US006090392A

United States Patent [19]
Berman

[11] Patent Number: 6,090,392
[45] Date of Patent: Jul. 18, 2000

[54] HIV ENVELOPE POLYPEPTIDES AND VACCINE

[75] Inventor: Phillip W. Berman, Portola Valley, Calif.

[73] Assignee: Genentech, Inc., South San Francisco, Calif.

[21] Appl. No.: 08/889,841

[22] Filed: Jul. 8, 1997

Related U.S. Application Data

[60] Provisional application No. 60/676,737, Jul. 8, 1996.

[51] Int. Cl.[7] .......................... A61K 39/21; A61K 39/12; A61K 39/00; A61K 39/38

[52] U.S. Cl. .................................... 424/208.1; 424/184.1; 424/188.1; 424/204.1; 530/395; 530/350; 530/326; 530/327; 530/329

[58] Field of Search .................................... 530/395, 350, 530/326, 327, 329; 424/184.1, 188.1, 204.1, 208.1

[56] References Cited

FOREIGN PATENT DOCUMENTS

| | | |
|---|---|---|
| 33320/89 | 11/1989 | Australia . |
| 0 187 041 A1 | 7/1986 | European Pat. Off. . |
| 0327180 | 8/1989 | European Pat. Off. . |
| 0 394 386 B1 | 9/1995 | European Pat. Off. . |
| 0 187 041 B1 | 5/1996 | European Pat. Off. . |
| 0 279 688 B1 | 4/1997 | European Pat. Off. . |
| 9115512 | of 1991 | WIPO . |
| WO 91/04273 | 4/1991 | WIPO . |
| WO 91/15238 | 10/1991 | WIPO . |
| WO 94/28929 | 12/1994 | WIPO . |

OTHER PUBLICATIONS

Berman et al., "Genetic and Immunologic Characterization of Viruses Infecting MN–rgp120 Vaccinated Volunteers," *One World, One Hope: XI International Conference on AIDS*, 10:3:10 (Jul. 7–12, 1996).

Berman et al., "Genetic and Immunologic Characterization of Viruses Infecting MN–rpg120–Vaccinated Volunteers," *The Journal of Infectious Diseases*, 176:2:384–397 (Aug., 1997).

McElrath et al., "Human immunodeficiency virus type 1 infection despite prior immunization with a recombinant envelope vaccine regimen," *Proc. Natl. Acad. Sci. USA*, 93:3972–3977 (Apr., 1996).

Kitchen et al., "Aetiology of AIDS—Antibodies to Human T–cell Leukaemia Virus (Type III) in Haemophiliacs," *Nature* 312:367–369 (Nov. 22, 1984).

Moore, "Enhanced: Coreceptors—Implications for HIV Pathogenesis and Therapy," *Science* 276:51 (1996).

Vandenbark et al., "Immunization with a Synthetic T–cell Receptor V–region Peptide Protects Against Experimental Autoimmune Encephalmyelitis," *Nature* 341:541–544 (Oct. 12, 1989).

*Primary Examiner*—Chris Eisenschenk
*Assistant Examiner*—Brett Nelson
*Attorney, Agent, or Firm*—McCutchen, Doyle, Brown & Enersen, LLP; Emily M. Haliday

[57] ABSTRACT

Oligonucleotide sequences encoding gp120 polypeptides from breakthrough isolates of vaccine trials using MN-rgp120 and the encoded gp120 polypeptides are provided. Use of the gp120 polypeptides from one or more of the isolates in a subunit vaccine, usually together with MN-rgp120, can provide protection against HIV strains that are sufficiently different from the vaccine strain (e.g.; MN-rgp120) that the vaccine does not confer protection against those strains. Antibodies induced by the polypeptides are also provided.

33 Claims, 22 Drawing Sheets

|       |    |                                                              |
|-------|----|--------------------------------------------------------------|
| C6.1  | 41 | V P V W K E A T T L F C C A S D A K K A Y D D T E V H N V W A T H A C V P T D P N P Q E M V L E |
| C6.5  | 41 | V P V W K E A T T L F C C A S D A K K A Y D D T E V H N V W A T H A C V P T D P N P Q E M V L E |
| C8.3  | 41 | V P V W K E A T T L F C C A S D A K K A Y D D T E V H N V W A T H A C V P T D P N P Q E V V L E |
| C8.6  | 41 | V P V W K E A T T L F C C A S D A K K A Y N D T E V H N V W A T H A C V P T D P N P Q E V V L G |
| C15.2 | 41 | V P V W K E A T T L F C C A S D A K K A Y N D T E V H K V W A T H A C V P T D P N P Q E V V L G |
| C15.3 | 41 | V P V W K E A T T L F C C A S D A K K A Y D D T E V H K V W A T H A C V P T D P S P Q E V V L G |
| C7.2  | 41 | V P V W K E A T T L F C C A S D A A R A Y D D T E V H N V W A T H A C V P T D P S P Q E V F L G |
| C7.10 | 41 | V P V W K E A T T L F C C A S D A K R A Y D D T G V H N V W A T H A C V P T D P N P Q E — — L E |
| C11.5 | 41 | V P V W K E A T T L F C C A S D A K K A Y D D T E V H N V W A T H A C V P T D P N P Q E — — L V |
| C11.7 | 41 | V P V W K E A N T L F C C A S D A K K A Y D D R E V H N V W A T H A C V P T D P N P Q E V V L G |
| C10.5 | 41 | V P V W K E A N T L F C C A S D A K K A Y D D R E V H N V W A T H A C V P T D P N P Q E V V L G |
| C10.7 | 41 | V P V W K E A T T L F C C A S D A K K A Y D D S E A H N V W A T H A C V P T D P N P Q E V E L E |
| C17.1 | 41 | V P V W K E A T T L F C C A S D A K K A Y D D S E A H N V W A T H A C V P T D P N P Q E V E L L |
| C17.3 | 41 | V P V W K E A T T L E C A S D A K K A Y D T E A H N V W A T H A C V P T D P N P Q E V E L V |
| MNGNE | 41 | V P V W K E A T T L F C A S D A K K A Y D T E A H N V W A T H A C V P T D P N P Q E V E L V |

| | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| C6.1 | 240 | A | G | F | A | I | L | K | C | R | D | K | K | F | N | G | T | G | P | C | K | N | V | S | T | V | Q | C | A | H | G | I | K | P | V | V | S | T | Q | L | L | N | G | S | L | A |
| C6.5 | 240 | A | G | F | A | I | L | K | C | K | D | K | K | F | N | G | T | G | P | C | K | N | V | S | T | V | Q | C | T | H | G | I | K | P | V | V | S | T | Q | L | L | N | G | S | L | A |
| C8.3 | 223 | A | G | F | A | I | L | K | C | K | D | K | K | F | N | G | T | G | P | C | K | N | V | S | T | V | Q | C | T | H | G | I | R | P | V | V | S | T | Q | L | L | N | G | S | L | A |
| C8.6 | 223 | A | G | F | A | I | L | K | C | K | D | K | K | F | N | G | T | G | P | C | K | N | V | R | T | V | Q | C | T | H | G | I | R | P | V | V | S | T | Q | L | L | N | G | S | L | A |
| C15.2 | 225 | A | G | F | A | I | L | K | C | N | N | K | T | F | E | G | K | G | P | C | K | N | V | S | T | V | Q | C | T | H | G | I | R | P | V | V | S | T | Q | L | L | N | G | S | L | A |
| C15.3 | 225 | A | G | F | A | I | L | K | C | N | N | K | T | F | E | G | K | G | P | E | K | N | V | S | T | V | Q | C | T | H | G | I | R | P | V | V | S | T | Q | L | L | N | G | S | L | A |
| C7.2 | 223 | A | G | F | A | I | L | K | C | N | D | K | K | F | S | G | K | G | P | E | K | N | V | S | T | V | Q | C | T | H | G | I | R | P | V | V | S | T | Q | L | L | N | G | S | L | A |
| C7.10 | 223 | A | G | F | A | I | L | K | C | N | D | K | K | F | S | G | K | G | P | C | S | K | V | S | T | V | Q | C | T | H | G | I | R | P | V | V | S | T | Q | L | L | N | G | S | L | A |
| C11.5 | 236 | A | G | F | A | I | L | K | C | K | D | K | K | F | N | G | T | G | P | C | S | K | V | S | T | V | Q | C | T | H | G | I | R | P | V | V | S | T | Q | L | L | N | G | S | L | A |
| C11.7 | 236 | A | G | F | A | I | L | K | C | K | D | K | K | F | N | G | T | G | P | C | K | N | V | S | T | V | Q | C | T | H | G | I | R | P | V | V | S | T | Q | L | L | N | G | S | L | A |
| C10.5 | 224 | A | G | F | A | I | L | K | C | K | D | K | K | F | N | G | T | G | P | C | K | N | V | S | T | V | Q | C | T | H | G | I | R | P | V | V | S | T | Q | L | L | N | G | S | L | A |
| C10.7 | 224 | A | G | F | A | I | L | K | C | K | D | K | K | F | N | G | T | G | P | C | K | N | V | S | T | V | Q | C | T | H | G | I | R | P | V | V | S | T | Q | L | L | N | G | S | L | A |
| C17.1 | 214 | A | G | F | A | I | L | K | C | K | D | K | K | F | N | G | T | G | P | C | T | N | V | S | T | V | Q | C | T | H | G | I | K | P | V | V | S | T | Q | L | L | N | G | S | L | A |
| C17.3 | 214 | A | G | F | A | I | L | K | C | K | D | K | K | F | N | G | T | G | P | C | T | N | V | S | T | V | Q | C | T | H | G | I | K | P | V | V | S | T | Q | L | L | N | G | S | L | A |
| MNGNE | 226 | A | G | F | A | I | L | K | C | N | D | K | K | F | S | G | K | G | S | C | K | N | V | S | T | V | Q | C | T | H | G | I | R | P | V | V | S | T | Q | L | L | N | G | S | L | A |

| | | | | | | | | | | | | | | | | | | | | | C4 | | | | | | | | | | | | | | | | | | V5 | | |
|---|---|---|---|---|---|---|---|---|---|---|---|---|---|---|---|---|---|---|---|---|---|---|---|---|---|---|---|---|---|---|---|---|---|---|---|---|---|---|---|---|---|
| C6.1 | 429 | C | R | I | K | Q | I | N | M | W | Q | E | I | G | K | A | M | Y | A | P | P | T | R | G | E | I | K | C | S | S | N | I | T | G | L | L | L | T | R | D | G | G | I | N | T | S |
| C6.5 | 429 | C | R | I | K | Q | I | N | M | W | Q | E | V | G | K | A | M | Y | A | P | P | I | R | G | E | I | K | C | S | S | N | I | T | G | L | L | L | T | R | D | G | G | I | N | T | S |
| C8.3 | 417 | C | R | I | K | Q | I | N | L | W | Q | E | V | G | K | A | M | Y | A | P | P | I | R | G | Q | I | R | C | S | S | N | I | T | G | L | L | L | T | R | D | G | G | I | N | T | G |
| C8.6 | 417 | C | R | I | K | Q | I | N | L | W | Q | E | V | G | K | A | M | Y | A | P | P | I | R | G | Q | I | R | C | S | S | N | I | T | G | L | L | L | T | R | D | G | G | S | N | T | S |
| C15.2 | 424 | C | R | I | K | Q | I | N | M | W | Q | E | V | G | K | A | M | Y | A | P | P | I | R | G | Q | I | R | C | S | S | N | I | T | G | L | M | I | R | R | D | G | G | G | K | N | E |
| C15.3 | 424 | C | R | I | K | Q | I | N | R | W | Q | E | V | G | K | A | M | Y | A | P | P | I | R | G | Q | I | K | C | S | S | N | I | T | G | L | M | L | T | R | D | G | G | N | E | N | N |
| C7.2 | 417 | C | R | I | K | Q | I | N | R | W | Q | E | V | G | K | A | T | Y | A | P | P | I | S | G | Q | I | R | C | T | S | N | I | T | G | L | L | L | T | R | D | G | G | N | E | N | N |
| C7.10 | 417 | C | R | I | K | Q | I | N | M | W | Q | E | V | G | K | A | M | Y | A | P | P | I | S | G | Q | I | K | C | S | S | N | I | T | G | L | L | L | T | R | D | G | G | N | V | T |
| C11.5 | 427 | C | R | I | K | Q | I | N | M | W | Q | E | V | G | K | A | M | Y | A | P | P | I | R | G | R | I | R | C | S | S | N | I | T | G | L | L | L | T | R | D | G | G | R | N | V | T |
| C11.7 | 427 | C | R | I | K | Q | I | N | M | W | Q | E | V | G | K | A | M | Y | A | P | P | I | R | G | R | I | R | C | S | S | N | I | T | G | L | L | L | T | R | D | G | G | N | D | D | G |
| C10.5 | 414 | C | R | I | K | Q | I | N | M | W | Q | E | V | G | K | A | M | Y | A | P | P | I | R | G | E | I | R | C | S | S | N | I | T | G | L | L | L | T | R | D | G | G | N | D | D | G |
| C10.7 | 414 | C | R | I | K | Q | I | N | M | W | Q | E | V | G | K | A | M | Y | A | P | P | I | R | G | E | I | R | C | S | S | N | I | T | G | L | L | L | T | R | D | G | G | N | D | G |
| C17.1 | 403 | C | R | I | R | Q | I | N | M | W | Q | E | V | G | K | A | M | Y | A | P | P | I | K | G | Q | I | R | C | S | S | N | I | T | G | L | L | L | T | R | D | G | G | N | N | M |
| C17.3 | 403 | C | R | I | R | Q | I | N | M | W | Q | E | K | I | G | K | A | M | Y | A | P | P | I | K | G | Q | I | R | C | S | S | N | I | T | G | L | L | I | L | T | R | D | G | G | N | N | M |
| MNgNE | 418 | C | K | L | K | Q | I | N | M | W | Q | R | V | G | K | A | M | Y | A | P | P | I | E | G | Q | I | R | C | S | S | N | I | T | G | L | L | L | T | R | D | G | G | E | D | T | D |

| FIG. 3A | FIG. 3B |
|---------|---------|
| FIG. 3C | FIG. 3D |
| FIG. 3E | FIG. 3F |
| FIG. 3G | FIG. 3H |
| FIG. 3I | FIG. 3J |

FIG. 3

HIV ENVELOPE POLYPEPTIDES AND VACCINE

CROSS-REFERENCE TO RELATED APPLICATIONS

This application claims the benefit of U.S. Provisional Application No. 60/676,737 (formerly application Ser. No. 08/676,737, filed Jul. 8, 1996, entitled "HIV Envelope Polypeptides and Vaccine" and naming Phillip W. Berman as the inventor.

BACKGROUND OF THE INVENTION

1. Field of the Invention

This invention relates to HIV envelope polypeptides and vaccines containing the polypeptides.

2. Description of the Related Art

Acquired immunodeficiency syndrome (AIDS) is caused by a retrovirus identified as the human immunodeficiency virus (HIV). There have been intense efforts to develop a vaccine that induces a protective immune response based on induction of antibodies or cellular responses. Recent efforts have used subunit vaccines where an HIV protein, rather than attenuated or killed virus, is used as the immunogen in the vaccine for safety reasons. Subunit vaccines generally include gp120, the portion of the HIV envelope protein which is on the surface of the virus.

The HIV envelope protein has been extensively described, and the amino acid and nucleic acid sequences encoding HIV envelope from a number of HIV strains are known (Myers, G. et al., 1992. Human Retroviruses and AIDS. A compilation and analysis of nucleic acid and amino acid sequences. Los Alamos National Laboratory, Los Alamos, N. Mex.). The HIV envelope protein is a glycoprotein of about 160 kd (gp160) which is anchored in the membrane bilayer at its carboxyl terminal region. The N-terminal segment, gp120, protrudes into the aqueous environment surrounding the virion and the C-terminal segment, gp41, spans the membrane. Via a host-cell mediated process, gp160 is cleaved to form gp120 and the integral membrane protein gp41. As there is no covalent attachment between gp120 and gp41, free gp120 is sometimes released from the surface of virions and infected cells.

The gp120 molecule consists of a polypeptide core of 60,000 daltons which is extensively modified by N-linked glycosylation to increase the apparent molecular weight of the molecule to 120,000 daltons. The amino acid sequence of gp120 contains five relatively conserved domains interspersed with five hypervariable domains. The positions of the 18 cysteine residues in the gp120 primary sequence, and the positions of 13 of the approximately 24 N-linked glycosylation sites in the gp120 sequence are common to all gp120 sequences. The hypervariable domains contain extensive amino acid substitutions, insertions and deletions. Sequence variations in these domains result in up to 30% overall sequence variability between gp120 molecules from the various viral isolates. Despite this variation, all gp120 sequences preserve the ability of the virus to bind to the viral receptor CD4 and to interact with gp41 to induce fusion of the viral and host cell membranes.

gp120 has been the object of intensive investigation as a vaccine candidate for subunit vaccines, as the viral protein which is most likely to be accessible to immune attack. At present, clinical trials using gp120 MN strain are underway. However, to date no human vaccine trial has been of sufficient size to confirm or refute vaccine efficacy.

The development of candidate HIV-1 vaccines is burdened by the lack of in vivo or in vitro models of HIV-1 infection that accurately approximate the conditions of natural infection in humans. Several candidate HIV-1 vaccines [Berman et al.; *J. Virol.* 7:4464–9 (1992); Haigwood et al.; *J. Virol.* 66:172–82 (1992); Salmon-Ceron et al.; *AIDS Res. and Human Retroviruses* 11:1479–86 (1995)] have been described that elicit broadly cross-reactive antibodies able to neutralize a variety of diverse HIV-1 isolates in vitro. However, the relevance of in vitro assays to protective immunity in vivo is uncertain. Although several vaccines have provided chimpanzees with protection from challenge by homologous and heterologous strains of HIV-1, protection has not always correlated with in vitro neutralization assays carried out in T cell lines, or in lectin- and cytokine-activated peripheral blood mononuclear cells (PBMCs) [Berman et al.; *Nature* 345:622–5 (1990); Bruck et al.; *Vaccine* 12(12):1141–8 (1994); El-Amad et al.; *AIDS* 9:1313–22 (1995); Girard et al.; *J. Virol.* 69:6239–48 (1995); and Fulz et al; *Science* 256:1687–1690 (1992)]. While successful protection of chimpanzees is encouraging and has historically proved to be a reliable indicator of vaccine efficacy, the conditions of infection in all experimental models of HIV-1 infection differ significantly from natural infection in humans.

Experimental HIV-1 infection in vivo and in vitro both suffer from the limitation that the in vitro amplification of HIV-1, which is required to prepare virus stocks for in vitro or in vivo infectivity experiments, imposes a genetic selection that results in a spectrum of virus quasi-species that differ from the spectrum of variants present in the clinical specimens used to establish the culture [Kusumi et al.; *J. Virol.* 66:875 (1992); Meyerhans et al.; *Cell* 58:901–10 (1989)]. Because of these uncertainties, and even greater uncertainties related to the amount of virus transmitted, the site and cell type involved in initial replication, and the kinetics of virus dissemination, the ability of currently available in vitro or in vivo assays to reliably predict vaccine efficacy is questionable.

One of the candidate HIV-1 vaccines that have entered human clinical trials is recombinant gp120 prepared in Chinese hamster ovary (CHO) cells from the MN strain of HIV-1 (MN-rgp120) (Berman et al.; *J. Virol.* 7:4464–9 (1992)). To date, approximately 499 adults have participated in Phase 1 and 2 immunogenicity and safety trials of this vaccine. The data collected thus far suggest that MN-rgp120 is safe, immunogenic, and elicits high titers of neutralizing antibodies in greater than 95% of individuals immunized according to a 0, 1, and 6 month immunization schedule [Belshe et al.; *JAMA* 272(6):475–80 (1994); McElrath; *Seminars in Cancer Biol.* 6:1–11 (1995)]. However, during the course of these trials, nine vaccinees who received MN-rgp120 have become infected with HIV-1 through high risk behavior. Small trials, such as these, in populations with low rates of infection and minimally sized placebo control groups do not have sufficient statistical power to confirm or refute vaccine efficacy.

However, effective vaccines based on gp120 or another HIV protein for protection against additional strains of HIV are still being sought to prevent the spread of this disease.

DESCRIPTION OF THE BACKGROUND ART

Recombinant subunit vaccines are described in Berman et al., PCT/US91/02250 (published as number WO91/15238 on Oct. 17, 1991). See also, e.g. Hu et al., Nature 328:721–724 (1987) (vaccinia virus-HIV envelope recombinant vaccine); Arthur et al., J. Virol. 63(12): 5046–5053 (1989) (purified gp120); and Berman et al., Proc. Natl. Acad. Sci. U.S.A. 85:5200–5204 (1988) (recombinant envelope glycoprotein gp120).

Numerous sequences for gp120 are known. The sequence of gp120 from the IIIB substrain of HIV-1$_{LAI}$ referred to herein is that determined by Muesing et al., "Nucleic acid structure and expression of the human AIDS/lymphadenopathy retrovirus, *Nature* 313:450–458 (1985). The sequences of gp120 from the NY-5, Jrcsf, Z6, Z321, and HXB2 strains of HIV-1 are listed by Myers et al., "Human Retroviruses and AIDS; A compilation and analysis of nucleic acid and amino acid sequences," Los Alamos National Laboratory, Los Alamos, N. Mex. (1992). The sequence of the Thai isolate A244 is provided by McCutchan et al., "Genetic Variants of HIV-1 in Thailand," AIDS Res. and Human Retroviruses 8:1887–1895 (1992). The MN$_{1984}$ clone is described by Gurgo et al., "Envelope sequences of two new United States HIV-1 isolates," *Virol.* 164: 531–536 (1988). As used herein, MN, MN-rgp120, the MN clone or isolate refers to MN$_{GNE}$. The MN$_{GNE}$ amino acid sequence is Sequence ID NO:41.

Each of the above-described references is incorporated herein by reference in its entirety.

SUMMARY OF THE INVENTION

Oligonucleotide sequences encoding gp120 polypeptides from breakthrough isolates of vaccine trials using MN-rgp120 and the encoded gp120 polypeptides are provided. Use of the gp120 polypeptides from one or more of the isolates in a subunit vaccine, usually together with MN-rgp120, can provide protection against HIV strains that are sufficiently different from the vaccine strain (e.g.; MN-rgp120) that the vaccine does not confer protection against those strains. Antibodies induced by the polypeptides are also provided.

BRIEF DESCRIPTION OF THE DRAWINGS

Figure 3B:
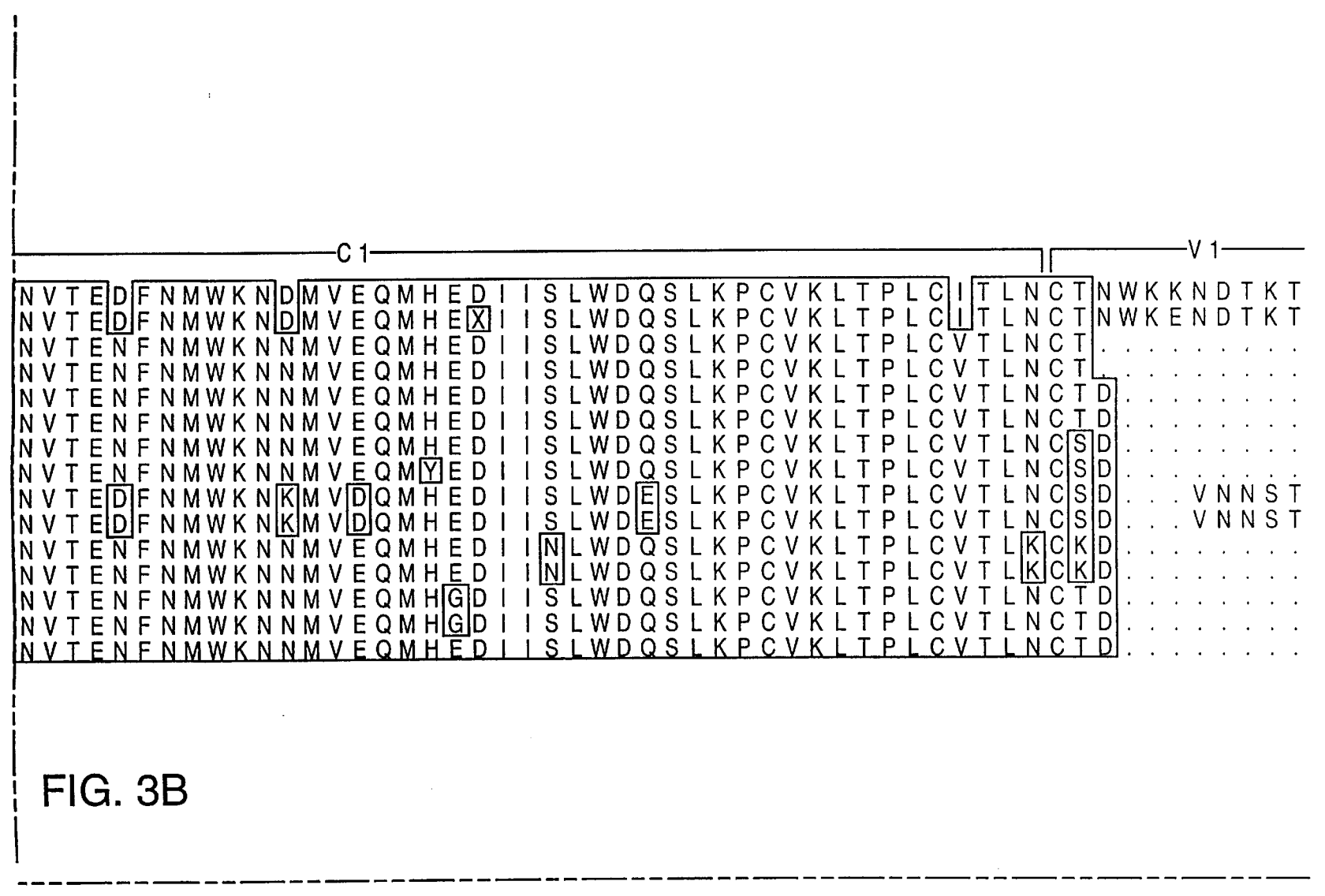
Figure 3C:
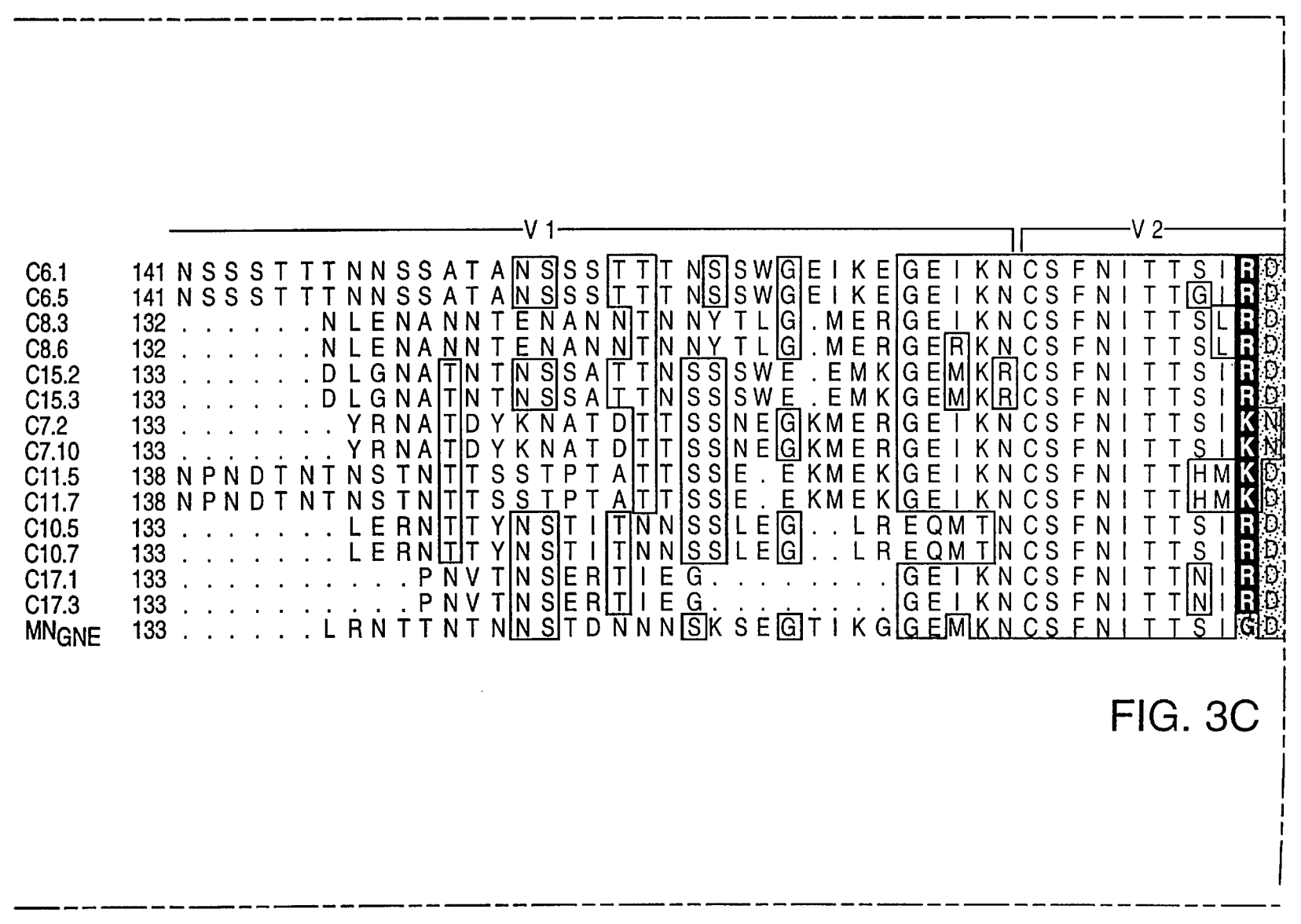
Figure 3G:
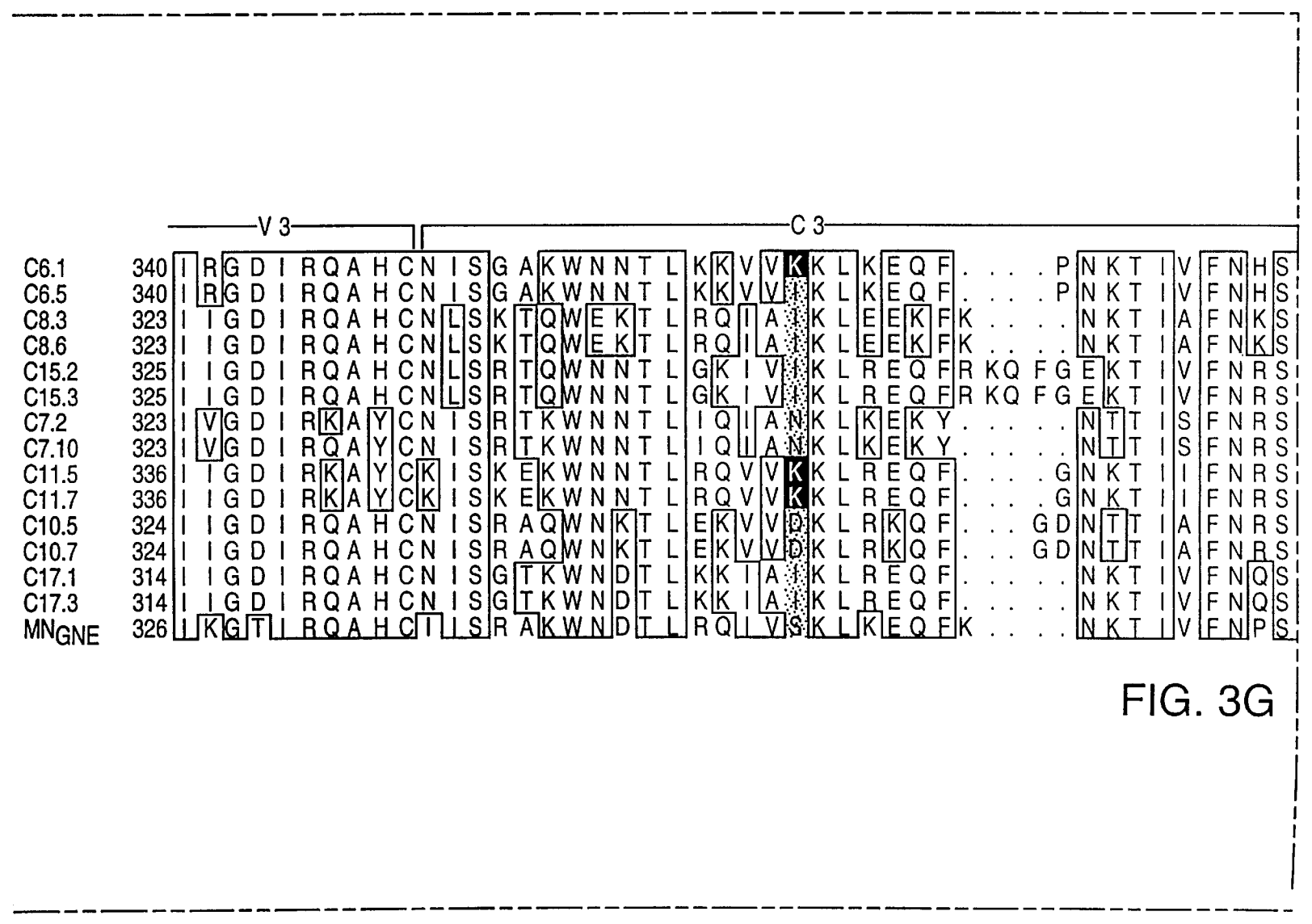
Figure 3H:
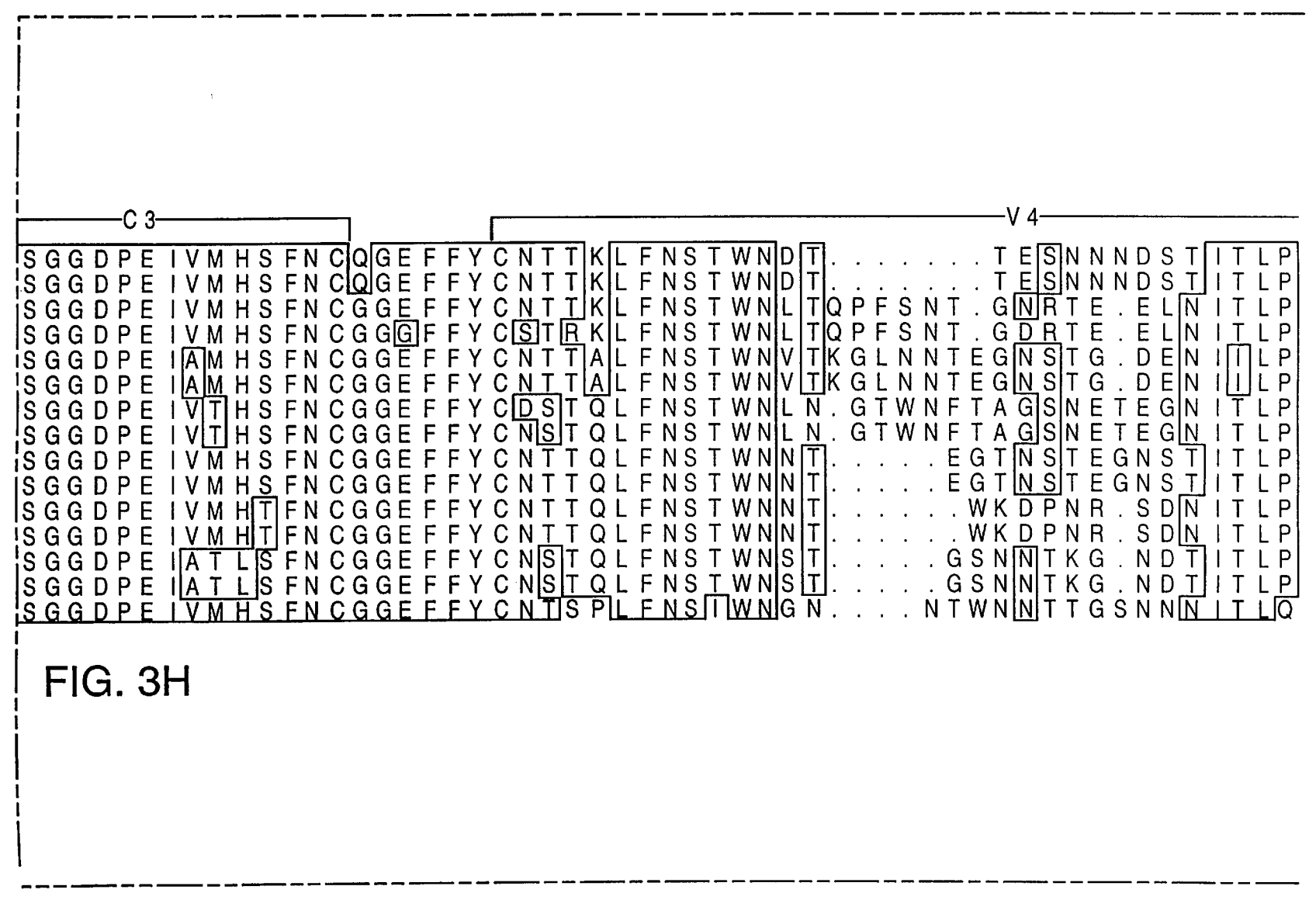

FIGS. 3A–3J illustrate predicted amino acid sequences of envelope glycoproteins (gp120) from breakthrough viruses. Proviral DNA sequences were amplified by PCR from PBMCs and cloned into the PRK5 expression plasmid. Two clones from each infected vaccinee were sequenced from double stranded plasmid DNA. Sequence numbering is with reference to the initiator methionine residue of gp120. For the purpose of comparison, the sequences shown begin at amino acid 12 of the mature, fully processed, envelope glycoproteins (corresponding to position 41 of the gp120 open reading frame). Shaded areas indicate sequences at neutralizing epitopes, dark boxes indicate polymorphisms thought to be important for the binding of virus neutralizing MAbs reactive with MN-rgp120. Conserved (C) regions and variable (V) regions are indicated above the sequences. Boxes indicate sequence homologies and polymorphisms.

FIG. 5A, binding by MAb (5B6) specific for the HSV-1 glycoprotein D flag epitope; FIG. 5B, binding by MAb (1034) against the V3 domain of MN-rgp120; FIG. 5C binding by MAb (50.1) raised against a synthetic peptide corresponding to the V3 domain of MN-rgp120; FIG. 5D, binding by a human MAb (15e) known to block the binding of gp120 to CD4.

DETAILED DESCRIPTION OF THE INVENTION

Figure 1A:
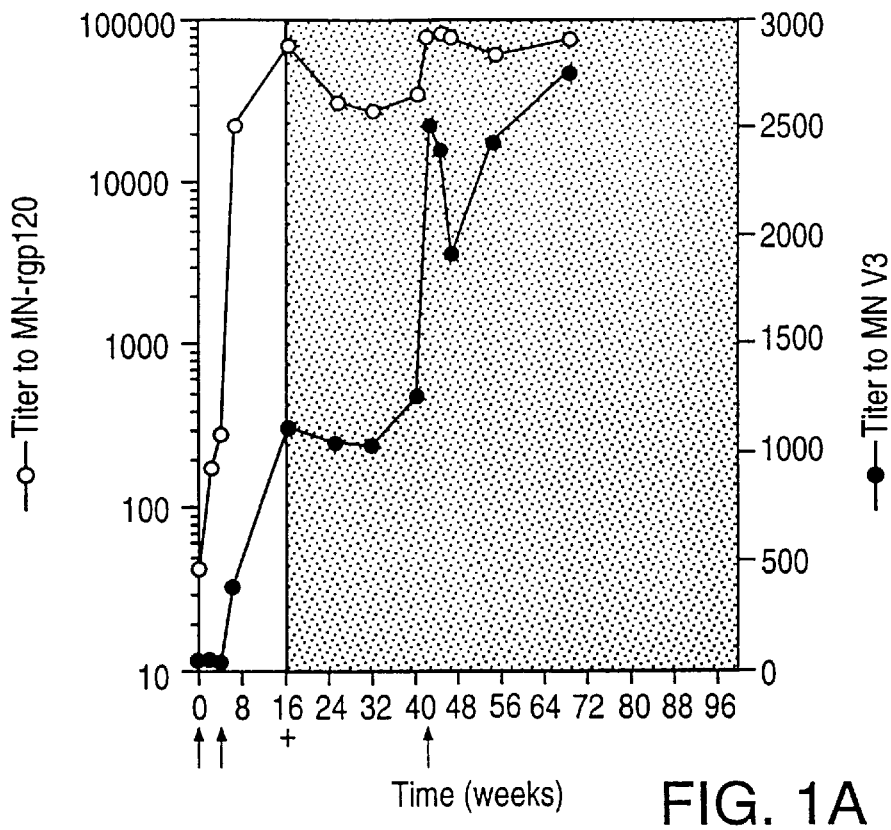
FIGS. 1A–1G illustrate the kinetics of antibody response to MN-rgp120 in vaccinees infected with HIV-1. Sera were collected at the time points indicated and assayed for antibodies reactive with MN-rgp120 (open circles) or a synthetic peptide derived from the V3 domain of MN-rgp120 (closed circles). Arrows indicate dates of injection. Plus sign indicates the first time HIV-1 infection was detected. Shaded area indicates data collected after HIV-1 infection. Data from vaccinee C6 is shown in FIG. 1A; C8 in FIG. 1B; C7, FIG. 1C; C11, FIG. 1D; C10, FIG. 1E; C17, FIG. 1F; and C15, FIG. 1G.

The present invention provides gp120 polypeptides from breakthrough isolates of HIV vaccine trials. Novel oligonucleotide sequences encoding gp120 from breakthrough isolates which can be used to express gp120 are also provided. Use of gp120 polypeptides from one or more of the isolates in a subunit vaccine, usually together with MN-rgp120, can provide protection against HIV strains that are sufficiently different from the vaccine strain (e.g.; MN-rgp120) that the vaccine does not confer protection against those strains.

In one embodiment, the vaccine is based on the use of the MN-rgp120 polypeptide (Sequence ID No:41) and gp120 polypeptides from MN-like viruses that include neutralizing epitopes that are not present in the initial vaccine strain, and are sufficiently different from those of the vaccine strain, to have been able to cause HIV-1 infections in MN-rgp120 vaccinated individuals (i.e.; to result in breakthrough infections). Use of the initial vaccine strain empirically determines the viruses present in the population that contain additional neutralizing epitopes sufficiently different from those of the vaccine strain to escape protection induced by the vaccine strain. Use of an initial representative gp120 polypeptide in a vaccine acts as a sieve so that viruses that are not effectively protected against by the vaccine strain breakthrough the vaccine, empirically resulting in determination of additional strains in a given geographic region that are not protected against by the initial vaccine strain. Use of gp120 from those breakthrough isolates complements the vaccine isolate by providing additional neutralizing epitopes not present in the initial vaccine strain, therefore creating a more complete vaccine that confers protection against multiple different virus strains in the region.

Prior HIV-1 vaccine strategies were based on selection of appropriate candidate vaccine polypeptides based on homology alignment studies. However, since some of the neutralizing epitopes are conformation-dependent and the location of all of these epitopes is not known, this approach necessarily cannot determine all of the neutralizing epitopes that should be included in a vaccine for a particular region. In contrast, the present approach uses a selected representative strain and empirically determines strains that are sufficiently different and therefore breakthrough the barrier of protection provided by the initial vaccination program. Those strains can be included in the vaccine to confer more complete protection from HIV strains in the region. In addition, those strains can be used alone to confer protection against the breakthrough virus.

In another embodiment, the invention comprises a vaccine containing a first HIV gp120 polypeptide sequence and a breakthrough isolate HIV gp120 polypeptide sequence from a vaccinee vaccinated with a vaccine including the first HIV gp120 polypeptide sequence, the HIV gp120 polypeptide sequences being in a suitable carrier. Fragments of one or both HIV gp120 polypeptide sequences can be substituted for one or both of the corresponding HIV gp120 polypeptide sequences.

Preferably, the first gp120 polypeptide sequence contains neutralizing epitopes found in one or more gp120 polypeptides present in isolates from the geographical region where the initial vaccine (i.e., the vaccine that gives rise to the breakthrough isolate) is administered. More preferably, the first gp120 polypeptide sequence contains at least one of the more common neutralizing epitopes for the region, and most preferably the first gp120 polypeptide sequence contains at least one of the three most common neutralizing epitopes.

gp120 polypeptide sequences suitable for use as the first gp120 polypeptide sequence include gp120 MN, the Thai isolate A244 sequence (hereinafter "gp120 A244"), gp120 MN-GNE6 (Sequences ID NOs:43 and 44; also known in the art as "gp120 GNE6"), and gp120 MN-GNE8 (Sequence ID NO:46; also known in the art as "gp120 GNE8"), and the like. gp120 MN, gp120 MN-GNE6, and gp120 MN-GNE8 are especially preferred for use as the first gp120 polypeptide sequence in initial vaccines for North America. gp120 A244 is especially preferred for use as the first gp120 polypeptide sequence in initial vaccines for Thailand.

In a variation of this embodiment, the vaccine includes two different (i.e., first and second) gp120 polypeptide sequences, or fragments thereof, in combination with a breakthrough isolate HIV gp120 polypeptide sequence. The latter can be from a vaccinee vaccinated with either or both of the first and second HIV gp120 polypeptide sequences.

Exemplary vaccines include those containing combinations of gp120 MN, gp120 A244, gp120 MN-GNE6 (Sequence ID NOs:43 and 44), and gp120 MN-GNE8 (Sequence ID NO:46). Combinations of gp120 MN and gp120 A244 or gp120 MN-GNE8 (Sequence ID NO:46) with a breakthrough isolate HIV gp120 polypeptide sequence are especially preferred.

In vaccines containing gp120 MN, the breakthrough isolate HIV gp120 polypeptide sequence can be an HIV gp120 polypeptide sequence selected from the group consisting of Sequence ID NOs:2, 5, 8, 10, 12, 16, 19, 23, 25, 28, 31, 33, 36, and 39, and fragments thereof.

The term "subunit vaccine" is used herein, as in the art, to refer to a viral vaccine that does not contain virus, but rather contains one or more viral proteins or fragments of viral proteins. As used herein, the term "multivalent", means that the vaccine contains gp120 from at least two HIV isolates having different amino acid sequences.

The term "breakthrough isolate" or "breakthrough virus" is used herein, as in the art, to refer to a virus isolated from a vaccinee.

The terms "amino acid sequence", "polypeptide sequence", and "polypeptide" are used interchangeably herein as in the art, as are the terms "nucleic acid sequence", "nucleotide sequence", and "oligonucleotide".

Polypeptides from Breakthrough Isolates

The gp120 polypeptides of this invention correspond to the amino acid sequences of seven breakthrough isolates which are illustrated below in Table 1. A polypeptide of this invention includes an HIV gp120 amino acid sequence illustrated in Table 1 (Sequence ID NOs:1, 4, 7, 9, 11, 15, 18, 22, 24, 27, 30, 32, 35, and 38) and fragments thereof. The polypeptides of this invention can include fused sequences from two or more HIV gp120 or gp160 amino acid sequences.

The polypeptide can also be joined to another viral protein, such as a flag epitope amino acid sequence. The term "flag epitope" is used herein, as in the art, to denote an amino acid sequence that includes an epitope recognized by a monoclonal antibody. Flag epitopes facilitate using single monoclonal antibody affinity purification of a plurality of different recombinant proteins, each having the flag epitope recognized by the monoclonal antibody. Numerous amino acid sequences can function as flag epitopes. The N-terminal sequences of Herpes Simplex Virus Type 1 (HSV-1) glycoprotein D (gD-1) is conveniently used as the flag epitope and its use is described in detail in the examples. The flag epitope is conveniently fused to the N terminus of the HIV gp120 polypeptide sequence. Alternatively, however, monoclonal antibodies that recognize neutralizing epitopes in the rgp120 sequences can be used to affinity purify the amino acid sequences, and a flag epitope can be omitted.

In addition, various signal sequences can be joined to a polypeptide of this invention. Although rgp120 is secreted to some extent in HIV cultures, the amount of the envelope glycoprotein released from (secreted by) the host cells varies widely from strain to strain. Various signal sequences can be introduced into the polypeptide by joining a nucleotide sequence encoding the signal sequence to the nucleotide sequence encoding the rgp120 to facilitate secretion of rgp120 from the cells. For example, Chiron HIV gp120 polypeptides include a signal sequence from tissue plasminogen activator (TPA) that provides good secretion of rgp120. Additional signal sequences are well known and include the N-terminal domain of murine leukemia virus surface protein gp70 described by Kayman et al., *J. Virol.* 68:400–410 (1984).

Table 1 illustrates the nucleotide and deduced amino acid sequences for two clones of each the seven breakthrough isolates of this invention. The clones are: C6.1; C6.5; C8.3; C8.6; C15.2; C15.3; C7.2; C7.10; C11.5; C11.7; C10.5; C10.7; C17.1; and C17.3. These sequences are SEQ. ID. NOs:1–40. The amino acid sequence for MN and the nucleotide and deduced amino acid sequences for MN-GNE6 and MN-GNE8 are illustrated in the sequence listing hereinafter. In the listing for MN-GNE6, a stop codon appears at amino acid residue position 51. This stop codon can be replaced with a codon encoding the corresponding amino acid from MN or MN-GNE8 or another isolate.

TABLE 1

CLONE C6.1

| GGG | GTA | CCT | GTG | TGG | AAG | GAA | GCA | ACC | ACC | ACT | CTA | 36 |
|---|---|---|---|---|---|---|---|---|---|---|---|---|
| Gly | Val | Pro | Val | Trp | Lys | Glu | Ala | Thr | Thr | Thr | Leu | |
| 1 | | | | 5 | | | | | 10 | | | |
| TTT | TGT | GCA | TCA | GAT | GCT | AAA | GCA | TAT | GAC | ACA | GAG GTG | 75 |
| Phe | Cys | Ala | Ser | Asp | Ala | Lys | Ala | Tyr | Asp | Thr | Glu Val | |
| | | 15 | | | | 20 | | | | | 25 | |
| CAT | AAT | GTT | TGG | GCC | ACA | CAT | GCT | TGT | GTA | CCC | ACA GAC | 114 |
| His | Asn | Val | Trp | Ala | Thr | His | Ala | Cys | Val | Pro | Thr Asp | |
| | | | | 30 | | | | | 35 | | | |
| CCA | AAC | CCA | CAA | GAA | ATG | GTA | TTG | GAA | AAT | GTG | ACA GAA | 153 |
| Pro | Asn | Pro | Gln | Glu | Met | Val | Leu | Glu | Asn | Val | Thr Glu | |
| | | 40 | | | | 45 | | | | | 50 | |
| GAT | TTT | AAC | ATG | TGG | AAA | AAT | GAC | ATG | GTA | GAA | CAG ATG | 192 |
| Asp | Phe | Asn | Met | Trp | Lys | Asn | Asp | Met | Val | Glu | Gln Met | |
| | | | | 55 | | | | | 60 | | | |
| CAT | GAG | GAT | ATA | ATC | AGT | TTA | TGG | GAT | CAA | AGC | CTA AAA | 231 |
| His | Glu | Asp | Ile | Ile | Ser | Leu | Trp | Asp | Gln | Ser | Leu Lys | |
| 65 | | | | | 70 | | | | | 75 | | |
| CCA | TGT | GTA | AAA | TTA | ACC | CCA | CTC | TGT | ATT | ACT | TTA AAT | 270 |
| Pro | Cys | Val | Lys | Leu | Thr | Pro | Leu | Cys | Ile | Thr | Leu Asn | |
| | | 80 | | | | 85 | | | | | 90 | |
| TGC | ACC | AAT | TGG | AAG | AAG | AAT | GAT | ACT | AAA | ACT | AAT AGT | 309 |
| Cys | Thr | Asn | Trp | Lys | Lys | Asn | Asp | Thr | Lys | Thr | Asn Ser | |
| | | | | 95 | | | | | 100 | | | |
| AGT | AGT | ACT | ACA | ACT | AAT | AAT | AGT | AGT | GCT | ACA | GCT AAT | 348 |
| Ser | Ser | Thr | Thr | Thr | Asn | Asn | Ser | Ser | Ala | Thr | Ala Asn | |
| | | 105 | | | | 110 | | | | | 115 | |
| AGT | AGT | AGT | ACT | ACA | ACT | AAT | AGT | AGT | TGG | GGA | GAG ATA | 387 |
| Ser | Ser | Ser | Thr | Thr | Thr | Asn | Ser | Ser | Trp | Gly | Glu Ile | |
| | | | | 120 | | | | | 125 | | | |
| AAG | GAG | GGA | GAA | ATA | AAG | AAC | TGC | TCT | TTC | AAT | ATC ACC | 426 |
| Lys | Glu | Gly | Glu | Ile | Lys | Asn | Cys | Ser | Phe | Asn | Ile Thr | |
| 130 | | | | | 135 | | | | | 140 | | |
| ACA | AGC | ATA | AGA | GAC | AAG | GTG | AAG | AAA | GAA | TAT | GCA CTT | 465 |
| Thr | Ser | Ile | Arg | Asp | Lys | Val | Lys | Lys | Glu | Tyr | Ala Leu | |
| | | 145 | | | | 150 | | | | | 155 | |
| TTT | TAT | AGC | CTT | GAT | GTA | GTA | CCA | ATA | GAA | AAT | GAT AAT | 504 |
| Phe | Tyr | Ser | Leu | Asp | Val | Val | Pro | Ile | Glu | Asn | Asp Asn | |
| | | | | 160 | | | | | 165 | | | |
| ACT | AGC | TAT | AGG | TTG | AGA | AGT | TGT | AAC | ACC | TCA | GTC ATT | 543 |
| Thr | Ser | Tyr | Arg | Leu | Arg | Ser | Cys | Asn | Thr | Ser | Val Ile | |
| | | 170 | | | | 175 | | | | | 180 | |
| ACA | CAA | GCC | TGT | CCA | AAG | GTA | ACT | TTT | GAG | CCA | ATT CCC | 582 |
| Thr | Gln | Ala | Cys | Pro | Lys | Val | Thr | Phe | Glu | Pro | Ile Pro | |
| | | | 185 | | | | | 190 | | | | |
| ATA | CAT | TAT | TGT | ACC | CCG | GCT | GGT | TTT | GCG | ATT | CTG AAG | 621 |
| Ile | His | Tyr | Cys | Thr | Pro | Ala | Gly | Phe | Ala | Ile | Leu Lys | |
| 195 | | | | | 200 | | | | | 205 | | |
| TGT | AGA | GAT | AAA | AAG | TTC | AAT | GGA | ACA | GGA | CCA | TGC AAA | 660 |
| Cys | Arg | Asp | Lys | Lys | Phe | Asn | Gly | Thr | Gly | Pro | Cys Lys | |

TABLE 1-continued

|  |  |  |  |  |  |  |  |  |  |  |
|---|---|---|---|---|---|---|---|---|---|---|
|  |  | 210 |  |  | 215 |  |  |  | 220 |  |
| AAT | GTT | AGC | ACA | GTA | CAA | TGT | GCA | CAT | GGA | ATT | AAG | CCA | 699 |
| Asn | Val | Ser | Thr | Val | Gln | Cys | Ala | His | Gly | Ile | Lys | Pro |  |
|  |  |  | 225 |  |  |  |  | 230 |  |  |  |  |  |
| GTA | GTG | TCA | ACT | CAA | CTG | CTG | TTA | AAT | GGC | AGC | CTA | GCA | 738 |
| Val | Val | Ser | Thr | Gln | Leu | Leu | Leu | Asn | Gly | Ser | Leu | Ala |  |
|  |  | 235 |  |  |  | 240 |  |  |  |  | 245 |  |  |
| GAA | GAA | GAG | GTA | ATA | ATT | AGA | TCT | GCC | AAT | TTC | TCA | AAC | 777 |
| Glu | Glu | Glu | Val | Ile | Ile | Arg | Ser | Ala | Asn | Phe | Ser | Asn |  |
|  |  |  |  | 250 |  |  |  |  | 255 |  |  |  |  |
| AAT | GCT | AAA | ATC | ATA | ATA | GTA | CAG | TTG | AGG | GAA | CCT | GTA | 816 |
| Asn | Ala | Lys | Ile | Ile | Ile | Val | Gln | Leu | Arg | Glu | Pro | Val |  |
| 260 |  |  |  |  | 265 |  |  |  |  | 270 |  |  |  |
| GAA | ATT | AAT | TGT | ACA | AGA | CCC | AGC | AAC | AAT | ACA | ATA | AAA | 855 |
| Glu | Ile | Asn | Cys | Thr | Arg | Pro | Ser | Asn | Asn | Thr | Ile | Lys |  |
|  |  |  | 275 |  |  |  |  | 280 |  |  |  |  | 285 |
| GGT | ATA | CAC | ATA | GGA | CCA | GGG | AGA | GCA | TTT | TAT | GCA | ACA | 894 |
| Gly | Ile | His | Ile | Gly | Pro | Gly | Arg | Ala | Phe | Tyr | Ala | Thr |  |
|  |  |  |  | 290 |  |  |  |  | 295 |  |  |  |  |
| GGA | GAC | ATA | CGA | GGA | GAT | ATA | AGA | CAA | GCA | CAT | TGT | AAC | 933 |
| Gly | Asp | Ile | Arg | Gly | Asp | Ile | Arg | Gln | Ala | His | Cys | Asn |  |
|  |  | 300 |  |  |  |  | 305 |  |  |  |  | 310 |  |
| ATT | AGT | GGA | GCA | AAA | TGG | AAT | AAC | ACT | TTA | AAG | AAG | GTA | 972 |
| Ile | Ser | Gly | Ala | Lys | Trp | Asn | Asn | Thr | Leu | Lys | Lys | Val |  |
|  |  |  | 315 |  |  |  |  | 320 |  |  |  |  |  |
| GTT | AAA | AAA | TTA | AAA | GAA | CAA | TTT | CCA | AAT | AAA | ACA | ATA | 1011 |
| Val | Lys | Lys | Leu | Lys | Glu | Gln | Phe | Pro | Asn | Lys | Thr | Ile |  |
| 325 |  |  |  |  | 330 |  |  |  |  | 335 |  |  |  |
| GTC | TTT | AAC | CAT | TCC | TCA | GGA | GGG | GAC | CCA | GAA | ATT | GTA | 1050 |
| Val | Phe | Asn | His | Ser | Ser | Gly | Gly | Asp | Pro | Glu | Ile | Val |  |
|  |  |  | 340 |  |  |  |  | 345 |  |  |  |  | 350 |
| ATG | CAC | AGT | TTT | AAT | TGT | CAA | GGG | GAA | TTT | TTC | TAC | TGT | 1089 |
| Met | His | Ser | Phe | Asn | Cys | Gln | Gly | Glu | Phe | Phe | Tyr | Cys |  |
|  |  |  |  | 355 |  |  |  |  | 360 |  |  |  |  |
| AAT | ACA | ACA | AAG | CTG | TTT | AAT | AGT | ACT | TGG | AAT | GAT | ACT | 1128 |
| Asn | Thr | Thr | Lys | Leu | Phe | Asn | Ser | Thr | Trp | Asn | Asp | Thr |  |
|  |  | 365 |  |  |  |  | 370 |  |  |  |  | 375 |  |
| ACA | GAG | TCA | AAT | AAC | AAT | GAT | AGT | ACT | ATT | ACA | CTC | CCA | 1167 |
| Thr | Glu | Ser | Asn | Asn | Asn | Asp | Ser | Thr | Ile | Thr | Leu | Pro |  |
|  |  |  | 380 |  |  |  |  | 385 |  |  |  |  |  |
| TGC | AGA | ATA | AAA | CAA | ATT | ATA | AAC | ATG | TGG | CAG | GAA | ATA | 1206 |
| Cys | Arg | Ile | Lys | Gln | Ile | Ile | Asn | Met | Trp | Gln | Glu | Ile |  |
| 390 |  |  |  |  | 395 |  |  |  |  | 400 |  |  |  |
| GGA | AAA | GCA | ATG | TAT | GCC | CCT | CCC | ACC | AGA | GGA | GAA | ATT | 1245 |
| Gly | Lys | Ala | Met | Tyr | Ala | Pro | Pro | Thr | Arg | Gly | Glu | Ile |  |
|  |  |  | 405 |  |  |  |  | 410 |  |  |  |  | 415 |
| AAA | TGT | TCA | TCA | AAT | ATT | ACA | GGA | CTA | CTG | TTA | ATA | AGA | 1284 |
| Lys | Cys | Ser | Ser | Asn | Ile | Thr | Gly | Leu | Leu | Leu | Ile | Arg |  |
|  |  |  |  | 420 |  |  |  |  | 425 |  |  |  |  |
| GAT | GGT | GGT | ATT | AAC | ACT | AGC | GAT | GCC | ACC | GAG | ACC | TTC | 1323 |
| Asp | Gly | Gly | Ile | Asn | Thr | Ser | Asp | Ala | Thr | Glu | Thr | Phe |  |
|  |  | 430 |  |  |  |  | 435 |  |  |  |  | 440 |  |
| AGA | CCG | GGA | GGA | GGA | GAT | ATG | AGG | GAC | AAT | TGG | AGA | AGT | 1362 |
| Arg | Pro | Gly | Gly | Gly | Asp | Met | Arg | Asp | Asn | Trp | Arg | Ser |  |
|  |  |  | 445 |  |  |  |  | 450 |  |  |  |  |  |
| GAA | TTA | TAT | AAA | TAT | AAA | GTA | GTG | AAA | ATT | GAG | CCA | TTA | 1401 |
| Glu | Leu | Tyr | Lys | Tyr | Lys | Val | Val | Lys | Ile | Glu | Pro | Leu |  |
| 455 |  |  |  |  | 460 |  |  |  |  | 465 |  |  |  |
| GGA | GTA | GCA | CCC | ACC | AAG | GCA | AAG | AGA | AGA | GTG | GTG | CAG | 1440 |

TABLE 1-continued

```
Gly Val Ala Pro Thr Lys Ala Lys Arg Arg Val Val Gln
        470             475             480

AGA GAA AAA AGA GCA GTA ACA CTA GGA GCT ATG TTC CTT    1479
Arg Glu Lys Arg Ala Val Thr Leu Gly Ala Met Phe Leu
            485             490

GGG TTC TTA GGA GCA TAA AGC TTC    1503
Gly Phe Leu Gly Ala Xaa Ser Phe
    495             500 501
```

CLONE C6.5

```
    GGG GTA CCT GTA TGG AAA GAA GCA ACC ACC ACT CTA    36
    Gly Val Pro Val Trp Lys Glu Ala Thr Thr Thr Leu
    1            5                  10

TTT TGT GCA TCA GAT GCT AAA GCA TAT GAC ACA GAG GTG    75
Phe Cys Ala Ser Asp Ala Lys Ala Tyr Asp Thr Glu Val
            15              20              25

CAT AAT GTT TGG GCC ACA CAT GCT TGT GTA CCC ACA GAC    114
His Asn Val Trp Ala Thr His Ala Cys Val Pro Thr Asp
                30              35

CCA AAC CCA CAA GAA ATG GTA TTG GAA AAT GTG ACA GAA    153
Pro Asn Pro Gln Glu Met Val Leu Glu Asn Val Thr Glu
        40              45              50

GAT TTT AAC ATG TGG AAA AAT GAC ATG GTA GAA CAG ATG    192
Asp Phe Asn Met Trp Lys Asn Asp Met Val Glu Gln Met
            55              60

CAT GAG ANT ATA ATC AGT TTA TGG GAT CAA AGC CTA AAA    231
His Glu Xaa Ile Ile Ser Leu Trp Asp Gln Ser Leu Lys
65              70              75

CCA TGT GTA AAA TTA ACC CCA CTC TGT ATT ACT TTA AAT    270
Pro Cys Val Lys Leu Thr Pro Leu Cys Ile Thr Leu Asn
            80              85              90

TGC ACC AAT TGG AAG GAG AAT GAT ACT AAA ACT AAT AGT    309
Cys Thr Asn Trp Lys Glu Asn Asp Thr Lys Thr Asn Ser
                95              100

AGT AGT ACT ACA ACT AAT AAT AGT AGT GCT ACA GCT AAT    348
Ser Ser Thr Thr Thr Asn Asn Ser Ser Ala Thr Ala Asn
            105             110             115

AGT AGT AGT ACT ACA ACT AAT AGT AGT TGG GGA GAG ATA    387
Ser Ser Ser Thr Thr Thr Asn Ser Ser Trp Gly Glu Ile
            120             125

AAG GAG GGA GAA ATA AAG AAC TGC TCT TTC AAT ATC ACC    426
Lys Glu Gly Glu Ile Lys Asn Cys Ser Phe Asn Ile Thr
130             135             140

ACA GGC ATA AGA GAC AAG GTG AAG AAA GAA TAT GCA CTT    465
Thr Gly Ile Arg Asp Lys Val Lys Lys Glu Tyr Ala Leu
            145             150             155

TTT TAT AGC CTT GAT GTA GTA CCA ATA GAA AAT GAT AAT    504
Phe Tyr Ser Leu Asp Val Val Pro Ile Glu Asn Asp Asn
                160             165

ACT AGC TAT AGG TTG AGA AGT TGT AAC ACC TCA GTC ATT    543
Thr Ser Tyr Arg Leu Arg Ser Cys Asn Thr Ser Val Ile
            170             175             180

ACA CAA GCC TGT CCA AAG GTA ACT TTT GAG CCA ATT CCC    582
Thr Gln Ala Cys Pro Lys Val Thr Phe Glu Pro Ile Pro
                185             190

ATA CAT TAT TGT ACC CCG GCT GGT TTT GCG ATT CTG AAG    621
Ile His Tyr Cys Thr Pro Ala Gly Phe Ala Ile Leu Lys
195             200             205

TGT AAA GAT AAA AAG TTC AAT GGA ACA GGA CCA TGC AAA    660
Cys Lys Asp Lys Lys Phe Asn Gly Thr Gly Pro Cys Lys
```

TABLE 1-continued

| | | | | | | | | | | | |
|---|---|---|---|---|---|---|---|---|---|---|---|
| | | 210 | | | | 215 | | | | 220 | |
| AAT | GTT | AGC | ACA | GTA | CAA | TGT | ACA | CAT | GGA | ATT | AAG CCA | 699 |
| Asn | Val | Ser | Thr | Val | Gln | Cys | Thr | His | Gly | Ile | Lys Pro |
| | | | | 225 | | | | 230 | | | |
| GTA | GTG | TCA | ACT | CAA | CTG | CTG | TTA | AAT | GGC | AGC | CTA GCA | 738 |
| Val | Val | Ser | Thr | Gln | Leu | Leu | Leu | Asn | Gly | Ser | Leu Ala |
| | | 235 | | | | 240 | | | | 245 | |
| GAA | GAA | GAG | GTA | ATA | ATT | AGA | TCT | GCC | AAT | TTC | TCA AAC | 777 |
| Glu | Glu | Glu | Val | Ile | Ile | Arg | Ser | Ala | Asn | Phe | Ser Asn |
| | | | 250 | | | | 255 | | | | |
| AAT | GCT | AAA | ATC | ATA | ATA | GTA | CAG | TTG | AAG | GAA | CCT GTA | 816 |
| Asn | Ala | Lys | Ile | Ile | Ile | Val | Gln | Leu | Lys | Glu | Pro Val |
| 260 | | | | 265 | | | | | 27 | | |
| GAA | ATT | AAT | TGT | ACA | AGA | CCC | AGC | AAC | AAT | ACA | ATA AAA | 855 |
| Glu | Ile | Asn | Cys | Thr | Arg | Pro | Ser | Asn | Asn | Thr | Ile Lys |
| | | 275 | | | | 280 | | | | 285 | |
| GGT | ATA | CAC | ATA | GGA | CCA | GGG | AGA | GCA | TTT | TAT | GCA ACA | 894 |
| Gly | Ile | His | Ile | Gly | Pro | Gly | Arg | Ala | Phe | Tyr | Ala Thr |
| | | | 290 | | | | 295 | | | | |
| GGA | GAC | ATA | CGA | GGA | GAT | ATA | AGA | CAA | GCA | CAT | TGT AAC | 933 |
| Gly | Asp | Ile | Arg | Gly | Asp | Ile | Arg | Gln | Ala | His | Cys Asn |
| | 300 | | | | 305 | | | | 310 | | |
| ATT | AGT | GGA | GCA | AAA | TGG | AAT | AAC | ACT | TTA | AAG | AAG GTA | 972 |
| Ile | Ser | Gly | Ala | Lys | Trp | Asn | Asn | Thr | Leu | Lys | Lys Val |
| | | 315 | | | | 320 | | | | | |
| GTT | ATA | AAA | TTA | AAA | GAA | CAA | TTT | CCA | AAT | AAA | ACA ATA | 1011 |
| Val | Ile | Lys | Leu | Lys | Glu | Gln | Phe | Pro | Asn | Lys | Thr Ile |
| 325 | | | | 330 | | | | | 335 | | |
| GTC | TTT | AAC | CAT | TCC | TCA | GGA | GGG | GAC | CCA | GAA | ATT GTA | 1050 |
| Val | Phe | Asn | His | Ser | Ser | Gly | Gly | Asp | Pro | Glu | Ile Val |
| | | 340 | | | | 345 | | | | | 350 |
| ATG | CAC | AGT | TTT | AAT | TGT | CAA | GGG | GAA | TTT | TTC | TAC TGT | 1089 |
| Met | His | Ser | Phe | Asn | Cys | Gln | Gly | Glu | Phe | Phe | Tyr Cys |
| | | | 355 | | | | 360 | | | | |
| AAT | ACA | ACG | AAG | CTG | TTT | AAT | AGT | ACT | TGG | AAT | GAT ACT | 1128 |
| Asn | Thr | Thr | Lys | Leu | Phe | Asn | Ser | Thr | Trp | Asn | Asp Thr |
| | 365 | | | | 370 | | | | 375 | | |
| ACA | GAG | TCA | AAT | AAC | AAT | GAT | AGT | ACT | ATT | ACA | CTC CCA | 1167 |
| Thr | Glu | Ser | Asn | Asn | Asn | Asp | Ser | Thr | Ile | Thr | Leu Pro |
| | | 380 | | | | 385 | | | | | |
| TGC | AGA | ATA | AAA | CAA | ATT | ATA | AAC | ATG | TGG | CAG | GAA GTA | 1206 |
| Cys | Arg | Ile | Lys | Gln | Ile | Ile | Asn | Met | Trp | Gln | Glu Val |
| 390 | | | | 395 | | | | | 400 | | |
| GGA | AAA | GCA | ATG | TAT | GCC | CCT | CCC | ATC | AGA | GGA | GAA ATT | 1245 |
| Gly | Lys | Ala | Met | Tyr | Ala | Pro | Pro | Ile | Arg | Gly | Glu Ile |
| | | 405 | | | | 410 | | | | 415 | |
| AAA | TGT | TCA | TCA | AAT | ATT | ACA | GGA | CTA | CTG | TTA | ACA AGA | 1284 |
| Lys | Cys | Ser | Ser | Asn | Ile | Thr | Gly | Leu | Leu | Leu | Thr Arg |
| | | | 420 | | | | 425 | | | | |
| GAT | GGT | GGT | ATT | AAC | ACT | AGC | GAT | GCC | ACC | GAG | ACC TTC | 1323 |
| Asp | Gly | Gly | Ile | Asn | Thr | Ser | Asp | Ala | Thr | Glu | Thr Phe |
| | 430 | | | | 435 | | | | 440 | | |
| AGA | CCG | GGA | GGA | GGA | GAT | ATG | AGG | GAC | AAT | TGG | AGA AGT | 1362 |
| Arg | Pro | Gly | Gly | Gly | Asp | Met | Arg | Asp | Asn | Trp | Arg Ser |
| | | | 445 | | | | 450 | | | | |
| GAA | TTA | TAT | AAA | TAT | AAA | GTA | GTG | AAA | ATT | GAG | CCA TTA | 1401 |
| Glu | Leu | Tyr | Lys | Tyr | Lys | Val | Val | Lys | Ile | Glu | Pro Leu |
| 455 | | | | 460 | | | | | 465 | | |
| GGA | GTA | GCA | CCC | ACC | AAG | GCA | AAG | AGA | AGA | GTG | GTG CAG | 1440 |

TABLE 1-continued

```
Gly Val Ala Pro Thr Lys Ala Lys Arg Arg Val Val Gln
        470             475             480

AGA GAA AAA AGA GCA GTA ACA CTA GGA GCT ATG TTC CTT    1479
Arg Glu Lys Arg Ala Val Thr Leu Gly Ala Met Phe Leu
            485             490

GGG TTC TTG GGA GCA TAA AGC TTC                         1503
Gly Phe Leu Gly Ala Xaa Ser Phe
    495             500 501
```

CLONE C8.3

```
  G GTA CCT GTA TGG AAA GAA GCA ACC ACC ACT CTA TTT    37
    Val Pro Val Trp Lys Glu Ala Thr Thr Thr Leu Phe
     1           5                  10

TGT GCA TCA GAT GCT AAA GCA TAT GAT ACA GAG GTA CAT    76
Cys Ala Ser Asp Ala Lys Ala Tyr Asp Thr Glu Val His
            15              20              25

AAT GTT TGG GCT ACA CAT GCC TGT GTA CCC ACA GAC CCC    115
Asn Val Trp Ala Thr His Ala Cys Val Pro Thr Asp Pro
                30              35

AAC CCA CAA GAA GTA GTA TTG GAA AAT GTA ACA GAA AAT    154
Asn Pro Gln Glu Val Val Leu Glu Asn Val Thr Glu Asn
        40              45              50

TTT AAC ATG TGG AAA AAT AAC ATG GTA GAA CAG ATG CAT    193
Phe Asn Met Trp Lys Asn Asn Met Val Glu Gln Met His
            55              60

GAG GAT ATA ATC AGT TTA TGG GAT CAA AGT CTA AAG CCA    232
Glu Asp Ile Ile Ser Leu Trp Asp Gln Ser Leu Lys Pro
 65              70              75

TGT GTA AAA TTA ACC CCA CTC TGT GTT ACT TTA AAT TGC    271
Cys Val Lys Leu Thr Pro Leu Cys Val Thr Leu Asn Cys
        80              85              90

ACT AAT TTG GAG AAT GCT AAT AAT ACC GAG AAT GCT AAT    310
Thr Asn Leu Glu Asn Ala Asn Asn Thr Glu Asn Ala Asn
            95              100

AAT ACC AAT AAT TAT ACC TTG GGG ATG GAG AGA GGT GAA    349
Asn Thr Asn Asn Tyr Thr Leu Gly Met Glu Arg Gly Glu
        105             110             115

ATA AAA AAC TGC TCT TTC AAT ATC ACC ACA AGC TTA AGA    388
Ile Lys Asn Cys Ser Phe Asn Ile Thr Thr Ser Leu Arg
            120             125

GAT AAG GTG AAA AAA GAA TAT GCA TTG TTT TAT AAA CTT    427
Asp Lys Val Lys Lys Glu Tyr Ala Leu Phe Tyr Lys Leu
130             135             140

GAT GTA GTA CAA ATA GAT AAT AGT ACC AAC TAT AGG CTG    466
Asp Val Val Gln Ile Asp Asn Ser Thr Asn Tyr Arg Leu
        145             150             155

ATA AGT TGT AAT ACC TCA GTC ATT ACA CAG GCC TGT CCA    505
Ile Ser Cys Asn Thr Ser Val Ile Thr Gln Ala Cys Pro
            160             165

AAG GTA TCC TTT GAG CTA ATT CCC ATA CAT TAT TGT GCC    544
Lys Val Ser Phe Glu Leu Ile Pro Ile His Tyr Cys Ala
        170             175             180

CCG GCT GGT TTT GCG ATT CTA AAG TGT AAA GAT AAG AAG    583
Pro Ala Gly Phe Ala Ile Leu Lys Cys Lys Asp Lys Lys
            185             190

TTC AAT GGA ACA GGA CCA TGT AAA AAT GTC AGC ACA GTA    622
Phe Asn Gly Thr Gly Pro Cys Lys Asn Val Ser Thr Val
195             200             205

CAA TGT ACA CAT GGA ATT AGA CCA GTA GTA TCA ACT CAA    661
Gln Cys Thr His Gly Ile Arg Pro Val Val Ser Thr Gln
```

TABLE 1-continued

|  | 210 |  |  |  | 215 |  |  |  | 220 |  |  |
|---|---|---|---|---|---|---|---|---|---|---|---|
| CTA | CTG | TTA | AAT | GGC | AGT | CTA | GCA | GAA | GAA | GAG | ATA | GTA | 700 |
| Leu | Leu | Leu | Asn | Gly | Ser | Leu | Ala | Glu | Glu | Glu | Ile | Val |  |
|  |  |  |  | 225 |  |  |  | 230 |  |  |  |  |  |

```
ATT AGA TCT GAA AAT ATC ACA GAC AAT GCT AAA ACC ATA    739
Ile Arg Ser Glu Asn Ile Thr Asp Asn Ala Lys Thr Ile
    235             240             245

ATA GTG CAG CTA AAT GAA TCT ATA GTG ATT AAT TGT ACA    778
Ile Val Gln Leu Asn Glu Ser Ile Val Ile Asn Cys Thr
        250             255

AGA CCC AAT AAC AAC ACA AGA AAA AGT ATA AAT ATA GGA    817
Arg Pro Asn Asn Asn Thr Arg Lys Ser Ile Asn Ile Gly
260             265             270

CCA GGG AGA GCA TTC TAT ACA ACA GGA GAC ATA ATA GGA    856
Pro Gly Arg Ala Phe Tyr Thr Thr Gly Asp Ile Ile Gly
        275             280             285

GAT ATA AGA CAA GCA CAT TGT AAC CTT AGT AAA ACA CAA    895
Asp Ile Arg Gln Ala His Cys Asn Leu Ser Lys Thr Gln
            290             295

TGG GAA AAA ACG TTA AGA CAG ATA GCT ATA AAA TTA GAA    934
Trp Glu Lys Thr Leu Arg Gln Ile Ala Ile Lys Leu Glu
300             305             310

GAA AAA TTT AAG AAT AAA ACA ATA GCC TTT AAT AAA TCC    973
Glu Lys Phe Lys Asn Lys Thr Ile Ala Phe Asn Lys Ser
        315             320

TCA GGA GGG GAC CCA GAA ATT GTA ATG CAC AGT TTT AAT   1012
Ser Gly Gly Asp Pro Glu Ile Val Met His Ser Phe Asn
325             330             335

TGT GGA GGG GAA TTT TTC TAC TGT AAT ACA ACA AAA CTG   1051
Cys Gly Gly Glu Phe Phe Tyr Cys Asn Thr Thr Lys Leu
        340             345             350

TTT AAT AGT ACC TGG AAT TTA ACA CAA CCG TTT AGT AAT   1090
Phe Asn Ser Thr Trp Asn Leu Thr Gln Pro Phe Ser Asn
            355             360

ACC GGG AAT CGT ACT GAA GAG TTA AAT ATT ACA CTC CCA   1129
Thr Gly Asn Arg Thr Glu Glu Leu Asn Ile Thr Leu Pro
        365             370             375

TGC AGA ATA AAA CAA ATC ATA AAC TTG TGG CAG GAA GTA   1168
Cys Arg Ile Lys Gln Ile Ile Asn Leu Trp Gln Glu Val
            380             385

GGC AAA GCA ATG TAT GCC CCT CCC ATC AGA GGA CAA ATT   1207
Gly Lys Ala Met Tyr Ala Pro Pro Ile Arg Gly Gln Ile
390             395             400

AGA TGT TCA TCA AAT ATT ACA GGG CTA CTA TTA ACA AGA   1246
Arg Cys Ser Ser Asn Ile Thr Gly Leu Leu Leu Thr Arg
        405             410             415

GAT GGT GGA AGT AAC ACC GGT GAC AAC AGG ACT GAG ACC   1285
Asp Gly Gly Ser Asn Thr Gly Asp Asn Arg Thr Glu Thr
            420             425

TTT AGA CCT GGA GGA GGA GAT ATG AGG GAC AAT TGG AGA   1324
Phe Arg Pro Gly Gly Gly Asp Met Arg Asp Asn Trp Arg
        430             435             440

AGT GAA TTA TAT AAA TAT AAA GTA GTA AGA ATT GAA CCA   1363
Ser Glu Leu Tyr Lys Tyr Lys Val Val Arg Ile Glu Pro
            445             450

TTA GGA GTA GCA CCC ACC CAG GCA AAG AGA AGA GTG GTG   1402
Leu Gly Val Ala Pro Thr Gln Ala Lys Arg Arg Val Val
455             460             465

CAA AGA GAA AAA AGA GCA GTG GGA ATA GGA GCT ATG TTC   1441
```

TABLE 1-continued

```
Gln Arg Glu Lys Arg Ala Val Gly Ile Gly Ala Met Phe
        470             475             480

CTT GGG TTC TTG GGA GAT AA                              1461
Leu Gly Phe Leu Gly Asp
                485 486
```

CLONE C8.6

```
G   GTA CCT GTG TGG AAA GAA GCA ACC ACC ACT CTA TTT     37
    Val Pro Val Trp Lys Glu Ala Thr Thr Thr Leu Phe
     1               5                  10

TGT GCA TCA GAT GCT AAA GCA TAT GAT ACA GAG GTA CAT     76
Cys Ala Ser Asp Ala Lys Ala Tyr Asp Thr Glu Val His
            15              20                  25

AAT GTT TGG GCT ACA CAT GCC TGT GTA CCC ACA GAC CCC     115
Asn Val Trp Ala Thr His Ala Cys Val Pro Thr Asp Pro
                30              35

AAC CCA CAA GAA GTA GTA TTG GAA AAT GTA ACA GAA AAT     154
Asn Pro Gln Glu Val Val Leu Glu Asn Val Thr Glu Asn
        40              45              50

TTT AAC ATG TGG AAA AAT AAC ATG GTA GAA CAG ATG CAT     193
Phe Asn Met Trp Lys Asn Asn Met Val Glu Gln Met His
                55              60

GAG GAT ATA ATC AGT TTA TGG GAT CAA AGT CTA AAG CCA     232
Glu Asp Ile Ile Ser Leu Trp Asp Gln Ser Leu Lys Pro
 65                 70                  75

TGT GTA AAA TTA ACC CCA CTC TGT GTT ACT TTA AAT TGC     271
Cys Val Lys Leu Thr Pro Leu Cys Val Thr Leu Asn Cys
            80              85                  90

ACT AAT TTG GAG AAT GCT AAT AAT ACC GAG AAT GCT AAT     310
Thr Asn Leu Glu Asn Ala Asn Asn Thr Glu Asn Ala Asn
                95                 100

AAT ACC AAT AAT TAT ACC TTG GGG ATG GAG AGA GGT GAA     349
Asn Thr Asn Asn Tyr Thr Leu Gly Met Glu Arg Gly Glu
        105             110             115

AGA AAA AAC TGC TCT TTC AAT ATC ACC ACA AGC TTA AGA     388
Arg Lys Asn Cys Ser Phe Asn Ile Thr Thr Ser Leu Arg
            120             125

GAT AAG GGG AAA AAA GAA TAT GCA TTG TTT TAT AAA CTT     427
Asp Lys Gly Lys Lys Glu Tyr Ala Leu Phe Tyr Lys Leu
130             135             140

GAT GTA GTA CAA ATA GAT AAT AGT ACC AAC TAT AGG CTG     466
Asp Val Val Gln Ile Asp Asn Ser Thr Asn Tyr Arg Leu
        145             150             155

ATA AGT TGT AAT ACC TCA GTC ATT ACA CAG GCC TGT CCA     505
Ile Ser Cys Asn Thr Ser Val Ile Thr Gln Ala Cys Pro
            160             165

AAG GTA TCC TTT GAG CCA ATT CCC ATA CAT TAT TGT GCC     544
Lys Val Ser Phe Glu Pro Ile Pro Ile His Tyr Cys Ala
        170             175             180

CCG GCT GGT TTT GCG ATT CTA AAG TGT AAA GAT AAG AAG     583
Pro Ala Gly Phe Ala Ile Leu Lys Cys Lys Asp Lys Lys
                185             190

TTC AAT GGA ACA GGA CCA TGT AAA AAT GTC AGG ACA GTA     622
Phe Asn Gly Thr Gly Pro Cys Lys Asn Val Arg Thr Val
195             200             205

CAA TGT ACA CAT GGA ATT AGA CCA GTA GTA TCA ACT CAA     661
Gln Cys Thr His Gly Ile Arg Pro Val Val Ser Thr Gln
            210             215             220

CTA CTG TTA AAT GGC AGT CTA GCA GAA GAA GAG ATA GTA     700
Leu Leu Leu Asn Gly Ser Leu Ala Glu Glu Glu Ile Val
```

TABLE 1-continued

```
                    225                     230
ATT AGA TCT GAA AAT ATC ACA GAC AAT GCT AAA ACC ATA    739
Ile Arg Ser Glu Asn Ile Thr Asp Asn Ala Lys Thr Ile
    235                     240                 245

ATA GTG CAG CTA AAT GAA TCT ATA GTG ATT AAT TGT ACA    778
Ile Val Gln Leu Asn Glu Ser Ile Val Ile Asn Cys Thr
                250                     255

AGA CCC AAT AAC AAC ACA AGA AAA AGT ATA AAT ATA GGA    817
Arg Pro Asn Asn Asn Thr Arg Lys Ser Ile Asn Ile Gly
260                     265                     270

CCA GGG AGA GCA TTC TAT ACA ACA GGA GAC ATA ATA GGA    856
Pro Gly Arg Ala Phe Tyr Thr Thr Gly Asp Ile Ile Gly
            275                     280                 285

GAT ATA AGA CAA GCA CAT TGT AAC CTT AGT AAA ACA CAA    895
Asp Ile Arg Gln Ala His Cys Asn Leu Ser Lys Thr Gln
                290                     295

TGG GAA AAA ACG TTA AGA CAG ATA GCT ATA AAA TTA GAA    934
Trp Glu Lys Thr Leu Arg Gln Ile Ala Ile Lys Leu Glu
    300                     305                 310

GAA AAA TTT AAG AAT AAA ACA ATA GCC TTT AAT AAA TCC    973
Glu Lys Phe Lys Asn Lys Thr Ile Ala Phe Asn Lys Ser
                315                     320

TCA GGA GGG GAC CCA GAA ATT GTA ATG CAC AGT TTT AAT   1012
Ser Gly Gly Asp Pro Glu Ile Val Met His Ser Phe Asn
325                     330                     335

TGT GGA GGG GGA TTT TTC TAC TGT AGT ACG AGA AAA CTG   1051
Cys Gly Gly Gly Phe Phe Tyr Cys Ser Thr Arg Lys Leu
            340                     345                 350

TTT AAT AGT ACC TGG AAT TTA ACA CAA CCG TTT AGT AAT   1090
Phe Asn Ser Thr Trp Asn Leu Thr Gln Pro Phe Ser Asn
                355                     360

ACC GGG GAT CGT ACT GAA GAG TTA AAT ATT ACA CTC CCA   1129
Thr Gly Asp Arg Thr Glu Glu Leu Asn Ile Thr Leu Pro
    365                     370                 375

TGC AGA ATA AAA CAA ATC ATA AAC TTG TGG CAG GAA GTA   1168
Cys Arg Iie Lys Gln Ile Ile Asn Leu Trp Gln Glu Val
                380                     385

GGC AAA GCA ATG TAT GCC CCT CCC ATC AGA GGA CAA ATT   1207
Gly Lys Ala Met Tyr Ala Pro Pro Ile Arg Gly Gln Ile
390                     395                     400

AGA TGT TCA TCA AAT ATT ACA GGG CTA CTA TTA AGG AGA   1246
Arg Cys Ser Ser Asn Ile Thr Gly Leu Leu Leu Arg Arg
            405                     410                 415

GAT GGT GGA AGT AAC ACC AGT GAC AAC CAG ACT GAG ACC   1285
Asp Gly Gly Ser Asn Thr Ser Asp Asn Gln Thr Glu Thr
                420                     425

TTT AGA CCT GGG GGA GGA GAT ATG AGG GAC AAG TGG AGA   1324
Phe Arg Pro Gly Gly Gly Asp Met Arg Asp Lys Trp Arg
    430                     435                 440

AGT GAA TTA TAT AAA TAT AAA GTA GTA AGA ATT GAA CCA   1363
Ser Glu Leu Tyr Lys Tyr Lys Val Val Arg Ile Glu Pro
                445                     450

TTA GGA GTA GCA CCC ACC CAG GCA AAG AGA AGA GTG GTG   1402
Leu Gly Val Ala Pro Thr Gln Ala Lys Arg Arg Val Val
455                     460                     465

CAA AGA GAA AAA AGA GCA GTG GGA ATA GGA GCT ATG TTC   1441
Gln Arg Glu Lys Arg Ala Val Gly Ile Gly Ala Met Phe
            470                     475                 480

CTT AGG TTC TTA GGA GAT AAA GCT TCT AGA GTC   1474
```

TABLE 1-continued

```
Leu Arg Phe Leu Gly Asp Lys Ala Ser Arg Val
            485                 490 491
```

CLONE C15.2

```
    CTC GAG GTA CCT GTA TGG AAA GAA GCA ACT ACC ACT   36
    Leu Glu Val Pro Val Trp Lys Glu Ala Thr Thr Thr
      1               5                      10

CTA TTT TGT GCA TCA GAT GCT AAA GCA TAT AAT ACA GAG   75
Leu Phe Cys Ala Ser Asp Ala Lys Ala Tyr Asn Thr Glu
            15              20                  25

AAA CAT AAT GTT TGG GCC ACA CAC GCC TGT GTA CCC ACA  114
Lys His Asn Val Trp Ala Thr His Ala Cys Val Pro Thr
                30              35

GAT CCC AAC CCA CAA GAA GTA GTA TTG GGA AAT GTG ACA  153
Asp Pro Asn Pro Gln Glu Val Val Leu Gly Asn Val Thr
 40                  45                  50

GAA AAT TTT AAC ATG TGG AAA AAT AAC ATG GTA GAA CAA  192
Glu Asn Phe Asn Met Trp Lys Asn Asn Met Val Glu Gln
            55                  60

ATG CAT GAA GAT ATA ATC AGT TTA TGG GAT CAA AGT CTA  231
Met His Glu Asp Ile Ile Ser Leu Trp Asp Gln Ser Leu
 65                  70                  75

AAG CCA TGT GTA AAA TTA ACC CCA CTC TGT GTT ACT TTA  270
Lys Pro Cys Val Lys Leu Thr Pro Leu Cys Val Thr Leu
            80                  85              90

AAT TGC ACT GAT GAT TTA GGG AAT GCT ACT AAT ACC AAT  309
Asn Cys Thr Asp Asp Leu Gly Asn Ala Thr Asn Thr Asn
                95                  100

AGT AGT GCC ACT ACC AAT AGT AGT AGT TGG GAA GAA ATG  348
Ser Ser Ala Thr Thr Asn Ser Ser Ser Trp Glu Glu Met
    105                 110                 115

AAG GGG GAA ATG AAA AGA TGC TCT TTC AAT ATC ACC ACA  387
Lys Gly Glu Met Lys Arg Cys Ser Phe Asn Ile Thr Thr
            120                 125

AGC ATA AGA GAT AAG ATT AAG AAA GAA CAT GCA CTT TTC  426
Ser Ile Arg Asp Lys Ile Lys Lys Glu His Ala Leu Phe
130                 135                 140

TAT AGA CTT GAT GTA GTA CCA ATA GAT AAT GAT AAT ACC  465
Tyr Arg Leu Asp Val Val Pro Ile Asp Asn Asp Asn Thr
            145                 150                 155

ACA TAT AGG TTG ATA AAT TGT AAT ACC TCA GTC ATT ACA  504
Thr Tyr Arg Leu Ile Asn Cys Asn Thr Ser Val Ile Thr
                160                 165

CAG GCC TGT CCA AAG GTA TCA TTT GAG CCA ATT CCC ATA  543
Gln Ala Cys Pro Lys Val Ser Phe Glu Pro Ile Pro Ile
    170                 175                 180

CAT TTT TGT GCC CCG GCT GGT TTT GCG ATT CTA AAG TGT  582
His Phe Cys Ala Pro Ala Gly Phe Ala Ile Leu Lys Cys
                185                 190

AAT AAT AAG ACG TTC GAG GGA AAA GGA CCA TGT AAA AAT  621
Asn Asn Lys Thr Phe Glu Gly Lys Gly Pro Cys Lys Asn
195                 200                 205

GTC AGT ACA GTA CAA TGC ACA CAT GGA ATT AGG CCA GTA  660
Val Ser Thr Val Gln Cys Thr His Gly Ile Arg Pro Val
            210                 215                 220

GTG TCA ACT CAA CTG CTG TTA AAT GGC AGT CTA GCA GAA  699
Val Ser Thr Gln Leu Leu Leu Asn Gly Ser Leu Ala Glu
                225                 230

GAA GAG GTA ATA ATT AGA TCT GAC AAT ATC ACA GAC AAT  738
Glu Glu Val Ile Ile Arg Ser Asp Asn Ile Thr Asp Asn
```

TABLE 1-continued

```
      235                     240                     245
ACT AAA ACC ATT ATA GTA CAG CTA AAC GAA TCT GTA GTA    777
Thr Lys Thr Ile Ile Val Gln Leu Asn Glu Ser Val Val
            250                     255

ATT AAT TGT ACA AGA CCC AAC AAC AAT ACA AGA AAA AGT    816
Ile Asn Cys Thr Arg Pro Asn Asn Asn Thr Arg Lys Ser
260                     265                     270

ATA CAT ATA GGA CCA GGG AGT GCA TTT TTT GCA ACA GGA    855
Ile His Ile Gly Pro Gly Ser Ala Phe Phe Ala Thr Gly
            275                     280                     285

GAA ATA ATA GGA GAT ATA AGA CAA GCA CAC TGT AAC CTT    894
Glu Ile Ile Gly Asp Ile Arg Gln Ala His Cys Asn Leu
                    290                     295

AGT AGA ACA CAA TGG AAT AAC ACT TTA GGA AAG ATA GTC    933
Ser Arg Thr Gln Trp Asn Asn Thr Leu Gly Lys Ile Val
            300                     305                     310

ATA AAA TTA AGA GAA CAA TTT AGA AAA CAA TTT GGA GAA    972
Ile Lys Leu Arg Glu Gln Phe Arg Lys Gln Phe Gly Glu
                    315                     320

AAA ACA ATA GTC TTT AAT CGA TCC TCA GGA GGG GAC CCG    1011
Lys Thr Ile Val Phe Asn Arg Ser Ser Gly Gly Asp Pro
325                     330                     335

GAA ATT GCA ATG CAC AGT TTT AAT TGT GGA GGG GAA TTT    1050
Glu Ile Ala Met His Ser Phe Asn Cys Gly Gly Glu Phe
            340                     345                     350

TTC TAC TGT AAC ACA ACA GCA CTG TTT AAT AGT ACC TGG    1089
Phe Tyr Cys Asn Thr Thr Ala Leu Phe Asn Ser Thr Trp
                    355                     360

AAT GTT ACT AAA GGG TTG AAT AAC ACT GAA GGA AAT AGC    1128
Asn Val Thr Lys Gly Leu Asn Asn Thr Glu Gly Asn Ser
365                     370                     375

ACA GGA GAT GAA AAT ATC ATA CTC CCA TGT AGA ATA AAA    1167
Thr Gly Asp Glu Asn Ile Ile Leu Pro Cys Arg Ile Lys
            380                     385

CAA ATT ATA AAC ATG TGG CAG GAA GTA GGA AAA GCA ATG    1206
Gln Ile Ile Asn Met Trp Gln Glu Val Gly Lys Ala Met
390                     395                     400

TAT GCC CCT CCC ATC AGT GGA CAA ATT AGA TGT TCA TCA    1245
Tyr Ala Pro Pro Ile Ser Gly Gln Ile Arg Cys Ser Ser
            405                     410                     415

AAC ATT ACA GGG CTG CTA CTA ACA AGA GAT GGT GGT AGT    1284
Asn Ile Thr Gly Leu Leu Leu Thr Arg Asp Gly Gly Ser
                    420                     425

AAG AAC GAG AGC ATC ACC ACC GAG GTC TTC AGA CCT GGA    1323
Lys Asn Glu Ser Ile Thr Thr Glu Val Phe Arg Pro Gly
            430                     435                     440

GGA GGA GAT ATG AGG GAC AAT TGG AGA AGT GAA TTA TAT    1362
Gly Gly Asp Met Arg Asp Asn Trp Arg Ser Glu Leu Tyr
                    445                     450

AAA TAT AAA GTA GTA AAA ATT GAA CCA TTA GGA GTA GCG    1401
Lys Tyr Lys Val Val Lys Ile Glu Pro Leu Gly Val Ala
455                     460                     465

CCC ACC AAG GCA AAG AGA AGA GTG GTG CAG AGA GAA AAA    1440
Pro Thr Lys Ala Lys Arg Arg Val Val Gln Arg Glu Lys
            470                     475                     480

AGA GCA GTG GGA ACA ATA GGA GCT ATG TTC CTT GGG TTC    1479
Arg Ala Val Gly Thr Ile Gly Ala Met Phe Leu Gly Phe
                    485                     490

TTG GGA GCA TAA AGC TTC TAG AGT CGA CCT GCA             1512
```

TABLE 1-continued

Leu Gly Ala Xaa Ser Phe Xaa Ser Arg Pro Ala
    495             500             504

CLONE C15.3

| | | | | | | | | | | |
|---|---|---|---|---|---|---|---|---|---|---|
| CTC | GAG | GTA | CCT | GTG | TGG | AAA | GAA | GCA | ACT | ACC | ACT | 36
| Leu | Glu | Val | Pro | Val | Trp | Lys | Glu | Ala | Thr | Thr | Thr |
|  1  |     |     |     |  5  |     |     |     |     | 10  |     |     |

CTA TTT TGT GCA TCA GAT GCT AAA GCA TAT AAT ACA GAG    75
Leu Phe Cys Ala Ser Asp Ala Lys Ala Tyr Asn Thr Glu
        15              20                      25

AAA CAT AAT GTT TGG GCC ACA CAC GCC TGT GTA CCC ACA    114
Lys His Asn Val Trp Ala Thr His Ala Cys Val Pro Thr
                30              35

GAT CCC AAC CCA CAA GAA GTA GTA TTG GGA AAT GTG ACA    153
Asp Pro Asn Pro Gln Glu Val Val Leu Gly Asn Val Thr
    40              45                      50

GAA AAT TTT AAC ATG TGG AAA AAT AAC ATG GTA GAA CAA    192
Glu Asn Phe Asn Met Trp Lys Asn Asn Met Val Glu Gln
            55                      60

ATG CAT GAA GAT ATA ATC AGT TTA TGG GAT CAA AGT CTA    231
Met His Glu Asp Ile Ile Ser Leu Trp Asp Gln Ser Leu
 65                  70                  75

AAG CCA TGT GTA AAA TTA ACC CCA CTC TGT GTT ACT TTA    270
Lys Pro Cys Val Lys Leu Thr Pro Leu Cys Val Thr Leu
            80                  85                  90

AAT TGC ACT GAT GAT TTA GGG AAT GCT ACT AAT ACC AAT    309
Asn Cys Thr Asp Asp Leu Gly Asn Ala Thr Asn Thr Asn
                95                      100

AGC AGT GCC ACT ACC AAT AGT AGT AGT TGG GAA GAA ATG    348
Ser Ser Ala Thr Thr Asn Ser Ser Ser Trp Glu Glu Met
    105                     110                 115

AAG GGG GAA ATG AAA AGG TGC TCT TTC AAT ATC ACC ACA    387
Lys Gly Glu Met Lys Arg Cys Ser Phe Asn Ile Thr Thr
                120                 125

AGC ATA AGA GAT AAG ATT AAG AAA GAA CAT GCA CTT TTC    426
Ser Ile Arg Asp Lys Ile Lys Lys Glu His Ala Leu Phe
130                 135                 140

TAT AGA CTT GAT GTA GTA CCA ATA GAT AAT GAT AAT ACC    465
Tyr Arg Leu Asp Val Val Pro Ile Asp Asn Asp Asn Thr
        145                 150                 155

ACA TAT AGG TTG ATA AAT TGT AAT ACC TCA GTC ATT ACA    504
Thr Tyr Arg Leu Ile Asn Cys Asn Thr Ser Val Ile Thr
                160                 165

CAG GCC TGT CCA AAG GTA TCA TTT GAG CCA ATT CCC ATA    543
Gln Ala Cys Pro Lys Val Ser Phe Glu Pro Ile Pro Ile
    170                 175                 180

CAT TTT TGT GCC CCG GCT GGT TTT GCG ATT CTA AAG TGT    582
His Phe Cys Ala Pro Ala Gly Phe Ala Ile Leu Lys Cys
                185                 190

AAT AAT AAG ACG TTC GAG GGA AAA GGA CCA TGT AAA AAT    621
Asn Asn Lys Thr Phe Glu Gly Lys Gly Pro Cys Lys Asn
195                 200                 205

GTC AGT ACA GTA CAA TGC ACA CAT GGA ATT AGG CCA GTA    660
Val Ser Thr Val Gln Cys Thr His Gly Ile Arg Pro Val
        210                 215                 220

GTG TCA ACT CAA CTG CTG TTA AAT GGC AGT CTA GCA GAA    699
Val Ser Thr Gln Leu Leu Leu Asn Gly Ser Leu Ala Glu
                225                 230

GAA GAG GTA ATA ATT AGA TCT GGC AAT ATC ACA GAC AAT    738
Glu Glu Val Ile Ile Arg Ser Gly Asn Ile Thr Asp Asn

TABLE 1-continued

```
           235                      240                      245
ACT AAA ACC ATT ATA GTA CAG CTA AAC GAA TCT GTA GTA    777
Thr Lys Thr Ile Ile Val Gln Leu Asn Glu Ser Val Val
            250                     255

ATT AAT TGT ACA AGA TCC AAC AAC AAT ACA AGA AAA AGT    816
Ile Asn Cys Thr Arg Ser Asn Asn Asn Thr Arg Lys Ser
260                     265                     270

ATA CAT ATA GGA CCA GGG AGT GCA TTT TTT GCA ACA GGA    855
Ile His Ile Gly Pro Gly Ser Ala Phe Phe Ala Thr Gly
            275                     280                     285

GAA ATA ATA GGA GAT ATA AGA CAA GCA CAC TGT AAC CTT    894
Glu Ile Ile Gly Asp Ile Arg Gln Ala His Cys Asn Leu
                    290                     295

AGT AGA ACA CAA TGG AAT AAC ACT TTA GGA AAG ATA GTC    933
Ser Arg Thr Gln Trp Asn Asn Thr Leu Gly Lys Ile Val
        300                     305                     310

ATA AAA TTA AGA GAA CAA TTT AGA AAA CAA TTT GGA GAA    972
Ile Lys Leu Arg Glu Gln Phe Arg Lys Gln Phe Gly Glu
                315                     320

AAA ACA ATA GTC TTT AAT CGA TCC TCA GGA GGG GAC CCG   1011
Lys Thr Ile Val Phe Asn Arg Ser Ser Gly Gly Asp Pro
325                     330                     335

GAA ATT GCA ATG CAC AGT TTT AAT TGT GGA GGG GAA TTT   1050
Glu Ile Ala Met His Ser Phe Asn Cys Gly Gly Glu Phe
            340                     345                     350

TTC TAC TGT AAC ACA ACA GCA CTG TTT AAT AGT ACC TGG   1089
Phe Tyr Cys Asn Thr Thr Ala Leu Phe Asn Ser Thr Trp
                    355                     360

AAT GTT ACT AAA GGG TTG AAT AAC ACT GAA GGA AAT AGC   1128
Asn Val Thr Lys Gly Leu Asn Asn Thr Glu Gly Asn Ser
365                     370                     375

ACA GGG GAT GAA AAT ATC ATA CTC CCA TGT AGA ATA AAA   1167
Thr Gly Asp Glu Asn Ile Ile Leu Pro Cys Arg Ile Lys
            380                     385

CAA ATT ATA AAC ATG TGG CAG GAA GTA GGA AAA GCA ATG   1206
Gln Ile Ile Asn Met Trp Gln Glu Val Gly Lys Ala Met
390                     395                     400

TAT GCC CCT CCC ATC AGT GGA CAA ATT AGA TGT TCA TCA   1245
Tyr Ala Pro Pro Ile Ser Gly Gln Ile Arg Cys Ser Ser
            405                     410                     415

AAT ATT ACA GGG CTG CTA CTA ACA AGA GAT GGT GGT AGT   1284
Asn Ile Thr Gly Leu Leu Leu Thr Arg Asp Gly Gly Ser
                    420                     425

AAG AAC GAG AGC ATC ACC ACC GAG GTC TTC AGA CCT GGA   1323
Lys Asn Glu Ser Ile Thr Thr Glu Val Phe Arg Pro Gly
        430                     435                     440

GGA GGA GAT ATG AGG GAC AAT TGG AGA AGT GAA TTA TAT   1362
Gly Gly Asp Met Arg Asp Asn Trp Arg Ser Glu Leu Tyr
                445                     450

AAA TAT AAA GTA GTA AAA ATT GAA CCA TTA GGA GTA GCG   1401
Lys Tyr Lys Val Val Lys Ile Glu Pro Leu Gly Val Ala
455                     460                     465

CCC ACC AAG GCA AAG AGA AGA GTG GTG CAG AGA GAA AAA   1440
Pro Thr Lys Ala Lys Arg Arg Val Val Gln Arg Glu Lys
            470                     475                     480

AGA GCA GTG GGA ACA ATA GGA GCT ATG TTC CTT GGG TTC   1479
Arg Ala Val Gly Thr Ile Gly Ala Met Phe Leu Gly Phe
                    485                     490

TTA GGA GCA TAA AGC TTC TAG A                         1501
```

TABLE 1-continued

```
Leu Gly Ala Xaa Ser Phe Xaa
    495             500
```

CLONE C7.2

| | | | | | | | | | | |
|---|---|---|---|---|---|---|---|---|---|---|
| GG GAA TTC GGA TCC GGG GTA CCT GTG TGG AAG GAA GCA | | | | | | | | | | 38 |
| Glu Phe Gly Ser Gly Val Pro Val Trp Lys Glu Ala | | | | | | | | | | |
| 1 | | | | 5 | | | | 10 | | |

```
GG GAA TTC GGA TCC GGG GTA CCT GTG TGG AAG GAA GCA      38
   Glu Phe Gly Ser Gly Val Pro Val Trp Lys Glu Ala
    1               5                   10

ACC ACC ACT CTA TTC TGT GCA TCA GAT GCT AGA GCA TAT     77
Thr Thr Thr Leu Phe Cys Ala Ser Asp Ala Arg Ala Tyr
            15                  20                  25

GAC ACA GAG GTA CAT AAT GTT TGG GCC ACA CAT GCC TGT    116
Asp Thr Glu Val His Asn Val Trp Ala Thr His Ala Cys
                30                  35

GTA CCC ACA GAC CCT AGT CCA CAA GAA GTA GTT TTG GAA    155
Val Pro Thr Asp Pro Ser Pro Gln Glu Val Val Leu Glu
    40                  45                  50

AAT GTG ACA GAA AAT TTT AAC ATG TGG AAA AAT AAC ATG    194
Asn Val Thr Glu Asn Phe Asn Met Trp Lys Asn Asn Met
                55                  60

GTA GAA CAA ATG CAT GAG GAT ATA ATT AGT TTA TGG GAT    233
Val Glu Gln Met His Glu Asp Ile Ile Ser Leu Trp Asp
65                  70                  75

CAA AGC TTA AAG CCA TGT GTA AAA TTA ACC CCA CTC TGT    272
Gln Ser Leu Lys Pro Cys Val Lys Leu Thr Pro Leu Cys
            80                  85                  90

GTT ACT TTA AAT TGC AGT GAT TAT AGG AAT GCT ACT GAT    311
Val Thr Leu Asn Cys Ser Asp Tyr Arg Asn Ala Thr Asp
                95                  100

TAT AAG AAT GCT ACT GAT ACC ACT AGT AGT AAC GAG GGA    350
Tyr Lys Asn Ala Thr Asp Thr Thr Ser Ser Asn Glu Gly
    105                 110                 115

AAG ATG GAG AGA GGA GAA ATA AAA AAC TGC TCT TTC AAT    389
Lys Met Glu Arg Gly Glu Ile Lys Asn Cys Ser Phe Asn
                120                 125

ATT ACC ACA AGC ATA AAA AAT AAG ATG CAG AAA GAA TAT    428
Ile Thr Thr Ser Ile Lys Asn Lys Met Gln Lys Glu Tyr
130                 135                 140

GCA CTT TTC TAT AAA CTT GAT ATA GTA CCA ATA GAT AAT    467
Ala Leu Phe Tyr Lys Leu Asp Ile Val Pro Ile Asp Asn
            145                 150                 155

ACA AGC TAT ACA TTG ATA AGT TGT AAC ACC TCA GTC ATT    506
Thr Ser Tyr Thr Leu Ile Ser Cys Asn Thr Ser Val Ile
                160                 165

ACA CAG GCC TGT CCA AAG GTA TCC TTT GAA CCA ACT CCC    545
Thr Gln Ala Cys Pro Lys Val Ser Phe Glu Pro Thr Pro
    170                 175                 180

ATA CAT TAT TGT GCT CCG GCT GGT TTT GCG ATT CTA AAG    584
Ile His Tyr Cys Ala Pro Ala Gly Phe Ala Ile Leu Lys
                185                 190

TGT AAT GAT AAG AAG TTC AGT GGA AAA GGA GAA TGT AAA    623
Cys Asn Asp Lys Lys Phe Ser Gly Lys Gly Glu Cys Lys
195                 200                 205

AAT GTC AGC ACA GTA CAA TGT ACA CAT GGA ATT AGG CCA    662
Asn Val Ser Thr Val Gln Cys Thr His Gly Ile Arg Pro
            210                 215                 220

GTA GTA TCA ACT CAA CTG CTG TTA AAT GGC AGT CTA GCA    701
Val Val Ser Thr Gln Leu Leu Leu Asn Gly Ser Leu Ala
                225                 230

GAA GAA GAG GTG GTA ATT AGA TCT GAC AAT TTC ATA GAC    740
Glu Glu Glu Val Val Ile Arg Ser Asp Asn Phe Ile Asp
```

TABLE 1-continued

```
      235                 240                      245
AAT ACT AAA ACC ATA ATA GTA CAG CTG AAA GAA TCT GTA    779
Asn Thr Lys Thr Ile Ile Val Gln Leu Lys Glu Ser Val
            250                 255

GAA ATT AAT TGT ATA AGA CCC AAC AAT AAT ACA AGA AAA    818
Glu Ile Asn Cys Ile Arg Pro Asn Asn Asn Thr Arg Lys
260                 265                 270

GGT ATA CAT ATA GGA CCA GGG AGA GCA TGG TAT GCA ACA    857
Gly Ile His Ile Gly Pro Gly Arg Ala Trp Tyr Ala Thr
            275                 280             285

GGA GAA ATA GTA GGA GAT ATA AGA AAG GCA TAT TGT AAC    896
Gly Glu Ile Val Gly Asp Ile Arg Lys Ala Tyr Cys Asn
                290                 295

ATT AGT AGA ACA AAA TGG AAT AAC ACT TTA ATA CAG ATA    935
Ile Ser Arg Thr Lys Trp Asn Asn Thr Leu Ile Gln Ile
    300                 305                 310

GCT AAC AAA TTA AAA GAA AAA TAT AAT ACA ACA ATA AGC    974
Ala Asn Lys Leu Lys Glu Lys Tyr Asn Thr Thr Ile Ser
            315                 320

TTT AAT CGA TCC TCA GGA GGG GAC CCA GAA ATT GTA ACG   1013
Phe Asn Arg Ser Ser Gly Gly Asp Pro Glu Ile Val Thr
325                 330                 335

CAT AGT TTT AAT TGT GGA GGG GAG TTT TTC TAC TGT GAT   1052
His Ser Phe Asn Cys Gly Gly Glu Phe Phe Tyr Cys Asp
            340                 345             350

TCA ACA CAA CTG TTT AAT AGT ACT TGG AAT TTA AAT GGT   1091
Ser Thr Gln Leu Phe Asn Ser Thr Trp Asn Leu Asn Gly
                355                 360

ACT TGG AAT TTT ACT GCA GGG TCA AAT GAA ACT GAA GGC   1130
Thr Trp Asn Phe Thr Ala Gly Ser Asn Glu Thr Glu Gly
    365                 370                 375

AAT ATC ACA CTC CCA TGC AGA ATA AAA CAA ATT ATA AAC   1169
Asn Ile Thr Leu Pro Cys Arg Ile Lys Gln Ile Ile Asn
            380                 385

AGG TGG CAG GAA GTA GGG AAA GCA ATG TAT GCC CCT CCC   1208
Arg Trp Gln Glu Val Gly Lys Ala Met Tyr Ala Pro Pro
390                 395                 400

ATC AGT GGA CAA ATA AAA TGC TCA TCA AAC ATT ACA GGG   1247
Ile Ser Gly Gln Ile Lys Cys Ser Ser Asn Ile Thr Gly
            405                 410             415

ATG ATA TTA ACA AGG GAT GGT GGT AAC GAG AAC AAT AAT   1286
Met Ile Leu Thr Arg Asp Gly Gly Asn Glu Asn Asn Asn
                420                 425

GAG AGC AGT ACT ACT GAG ACC TTC AGA CCG GGA GGA GGA   1325
Glu Ser Ser Thr Thr Glu Thr Phe Arg Pro Gly Gly Gly
            430                 435             440

GAT ATG AGG AAC AAT TGG AGA AGT GAA TTA TAT AAA TAT   1364
Asp Met Arg Asn Asn Trp Arg Ser Glu Leu Tyr Lys Tyr
                445                 450

AAA GTA GTA AAA ATT GAA CCA TTA GGA GTA GCA CCC ACC   1403
Lys Val Val Lys Ile Glu Pro Leu Gly Val Ala Pro Thr
455                 460                 465

AAG GCA AAG AGA AGA GTG GTG CAG AGA GAA AAA AGA GCA   1442
Lys Ala Lys Arg Arg Val Val Gln Arg Glu Lys Arg Ala
            470                 475             480

GTG GGA GCG CTA GGA GCT ATG TTC CTT GGG TTC TTA GGA   1481
Val Gly Ala Leu Gly Ala Met Phe Leu Gly Phe Leu Gly
                485                 490

GCA TAA AGC TTC TAG ACC GAC TCT AGA GGA TCC           1514
```

TABLE 1-continued

```
Ala Xaa Ser Phe Xaa Thr Asp Ser Arg Gly Ser
    495             500             504
```

CLONE C7.10

```
G   GTA CCT GTG TGG AAG GAA GCA ACC ACC ACT CTA TTC     37
    Val Pro Val Trp Lys Glu Ala Thr Thr Thr Leu Phe
    1               5                   10

TGT GCA TCA GAT GCT AGA GCA TAT GAC ACA GAG GTA CAT     76
Cys Ala Ser Asp Ala Arg Ala Tyr Asp Thr Glu Val His
            15                  20                  25

AAT GTT TGG GCC ACA CAT GCC TGT GTA CCC ACA GAC CCT    115
Asn Val Trp Ala Thr His Ala Cys Val Pro Thr Asp Pro
                30                  35

AGT CCA CAA GAA GTA TTT TTG GGA AAT GTG ACA GAA AAT    154
Ser Pro Gln Glu Val Phe Leu Gly Asn Val Thr Glu Asn
    40                  45                  50

TTT AAT ATG TGG AAA AAT AAC ATG GTA GAA CAA ATG TAT    193
Phe Asn Met Trp Lys Asn Asn Met Val Glu Gln Met Tyr
            55                  60

GAG GAT ATA ATT AGT TTA TGG GAT CAA AGC TTA AAG CCA    232
Glu Asp Ile Ile Ser Leu Trp Asp Gln Ser Leu Lys Pro
65                  70                  75

TGT GTA AAA TTA ACC CCA CTC TGT GTT ACT TTA AAT TGC    271
Cys Val Lys Leu Thr Pro Leu Cys Val Thr Leu Asn Cys
            80                  85                  90

AGT GAT TAT AGG AAT GCT ACT GAT TAT AAG AAT GCT ACT    310
Ser Asp Tyr Arg Asn Ala Thr Asp Tyr Lys Asn Ala Thr
                95                  100

GAT ACC ACT AGT AGT AAC GAG GGA AAG ATG GAG AGA GGA    349
Asp Thr Thr Ser Ser Asn Glu Gly Lys Met Glu Arg Gly
    105                 110                 115

GAA ATA AAA AAC TGC TCT TTC AAT ATC ACC ACA AGC ATA    388
Glu Ile Lys Asn Cys Ser Phe Asn Ile Thr Thr Ser Ile
                120                 125

AAA AAT AAG ATG CAG AAA GAA TAT GCA CTT TTC TAT AAA    427
Lys Asn Lys Met Gln Lys Glu Tyr Ala Leu Phe Tyr Lys
130                 135                 140

CTT AAT ATA GTA CCA ATA GAT AAT ACA AGC TAT ACA TTG    466
Leu Asn Ile Val Pro Ile Asp Asn Thr Ser Tyr Thr Leu
            145                 150                 155

ATA AGT TGT AAC ACC TCA GTC ATT ACA CAG GCC TGT CCA    505
Ile Ser Cys Asn Thr Ser Val Ile Thr Gln Ala Cys Pro
                160                 165

AAG GTA TCC TTT GAA CCA ATT CCC ATA CAT TAT TGT GCT    544
Lys Val Ser Phe Glu Pro Ile Pro Ile His Tyr Cys Ala
    170                 175                 180

CCG GCT GGT TTT GCG ATT CTA AAG TGT AAT GAT AAG AAG    583
Pro Ala Gly Phe Ala Ile Leu Lys Cys Asn Asp Lys Lys
                185                 190

TTC AGT GGA AAA GGA GAA TGT AAA AAT GTC AGC ACA GTA    622
Phe Ser Gly Lys Gly Glu Cys Lys Asn Val Ser Thr Val
195                 200                 205

CAA TGT ACA CAT GGA ATT AGG CCA GTA GTA TCA ACT CAA    661
Gln Cys Thr His Gly Ile Arg Pro Val Val Ser Thr Gln
            210                 215                 220

CTG CTG TTA AAT GGC AGT CTA GCA GAA GAA GAG GTG GTA    700
Leu Leu Leu Asn Gly Ser Leu Ala Glu Glu Glu Val Val
                225                 230

ATT AGA TCT GAC AAT TTC ACA GAC AAT ACT AAA ACC ATA    739
Ile Arg Ser Asp Asn Phe Thr Asp Asn Thr Lys Thr Ile
```

TABLE 1-continued

```
      235                 240                 245
ATA GTA CAG CTG AAA GAA TCT GTA GAA ATT AAT TGT ATA    778
Ile Val Gln Leu Lys Glu Ser Val Glu Ile Asn Cys Ile
            250                 255

AGA CCC AAC AAT AAT ACA AGA AAA GGT ATA CAT ATA GGA    817
Arg Pro Asn Asn Asn Thr Arg Lys Gly Ile His Ile Gly
260                 265                 270

CCA GGG AGA GCA TGG TAT GCA ACA GGA GAA ATA GTA GGA    856
Pro Gly Arg Ala Trp Tyr Ala Thr Gly Glu Ile Val Gly
        275                 280                 285

GAT ATA AGA CAG GCA TAT TGT AAC ATT AGT AGA ACA AAA    895
Asp Ile Arg Gln Ala Tyr Cys Asn Ile Ser Arg Thr Lys
                290                 295

TGG AAT AAC ACT TTA ATA CAG ATA GCT AAC AAA TTA AAA    934
Trp Asn Asn Thr Leu Ile Gln Ile Ala Asn Lys Leu Lys
        300                 305                 310

GAA AAA TAT AAT ACA ACA ATA AGC TTT AAT CGA TCC TCA    973
Glu Lys Tyr Asn Thr Thr Ile Ser Phe Asn Arg Ser Ser
                315                 320

GGA GGG GAC CCA GAA ATT GTA ACC CAT AGT TTT AAT TGT    1012
Gly Gly Asp Pro Glu Ile Val Thr His Ser Phe Asn Cys
325                 330                 335

GGA GGG GAA TTT TTC TAC TGT AAT TCA ACA CAA CTG TTT    1051
Gly Gly Glu Phe Phe Tyr Cys Asn Ser Thr Gln Leu Phe
        340                 345                 350

AAT AGT ACT TGG AAT TTA AAT GGT ACT TGG AAT TTT ACT    1090
Asn Ser Thr Trp Asn Leu Asn Gly Thr Trp Asn Phe Thr
                355                 360

GCA GGG TCA AAT GAA ACT GAA GGC AAT ATC ACA CTC CCA    1129
Ala Gly Ser Asn Glu Thr Glu Gly Asn Ile Thr Leu Pro
365                 370                 375

TGC AGA ATA AAA CAA ATT ATA AAC AGG TGG CAG GAA GTA    1168
Cys Arg Ile Lys Gln Ile Ile Asn Arg Trp Gln Glu Val
        380                 385

GGA AAA GCA ATG TAT GCC CCT CCC ATC AGT GGA CAA ATA    1207
Gly Lys Ala Met Tyr Ala Pro Pro Ile Ser Gly Gln Ile
390                 395                 400

AGA TGC TCA TCA AAC ATT ACA GGG ATG ATA TTA ACA AGG    1246
Arg Cys Ser Ser Asn Ile Thr Gly Met Ile Leu Thr Arg
            405                 410                 415

GAT GGT GGT AAC GAG AAC AAT AAT GAG AGC AGT ACT ACT    1285
Asp Gly Gly Asn Glu Asn Asn Asn Glu Ser Ser Thr Thr
                420                 425

GAG ACC TTC AGA CCG GGA GGA GGA GAT ATG AGG AAC AAT    1324
Glu Thr Phe Arg Pro Gly Gly Gly Asp Met Arg Asn Asn
        430                 435                 440

TGG AGA AGT GAA TTA TAT AAA TAT AAA GTA GTA AAA ATT    1363
Trp Arg Ser Glu Leu Tyr Lys Tyr Lys Val Val Lys Ile
                445                 450

GAG CCA TTA GGA GTA GCA CCC ACC GAC TCT AGA GGA TCC    1402
Glu Pro Leu Gly Val Ala Pro Thr Asp Ser Arg Gly Ser
455                 460                 465

TCT AGA     1408
Ser Arg
    469
```

CLONE C11.5

```
    GAG GTA CCT GTG TGG AAA GAA GCA ACC ACT ACT CTA    36
    Glu Val Pro Val Trp Lys Glu Ala Thr Thr Thr Leu
      1               5                  10
```

TABLE 1-continued

```
TTT TGT GCA TCA GAT GCT AAA GCA TAT GAC ACA GGG GTG    75
Phe Cys Ala Ser Asp Ala Lys Ala Tyr Asp Thr Gly Val
            15              20              25

CAT AAT GTT TGG GCC ACA CAT GCC TGT GTA CCC ACA GAC   114
His Asn Val Trp Ala Thr His Ala Cys Val Pro Thr Asp
                30              35

CCC AAC CCA CAA GAA ATA GAA TTG GTA AAT GTG ACA GAA   153
Pro Asn Pro Gln Glu Ile Glu Leu Val Asn Val Thr Glu
        40              45              50

GAT TTT AAC ATG TGG AAA AAT AAA ATG GTA GAC CAG ATG   192
Asp Phe Asn Met Trp Lys Asn Lys Met Val Asp Gln Met
                55              60

CAT GAG GAT ATA ATC AGT TTA TGG GAT GAA AGC CTA AAG   231
His Glu Asp Ile Ile Ser Leu Trp Asp Glu Ser Leu Lys
        65              70              75

CCA TGT GTA AAG TTA ACC CCA CTT TGT GTT ACT CTA AAC   270
Pro Cys Val Lys Leu Thr Pro Leu Cys Val Thr Leu Asn
                80              85              90

TGC AGT GAT GTG AAC AAT TCC ACA AAT CCT AAT GAT ACT   309
Cys Ser Asp Val Asn Asn Ser Thr Asn Pro Asn Asp Thr
                    95              100

AAT ACT AAT TCC ACT AAT ACT ACT TCC TCT ACT CCT ACG   348
Asn Thr Asn Ser Thr Asn Thr Thr Ser Ser Thr Pro Thr
        105             110             115

GCC ACT ACT AGT AGC GAG GAA AAG ATG GAG AAG GGA GAA   387
Ala Thr Thr Ser Ser Glu Glu Lys Met Glu Lys Gly Glu
                120             125

ATA AAA AAC TGC TCT TTC AAT ATC ACC ACA CAC ATG AAA   426
Ile Lys Asn Cys Ser Phe Asn Ile Thr Thr His Met Lys
130             135             140

GAT AAG GCA CAG AAA GAA TAT GCA CTT TTT TAT AAA CTT   465
Asp Lys Ala Gln Lys Glu Tyr Ala Leu Phe Tyr Lys Leu
            145             150             155

GAT ATA GTA CCA ATA GAT GAT AAT AAT GCC AGC TAT AGG   504
Asp Ile Val Pro Ile Asp Asp Asn Asn Ala Ser Tyr Arg
                160             165

TTG ATA AGT TGT AAT ACC TCA GAC ATT ACA CAG GCC TGT   543
Leu Ile Ser Cys Asn Thr Ser Asp Ile Thr Gln Ala Cys
        170             175             180

CCA AAG GTG ACC TTT GAG CCA ATT CCC ATA CAT TAT TGT   582
Pro Lys Val Thr Phe Glu Pro Ile Pro Ile His Tyr Cys
                185             190

GCC CCG GCT GGT TTT GCG ATT CTA AAG TGT AAA GAT AAG   621
Ala Pro Ala Gly Phe Ala Ile Leu Lys Cys Lys Asp Lys
195             200             205

AAG TTC AAT GGA ACA GGA CCA TGT TCA AAG GTC AGC ACA   660
Lys Phe Asn Gly Thr Gly Pro Cys Ser Lys Val Ser Thr
            210             215             220

GTA CAA TGT ACA CAT GGA ATT AGG CCA GTA GTA TCA ACT   699
Val Gln Cys Thr His Gly Ile Arg Pro Val Val Ser Thr
                225             230

CAA CTG TTG TTA AAT GGC AGT CTT GCA GAA GAA GAA GTA   738
Gln Leu Leu Leu Asn Gly Ser Leu Ala Glu Glu Glu Val
        235             240             245

GTA ATT AGA TCT GTC AAT TTC ACA GAC AAT GCT AAA ATC   777
Val Ile Arg Ser Val Asn Phe Thr Asp Asn Ala Lys Ile
                250             255

ATA ATA GTA CAG CTG AAA GAA CCT GTA GCA ATT AAT TGT   816
Ile Ile Val Gln Leu Lys Glu Pro Val Ala Ile Asn Cys
```

TABLE 1-continued

```
260                 265                 270
ACA AGA CCC AAC AAC AAT ACA AGA AAA GGT ATA CAT CTA   855
Thr Arg Pro Asn Asn Asn Thr Arg Lys Gly Ile His Leu
        275                 280                 285

GGA CCA GGG AGC ACA TTT TAT ACA ACA GGA GAA ATA ATA   894
Gly Pro Gly Ser Thr Phe Tyr Thr Thr Gly Glu Ile Ile
                290                 295

GGA GAC ATA AGA AAA GCA TAT TGC AAG ATT AGT AAA GAA   933
Gly Asp Ile Arg Lys Ala Tyr Cys Lys Ile Ser Lys Glu
    300                 305                 310

AAA TGG AAT AAC ACT TTA AGA CAG GTA GTT AAA AAA TTA   972
Lys Trp Asn Asn Thr Leu Arg Gln Val Val Lys Lys Leu
                315                 320

AGA GAA CAA TTT GGG AAT AAA ACA ATA ATT TTT AAT CGA  1011
Arg Glu Gln Phe Gly Asn Lys Thr Ile Ile Phe Asn Arg
325                 330                 335

TCC TCA GGA GGG GAC CCA GAA ATT GTA ATG CAC AGT TTT  1050
Ser Ser Gly Gly Asp Pro Glu Ile Val Met His Ser Phe
        340                 345                 350

AAC TGT GGA GGG GAG TTT TTC TAC TGT AAT ACA ACA CAA  1089
Asn Cys Gly Gly Glu Phe Phe Tyr Cys Asn Thr Thr Gln
                355                 360

CTG TTT AAT AGT ACT TGG AAT AAT ACT GAA GGG ACA AAT  1128
Leu Phe Asn Ser Thr Trp Asn Asn Thr Glu Gly Thr Asn
    365                 370                 375

AGC ACT GAA GGA AAT AGC ACA ATC ACA CTC CCA TGC AGA  1167
Ser Thr Glu Gly Asn Ser Thr Ile Thr Leu Pro Cys Arg
                380                 385

ATA AAA CAA ATT ATA AAT ATG TGG CAG GAA GTA GGA AAA  1206
Ile Lys Gln Ile Ile Asn Met Trp Gln Glu Val Gly Lys
390                 395                 400

GCA ACG TAT GCC CCT CCC ATC AGA GGA CGA ATT AGA TGC  1245
Ala Thr Tyr Ala Pro Pro Ile Arg Gly Arg Ile Arg Cys
        405                 410                 415

ATA TCA AAT ATT ACA GGA CTG CTA TTA ACA AGA GAT GGT  1284
Ile Ser Asn Ile Thr Gly Leu Leu Leu Thr Arg Asp Gly
                420                 425

GGT AGG AAT GTC ACA AAC AAT ACC GAA ACC TTC AGA CCT  1323
Gly Arg Asn Val Thr Asn Asn Thr Glu Thr Phe Arg Pro
    430                 435                 440

GGA GGA GGA GAC ATG AGG GAC AAT TGG AGA AGT GAA TTA  1362
Gly Gly Gly Asp Met Arg Asp Asn Trp Arg Ser Glu Leu
                445                 450

TAT AAA TAT AAA GTA GTA AAA GTT GAA CCA TTA GGA ATA  1401
Tyr Lys Tyr Lys Val Val Lys Val Glu Pro Leu Gly Ile
455                 460                 465

GCA CCC ACC AAG GCA AAG AGA AGA GTG GTG CAC AGA GAC  1440
Ala Pro Thr Lys Ala Lys Arg Arg Val Val His Arg Asp
        470                 475                 480

AAA AGA GCA GCA CTA GGA GCC TTG TTC CTT GGG TTC TTA  1479
Lys Arg Ala Ala Leu Gly Ala Leu Phe Leu Gly Phe Leu
                485                 490

GGA GCA TAA AAG CTT CTA GA  1499
Gly Ala Xaa Lys Leu Leu
    495                 499

CLONE C11.7

GAG GTA CCT GTA TGG AAA GAA GCA ACC ACT ACT CTA    36
    Glu Val Pro Val Trp Lys Glu Ala Thr Thr Thr Leu
      1               5                  10
```

TABLE 1-continued

```
TTT TGT GCA TCA GAT GCT AAA GCA TAT GAC ACA GAG GTG    75
Phe Cys Ala Ser Asp Ala Lys Ala Tyr Asp Thr Glu Val
            15              20              25

CAT AAT GTT TGG GCC ACA CAT GCC TGT GTA CCC ACA GAC   114
His Asn Val Trp Ala Thr His Ala Cys Val Pro Thr Asp
                30              35

CCC AAC CCA CAA GAA ATA GAA TTG GTA AAT GTG ACA GAA   153
Pro Asn Pro Gln Glu Ile Glu Leu Val Asn Val Thr Glu
        40              45              50

GAT TTT AAC ATG TGG AAA AAT AAA ATG GTA GAC CAG ATG   192
Asp Phe Asn Met Trp Lys Asn Lys Met Val Asp Gln Met
                55              60

CAT GAG GAT ATA ATC AGT TTA TGG GAT GAA AGC CTA AAG   231
His Glu Asp Ile Ile Ser Leu Trp Asp Glu Ser Leu Lys
65              70              75

CCA TGT GTA AAG TTA ACC CCA CTT TGT GTT ACT CTA AAC   270
Pro Cys Val Lys Leu Thr Pro Leu Cys Val Thr Leu Asn
            80              85              90

TGC AGT GAT GTG AAC AAT TCC ACA AAT CCT AAT GAT ACT   309
Cys Ser Asp Val Asn Asn Ser Thr Asn Pro Asn Asp Thr
                95              100

AAT ACT AAT TCC ACT AAT ACT ACT TCC TCT ACT CCT ACG   348
Asn Thr Asn Ser Thr Asn Thr Thr Ser Ser Thr Pro Thr
        105             110             115

GCC ACT ACT AGT AGC GAG GAA AAG ATG GAG AAG GGA GAA   387
Ala Thr Thr Ser Ser Glu Glu Lys Met Glu Lys Gly Glu
                120             125

ATA AAA AAC TGC TCT TTC AAT ATC ACC ACA CAC ATG AAA   426
Ile Lys Asn Cys Ser Phe Asn Ile Thr Thr His Met Lys
130             135             140

GAT AAG GTA CAG AAA GAA TAT GCA CTT TTT TAT AAA CTT   465
Asp Lys Val Glfl Lys Glu Tyr Ala Leu Phe Tyr Lys Leu
            145             150             155

GAT ATA GTA CCA ATA GAT GAT AAT AAT ACC AGC TAT AGG   504
Asp Ile Val Pro Ile Asp Asp Asn Asn Thr Ser Tyr Arg
                160             165

TTG ATA AGT TGT AAT ACC TCA GTC ATT ACA CAG GCC TGT   543
Leu Ile Ser Cys Asn Thr Ser Val Ile Thr Gln Ala Cys
        170             175             180

CCA ATG GTG ACC TTT GAG CCA ATT CCC ATA CAT TAT TGT   582
Pro Met Val Thr Phe Glu Pro Ile Pro Ile His Tyr Cys
                185             190

GCC CCG GCT GGT TTT GCG ATT CTA AAG TGT AAA GAT AAG   621
Ala Pro Ala Gly Phe Ala Ile Leu Lys Cys Lys Asp Lys
195             200             205

AAG TTC AAT GGA ACA GGA CCA TGT TCA AAG GTC AGC ACA   660
Lys Phe Asn Gly Thr Gly Pro Cys Ser Lys Val Ser Thr
            210             215             220

GTA CAA TGT ACA CAT GGA ATT AGG CCA GTA GTA TCA ACT   699
Val Gln Cys Thr His Gly Ile Arg Pro Val Val Ser Thr
                225             230

CAA CTG TTG TTA AAT GGC AGT CTT GCA GAA GAA GAA GTA   738
Gln Leu Leu Leu Asn Gly Ser Leu Ala Glu Glu Glu Val
        235             240             245

GTA ATT AGA TCT GTC AAT TTC ACA GAC AAT GCT AAA ATC   777
Val Ile Arg Ser Val Asn Phe Thr Asp Asn Ala Lys Ile
                250             255

ATA ATA GTA CAG CTG AAA GAA CCT GTA GCA ATT AAT TGT   816
Ile Ile Val Gln Leu Lys Glu Pro Val Ala Ile Asn Cys
```

TABLE 1-continued

```
260                 265                 270
ACA AGA CCC AAC AAC AAT ACA AGA AAA GGT ATA CAT CTA    855
Thr Arg Pro Asn Asn Asn Thr Arg Lys Gly Ile His Leu
        275                 280                 285

GGA CCA GGG AGC ACA TTT TAT ACA ACA GGA GAA ATA ATA    894
Gly Pro Gly Ser Thr Phe Tyr Thr Thr Gly Glu Ile Ile
                290                 295

GGA GAC ATA AGA AAA GCA TAT TGC AAG ATT AGT AAA GAA    933
Gly Asp Ile Arg Lys Ala Tyr Cys Lys Ile Ser Lys Glu
    300                 305                 310

AAA TGG AAT AAC ACT TTA AGA CAG GTA GTT AAA AAA TTA    972
Lys Trp Asn Asn Thr Leu Arg Gln Val Val Lys Lys Leu
                315                 320

AGA GAA CAA TTT GGG AAT AAA ACA ATA ATT TTT AAT CGA    1011
Arg Glu Gln Phe Gly Asn Lys Thr Ile Ile Phe Asn Arg
325                 330                 335

TCC TCA GGA GGG GAC CCA GAA ATT GTA ATG CAC AGT TTT    1050
Ser Ser Gly Gly Asp Pro Glu Ile Val Met His Ser Phe
        340                 345                 350

AAC TGT GGA GGG GAG TTT TTC TAC TGT AAT ACA ACA CAA    1089
Asn Cys Gly Gly Glu Phe Phe Tyr Cys Asn Thr Thr Gln
                355                 360

CTG TTT AAT AGT ACT TGG AAT AAT ACT GAA GGG ACA AAT    1128
Leu Phe Asn Ser Thr Trp Asn Asn Thr Glu Gly Thr Asn
365                 370                 375

AGC ACT GAA GGA AAT AGC ACA ATC ACA CTC CCA TGC AGA    1167
Ser Thr Glu Gly Asn Ser Thr Ile Thr Leu Pro Cys Arg
        380                 385

ATA AAA CAA ATT ATA AAT ATG TGG CAG GAA GTA GGA AAA    1206
Ile Lys Gln Ile Ile Asn Met Trp Gln Glu Val Gly Lys
390                 395                 400

GCA ACG TAT GCC CCT CCC ATC AGA GGA CGA ATT AGA TGC    1245
Ala Thr Tyr Ala Pro Pro Ile Arg Gly Arg Ile Arg Cys
                405                 410                 415

ATA TCA AAT ATT ACA GGA CTG CTA TTA ACA AGA GAT GGT    1284
Ile Ser Asn Ile Thr Gly Leu Leu Leu Thr Arg Asp Gly
                420                 425

GGT AGG AAT GTC ACA AAC AAT ACC GAN NCC TTC AGA CCT    1323
Gly Arg Asn Val Thr Asn Asn Thr Xaa Xaa Phe Arg Pro
        430                 435                 440

GGA GGA GGA GAC ATG AGG GAC AAT TGG AGA AGT GAA TTA    1362
Gly Gly Gly Asp Met Arg Asp Asn Trp Arg Ser Glu Leu
                445                 450

TAT AAA TAT AAA GTA GTA AAA GTT GAA CCA TTA GGA ATA    1401
Tyr Lys Tyr Lys Val Val Lys Val Glu Pro Leu Gly Ile
455                 460                 465

GCA CCC ACC AAG GCA AAG AGA AGA GTG GTG CAC AGA GAC    1440
Ala Pro Thr Lys Ala Lys Arg Arg Val Val His Arg Asp
        470                 475                 480

AAA AGA GCA GCA CTA GGA GCT TTG TTC CTT GGG TTC TTA    1479
Lys Arg Ala Ala Leu Gly Ala Leu Phe Leu Gly Phe Leu
                485                 490

GGA GCA TAA AAG CTT CTA GA    1499
Gly Ala Xaa Lys Leu Leu
        495                 499
```

CLONE C10.5

```
G   GTA CCT GTG TGG AAA GAA GCA AAC ACA ACT CTA TTT    37
    Val Pro Val Trp Lys Glu Ala Asn Thr Thr Leu Phe
    1               5                   10
```

TABLE 1-continued

```
TGT GCA TCA GAT GCT AAA GCA TAT GAT AGA GAA GTA CAT    76
Cys Ala Ser Asp Ala Lys Ala Tyr Asp Arg Glu Val His
            15              20              25

AAT GTT TGG GCA ACA CAT GCC TGT GTA CCC ACA GAC CCC   115
Asn Val Trp Ala Thr His Ala Cys Val Pro Thr Asp Pro
            30              35

AAC CCA CAA GAA ATA GTA TTG GGA AAT GTG ACA GAA AAT   154
Asn Pro Gln Glu Ile Val Leu Gly Asn Val Thr Glu Asn
    40              45              50

TTT AAC ATG TGG AAA AAT AAC ATG GTA GAA CAA ATG CAT   193
Phe Asn Met Trp Lys Asn Asn Met Val Glu Gln Met His
            55              60

GAG GAT ATA ATC AAT TTA TGG GAT CAA AGC TTA AAG CCA   232
Glu Asp Ile Ile Asn Leu Trp Asp Gln Ser Leu Lys Pro
 65             70              75

TGT GTA AAG TTA ACT CCA CTC TGT GTT ACT TTA AAG TGC   271
Cys Val Lys Leu Thr Pro Leu Cys Val Thr Leu Lys Cys
            80              85              90

AAG GAT CTG GAG AGG AAT ACT ACC TAT AAT AGC ACT ATT   310
Lys Asp Leu Glu Arg Asn Thr Thr Tyr Asn Ser Thr Ile
                95              100

ACC AAT AAT AGT AGT TTG GAG GGA CTA AGA GAA CAA ATG   349
Thr Asn Asn Ser Ser Leu Glu Gly Leu Arg Glu Gln Met
        105             110             115

ACA AAC TGC TCT TTC AAC ATC ACC ACA AGT ATA AGA GAT   388
Thr Asn Cys Ser Phe Asn Ile Thr Thr Ser Ile Arg Asp
            120             125

AAG GTG CAG AAA GAA TAT GCA CTT TTG TAT AAA CTT GAT   427
Lys Val Gln Lys Glu Tyr Ala Leu Leu Tyr Lys Leu Asp
130             135             140

GTA GTA CCA ATA GAA GAA GAT GAC AAT ACT AGC TAT AGA   466
Val Val Pro Ile Glu Glu Asp Asp Asn Thr Ser Tyr Arg
            145             150             155

TTG ATA AGT TGT AAC ACC TCA GTC ATT ACA CAG GCT TGT   505
Leu Ile Ser Cys Asn Thr Ser Val Ile Thr Gln Ala Cys
                160             165

CCA AAG ACA TCC TTT GAG CCA ATT CCC ATA CAT TAT TGT   544
Pro Lys Thr Ser Phe Glu Pro Ile Pro Ile His Tyr Cys
        170             175             180

GCC CCG GCT GGT TTT GCG ATT CTA AAG TGT AAT GAT AAG   583
Ala Pro Ala Gly Phe Ala Ile Leu Lys Cys Asn Asp Lys
            185             190

AAG TTC AAT GGA ACA GGA CCA TGT AAA AAT GTC AGC ACA   622
Lys Phe Asn Gly Thr Gly Pro Cys Lys Asn Val Ser Thr
195             200             205

GTA CAA TGT ACA CAT GGA ATT AGG CCA GTA GTA TCA ACT   661
Val Gln Cys Thr His Gly Ile Arg Pro Val Val Ser Thr
            210             215             220

CAA CTG TTG TTA AAT GGC AGT CTA GCA GAA GAA GAG GTA   700
Gln Leu Leu Leu Asn Gly Ser Leu Ala Glu Glu Glu Val
                225             230

GTA ATC AGA TCT GCC AAT TTC ACA GAC AAT GCT AAA ACC   739
Val Ile Arg Ser Ala Asn Phe Thr Asp Asn Ala Lys Thr
        235             240             245

ATA ATA GTA CAT CTA AAT GAA ACT GTA AAA ATT AAT TGT   778
Ile Ile Val His Leu Asn Glu Thr Val Lys Ile Asn Cys
            250             255

ACA AGA CTT GGC AAC AAT ACA AGA AAA AGT ATA AAT ATA   817
Thr Arg Leu Gly Asn Asn Thr Arg Lys Ser Ile Asn Ile
```

TABLE 1-continued

```
260                 265                      270
GGA CCA GGG AGA GTA CTC TAT GCA ACA GGA GAA ATA ATA    856
Gly Pro Gly Arg Val Leu Tyr Ala Thr Gly Glu Ile Ile
        275                 280                 285

GGA GAC ATA AGA CAA GCA CAT TGT AAC ATT AGT AGA GCA    895
Gly Asp Ile Arg Gln Ala His Cys Asn Ile Ser Arg Ala
                290                 295

CAA TGG AAT AAG ACT TTA GAA AAG GTA GTT GAC AAA TTA    934
Gln Trp Asn Lys Thr Leu Glu Lys Val Val Asp Lys Leu
    300                 305                 310

AGA AAA CAA TTT GGG GAT AAT ACA ACA ATA GCT TTT AAT    973
Arg Lys Gln Phe Gly Asp Asn Thr Thr Ile Ala Phe Asn
            315                 320

CGA TCC TCA GGA GGG GAC CCA GAA ATT GTA ATG CAC ACT   1012
Arg Ser Ser Gly Gly Asp Pro Glu Ile Val Met His Thr
325                 330                 335

TTT AAT TGT GGA GGG GAA TTT TTC TAC TGT AAT ACA ACA   1051
Phe Asn Cys Gly Gly Glu Phe Phe Tyr Cys Asn Thr Thr
        340                 345                 350

CAA CTG TTT AAT AGT ACT TGG AAT AAT ACT TGG AAG GAT   1090
Gln Leu Phe Asn Ser Thr Trp Asn Asn Thr Trp Lys Asp
                355                 360

CCT AAC AGG AGT GAC AAT ATC ACA CTC CCA TGC AGA ATA   1129
Pro Asn Arg Ser Asp Asn Ile Thr Leu Pro Cys Arg Ile
    365                 370                 375

AAA CAA ATT ATA AAC ATG TGG CAG GAA GTA GGA AAA GCA   1168
Lys Gln Ile Ile Asn Met Trp Gln Glu Val Gly Lys Ala
            380                 385

ATG TAC GCC CCT CCC ATC AGA GGG GAA ATT AGA TGT TCA   1207
Met Tyr Ala Pro Pro Ile Arg Gly Glu Ile Arg Cys Ser
390                 395                 400

TCA AAT ATC ACA GGG CTG CTA CTA ACA AGA GAT GGT GGT   1246
Ser Asn Ile Thr Gly Leu Leu Leu Thr Arg Asp Gly Gly
        405                 410                 415

AAT GAC GAT GGT AAT GAC ACG ACC ACA AAC AGG ACC GAG   1285
Asn Asp Asp Gly Asn Asp Thr Thr Thr Asn Arg Thr Glu
                420                 425

ATC TTC AGA CCT GGA GGA GGA GAT ATG AGG GAC AAT TGG   1324
Ile Phe Arg Pro Gly Gly Gly Asp Met Arg Asp Asn Trp
    430                 435                 440

AGA AGT GAA TTA TAT AGA TAT AAA GTA GTA AAA ATT GAA   1363
Arg Ser Glu Leu Tyr Arg Tyr Lys Val Val Lys Ile Glu
            445                 450

CCA TTA GGA ATA GCA CCC ACC AGG GCA AAG AGA AGA GTG   1402
Pro Leu Gly Ile Ala Pro Thr Arg Ala Lys Arg Arg Val
455                 460                 465

GTG CAG AGA GAA AAA AGA GCA GTA GGA CTA GGA GCT TTG   1441
Val Gln Arg Glu Lys Arg Ala Val Gly Leu Gly Ala Leu
        470                 475                 480

TTC CTT GGG T TCTTAGGAG CATAAAGCTT CTAGA              1475
Phe Leu Gly
        483
```

CLONE C10.7

```
G   GTA CCT GTG TGG AAA GAA GCA AAC ACA ACT CTA TTT    37
    Val Pro Val Trp Lys Glu Ala Asn Thr Thr Leu Phe
    1               5                   10

TGT GCA TCA GAT GCT AAA GCA TAT GAT AGA GAA GTA CAT    76
Cys Ala Ser Asp Ala Lys Ala Tyr Asp Arg Glu Val His
        15                  20                  25
```

TABLE 1-continued

```
AAT GTT TGG GCA ACA CAT GCC TGT GTA CCC ACA GAC CCC    115
Asn Val Trp Ala Thr His Ala Cys Val Pro Thr Asp Pro
                30                  35

AAC CCA CAA GAA ATA GTA TTG GGA AAT GTG ACA GAA AAT    154
Asn Pro Gln Glu Ile Val Leu Gly Asn Val Thr Glu Asn
     40              45                  50

TTT AAC ATG TGG AAA AAT AAC ATG GTA GAA CAA ATG CAT    193
Phe Asn Met Trp Lys Asn Asn Met Val Glu Gln Met His
             55                  60

GAG GAT ATA ATC AAT TTA TGG GAT CAA AGC TTA AAG CCA    232
Glu Asp Ile Ile Asn Leu Trp Asp Gln Ser Leu Lys Pro
 65                  70                  75

TGT GTA AAG TTA ACT CCA CTC TGT GTT ACT TTA AAG TGC    271
Cys Val Lys Leu Thr Pro Leu Cys Val Thr Leu Lys Cys
         80                  85                  90

AAG GAT CTG GAG AGG AAT ACT ACC TAT AAT AGC ACT ATT    310
Lys Asp Leu Glu Arg Asn Thr Thr Tyr Asn Ser Thr Ile
                 95                 100

ACC AAT AAT AGT AGT TTG GAG GGA CTA AGA GAA CAA ATG    349
Thr Asn Asn Ser Ser Leu Glu Gly Leu Arg Glu Gln Met
        105                 110                 115

ACA AAC TGC TCT TTC AAC ATC ACC ACA AGT ATA AGA GAT    388
Thr Asn Cys Ser Phe Asn Ile Thr Thr Ser Ile Arg Asp
        120                 125

AAG GTG CAG AAA GAA TAT GCA CTT TTG TAT AAA CTT GAT    427
Lys Val Gln Lys Glu Tyr Ala Leu Leu Tyr Lys Leu Asp
130                 135                 140

GTA GTA CCA ATA GAA GAA GAT GAC AAT ACT AGC TAT AGA    466
Val Val Pro Ile Glu Glu Asp Asp Asn Thr Ser Tyr Arg
        145                 150                 155

TTG ATA AGT TGT AAC ACC TCA GTC ATT ACA CAG GCT TGT    505
Leu Ile Ser Cys Asn Thr Ser Val Ile Thr Gln Ala Cys
                160                 165

CCA AAG ACA TCC TTT GAG CCA ATT CCC ATA CAT TAT TGT    544
Pro Lys Thr Ser Phe Glu Pro Ile Pro Ile His Tyr Cys
        170                 175                 180

GCC CCG GCT GGT TTT GCG ATT CTA AAG TGT AAT GAT AAG    583
Ala Pro Ala Gly Phe Ala Ile Leu Lys Cys Asn Asp Lys
                185                 190

AAG TTC AAT GGA ACA GGA CCA TGT AAA AAT GTC AGC ACA    622
Lys Phe Asn Gly Thr Gly Pro Cys Lys Asn Val Ser Thr
195                 200                 205

GTA CAA TGT ACA CAT GGA ATT AGG CCA GTA GTA TCA ACT    661
Val Gln Cys Thr His Gly Ile Arg Pro Val Val Ser Thr
        210                 215                 220

CAA CTG TTG TTA AAT GGC AGT CTA GCA GAA GAA GAG GTA    700
Gln Leu Leu Leu Asn Gly Ser Leu Ala Glu Glu Glu Val
                225                 230

GTA ATC AGA TCT GCC AAT TTC ACA GAC AAT GCT AAA ACC    739
Val Ile Arg Ser Ala Asn Phe Thr Asp Asn Ala Lys Thr
        235                 240                 245

ATA ATA GTA CAT CTA AAT GAA ACT GTA AAA ATT AAT TGT    778
Ile Ile Val His Leu Asn Glu Thr Val Lys Ile Asn Cys
                250                 255

ACA AGA CTT GGC AAC AAT ACA AGA AAA AGT ATA AAT ATA    817
Thr Arg Leu Gly Asn Asn Thr Arg Lys Ser Ile Asn Ile
260                 265                 270

GGA CCA GGG AGA GTA CTC TAT GCA ACA GGA GAA ATA ATA    856
Gly Pro Gly Arg Val Leu Tyr Ala Thr Gly Glu Ile Ile
```

TABLE 1-continued

```
              275                       280                       285
GGA GAC ATA AGA CAA GCA CAT TGT AAC ATT AGT AGA GCA         895
Gly Asp Ile Arg Gln Ala His Cys Asn Ile Ser Arg Ala
                    290                   295

CAA TGG AAT AAG ACT TTA GAA AAG GTA GTT GAC AAG TTA         934
Gln Trp Asn Lys Thr Leu Glu Lys Val Val Asp Lys Leu
        300                   305                   310

AGA AAA CAA TTT GGG GAT AAT ACA ACA ATA GCT TTT AAT         973
Arg Lys Gln Phe Gly Asp Asn Thr Thr Ile Ala Phe Asn
                315                   320

CGA TCC TCA GGA GGG GAC CCA GAA ATT GTA ATG CAC ACT        1012
Arg Ser Ser Gly Gly Asp Pro Glu Ile Val Met His Thr
325                   330                   335

TTT AAT TGT GGA GGG GAA TTT TTC TAC TGT AAT ACA ACA        1051
Phe Asn Cys Gly Gly Glu Phe Phe Tyr Cys Asn Thr Thr
            340                   345                   350

CAA CTG TTT AAT AGT ACT TGG AAT AAT ACT TGG AAG GAT        1090
Gln Leu Phe Asn Ser Thr Trp Asn Asn Thr Trp Lys Asp
                    355                   360

CCT AAC AGG AGT GAC AAT ATC ACA CTC CCA TGC AGA ATA        1129
Pro Asn Arg Ser Asp Asn Ile Thr Leu Pro Cys Arg Ile
        365                   370                   375

AAA CAA ATT ATA AAC ATG TGG CAG GAA GTA GGA AAA GCA        1168
Lys Gln Ile Ile Asn Met Trp Gln Glu Val Gly Lys Ala
                380                   385

ATG TAC GCC CCT CCC ATC AGA GGG GAA ATT AGA TGT TCA        1207
Met Tyr Ala Pro Pro Ile Arg Gly Glu Ile Arg Cys Ser
390                   395                   400

TCA AAT ATC ACA GGG CTG CTA CTA ACA AGA GAT GGT GGT        1246
Ser Asn Ile Thr Gly Leu Leu Leu Thr Arg Asp Gly Gly
            405                   410                   415

AAT GAC GAT GGT AAT GAC ACG ACC ACA AAC AGG ACC GAG        1285
Asn Asp Asp Gly Asn Asp Thr Thr Thr Asn Arg Thr Glu
                    420                   425

ATC TTC AGA CCT GGA GGA GGA GAT ATG AGG GAC AAT TGG        1324
Ile Phe Arg Pro Gly Gly Gly Asp Met Arg Asp Asn Trp
        430                   435                   440

AGA AGT GAA TTA TAT AGA TAT AAA GTA GTA AAA ATT GAA        1363
Arg Ser Glu Leu Tyr Arg Tyr Lys Val Val Lys Ile Glu
                445                   450

CCA TTA GGA ATA GCA CCC ACC AGG GCA AAG AGA AGA GTG        1402
Pro Leu Gly Ile Ala Pro Thr Arg Ala Lys Arg Arg Val
455                   460                   465

GTG CAG AGA GAA AAA AGA GCA GTA GGA CTA GGA GCT TTG        1441
Val Gln Arg Glu Lys Arg Ala Val Gly Leu Gly Ala Leu
            470                   475                   480

TTC CTT GGG TTC TTG GGA GCA TAA AGC TTC TAG A              1475
Phe Leu Gly Phe Leu Gly Ala Xaa Ser Phe Xaa
                485                       490 491
```

CLONE C17.1

```
    CTC GAG GTA CCT GTG TGG AAA GAA GCA ACC ACC ACT          36
    Leu Glu Val Pro Val Trp Lys Glu Ala Thr Thr Thr
    1                   5                   10

CTA TTT TGT GCA TCA GAT GCT AAA GCA TAT GAT TCA GAG         75
Leu Phe Cys Ala Ser Asp Ala Lys Ala Tyr Asp Ser Glu
            15                  20                  25

GCA CAT AAT GTT TGG GCC ACA CAT GCC TGT GTA CCC ACA        114
Ala His Asn Val Trp Ala Thr His Ala Cys Val Pro Thr
                30                  35
```

TABLE 1-continued

```
GAC CCC AAC CCA CAA GAA GTA GAA TTG GAA AAT GTG ACA    153
Asp Pro Asn Pro Gln Glu Val Glu Leu Glu Asn Val Thr
    40              45                  50

GAA AAT TTT AAC ATG TGG AAA AAT AAC ATG GTA GAA CAG    192
Glu Asn Phe Asn Met Trp Lys Asn Asn Met Val Glu Gln
            55              60

ATG CAT GGG GAT ATA ATT AGT TTA TGG GAT CAA AGC CTA    231
Met His Gly Asp Ile Ile Ser Leu Trp Asp Gln Ser Leu
65                  70                  75

AAG CCA TGT GTA AAA TTA ACC CCA CTC TGT GTT ACG TTA    270
Lys Pro Cys Val Lys Leu Thr Pro Leu Cys Val Thr Leu
        80                  85                  90

AAT TGC ACT GAC CCA AAT GTT ACT AAT AGC GAG AGA ACG    309
Asn Cys Thr Asp Pro Asn Val Thr Asn Ser Glu Arg Thr
                95                  100

ATA GAG GGG GGA GAA ATA AAA AAT TGC TCT TTC AAT ATC    348
Ile Glu Gly Gly Glu Ile Lys Asn Cys Ser Phe Asn Ile
    105                 110                 115

ACC ACA AAC ATA AGA GAT AGG TTT CAG AAA GAA TAT GCA    387
Thr Thr Asn Ile Arg Asp Arg Phe Gln Lys Glu Tyr Ala
            120                 125

CTT TTT TAT AAA CTT GAT GTA ATA CCA TTA GGT AAT GAT    426
Leu Phe Tyr Lys Leu Asp Val Ile Pro Leu Gly Asn Asp
130                 135                 140

AAT ACT AGC TAT AGG TTG ATA AGT TGT AAC ACC TCA GTC    465
Asn Thr Ser Tyr Arg Leu Ile Ser Cys Asn Thr Ser Val
        145                 150                 155

ATT ACA CAG GCC TGT CCA AAG GTA TCC TTT GAG CCA ATT    504
Ile Thr Gln Ala Cys Pro Lys Val Ser Phe Glu Pro Ile
                160                 165

CCC ATA CAT TAT TGT GCC CCG GCT GGT TTT GCG ATT CTA    543
Pro Ile His Tyr Cys Ala Pro Ala Gly Phe Ala Ile Leu
    170                 175                 180

AAG TGT AAA GAT AAG AAG TTC AAT GGA ACA GGA CCA TGT    582
Lys Cys Lys Asp Lys Lys Phe Asn Gly Thr Gly Pro Cys
            185                 190

ACA AAT GTC AGC ACA GTA CAA TGT ACA CAT GGA ATT AAG    621
Thr Asn Val Ser Thr Val Gln Cys Thr His Gly Ile Lys
195                 200                 205

CCA GTA GTA TCA ACT CAA CTG TTG TTA AAT GGC AGT CTA    660
Pro Val Val Ser Thr Gln Leu Leu Leu Asn Gly Ser Leu
        210                 215                 220

GCA GAA GAA GAC ATA GTA ATT AGA TCC GCC AAT CTC ACA    699
Ala Glu Glu Asp Ile Val Ile Arg Ser Ala Asn Leu Thr
                225                 230

GAC AAT GCT AAA AAC ATA ATA GTA CAG CTG AAT GAA TCT    738
Asp Asn Ala Lys Asn Ile Ile Val Gln Leu Asn Glu Ser
    235                 240                 245

GTA ACA ATG AAT TGT ACA AGA CCC AAC AAC AAT ACA ATG    777
Val Thr Met Asn Cys Thr Arg Pro Asn Asn Asn Thr Met
            250                 255

AAA AGT ATA CAT ATA GGA CCA GGC AGA GCA TTT TAT GCA    816
Lys Ser Ile His Ile Gly Pro Gly Arg Ala Phe Tyr Ala
260                 265                 270

ACA GGA AAC ATA ATA GGA GAT ATA AGA CAA GCA CAT TGT    855
Thr Gly Asn Ile Ile Gly Asp Ile Arg Gln Ala His Cys
        275                 280                 285

AAC ATT AGT GGA ACA AAA TGG AAT GAC ACT TTG AAA AAG    894
Asn Ile Ser Gly Thr Lys Trp Asn Asp Thr Leu Lys Lys
```

TABLE 1-continued

```
                    290                           295
ATA GCT ATA AAA TTA AGA GAA CAA TTT AAT AAG ACA ATA    933
Ile Ala Ile Lys Leu Arg Glu Gln Phe Asn Lys Thr Ile
        300                 305                 310

GTC TTT AAT CAA TCC TCA GGA GGG GAC CCA GAA ATT GCA    972
Val Phe Asn Gln Ser Ser Gly Gly Asp Pro Glu Ile Ala
            315                 320

ACG CTC AGT TTT AAT TGT GGA GGG GAA TTT TTC TAC TGT    1011
Thr Leu Ser Phe Asn Cys Gly Gly Glu Phe Phe Tyr Cys
325                 330                 335

AAT TCA ACA CAA CTG TTT AAT AGT ACT TGG AAT AGT ACT    1050
Asn Ser Thr Gln Leu Phe Asn Ser Thr Trp Asn Ser Thr
            340                 345                 350

GGG TCA AAT AAC ACT AAA GGA AAT GAC ACA ATC ACA CTC    1089
Gly Ser Asn Asn Thr Lys Gly Asn Asp Thr Ile Thr Leu
                355                 360

CCA TGC AGA ATA AGA CAA ATT ATA AAC ATG TGG CAG AAA    1128
Pro Cys Arg Ile Arg Gln Ile Ile Asn Met Trp Gln Lys
365                 370                 375

ATA GGA AAA GCA ATG TAT GCC CCT CCC ATC AAA GGG CAA    1167
Ile Gly Lys Ala Met Tyr Ala Pro Pro Ile Lys Gly Gln
            380                 385

ATT AGA TGT TCA TCA AAT ATT ACA GGG CTA ATA TTA ACA    1206
Ile Arg Cys Ser Ser Asn Ile Thr Gly Leu Ile Leu Thr
390                 395                 400

AGA GAT GGT GGT AAC AAC AAC ATG AGC AAG ACC ACC GAG    1245
Arg Asp Gly Gly Asn Asn Asn Met Ser Lys Thr Thr Glu
            405                 410                 415

ACC TTC AGA CCT GGA GGA GGA GAT ATG AGG GAC AAT TGG    1284
Thr Phe Arg Pro Gly Gly Gly Asp Met Arg Asp Asn Trp
                420                 425

AGA AGT GAA TTA TAT AAA TAT AAA GTA GTA AAA ATT GAA    1323
Arg Ser Glu Leu Tyr Lys Tyr Lys Val Val Lys Ile Glu
430                 435                 440

CCA TTA GGA GTA GCA CCC ACC AGG GCA AAG AGA AGA GTG    1362
Pro Leu Gly Val Ala Pro Thr Arg Ala Lys Arg Arg Val
            445                 450

GTG CAG AGA GAA AAA AGA GCA GTG GGA ATA GGA GCT GTG    1401
Val Gln Arg Glu Lys Arg Ala Val Gly Ile Gly Ala Val
455                 460                 465

TTC CTT GGG TTC TTG GGA GCA TAA AGC TTC TAG A          1435
Phe Leu Gly Phe Leu Gly Ala Xaa Ser Phe Xaa
            470                 475     478

CLONE C17.3

CTC GAG GTA CCT GTG TGG AAA GAA GCA ACC ACC ACT    36
    Leu Glu Val Pro Val Trp Lys Glu Ala Thr Thr Thr
     1               5                  10

CTA TTT TGT GCA TCA GAT GCT AAA GCA TAT GAT TCA GAG    75
Leu Phe Cys Ala Ser Asp Ala Lys Ala Tyr Asp Ser Glu
            15                  20                  25

GCA CAT AAT GTT TGG GCC ACA CAT GCC TGT GTA CCC ACA    114
Ala His Asn Val Trp Ala Thr His Ala Cys Val Pro Thr
                30                  35

GAC CCC AAC CCA CAA GAA GTA GAA TTG GAA AAT GTG ACA    153
Asp Pro Asn Pro Gln Glu Val Glu Leu Glu Asn Val Thr
40                  45                  50

GAA AAT TTT AAC ATG TGG AAA AAT AAC ATG GTA GAA CAG    192
Glu Asn Phe Asn Met Trp Lys Asn Asn Met Val Glu Gln
            55                  60
```

TABLE 1-continued

```
ATG CAT GGG GAT ATA ATT AGT TTA TGG GAT CAA AGC CTA    231
Met His Gly Asp Ile Ile Ser Leu Trp Asp Gln Ser Leu
 65              70                  75

AAG CCA TGT GTA AAA TTA ACC CCA CTC TGT GTT ACG TTA    270
Lys Pro Cys Val Lys Leu Thr Pro Leu Cys Val Thr Leu
         80                  85                  90

AAT TGC ACT GAC CCA AAT GTT ACT AAT AGC GAG AGA ACG    309
Asn Cys Thr Asp Pro Asn Val Thr Asn Ser Glu Arg Thr
                 95                 100

ATA GAG GGG GGA GAA ATA AAA AAT TGC TCT TTC AAT ATC    348
Ile Glu Gly Gly Glu Ile Lys Asn Cys Ser Phe Asn Ile
        105                 110                 115

ACC ACA AAC ATA AGA GAT AGG TTT CAG AAA GAA TAT GCA    387
Thr Thr Asn Ile Arg Asp Arg Phe Gln Lys Glu Tyr Ala
                120                 125

CTT TTT TAT AAA CTT GAT GTA ATA CCA TTA GGT AAT GAT    426
Leu Phe Tyr Lys Leu Asp Val Ile Pro Leu Gly Asn Asp
130                 135                 140

AAT ACT AGC TAT AGG TTG ATA AGT TGT AAC ACC TCA GTC    465
Asn Thr Ser Tyr Arg Leu Ile Ser Cys Asn Thr Ser Val
        145                 150                 155

ATT ACA CAG GCC TGT CCA AAG GTA TCC TTT GAG CCA ATT    504
Ile Thr Gln Ala Cys Pro Lys Val Ser Phe Glu Pro Ile
                160                 165

CCC ATA CAT TAT TGT GCC CCG GCT GGT TTT GCG ATT CTA    543
Pro Ile His Tyr Cys Ala Pro Ala Gly Phe Ala Ile Leu
        170                 175                 180

AAG TGT AAA GAT AAG AAG TTC AAT GGA ACA GGA CCA TGT    582
Lys Cys Lys Asp Lys Lys Phe Asn Gly Thr Gly Pro Cys
                185                 190

ACA AAT GTC AGC ACA GTA CAA TGT ACA CAT GGA ATT AAG    621
Thr Asn Val Ser Thr Val Gln Cys Thr His Gly Ile Lys
195                 200                 205

CCA GTA GTA TCA ACT CAA CTG TTG TTA AAT GGC AGT CTA    660
Pro Val Val Ser Thr Gln Leu Leu Leu Asn Gly Ser Leu
        210                 215                 220

GCA GAA GAA GAC ATA GTA ATT AGA TCC GCC AAT CTC ACA    699
Ala Glu Glu Asp Ile Val Ile Arg Ser Ala Asn Leu Thr
                225                 230

GAC AAT GCT AAA AAC ATA ATA GTA CAG CTG AAT GAA TCT    738
Asp Asn Ala Lys Asn Ile Ile Val Gln Leu Asn Glu Ser
235                 240                 245

GTA ACA ATG AAT TGT ACA AGA CCC AAC AAC AAT ACA ATG    777
Val Thr Met Asn Cys Thr Arg Pro Asn Asn Asn Thr Met
        250                 255

AAA AGT ATA CAT ATA GGA CCA GGC AGA GCA TTT TAT GCA    816
Lys Ser Ile His Ile Gly Pro Gly Arg Ala Phe Tyr Ala
260                 265                 270

ACA GGA AAC ATA ATA GGA GAT ATA AGA CAA GCA CAT TGT    855
Thr Gly Asn Ile Ile Gly Asp Ile Arg Gln Ala His Cys
                275                 280                 285

AAC ATT AGT GGA ACA AAA TGG AAT GAC ACT TTG AAA AAG    894
Asn Ile Ser Gly Thr Lys Trp Asn Asp Thr Leu Lys Lys
                290                 295

ATA GCT ATA AAA TTA AGA GAA CAA TTT AAT AAG ACA ATA    933
Ile Ala Ile Lys Leu Arg Glu Gln Phe Asn Lys Thr Ile
300                 305                 310

GTC TTT AAT CAA TCC TCA GGA GGG GAC CCA GAA ATT GCA    972
Val Phe Asn Gln Ser Ser Gly Gly Asp Pro Glu Ile Ala
```

TABLE 1-continued

|  | 315 |  |  |  |  |  |  | 320 |  |  |  |  |
|---|---|---|---|---|---|---|---|---|---|---|---|---|
| ACG | CTC | AGT | TTT | AAT | TGT | GGA | GGG | GAA | TTT | TTC | TAC | TGT | 1011 |
| Thr | Leu | Ser | Phe | Asn | Cys | Gly | Gly | Glu | Phe | Phe | Tyr | Cys |  |
| 325 |  |  |  |  | 330 |  |  |  |  | 335 |  |  |  |
| AAT | TCA | ACA | CAA | CTG | TTT | AAT | AGT | ACT | TGG | AAT | AGT | ACT | 1050 |
| Asn | Ser | Thr | Gln | Leu | Phe | Asn | Ser | Thr | Trp | Asn | Ser | Thr |  |
|  |  | 340 |  |  |  |  | 345 |  |  |  |  | 350 |  |
| GGG | TCA | AAT | AAC | ACT | AAA | GGA | AAT | GAC | ACA | ATC | ACA | CTC | 1089 |
| Gly | Ser | Asn | Asn | Thr | Lys | Gly | Asn | Asp | Thr | Ile | Thr | Leu |  |
|  |  |  |  | 355 |  |  |  |  | 360 |  |  |  |  |
| CCA | TGC | AGA | ATA | AGA | CAA | ATT | ATA | AAC | ATG | TGG | CAG | AAA | 1128 |
| Pro | Cys | Arg | Ile | Arg | Gln | Ile | Ile | Asn | Met | Trp | Gln | Lys |  |
|  | 365 |  |  |  |  | 370 |  |  |  |  | 375 |  |  |
| ATA | GGA | AAA | GCA | ATG | TAT | GCC | CCT | CCC | ATC | AAA | GGG | CAA | 1167 |
| Ile | Gly | Lys | Ala | Met | Tyr | Ala | Pro | Pro | Ile | Lys | Gly | Gln |  |
|  |  |  | 380 |  |  |  |  | 385 |  |  |  |  |  |
| ATT | AGA | TGT | TCA | TCA | AAT | ATT | ACA | GGG | CTA | ATA | TTA | ACA | 1206 |
| Ile | Arg | Cys | Ser | Ser | Asn | Ile | Thr | Gly | Leu | Ile | Leu | Thr |  |
| 390 |  |  |  |  | 395 |  |  |  |  | 400 |  |  |  |
| AGA | GAT | GGT | GGT | AAC | AAC | AAC | ATG | AGC | AAG | ACC | ACC | GAG | 1245 |
| Arg | Asp | Gly | Gly | Asn | Asn | Asn | Met | Ser | Lys | Thr | Thr | Glu |  |
|  |  | 405 |  |  |  |  | 410 |  |  |  |  | 415 |  |
| ACC | TTC | AGA | CCT | GGA | GGA | GGA | GAT | ATG | AGG | GAC | AAT | TGG | 1284 |
| Thr | Phe | Arg | Pro | Gly | Gly | Gly | Asp | Met | Arg | Asp | Asn | Trp |  |
|  |  |  | 420 |  |  |  |  | 425 |  |  |  |  |  |
| AGA | AGT | GAA | TTA | TAT | AAA | TAT | AAA | GTA | GTA | AAA | ATT | GAA | 1323 |
| Arg | Ser | Glu | Leu | Tyr | Lys | Tyr | Lys | Val | Val | Lys | Ile | Glu |  |
|  | 430 |  |  |  |  | 435 |  |  |  |  | 440 |  |  |
| CCA | TTA | GGA | GTA | GCA | CCC | ACC | AGG | GCA | AAG | AGA | AGA | GTG | 1362 |
| Pro | Leu | Gly | Val | Ala | Pro | Thr | Arg | Ala | Lys | Arg | Arg | Val |  |
|  |  |  | 445 |  |  |  |  | 450 |  |  |  |  |  |
| GTG | CAG | AGA | GAA | AAA | AGA | GCA | GTG | GGA | ATA | GGA | GCT | GTG | 1401 |
| Val | Gln | Arg | Glu | Lys | Arg | Ala | Val | Gly | Ile | Gly | Ala | Val |  |
| 455 |  |  |  |  | 460 |  |  |  |  | 465 |  |  |  |
| TTC | CTT | GGG | TTC | TTG | GGA | GCA | TAA | AGC | TTC | TAG | A | 1435 |  |
| Phe | Leu | Gly | Phe | Leu | Gly | Ala | Xaa | Ser | Phe | Xaa |  |  |  |
|  |  | 470 |  |  |  |  | 475 |  |  | 478 |  |  |  |

Figure 3D:
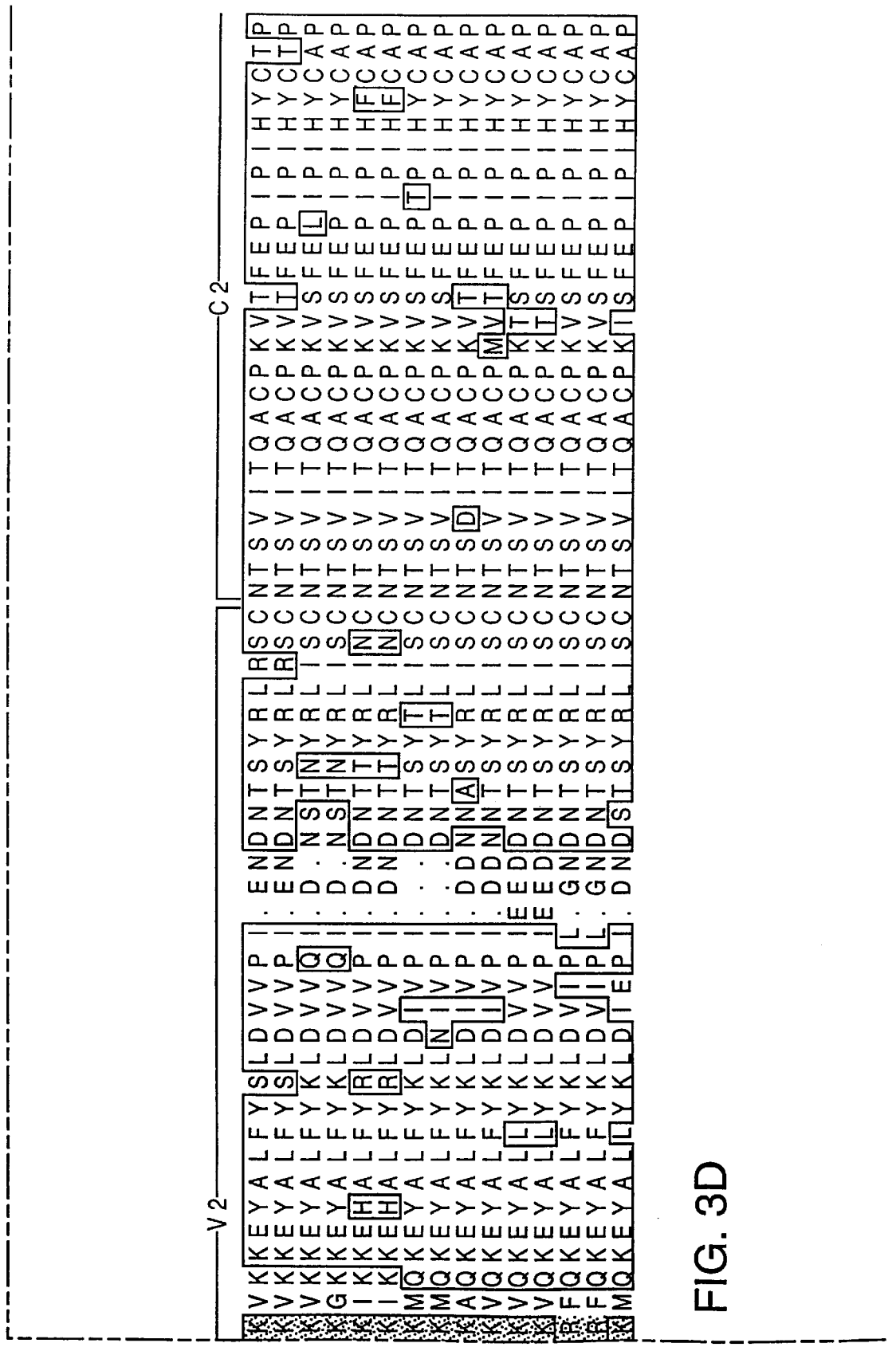
Figure 3F:
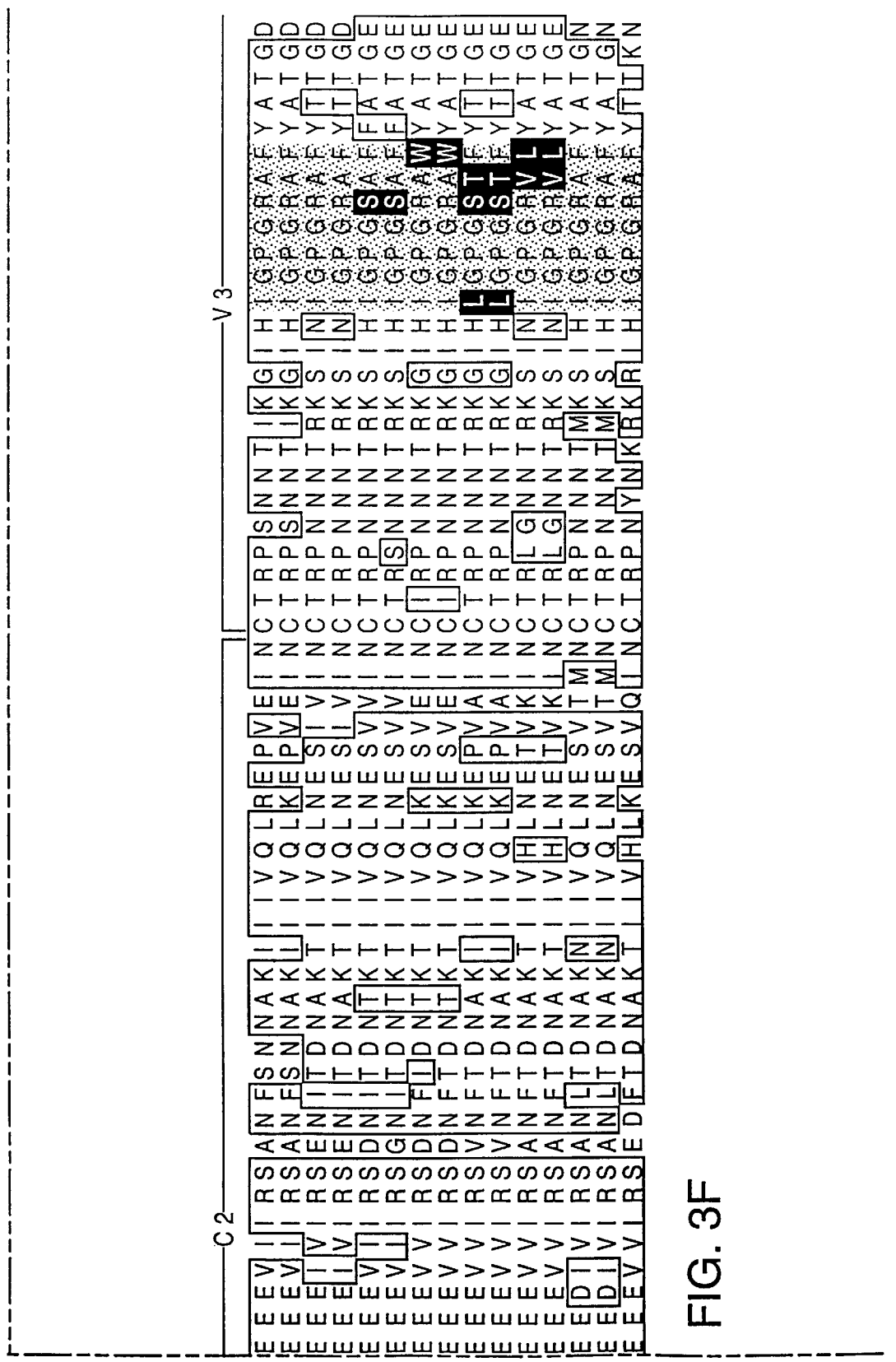

In addition to the listing in Table 1, FIG. 3 shows the alignment of the amino acid sequences of the clones of each of the seven isolates. Corresponding residues from various clones are in boxes. In the figure, the amino acid sequences are aligned against MN-rgp120 (SEQ. ID. NO:41).

In one embodiment, a gp120 polypeptide of this invention has the same amino acid sequence as the sequence of one of the breakthrough isolates. In another embodiment, the amino acid sequence is truncated, as described in detail hereinafter. In another embodiment, a gp120 polypeptide sequence of this invention contains a substitution, insertion, or deletion (alteration) of one or more amino acids in the sequence of a breakthrough isolate. Usually, with the exception of amino acids that are not present in a truncated amino acid sequence and eliminate an epitope, a gp120 polypeptide of this invention will include alterations in the amino acid sequence of a breakthrough isolate that do not alter the polypeptide's ability to induce the same neutralizing antibodies as the amino acid sequence of the isolate.

In general, substitutions in the amino acid sequence of a gp120 polypeptide of this invention are conservative substitutions, particularly for amino acid residues in the V2, V3, and C4 domains of gp120, which domains contain neutralizing epitopes. However, nonconservative substitutions, particularly in domains that do not contain neutralizing epitopes are contemplated.

Conservative substitutions replace an amino acid with an amino acid of similar size and character. For example, a hydrophobic residue or hydrophilic residue is replaced with another hydrophobic residue or hydrophilic residue, respectively. Amino acids can be divided into the following groups: positively charged residues (K, R and H); negatively charged residues (D and E); amides (N and Q); aromatics (F, Y, and W); hydrophobics (P, G, A, V, L, I, and M); and uncharged residues (S and T). Usually, residues within a group are replaced with another member of the group.

In one embodiment, critical amino acid residues in the V2, V3, and C4 domains of gp120 are identical to the corresponding residues in a breakthrough isolate sequence. Critical amino acid residues in the V2, V3, and C4 domains of gp120 are described in the experimental section. In another embodiment, all amino acid residues in the V2, V3, and C4 domains of gp120 are identical to corresponding residues in a breakthrough isolate sequence.

Oligonucleotide Encoding gp120 from Breakthrough Isolates

The present invention also provides novel oligonucleotides encoding gp120 from the breakthrough isolates which can be used to express gp120. An oligonucleotide of this invention encodes a polypeptide of this invention. The oligonucleotide can be DNA or RNA, usually DNA. Although numerous nucleotide sequences can encode the same amino acid sequence due to the degeneracy of the genetic code, conveniently, the oligonucleotides of this invention include a nucleotide sequence of a breakthrough isolate as illustrated in Table 1 (Sequence ID NOs:1, 4, 7, 9, 11, 15, 18, 22, 24, 27, 30, 32, 35, and 38). Usually, an oligonucleotide of this invention is less than about 5 kilobases (kb), preferably less than about 3 kb.

To express the encoded amino acid sequence, the oligonucleotide can be inserted into a transcription unit. The transcription unit can be inserted into a plasmid for production of cell lines, inserted into a virus (e.g.; vaccinia) or can be used directly as a DNA vaccine. Suitable transcription units for production of vaccine proteins are well known. A preferred expression vector, designated psvI6B5, is illustrated in Sequence ID NO:45. The vector includes an HSV-1 gD1 signal sequence joined to a linker sequence. The gp120 nucleotide sequence to be expressed starts with the Kpn I site of the gene. Since all gp120 or gp160 sequences contain this site, any gp120 nucleotide sequence can be analogously inserted into the vector and expressed. The vector ends with a polyA tail from SV40.

In addition to being useful to express a polypeptide sequence of this invention, the oligonucleotides of this invention can also be used in diagnostics to detect HIV isolates. For example, the oligonucleotide or a portion thereof encoding a neutralizing epitope can be used in branched chain DNA diagnostics or as a probe in in situ hybridization studies.

Vaccine Preparation

A gp120 polypeptide of this invention from a selected breakthrough isolate(s) in a suitable carrier is used to make a subunit vaccine. The polypeptide can be used alone, but is generally administered in a multivalent subunit vaccine that includes gp120 MN. In addition to one or more gp120 polypeptides of this invention, the vaccine generally includes the MN polypeptide (hereinafter, MN-rgp120). The vaccine usually includes about 3 to about 5 different gp120 polypeptides, but 30 or more different gp120 polypeptides can be used.

Preparation of gp120 polypeptides for use in a vaccine is well known and is described hereinafter. With the exception of the use of the selected HIV isolate, the gp120 subunit vaccine prepared in the method does not differ from gp120 subunit vaccines of the prior art.

As with prior art gp120 subunit vaccines, gp120 at the desired degree of purity and at a sufficient concentration to induce antibody formation is mixed with a physiologically acceptable carrier. A physiologically acceptable carrier is nontoxic to a recipient at the dosage and concentration employed in the vaccine. Generally, the vaccine is formulated for injection, usually intramuscular or subcutaneous injection. Suitable carriers for injection include sterile water, but preferably are physiologic salt solutions, such as normal saline or buffered salt solutions such as phosphate-buffered saline or ringer's lactate. The vaccine generally contains an adjuvant. Useful adjuvants include QS21 (*Quillaja saponaria*, commercially available from Cambridge Biotech, Worcester, Mass.), which stimulates cytotoxic T-cells, and alum (aluminum hydroxide adjuvant). Formulations with different adjuvants which enhance cellular or local immunity can also be used. In particular, immunopotentiators such as cytokines can be included in the vaccine. Examples of suitable immunopotentiating cytokines include interleukins, such as interleukin-2 (IL-2) and interleukin-12 (IL-12), and tumor necrosis factor-alpha (TNF-$\alpha$).

Additional excipients that can be present in the vaccine include low molecular weight polypeptides (less than about 10 residues), proteins, amino acids, carbohydrates including glucose or dextrans, chelating agents such as EDTA, and other excipients that stabilize the protein or inhibit growth of microorganisms.

The vaccine can also contain other HIV proteins. In particular, gp41 or the extracellular portion of gp41 or HIV-1 core proteins such as P24, P17, and P55 can be present in the vaccine. Although the amino acid sequence of gp41 is more conserved than that of gp120, gp41 contains neutralizing epitopes. Preferably, any gp41 present in the vaccine is from an HIV isolate present in the vaccine. gp160 from an isolate used in the vaccine can replace gp120 in the vaccine or be used together with gp120 from the isolate. Alternatively, gp160 from a different isolate than those in the vaccine can additionally be present in the vaccine.

Vaccines according to the invention can also contain one or more soluble gp120 polypeptide sequences, or fragments thereof, in combination with an engineered virus specifically designed to express proteins that induce a cytotoxic T-cell response. Suitable engineered viruses are derived from, for example, Canary Pox virus, vaccinia viruses, attenuated human herpes viruses (such as, e.g., herpes simplex viruses), and Varicella Zoster. Exemplary engineered viruses are modified to express any HIV protein capable of inducing a cytotoxic T-cell response, such as those described above. Typically, immunization with the gp120/engineered virus vaccine is followed by administration of one or more doses of the gp120 polypeptide sequence(s) to boost the immune response. If desired, viruses can be engineered to express one or more gp120 polypeptide sequences of the invention, or fragments thereof, and used in vaccines with or without soluble gp120 polypeptide sequences.

Vaccine formulations generally include a total of about 300 to 600 $\mu$g of gp120, conveniently in about 1.0 ml of carrier. Preferred formulations include use of twice the weight of a gp120 polypeptide in twice as600 $\mu$g alum. However, formulations having smaller amounts (e.g.; 50 $\mu$g per dose) are also used, generally with alum or other adjuvants. The amount of gp120 for any isolate present in the vaccine will vary depending on the immunogenicity of the gp120. For example, gp120 from some strains of HIV may be less immunogenic than gp120 from the MN strain (Sequence ID NO:41). If two strains having different immunogenicity are used in combination, empirical titration of the amount of each virus would be performed to determine the percent of the gp120 of each strain in the vaccine. For isolates having similar immunogenicity, approximately equal amounts of each isolate's gp120 would be present in the vaccine. For example, in a preferred embodiment, the vaccine includes gp120 from the MN and a strain of this invention at concentrations of about 300 $\mu$g per strain in about 1.0 ml of carrier. When the vaccine includes gp120 from about 30 isolates, about 10 to about 50 $\mu$g can be used. Methods of determining the relative amount of an immunogenic protein in multivalent vaccines are well known and have been used, for example, to determine relative proportions of various isolates in multivalent polio vaccines.

The vaccines of this invention are administered in the same manner as prior art HIV gp120 subunit vaccines. In particular, the vaccines are generally administered at 0, 1, and at 6, 8 or 12 months, depending on the protocol. A preferred protocol includes administration at 0, 1, 6, and 12 months. Following the immunization procedure, annual or bi-annual boosts can be administered. However, during the immunization process and thereafter, neutralizing antibody levels can be assayed and the protocol adjusted accordingly.

The vaccine is administered to uninfected individuals. In addition, the vaccine can be administered to seropositive individuals to augment immune response to the virus, as with prior art HIV vaccines. It is also contemplated that DNA encoding the strains of gp120 for the vaccine can be administered in a suitable vehicle for expression in the host. In this way, gp120 can be produced in the infected host, eliminating the need for repeated immunizations. Preparation of gp120 expression vehicles is described hereinafter.

Although the gp120 isolates described herein can be used as a vaccine as described above, the amino acid sequences can also be used alone or in combinations in the same type of formulation for use as an immunogen, to induce antibodies that recognize the isolate(s) present in the immunogen. Immunogens are formulated in the same manner as vaccines and can include the same excipients, etc. Antibodies induced by the immunogens can be used in a diagnostic to detect the HIV strain in the immunogen or to affinity purify the strain.

gp120 Polypeptide Sequences and Chemokine Receptors

While CD4 is the primary cellular receptor for HIV-1, it is not sufficient for entry of HIV-1 into cells. Co-receptors required in conjunction with CD4 have been identified. These co-receptors are members of the chemokine receptor family of seven-transmembrane G-protein coupled receptors. The chemokine superfamily is subdivided into two groups based on the amino terminal cysteine spacing. The CXC chemokines are primarily involved in neutrophil-mediated inflammation, and the CC chemokines tend to be involved in chronic inflammation. At least five CC chemokine receptors, designated CC-CKR1–5 (also known in the art as CCR1–5), and at least four CXC chemokine receptors, designated CXC-CKR1–4 (also known as CXCR-1–4), have been identified.

CXC-CKR-4 (CXCR-4), which has also been called the alpha-chemokine receptor fusin, serves as an entry cofactor for T-cell-tropic HIV-1 strains. CC-CKR-5 (CC-R5), which has been called beta-chemokine receptor, together with its related family members, such as CC-CKR-2b and CC-CKR3, serve as entry cofactors for macrophage-tropic HIV-1 strains. T-cell-tropic strains can infect primary T-cells and T-cell lines, but not macrophages, whereas macrophage-tropic strains can infect macrophages and primary T-cells, but not T-cell lines. T-cell- and macrophage-tropic strains are discussed more fully in Deng et. al., Nature 381:661–666 (1996), which is hereby incorporated by reference in its entirety. Examples of T-cell-tropic strains include laboratory isolates, such as IIIB and MN. Macrophage-tropic strains include primary isolates, including but not limited to A244, GNE6, GNE8, and breakthrough viruses from vaccinees immunized with gp120-based vaccines. Dual-tropic strains can use both types of co-receptors, entering cells via CXC-CKR-4 or via one or more CC-CKR family members, preferably CC-CKR-5, CC-CKR-2b, or CC-CKR-3. While the present invention is not intended to be bound or limited by any one theory, the entry of T-cell tropic and macrophagetropic HIV-1 strains is believed to provide a unifying explanation of the differences in cell tropism between viral strains, the resistance to HIV-1 infection by many CD4-transfected nonprimate cells, and the HIV-1 infection resistance of a portion of the human population.

Accordingly, in one embodiment is a vaccine containing (1) a first gp120 polypeptide sequence, or fragment thereof, from a macrophage-tropic HIV-1 strain and/or a second gp120 polypeptide sequence, or fragment thereof, from a T-cell tropic strain, in combination with (2) a breakthrough isolate HIV gp120 polypeptide sequence, or fragment thereof, from a vaccinee vaccinated with the first and/or second HIV gp120 polypeptide sequence. Preferably, the vaccine includes at least two gp120 polypeptide sequences that bind to different chemokine receptors. In one embodiment, the vaccine includes first and second gp120 polypeptide sequences that bind to different chemokine receptors. In addition, the breakthrough isolate gp120 polypeptide sequence can bind to a different chemokine receptor than the chemokine receptor(s) bound by either or both of the first and second gp120 polypeptide sequence(s).

A preferred T-cell tropic strain is a laboratory isolate, most preferably MN. Preferred macrophagetropic viruses for use in the invention are GNE6 and GNE8, which are representative of the breakthrough viruses disclosed herein and differ from MN in that their gp120s induce the formation of antibodies that recognize the gp120 sequences (e.g., the V3 domain) involved in binding to CC chemokine receptors, such as CXC-CKR-5.

In one embodiment, HIV infection is prevented by administering one or more chemokine receptor-binding gp120 polypeptide sequences, or fragment(s) thereof containing appropriate chemokine receptor-binding domains, in a vaccine, such as those described above. Preferably, the vaccine also includes one or more CD4-binding gp120 polypeptide sequences or appropriate fragments thereof. Such vaccines induce anti-HIV antibodies that inhibit viral gp120-chemokine receptor or -CD4 binding. In addition, such gp120 polypeptides can directly inhibit HIV infection by binding to one or more co-receptors for HIV infection, such as CD4 or a chemokine receptor, thus providing a prophylactic or therapeutic effect in treating HIV infection. Preferably, gp120 polypeptide sequences useful in this regard contain the T-cell binding (TCB) domain.

Various uses of chemokine receptor-binding gp120 polypeptides are discussed below with regard to the CC chemokine receptor family. However, those skilled in the art recognize that this discussion applies equally to CXC chemokine receptors that act as cofactors in HIV infection.

The gp120 polypeptides can be used as a composition containing one or more gp120 polypeptides, as described for use as a vaccine or immunogen. The composition can be administered, prophylactically or therapeutically, to a patient at risk of infection or in need of such treatment using the dosages and routes and means of administration described herein. However, chronic administration may be preferred and dosages can be adjusted accordingly. It is noted that in vivo administration can also induce antibodies that bind viral gp120, further inhibiting virus binding to CC-CKR.

The gp120 polypeptides can also be used in screening assays to identify antagonists of CC-CKR. For example, candidate antagonists can be screened for inhibition of binding of gp120 to a CC-CKR CC-CKR receptor that is isolated and attached to a surface (e.g., plastic dish) or recombinantly or naturally expressed on the surface of a cell. Antagonists can either bind gp120 or bind receptor. Preferred candidate antagonists include gp120 compounds, small gp120 peptides (5 to 20 amino acids in length, preferably 7 to 10 amino acids in length) or peptidomimetics of gp120 that bind receptor, monoclonal antibodies that bind gp120, and small organic molecules that bind either gp120 or receptor.

The antibodies induced by the gp120 polypeptides can also be used to induce anti-idiotype antibodies that bind CC chemokines. These anti-idiotype antibodies can be screened for binding to an anti-gp120 polypeptide antibody and inhibiting gp120 from binding CC-CKR receptor. Such anti-idiotype antibodies mimic gp120 by binding to CC-CKR receptor. Such antibodies, preferably human antibodies, can be obtained in a number of ways, such as human antibodies from combinatorial libraries (e.g., Burton et al. Adv. Immunolo. (1994) 57:191–280). It is now possible to produce transgenic animals (e.g., mice) that are capable, upon immunization, of producing a full repertoire of human antibodies in the absence of endogenous immunoglobulin production. For example, homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice results in the production of human antibodies upon antigen challenge as described in Jakobovitis et al., *Proc. Natl. Acad. Sci. USA* 90: 2551 (1993); Jakobovits et al., *Nature* 362:255–258 (1993); Bruggermann et al., *Year in Immuno.* 7: 33 (1993).

Alternatively, phage display technology as described by McCafferty et al., *Nature* 348:552–553 (1990) can be used to produce human antibodies and antibody fragments in vitro from immunoglobulin variable (V) domain gene repertoires from unimmunized donors. According to this technique, antibody V domain genes are closed in-frame either into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Phage display can be performed in a variety of formats as reviewed by, for example, Johnson, et al., *Current Opinion in Structural Biology* 3:564–571 (1993).

Several sources of V-gene segments can be used for phage display. Clackson et al., Nature, 352: 624–628 (1991) isolated a diverse array of anti-oxazolone antibodies from a small random combinatorial library of V genes derived from the spleens of immunized mice. A repertoire of V genes from unimmunized human donors (or embryonic cells) can be constructed. It has been demonstrated that antibodies to a diverse array of antigens (including self-antigens) can be isolated essentially following the techniques described by Marks et al., J. Mol. Biol., 222: 581–597 (1991), or Griffith et al., EMBO J., 12: 725–734 (1993).

In a natural immune response, antibody genes accumulate mutations at a high rate (somatic hypermutation). Some of the changes introduced confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10:779–783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires has been described by Waterhouse et al., Nucl. Acids Res., 21: 2265–2266 (1993).

Accordingly, antibodies that bind CC-CKR can be obtained by screening antibodies or fragments thereof expressed on the surface of bacteriophage in combinatorial libraries or in other systems as described above with a gp120 monoclonal antibody that inhibits gp120 binding to receptor.

In addition to screening antibodies with a gp-120 antibody, random or combinatorial peptide libraries can be screened with either a gp120 antibody or the gp120 compounds of the invention. Approaches are available for identifying peptide ligands from libraries that comprise large collections of peptides, ranging from 1 million to 1 billion difference sequences, which can be screened using monoclonal antibodies or target molecules. The power of this technology stems from the chemical diversity of the amino acids coupled with the large number of sequences in a library. See for example, Scott et al., Cur. Open. Biotechnol. 5(1):40–8 (1994); Kenan et al. Trends Biochem. Sci. (1994) 19(2):57–64. Accordingly, the monoclonal antibodies, preferably human monoclonals or fragments thereof, generated as discussed herein, find use in treatment by inhibiting or treating HIV infection or disease progression, as well as in screening assays to identify additional pharmaceuticals.

Production of gp120 gp120 for a vaccine can be produced by any suitable means, as with prior art HIV gp120 subunit vaccines. Recombinantly-produced or chemically synthesized gp120 is preferable to gp120 isolated directly from HIV for safety reasons. Methods for recombinant production of gp120 are described below.

Oligonucleotides encoding gp120 from breakthrough isolates and capable of expressing gp120 can be prepared by conventional means. For example, the nucleotide sequence can be synthesized. Alternatively, another HIV nucleotide sequence encoding gp120 can be used as a backbone and altered at any differing residues as by site-directed mutagenesis. Site-directed mutagenesis is described in Kunkel et al, *Proc. Natl. Acad. Sci. (USA)* 82:488–492 (1985) and Zoller et al, *Nuc. Acids Res.* 10:6487–6500 (1982) and is well known.

In a preferred embodiment, the nucleotide sequence is present in an expression construct containing DNA encoding gp120 under the transcriptional and translational control of a promoter for expression of the encoded protein. The promoter can be a eukaryotic promoter for expression in a mammalian cell. In cases where one wishes to expand the promoter or produce gp120 in a prokaryotic host, the promoter can be a prokaryotic promoter. Usually a strong promoter is employed to provide high-level transcription and expression.

The expression construct can be part of a vector capable of stable extrachromosomal maintenance in an appropriate cellular host or may be integrated into host genomes. Normally, markers are provided with the expression construct which allow for selection of a host containing the construct. The marker can be on the same or a different DNA molecule, desirably, the same DNA molecule.

The expression construct can be joined to a replication system recognized by the intended host cell. Various replication systems include viral replication systems such as those from retroviruses, simian virus, bovine papilloma virus, or the like. In addition, the construct may be joined to an amplifiable gene, e.g. the DHFR gene, so that multiple copies of the gp120 DNA can be made. Introduction of the construct into the host will vary depending on the construct and can be achieved by any convenient means. A wide variety of prokaryotic and eukaryotic hosts can be employed for expression of the proteins.

Preferably, the gp120 is expressed in mammalian cells that provide the same glycosylation and disulfide bonds as in native gp120. Expression of gp120 and fragments of gp120 in mammalian cells as fusion proteins incorporating N-terminal sequences of Herpes Simplex Virus Type 1 (HSV-1) glycoprotein D (gD-1) is described in Lasky, L. A. et al., 1986 (Neutralization of the AIDS retrovirus by antibodies to a recombinant envelope glycoprotein) Science 233: 209–212 and Haffar, O. K. et al., 1991 (The cytoplasmic tail of HIV-1 gp160 contains regions that associate with cellular membranes.) Virol. 180:439–441, respectively. A preferred method for expressing gp120 is described in the examples. In the examples, a heterologous signal sequence was used for convenient expression of the protein. However, the protein can also be expressed using the native signal sequence.

An isolated, purified gp120 polypeptide having one of the amino acid sequences illustrated in Table 1 can be produced by conventional methods. For example, the proteins can be chemically synthesized. In a preferred embodiment, the proteins are expressed in mammalian cells using an expression construct of this invention. The expressed proteins can be purified by conventional means. A preferred purification procedure is described in the examples.

gp120 Fragments

The present invention also provides gp120 fragments that are suitable for use in inducing antibodies for use in a vaccine formulation. A truncated gp120 sequence, as used herein, is a fragment of gp120 that is free from a portion of the intact gp120 sequence beginning at either the amino or carboxy terminus of gp120. A truncated gp120 sequence of this invention is free from the C5 domain. The C5 domain of gp120 is a major immunogenic site of the molecule. However, antibodies to the region do not neutralize virus. Therefore, elimination of this portion of gp120 from immunogens used to induce antibodies for serotyping is advantageous.

In another embodiment, the truncated gp120 sequence is additionally free from the carboxy terminal region through about amino acid residue 453 of the gp120 V5 domain. The portion of the V5 domain remaining in the sequence provides a convenient restriction site for preparation of expression constructs. However, a truncated gp120 sequence that is free from the entire gp120 V5 domain is also suitable for use in inducing antibodies.

In addition, portions of the amino terminus of gp120 can also be eliminated from the truncated gp120 sequence. In particular, the truncated gp120 sequence can be free from the gp120 signal sequence. The truncated gp120 sequence can be free from the carboxy terminus through amino acid residue 111 of the gp120 C1 domain, eliminating most of the C1 domain but preserving a convenient restriction site. However, the portion of the C1 domain through the V2 cysteine residue that forms a disulfide bond can additionally be removed, so that the truncated gp120 sequence is free from the carboxy terminus through amino acid residue 117 of the gp120 C1 domain. In a preferred embodiment, the truncated gp120 sequence is free from the amino terminus of gp120 through residue 111 of the C1 domain and residue 453 through the carboxy terminus of gp120.

The truncated gp120 sequences can be produced by recombinant engineering, as described previously. Conveniently, DNA encoding the truncated gp120 sequence is joined to a heterologous DNA sequence encoding a signal sequence.

It is understood that the application of the teachings of the present invention to a specific problem or situation is within the capabilities of one having ordinary skill in the art in light of the teachings contained herein. Examples of the products of the present invention and representative processes for their isolation, use, and manufacture appear below, but should not be construed to limit the invention. All literature citations herein are expressly incorporated by reference.

EXAMPLES

Materials and Methods

Specimen collection from human volunteers. Blood was collected from MN-rgp120-immunized individuals who were infected with HIV-1 while participating in Phase I (NIH Protocol AVEG 016) and Phase II (NIH Protocol AVEG 201) HIV-1 vaccine trials sponsored by the National Institutes of Health (NIH). The demographics of the subjects in the study, and the study design have been described in McElrath; *Seminars in Cancer Biol.* 6:1–11 (1995); McElrath et al.; *Abstracts from Eighth Annual Meeting of the National Cooperative Vaccine Development Groups for AIDS*. Bethseda, Md. 216 (1996). Specimens were obtained according to an informed consent protocol approved by the institutional review boards of the participating institutions. In the experimental section, the time of HIV-1 infection is specified with regard to data provided by the NIH AIDS Vaccine Evaluation Network where PCR (RNA) and/or serologic assays were used to detect HIV-1 infection.

Sample preparation for cloning HIV-1 envelope glycoproteins. Peripheral blood mononuclear cells (PBMCs) from HIV-1 infected vaccinees were prepared from heparinized venous blood by gradient centrifugation using FICOLL-HYPAQUE leukocyte seperation medium. Cell number and viability were determined. After separation, PBMCs were washed twice in phosphate-buffered saline and suspended at a cell density of $6\times10^6$ cells/ml in PCR lysis buffer (50 mM KCl, 10 mM Tris (pH 8.4), 2.5 mM $MgCl_2$, 0.1 mg/ml gelatin (Sigma), 0.45% NONIDET P40 detergent, 0.45% TWEEN 20 detergent (both detergents are commercially available from United States Biochemical Corp.) and 0.06 mg/ml Proteinase K (Gibco BRL) to lyse the cells. The lysate was incubated at 50–60° C. for 1 hour, followed by inactivation of the Proteinase K at 95° C. for 10 minutes. Lysates were shipped frozen and stored at −70° C. until use.

Polymerase chain reaction (PCR) amplification. Samples were subjected to two rounds of PCR amplification using the nested primers described below. In the first round, 25 μl aliquots of PBMC lysates (containing about 1 μg genomic DNA) were mixed with an equal volume of a PCR reaction mix containing 400 μM each dNTP, 200 μg/ml BSA (Sigma Chemical Corporation, RIA grade) and about 100 pmoles of each primer in 50 mM KCl, 20 mM Tris (pH 8.4) and 3 mM $MgCl_2$. After an initial 10 minute denaturation step at 95° C., 5 units of Taq polymerase (AMPLITAQ, Perkin Elmer Cetus) were added during an 55° C. soak step, and samples were overlayed with mineral oil.

The PCR profile was as follows: 2 cycles having 1 minute at 55° C., 2.5 minutes at 72° C. and 1 minute at 94° C., followed by 28 cycles with 30 seconds at 55° C., 2.5 minutes at 72° C. and 45 seconds at 94° C., and an extension step at 72° C. for 5 minutes.

Aliquots of 10 μl from the first-round reactions were re-amplified with appropriate nested primers in a final reaction volume of 100 μl, using either the reagents and profile described above or the reagents and profile described in the PCR Optimizer Kit (Invitrogen.) PCR reaction products were purified using QIAQUICK-spin columns (Qiagen Inc.) The primer pair used in the first round was either 120.os.F (5'-gggaattcggatccAGAGCAGAAGACAGTGGCAATGA with homologous sequence at position 6248–6270 of HIVPV22) (SEQ. ID. NO:47) or JM11A (5'-ctcgag-CTCCTGAAGACAGTCAGACTCATCAAG at position 6048–6074) (SEQ. ID. NO:48) in the forward direction [Kusumi et al.; J. Virol. 66:875 (1992)] combined with 120.os.R (5'-ggtctagaagctttaGCCCATAGTGCTTCCTGCTGCT-CC at position 7836–7859) (SEQ. ID. NO:49) in the reverse direction. The internal nested primers were 120.BX.F (5'-gggcggatcctcgaGGTACCTGTRTGGAAAGAAGCA at position 6389–6410; R: A or G) (SEQ. ID. NO:50) and 120.is.R (5'-ggtctagaagctttaTGCTCCYAAGAACCCAAGGAACA at position 7819–7841; Y: T or C) (SEQ. ID. NO:51). Heterologous primer sequences are shown in lower case letters.

Subcloning of PCR products and the expression of recombinant envelope glycoproteins as fusion proteins. The HIV-1 envelope glycoprotein gp120 sequences were cloned and expressed as chimeric genes and fusion proteins, where the signal sequence and 27 amino acids from the mature N terminus of herpes simplex virus type 1 (HSV-1) were fused to the N-terminal sequences of the gp120 genes, corresponding to amino acid 13 of the mature gp120 sequence. PCR products containing gp120 sequences from the breakthrough specimens were cloned into pRK5 expression plasmid as chimeric genes using combinations of restrictions sites engineered into the heterologous PCR primer tails and the Xho I site engineered into the N-terminal sequence of HSV-1 gD.

The resulting double-stranded DNA was sequenced with Sequenase and the dGTP Reagent Kit (United States Biochemical Corp.). Sequences from glycoprotein D were provided to enhance expression and to provide a flag epitope to facilitate protein analysis, as described in Berman et al.; *J. Virol.* 7:4464–9 (1992); Nakamura et al.; *AIDS and Human Retroviruses* 8:1875–85 (1992); and Nakamura et al.; *J. Virol.* 67:6179–91 (1993).

Briefly, isolated DNA fragments generated by the PCR reaction were ligated into a plasmid (pRK.gD-5, pRKgDstop) designed to fuse the gp120 fragments, in frame, to the 5' sequences of the glycoprotein D (gD) gene of Type 1 Herpes Simplex Virus (gD-1)and the 3' end to translational stop codons. The fragment of the gD-1 gene encoded the signal sequence and 25 amino acids of the mature form of HSV-1 protein. To allow for expression in mammalian cells, chimeric genes fragments were cloned into the pRK5 expression plasmid (Eaton et al., *Biochemistry* 291:8343–8347 (1986)) that contained a polylinker with cloning sites and translational stop codons located between a cytomegalovirus promotor and a simian virus 40 virus polyadenylation site.

The resulting plasmids were transfected into the 293s embryonic human kidney cell line (Graham et al., *J. Gen. Virol.* 36:59–77 (1977)) using a calcium phosphate technique (Graham et al., *Virology* 52:456–467 (1973)). Growth conditioned cell culture media was collected 48 hr after transfection, and the soluble proteins were detected by ELISA or by specific radioimmunoprecipitation where metabolically labeled proteins from cell culture supernatants were resolved by sodium dodecyl sulfate polyacrylamide gel electrophoresis (PAGE) and visualized by autoradiography as described in Berman et al., *J. Virol.* 63:3489–3498 (1989) and Laemmli, *Nature* 227:680–685 (1970).

Serologic assays. Sera were assayed for antibodies to rgp120, antibodies to synthetic gp120 V3 domain peptides corresponding to sequences from the gp120 V3 domain, and antibodies able to inhibit the binding of MN-rgp120 to cell surface CD4 using serologic assays described in Berman et al.; *J. Virol.* 7:4464–9 (1992); Nakamura et al.; *AIDS and Human Retroviruses* 8:1875–85 (1992); and Nakamura et al.; *J. Virol.* 67:6179–91 (1993). Endpoint titers of antibody binding to gp120 and V3 peptides were determined using three fold-serial dilutions of sera. The endpoint dilution titer was defined as the last dilution that produced an optical density value that was two times higher than the mean of the optical densities of 1:50 diluted, pooled, normal human sera. Antibody titers were calculated by a computer program that interpolated values between antibody dilutions. The inter-assay coefficient of variation of positive control standard sera was 35%.

Binding of monoclonal antibodies to rgp120 from breakthrough viruses. An ELISA similar to that described by Moore et al.; *AIDS* 3:155–63 (1989) was used to measure the binding of various monoclonal antibodies (MAbs) to rgp120s from breakthrough viruses. Briefly, Nunc-Immuno plates (Maxisorp, certified) were coated (100 μl at 5 μg/ml in PBS at 4° C. overnight) with an affinity-purified sheep polyclonal antiserum to a peptide at the C terminus of gp120 (D7324, International Enzymes, Fallbrook, Calif.). After washing once with PBS-0.05% TWEEN-20 detergent, the plates were blocked with PBS-1.0% BSA for 30–60 minutes at room temperature. Cell culture supernatants from 293s cells, diluted to contain equivalent amounts of the gD-rgp120 fusion protein, were added and incubated for 2 hours at room temperature followed by three washes with PBS-0.05% TWEEN-20 detergent. Various MAbs were diluted in PBS-1.0% BSA and 100 μL of the diluted MAbs were added to each well and incubated for 1 hour at room temperature.

The plates were washed 3 times and incubated with 100 μl of a horseradish peroxidase-conjugated second antibody (goat anti-mouse or anti-human IgG, Cappel) for 1 hour at room temperature. After 3 washes the plates were developed and the $OD_{492}$ (optical density at 492 nm) read in a plate reader. Growth conditioned cell culture supernatants were normalized by dilution based on binding by MAb 5B6 which is specific for HSV-1 glycoprotein D fusion protein.

Virus neutralization assays. The ability of vaccinee sera to inhibit infection of MT4 cells by HIV-$1_{MN}$ was measured in a cytopathicity assay where cell viability was quantitated using a calorimetric indicator dye, as described in Robertson et al.; *J. Virol. Methods* 20:195–202 (1988). Briefly, a virus stock of HIV-$1_{MN}$ (obtained from Dr. Michael Norcross, U.S. Food and Drug Administration) was prepared as the clarified supernatant from chronically infected H9/HIV-$1_{MN}$ cell culture. H9 cells chronically infected with HIV-MN were pelleted and resuspended in one-tenth the original volume of medium. Cell-associated virus was released by the mechanical shearing effects of rapid vortexing of the cells as described in Wrin et al.; *J. Virol.* 69:39–48 (1995).

An amount of virus sufficient to ensure complete cell lysis killing in 7 days was incubated with three-fold serial dilutions of test antisera, and then used to challenge MT4 T-lymphoid cells in 10% FCS/RPMI-1640 cell culture media. The cultures were incubated for 7 days at 37° C. in 5% $CO_2$, and then cell viability was tested by the dye MTT, as described by Robertson et al.; *J. Virol. Methods* 20:195–202 (1988). Virus neutralization endpoints were quantitated by measurement of OD at 570–650 nm, and then the endpoint titers were calculated as the reciprocal of the antiserum dilution giving a signal that was two-fold above the control signal with unprotected (killed) cells. These titers were typically twice those calculated at 50% protection.

RESULTS

Immunization history of infected subjects. Since 1992, 499 adults have been immunized with MN-rgp120 in Phase I trials in low or moderate risk individuals and in a Phase II clinical trial involving moderate to high risk individuals. The studies described herein entail the genetic and immunologic characterization of the first seven of nine individuals who became infected with HIV-1 through high risk behavior during the course of these trials. A listing of the trials and summary of the status of the vaccinees is presented in Table 2A. A listing of the analysis of the vaccinees is presented in Table 2B.

TABLE 2A

Description of Vaccinees Infected with HIV-1 After Immunization with MN-rgp120

| Study No. | Case No. | *Risk Group | ‡Antigen dose/ Adjuvant |
|---|---|---|---|
| 016 | C6 | M/H | 300/QS21 |
| 016 | C8 | M/H | 600/QS21 |
| 016 | C15 | M/H | 300/QS21 |
| 201 | C7 | M/H | 600/Alum |
| 201 | C11 | M/H | 600/Alum |
| 201 | C10 | M/IDU | 600/Alum |
| 201 | C17 | M/IDU | 600/Alum |

*M/H indicates male homosexual; M/IDU indicate male intravenous drug user.
‡numbers indicate dose in micrograms of MN-rgp120 injected per immunization; QS21 indicates antigen was formulated in QS21 adjuvant; Alum indicates MN-rgp120 formulated in aluminum hydroxide.

TABLE 2B

Description of Vaccinees Infected with HIV-1 After Immunization with MN-rgp120

| Case No. | Injection Schedule (months) | Injections before HIV-1+ | Time of HIV-1+ (months) | ¤Interval: to HIV-1+ (months) |
|---|---|---|---|---|
| C6 | 0,1,10.5 | 2 | 4.00 | 2.00 |
| C8 | 0,1 | 2 | 4.00 | 3.00 |
| C15 | 0,1,2 | 3 | 6.25 | 4.00 |
| C7 | 0,1,6,12 | 3 | 9.25 | 3.00 |
| C11 | 0,1,6,12 | 4 | 19.50 | 6.75 |
| C10 | 0,1,6,19 | 3 | 19.50 | 13.50 |
| C17 | 0,1,6,18 | 4 | 24.75 | 6.25 |

¤indicates interval between last immunization and detection of HIV-1 infection.

Three of the infections occurred in a Phase I trial (NIH Protocol AVEG 201) that compared the safety and immunogenicity of MN-rgp120 formulated in two different adjuvants (alum and QS21), and four of the infections occurred in a Phase II trial aimed at establishing the safety and immunogenicity of MN-rgp120 in various high risk groups (e.g., intravenous drug users, homosexual and bisexual males, and partners of HIV-1 infected individuals).

Of the seven infections studied (Table 3), two (C6 and C8) occurred after two injections, three (C7, C10 and C15) occurred after three injections, and two (C11 and C17) occurred after receiving the four scheduled injections. The interval between receiving the last immunization and becoming infected was 2 to 13.5 months.

TABLE 3

Peak Post Boost MN-rgp120 Antibody Titers in Vaccinees that Became Infected with HIV-1

| Injections | C6 | C8 | C15 | C7 | C11 | C10 | C17 |
|---|---|---|---|---|---|---|---|
| 1 | <50 | 2185 | 79 | <50 | 1890 | na | na |
| 2 | 21539 | 10125 | na | 413 | 32696 | 7771 | 7056 |
| 3 | # | # | 4460 | 9707 | 34728 | 11627 | 18413 |
| 4 | # | # | # | # | # | # | 11340 |

\# - indicates specimen not analyzed because of HIV-1 infection.
na - indicates the sample was not available for testing.
boldface - indicates unusually low antibody titers.

Antibody response to gp120 in vaccinated individuals. The magnitude and specificity of the antibody response to MN-rgp120 was measured by ELISA in all infected individuals throughout the course of the immunization regime (FIG. 1). Five of the seven subjects exhibited normal antibody response kinetics that included a small but reproducible primary response (1:100–1:2,000) and a strong secondary (booster) response (titters ranging from 1:7,000–1:32,000), and antibody responses following third and fourth injections that were similar or marginally higher than those achieved after the second immunization (FIG. 1, Table 3).

The antibody response observed in C7 (FIG. 1C) was unusual in that no antibodies were detectable after the primary injection and a titer of only 1:350 was detected after the second injection. It thus appeared that C7 did not respond to the primary immunization, and that the antibody response obtained after the second injection represented a primary immune response. Consistent with this hypothesis, the third injection elicited a titer of only 1:9,707, typical of those normally seen after two immunizations.

An atypical antibody response was also seen in subject C15 (FIG. 1G) who was immunized according to an accelerated immunization schedule of 0, 1, and 2 months. As expected, the antibody titer seen in this subject (1:4,460) was at the low end of what is typically achieved after two immunizations and was far below normal values for three immunizations. The lack of an effective booster response after the third immunization of C15 was not surprising in view of previous studies where an accelerated 0, 1, and 2 month immunization schedule in baboons [Anderson et al.; J. Infect. Dis. 160:960–9 ((1989)] similarly prolonged the secondary response and failed to elicit an effective tertiary booster response.

Figure 1B:
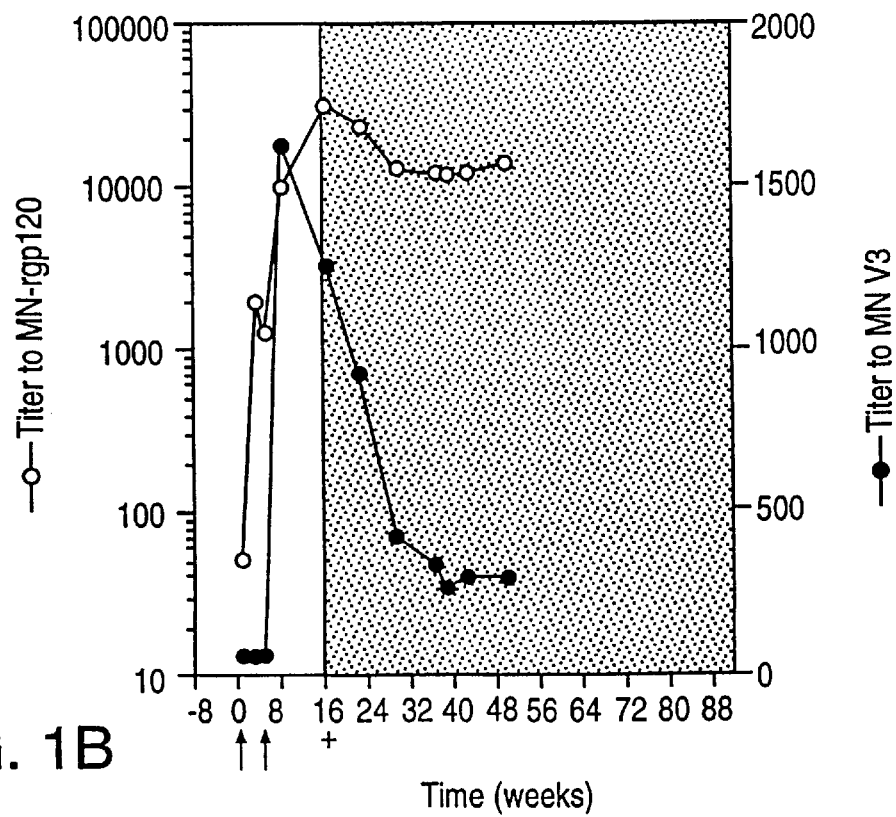
Figure 1C:
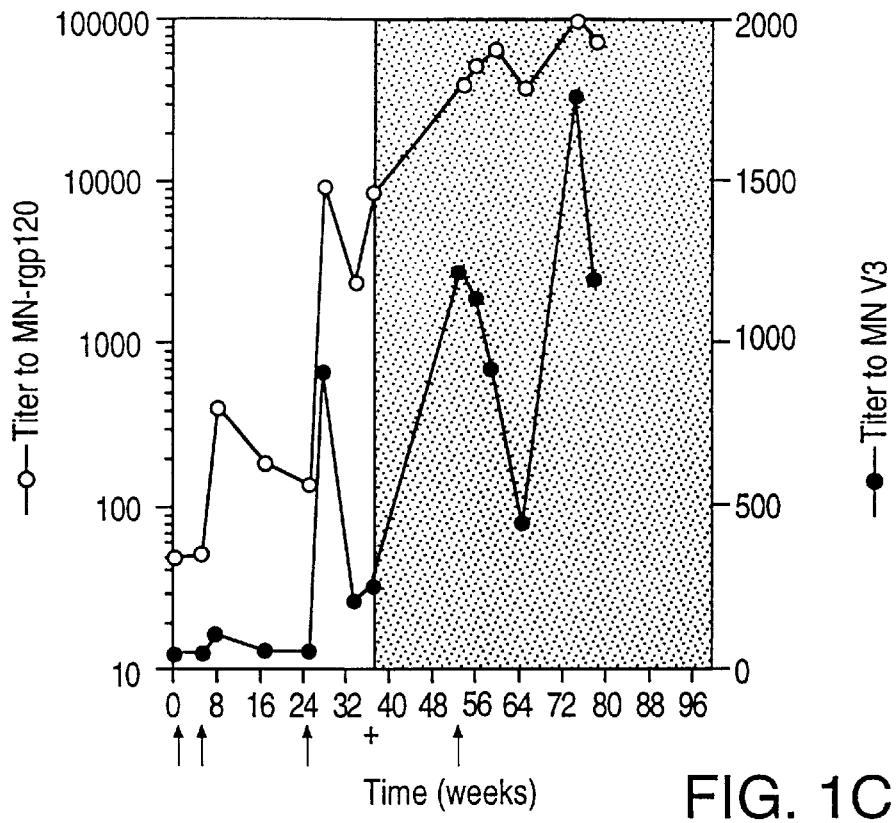

Retrospective analysis of serum and plasma from subjects C6 (FIG. 1A) and C8 (FIG. 1B) indicated that they became infected with HIV-1 at some point between the second and third immunizations. Serologic evidence of HIV-1 infection was evident in the gp120 antibody assays where the titers failed to decline two weeks after the second injection and instead formed an uncharacteristic high titer plateau (FIGS. 1A and 1B). A similar plateau in MN-rgp120 titer after the third injection, suggested that subject C7 became infected around week 36, approximately 16 weeks after receiving the third injection (FIG. 1C). Subjects C10 (FIG. 1E), C11 (FIG. 1D), C15 (FIG. 1G), and C17 (FIG. 1F) developed unexpected increases in gp120 titers, typical of HIV-1 infection, after either the third or fourth immunizations. The data obtained demonstrate that immunologic priming for MN-rgp120 antibody responses is insufficient to provide universal protection from HIV-1 infection.

Figure 1D:
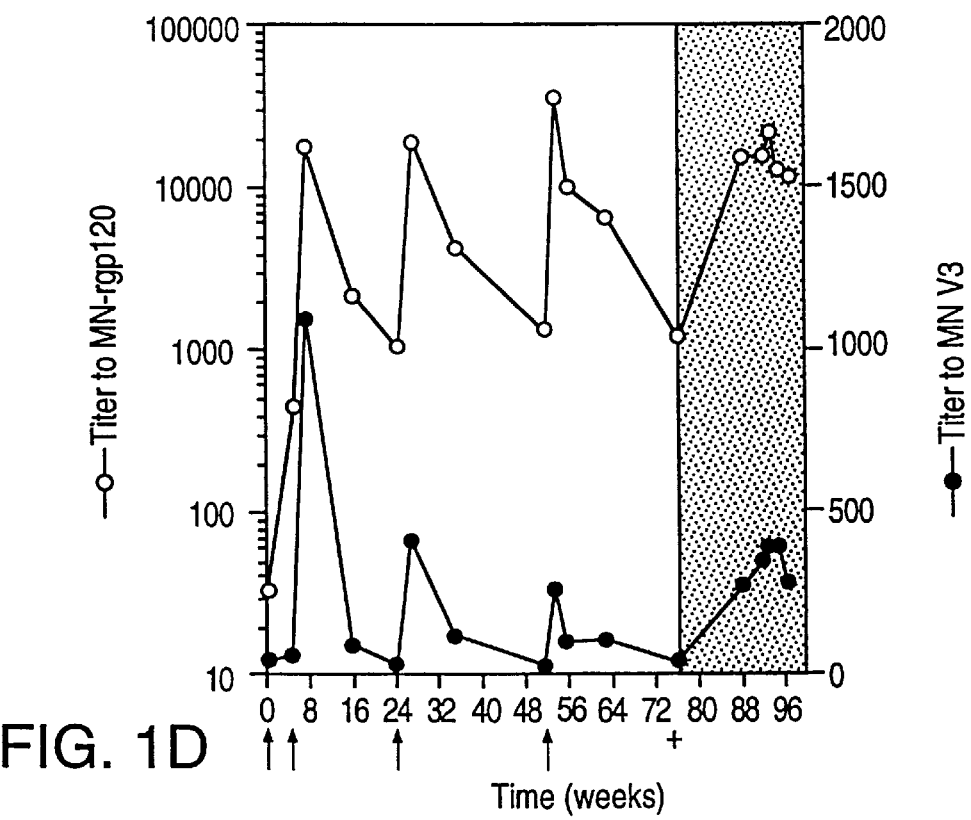
Figure 1E:
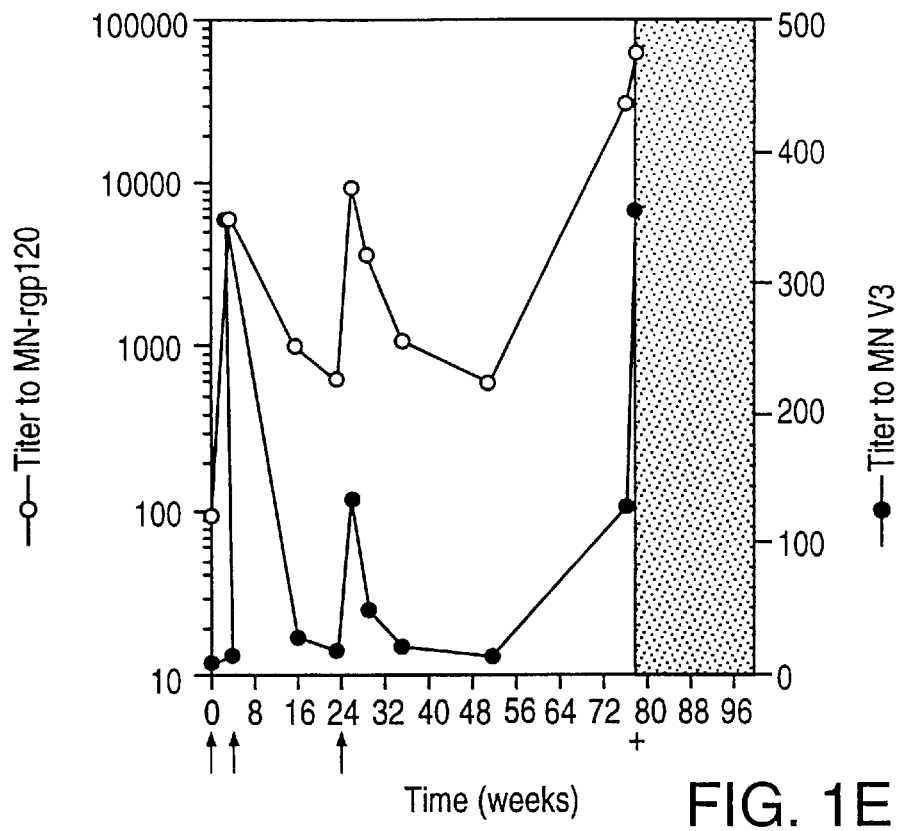
Figure 1F:
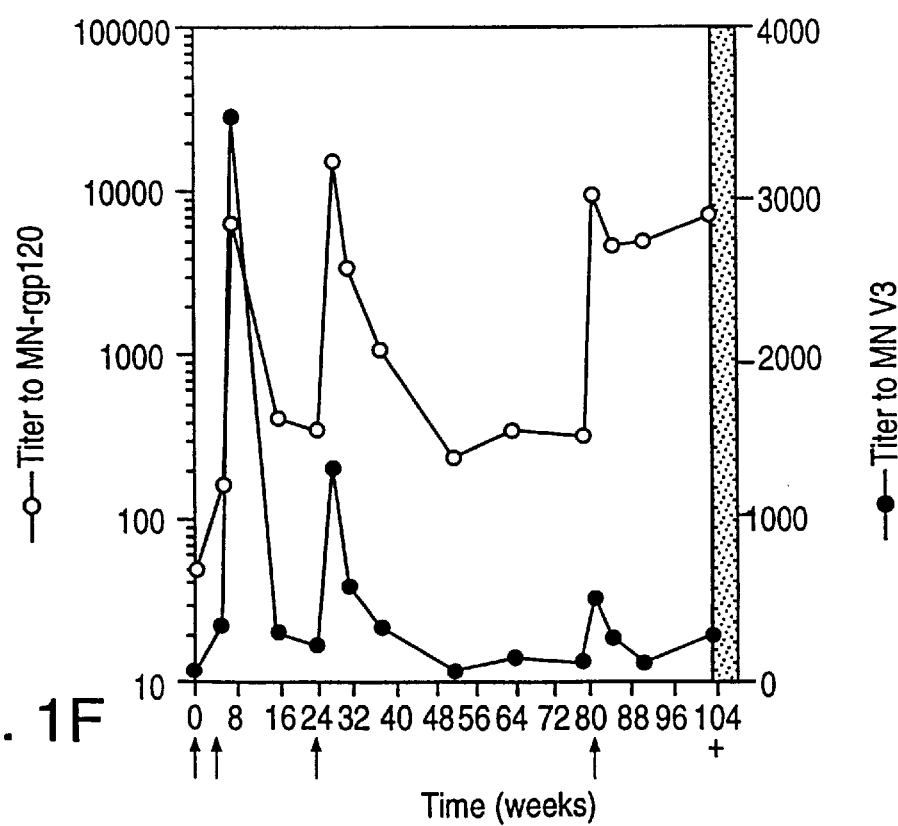
Figure 1G:
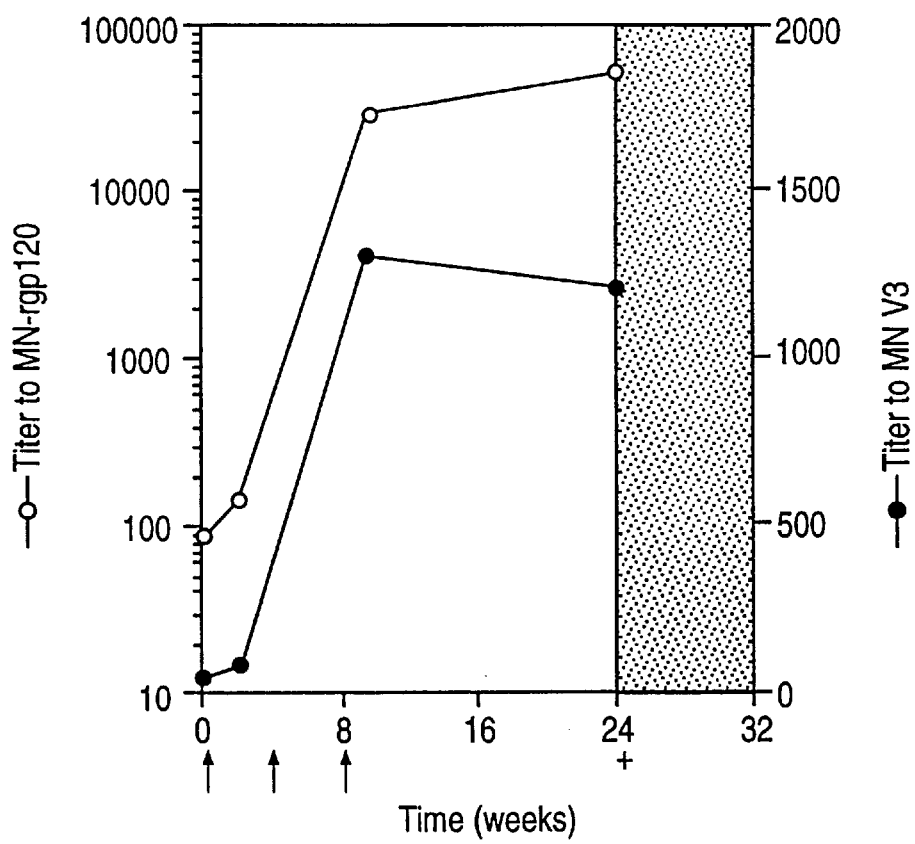

Antibody titers to the V3 domain. To further characterize the antibody response to gp120, antibody titers were measured to a synthetic V3 domain peptide of MN-rgp120 containing the principal neutralizing determinant (PND). Five of the seven subjects developed good V3 titers (1:400 to 1:4000) after the second immunization, however two subjects (C7 and C15) required three immunizations before developing significant tiers (FIGS. 1C and 1G). As had been observed previously (11), the peak V3 titers in some individuals (e.g. C11, C10, C17) appeared to decline with each successive immunization (FIGS. 1D, 1E, and 1F). After HIV-1 infection, two patterns of V3 reactivity were observed. Three subjects (C6, C7, and C10) showed large increases in titer to V3 domain peptides (FIGS. 1A, 1C, and 1E) whereas C8 (FIG. 1B) showed a large decrease in V3 titer. At the time of analysis, the data were insufficient to draw any conclusions regarding the changes in V3 titers in response to HIV-1 infection in subjects C11, C15 and C17.

The results obtained indicate that the ability to form antibodies reactive with the V3 domain at various timepoints prior to HIV-1 infection is not a valid correlate of protective immunity against all strains of HIV-1.

CD4 Inhibition titers. Antibodies that block the binding of gp120 to CD4 represent a heterogeneous class of virus neutralizing antibodies. Some are known to bind to the C4 domain of gp120 [Nakamura et al.; *J. Virol.* 67:6179–91 (1993); Anderson et al.; *J. Infect. Dis.* 160:960–9 ((1989)], and some are known to recognize conformation dependent discontinuous epitopes [Berman et al.; *J. Virol.* 7:4464–9 (1992); Nakamura et al.; *J. Virol.* 67:6179–91 (1993); McKeating et al.; *AIDS Research and Human Retroviruses* 8:451–9 (1992); Ho et al.; *J. Virol.* 65:489–93 (1991); Barbas et al.; *Proc. Natl. Acad. Sci. USA* 91:3809–13 (1994)].

Figure 2A:
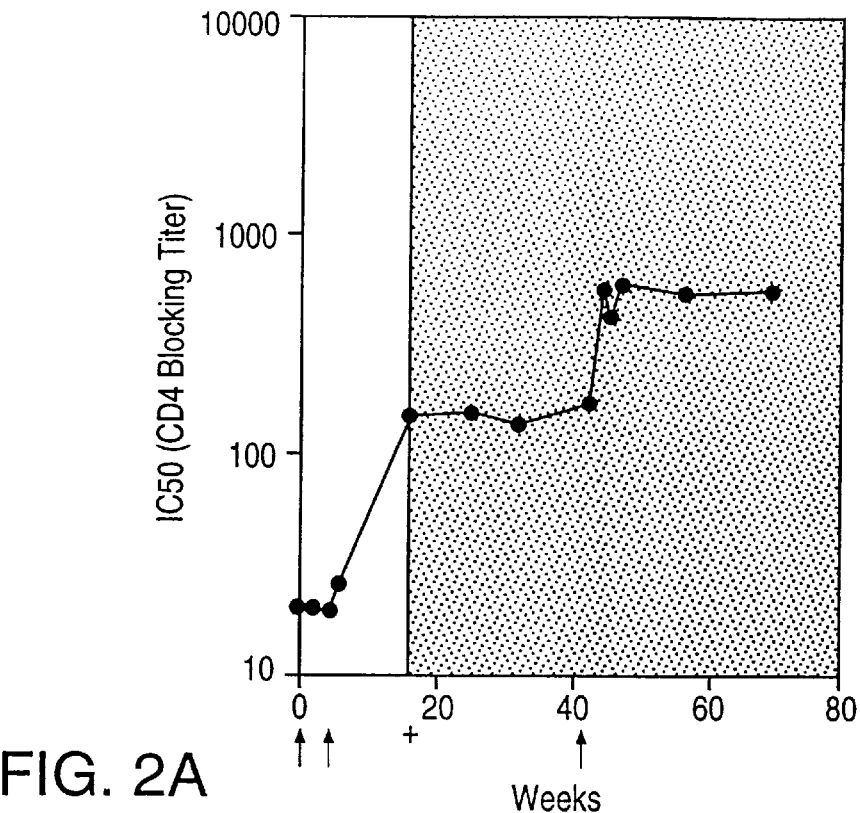
FIGS. 2A–2G illustrate the kinetics of CD4 blocking antibody response in vaccinees infected with HIV-1. Sera were collected at the time points indicated and assayed for antibodies able to block the binding of [$^{125}$I]-labeled MN-rgp120 to cell surface CD4. Arrows indicate dates of injection. Plus sign indicates the first time HIV-1 infection was detected. Shaded area indicates data collected after HIV-1 infection. Data from vaccinee C6 is shown in FIG. 2A; C8 in FIG. 2B; C7, FIG. 2C; C11, FIG. 2D; C10, FIG. 2E; C17, FIG. 2F; and C15, FIG. 2G.
Figure 2B:
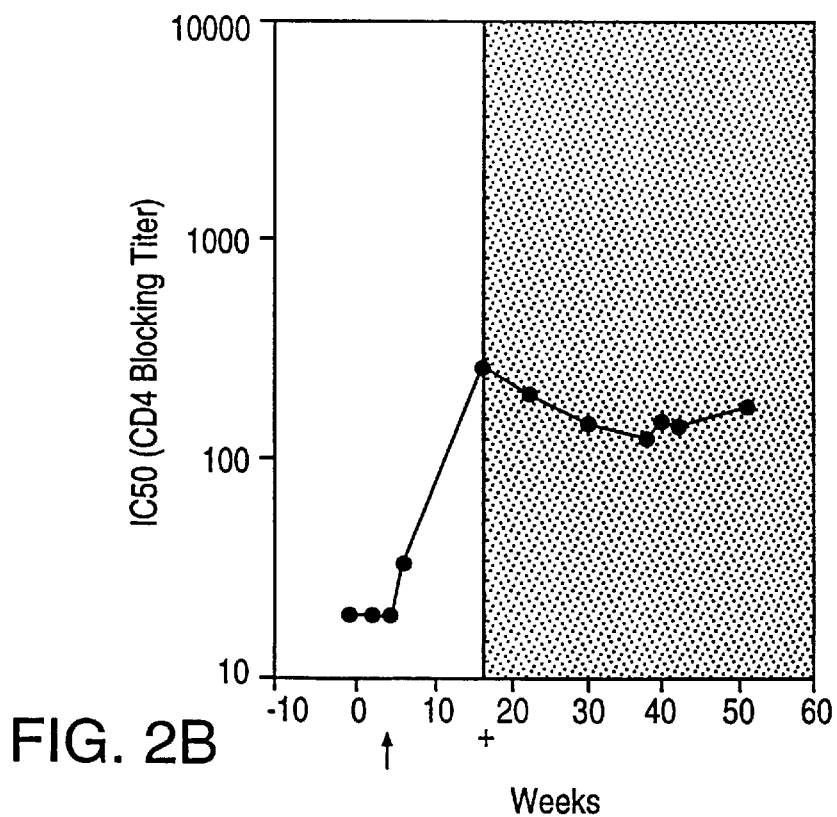
Figure 2C:
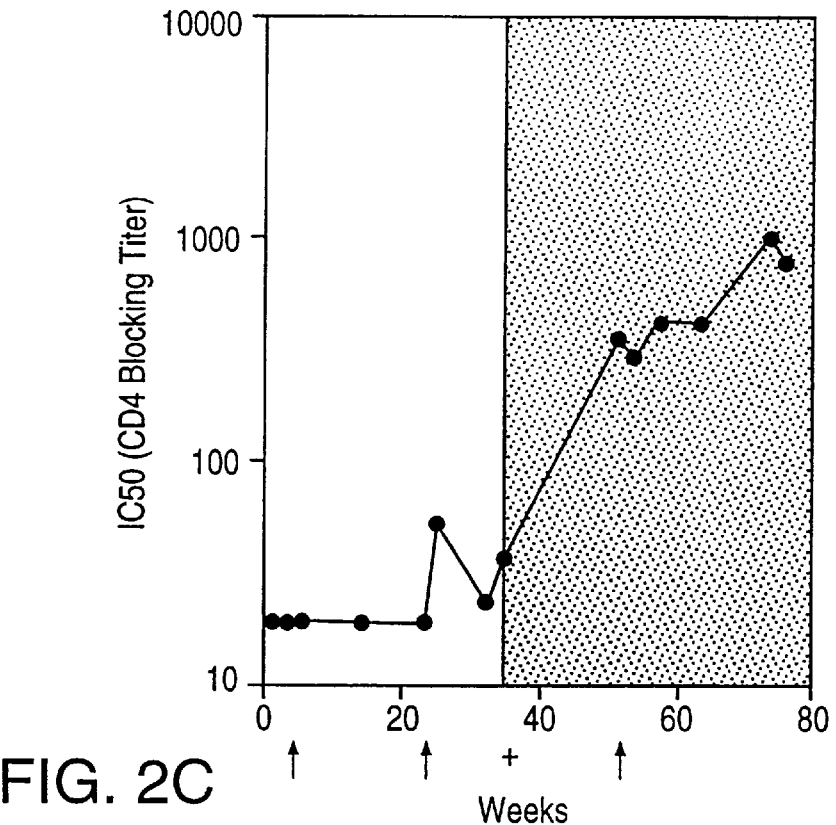
Figure 2D:
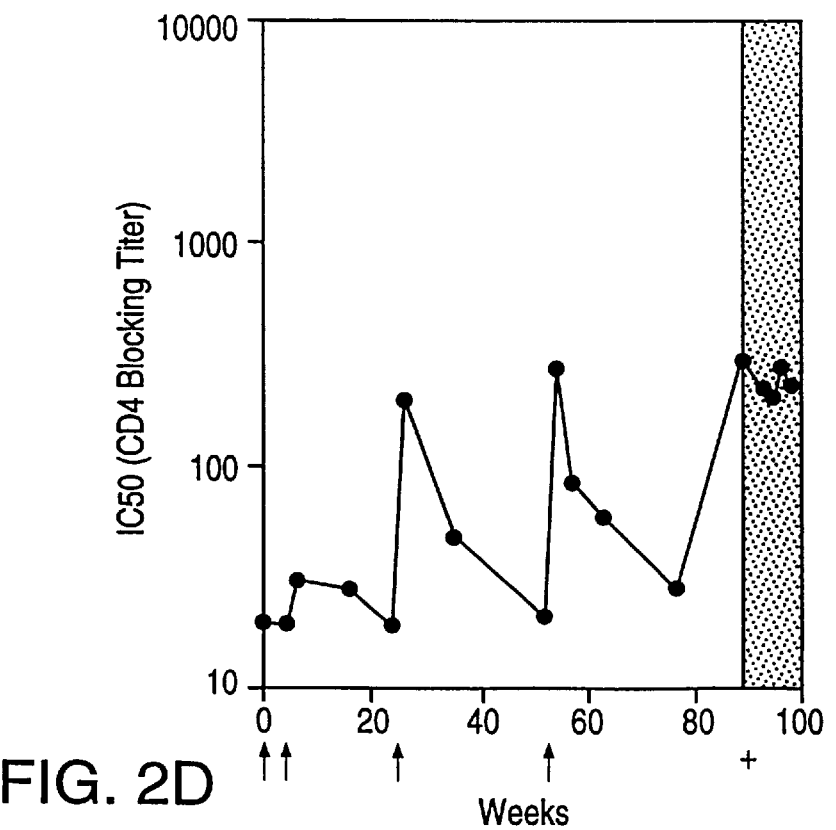
Figure 2E:
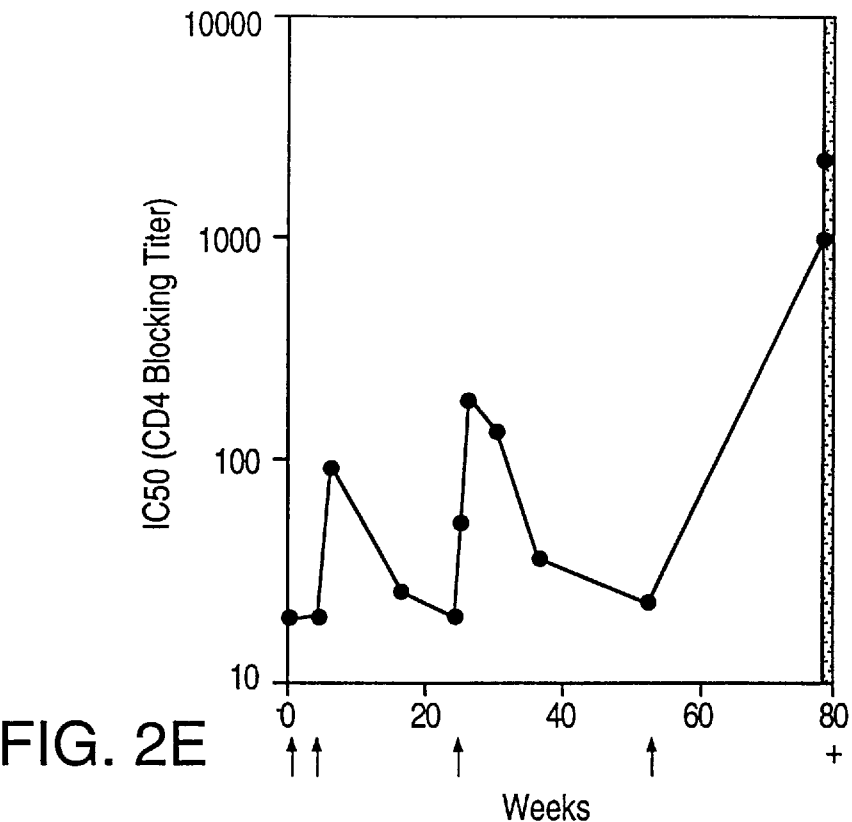
Figure 2F:
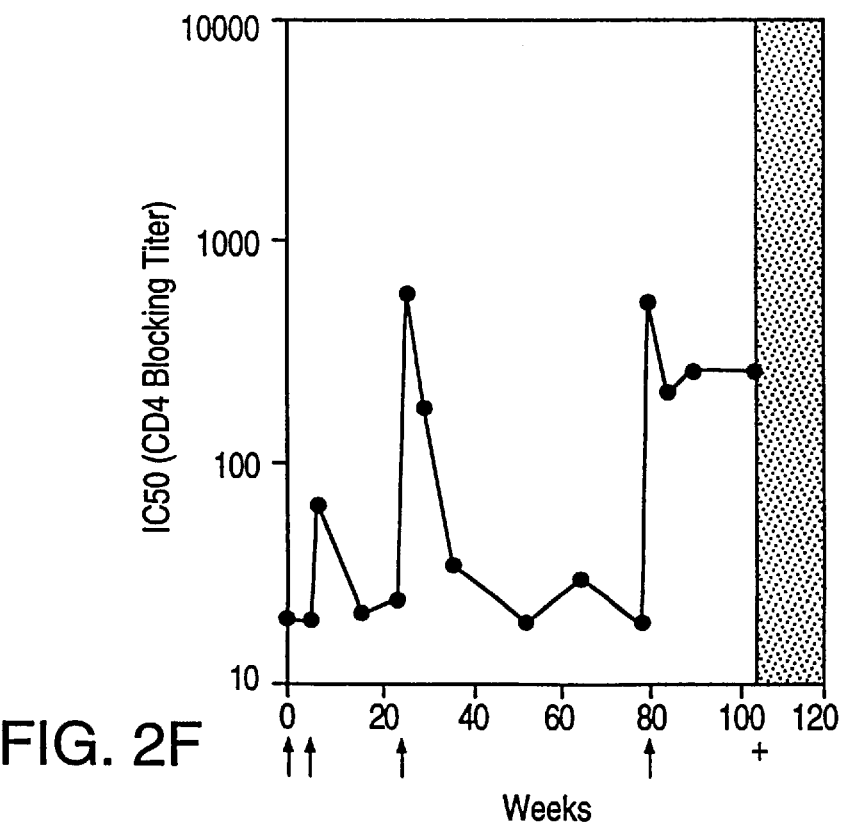
Figure 2G:
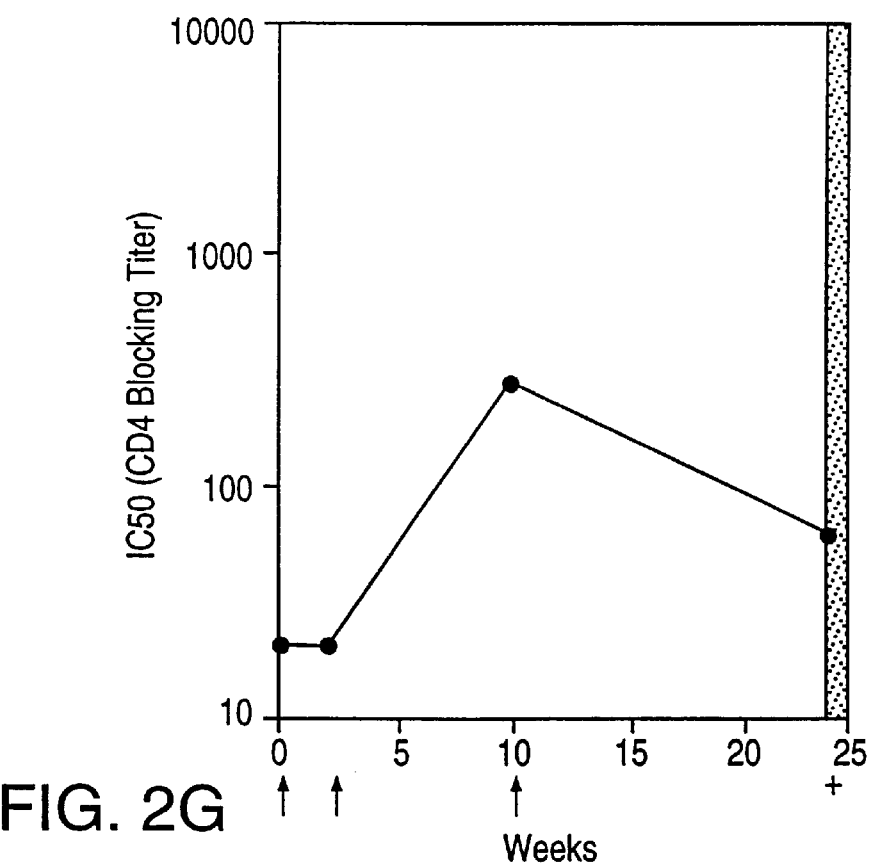

One way to detect antibodies to both types of epitopes is to measure the ability of vaccinee sera to prevent the binding of [$^{125}$I]-labeled gp120 to cell surface CD4 [[Nakamura et al.; *AIDS and Human Retroviruses* 81875–85 (1992); Nakamura et al.; *J. Virol.* 67:6179–91 (1993)]. CD4 blocking titers were detected in all seven of the vaccinees prior to infection (FIG. 2) with peak titers that ranged from 1:10–1:300. At the last time point prior to infection, the CD4 titers in five of the seven vaccinees was low (1:30 or less). One vaccinee (C17), however, possessed a CD4 blocking titer of about 1:300 prior to infection (FIG. 2F). Thus, the lack of antibodies that block the binding of MN-rgp120 to CD4 cannot account for all of the infections. Large increases in CD4 blocking titers (1:100–1:1,000) were seen in five of the seven subjects after HIV-1 infection. These included vaccinees C6, C7, C8, C10, and C11. These results demonstrate that the CD4 blocking titers elicited by MN-rgp120 were lower than those elicited by natural infection.

Virus neutralizing activity. The virus neutralizing activity of antisera from MN-rgp120-immunized subjects was measured using a calorimetric assay that measured the viability of MT-4 cells after incubation with antibody treated virus (HIV-1$_{MN}$). Since the actual date of infection was not known for any of the breakthrough infections, and serum samples were collected infrequently, the magnitude of the neutralizing antibody response at the time of infection is not known for any of the vaccinees.

Of the seven infections examined, the serum sample closest to the time of infection was that obtained from C7, where a neutralizing titer of 1:15 to HIV-1 was present three weeks prior to detection of HIV-1 infection (Table 4). In all other cases, however, the interval between the last injection and the time of infection was 10 to 25 weeks.

TABLE 4

Neutralization Activity of Sera from Vaccinees Infected with HIV-1

| Week | C6 | C8 | C15 | C7 | C11 | C10 | C17 |
|------|------|------|------|------|------|------|------|
| 0 | <10* | <10* | <10* | <10* | <10* | <10* | <10* |
| 2 | <10 | <10 | <10 | — | — | — | — |
| 4 | <10* | <10* | nd* | <10* | <10* | <10* | <10* |
| 6 | 10 | 80 | — | <10 | 30 | 150 | 150 |
| 8 | — | — | nd* | — | — | — | — |
| 10 | — | — | 35 | — | — | — | — |
| 15 | — | — | — | <10 | — | — | — |
| 16 | 150# | 250# | — | — | 30 | 10 | <10 |
| 24 | | | 150# | <10* | 20* | <10* | <10* |
| 26 | | | | 70 | 500 | 200 | 400 |
| 30 | | | | — | — | 40 | 100 |
| 33 | | | | 15 | — | — | — |
| 35 | | | | — | 100 | — | — |
| 36 | | | | 30# | — | 10 | 40 |
| 52 | | | | | 30* | <10 | <10 |
| 54 | | | | | 250 | — | — |
| 57 | | | | | 100 | — | — |
| 63 | | | | | 90 | — | — |
| 64 | | | | | — | — | <10 |
| 77 | | | | | 40# | — | — |
| 78 | | | | | | 500# | 10* |
| 80 | | | | | | | 100 |
| 84 | | | | | | | 60 |
| 90 | | | | | | | 150 |
| 104 | | | | | | | 150# |

* - indicates immunization.
- indicates HIV-1 positive.
nd - indicates not done.
— - indicates sample not available.

When sera from the two early infections were examined (Table 4), one individual (C6) had a peak neutralizing titer of 1:10 ten weeks prior to detection of HIV-1 infection, whereas the other individual (C8) had a neutralizing titer of 1:80 ten weeks prior to detection of HIV-1 infection. Subject C15, who was immunized according to an accelerated immunization schedule, developed a neutralizing titer of 1:35 after the third injection, 14 weeks prior to HIV-1 infection. Subject C10, who had a peak neutralizing titer of 1:200 following the third immunization (week 24), had no detectable titer at week 52, six months prior to the first indication of HIV-1 infection (week 78).

Subject C11 possessed a neutralizing titer of 1:90 at fourteen weeks prior to detection of HIV-1 and a peak titer of 1:500 following the third immunization. Similarly vaccinee C17 had a neutralizing titer of 1:150 fourteen weeks prior to infection and a peak titer of 1:400 at two weeks after the third immunization.

Based on the rate of decay of the gp120 response of approximately two months [Belshe et al.; *JAMA* 272(6):475–80 (1994)], as well as the observation that neutralizing titers of 1:150 decayed to 1:10 in 10 weeks in vaccinees C10 and C17, it appears that neutralizing titers in C8, C15, C11, and C17 could have declined to 1:10 or less in the intervals between the last pre-infection serum sample and the time of HIV-1 detection.

The results of these studies demonstrated that all vaccinees developed some level of virus-neutralizing antibodies at some time prior to HIV-1 infection, and that the magnitude of the neutralizing response was probably low at the time of infection. In general, the magnitude of the virus-neutralizing response observed in the individuals that became infected with HIV-1 was comparable to that seen in non-infected vaccinees as described in Belshe et al.; *JAMA* 272(6):475–80 (1994).

Sequences of Viruses. To evaluate the similarity of the breakthrough viruses with the vaccine antigen, nucleotide sequences for gp120 from all seven breakthrough viruses were determined. Envelope glycoprotein genes were amplified from proviral DNA using the polymerase chain reaction. Sequences were obtained by direct amplification of DNA from lysates of gradient-purified lymphocytes obtained directly from patient blood without any intermediate tissue culture or amplification step.

A listing of the complete gp120 sequences (two clones per specimen) is provided in FIG. 3. All seven envelope glycoproteins possessed sequences typical of subtype (clade) B viruses. The overall homology with MN-rgp120 ranged from 69–80% (Table 5).

TABLE 5

Comparison of MN-rgp120 Sequence with Sequences from Infected Vaccinees*

|       | MN  | C6.1 | C8.3 | C7.2 | C11.5 | C10.5 | C17.1 | C15.2 |
|-------|-----|------|------|------|-------|-------|-------|-------|
| MN    | 100 | 79   | 78   | 70   | 75    | 69    | 80    | 72    |
| C6.1  |     | 100  | 78   | 70   | 81    | 75    | 90    | 79    |
| C8.3  |     |      | 100  | 68   | 80    | 76    | 84    | 83    |
| C7.2  |     |      |      | 100  | 80    | 73    | 76    | 73    |
| C11.5 |     |      |      |      | 100   | 75    | 70    | 80    |
| C10.5 |     |      |      |      |       | 100   | 70    | 72    |
| C17.1 |     |      |      |      |       |       | 100   | 87    |
| C15.2 |     |      |      |      |       |       |       | 100   |

* - Data indicate percent identity.

Interestingly, a high percentage (four of seven) of the breakthrough viruses differed from MN-rgp120 by 25–30% [Myers et al.; *Retroviruses and AIDS Database*, Los Alamos National Laboratory (1992 and 1995)]. Historically this degree of sequence variation is typical of inter-subtype (intra-clade) variation rather than intra-subtype variation which is expected to be in the 10–20% range [Myers et al.; *Retroviruses and AIDS Database*, Los Alamos National Laboratory (1992 and 19950]. Of the viruses with the greatest homology to MN-rgp120, two (C6 and C8) occurred as early infections, prior to complete immunization, and one (C17) occurred as a late infection.

Polymorphism in the V3 Domain. Of particular interest were polymorphisms in regions known to contain epitopes recognized by virus neutralizing antibodies. The best characterized neutralizing epitope, the principal neutralizing determinant (PND), occurs at the tip of the V3 loop. In subtype B viruses, approximately 60% possess the MN serotype-defining signature sequence, IGPGRAF (SEQ. ID. NO:52), based on identity with the prototypic MN strain of HIV-1 [Berman et al.; *J. Virol.* 7:4464–9 (1992); Myers et al.; *Retroviruses and AIDS Database*, Los Alamos National Laboratory (1992 and 1995); La Rosa et al.; *Science* 249:932–5 (1990)].

Three of the viruses (C6, C8, and C17) possessed the MN serotype signature sequence (FIG. 3). In contrast, four viruses possessed sequences with radical amino acid substitutions in the PND [IGPGRAW (C7), LGPGSTF (C11), IGPGRVL (C10), and IGPGSAF (C15)] (SEQ. ID. NOs:53–56, respectively), and therefore were classified as "non-MN like" viruses. Of note, each of the four "non-MN-like" sequences were rare (Table 6) and were not typical of the most common "non-MN" variants of subtype B viruses [Myers et al.; *Retroviruses and AIDS Database*, Los Alamos National Laboratory (1992 and 1995)].

TABLE 6

Frequency of Polymorphisms at the Principal Neutralizing Determinant in HIV-1 Infected Individuals Immunized with MN-rgp120*

| V3 Sequence | Observed | | Dataset Frequency | | |
|---|---|---|---|---|---|
| | Fre- | GNE | LANL | LANL.1 | LaRosa |
| Sequence | n quency | (n = 52) | (n = 519) | (n = 160) | (n = 245) |
| GPGRAF | 3  0.42 | 0.67 | 0.57 | 0.66 | 0.60 |
| GPGRAW | 1  0.14 | 0.03 | 0.013 | 0.06 | 0.010 |

TABLE 6-continued

Frequency of Polymorphisms at the Principal Neutralizing Determinant in HIV-1 Infected Individuals Immunized with MN-rgp120*

| V3 Sequence | Observed | | Dataset Frequency | | |
|---|---|---|---|---|---|
| | Fre- | GNE | LANL | LANL.1 | LaRosa |
| Sequence | n quency | (n = 52) | (n = 519) | (n = 160) | (n = 245) |
| GPGRVL | 1  0.14 | <0.02 | 0.004 | <0.006 | <0.008 |
| GPGSTF** | 1  0.14 | <0.02 | <0.002 | <0.006 | <0.004 |
| GPGSAF | 1  0.14 | 0.02 | 0.011 | <0.006 | <0.004 |

*Data set GNE refers to a collection of 52 independent isolates collected in 1992; dataset LANL refers to a collection of 519 sequences reported by Myers et al., Retroviruses and AIDS Database, Los Alamos National Laboratory 1992 and 1995; LANL.1 refers to a collection of 160 epidemiologically unlinked individuals provided by B. Korber (personal communication); dataset La Rosa refers to sequence data reported by La Rosa et al., Science 249:932-5 (1990).
**Sequences were not present in the data sets examined.

The prevalence of viruses with PND sequences matching the breakthrough viruses ranged from a high of 1.3% (C7) to a low of 0.2% (C11) in a listing of 519 subtype B sequences compiled by the Los Alamos National Laboratory [Myers et al.; *Retroviruses and AIDS Database*, Los Alamos National Laboratory (1992 and 1995)]. Similarly low frequencies were observed in three other independently derived data sets (Table 6). The occurrence of these sequences did not differ significantly between data sets collected prior to 1985 [La Rosa et al.; *Science* 249:932–5 (1990)] and data collected 1992, or from a set of 160 epidemiologically unlinked individuals (B. Korber, personal communication). All four sets of data agreed that the prevalence of viruses with MN-like PND sequences was in the range of 60%. Based on this data, four of the seven breakthrough infections were determined to be caused by viruses that fell outside of the spectrum of viruses that the vaccine was expected to prevent.

Other features of breakthrough virus V3 domains. Like MN-rgp120, the V3 domains of all of the breakthrough viruses were 36 amino acids in length. However, all seven viruses differed from MN-rgp120 with respect to the number of glycosylation sites and with respect to the syncytium-inducing (SI) signature sequence.

The sequence of MN-rgp120 is somewhat unusual [Myers et al.; *Retroviruses and AIDS Database*, Los Alamos National Laboratory (1992 and 1995)] in that it lacks an N-linked glycosylation site at position 306 in the V3 domain. The lack of this glycosylation site does not appear to be antigenically significant since antisera to MN-rgp120 are known to neutralize a variety of viruses (e.g. SF-2, DU6587-5, DU4489-5, CC) that possess a glycosylation site at this position [Berman et al.; *J. Virol.* 7:4464–9 (1992)].

In addition, the V3 domain of MN-rgp120 possessed sequence polymorphisms (R at position 311, K at position 324, K at position 328) typical of syncytium inducing viruses [Fouchier et al.; *J. Virol.* 66:3183–87 (1992)], whereas all seven breakthrough viruses possessed sequences associated with non-syncytium-inducing viruses. Syncytium-inducing viruses have been associated with rapid disease progression [Tersmette et al.; *J. Virol.* 62:2026–32 (1988)] and T cell tropism [O'Brien et al.; *Nature* (London) 348:69–73 (1990); Shioda et al.; *Nature* (London) 349:167–9 (1991)]. To date viruses with these properties have not been recovered from any of the MN-rgp120 immunized volunteers.

Polymorphism in the V1, V2 and C4 domains. Previous investigations have identified additional neutralizing epitopes in the V1, V2 and C4 domains of gp120 [Nakamura et al.; *J. Virol.* 67:6179–91 (1993); McKeating et al.; *AIDS Research and Human Retroviruses* 8:451–9 (1992); Ho et al.; *J. Virol.* 65:489–93 (1991); Barbas et al.; *Proc. Natl. Acad. Sci. USA* 91:3809–13 (1994); McKeating et al.; *J. Virol.* 67:4932–44 (1993); Moore et al.; *J. Virol.* 67:6136–6151 (1993); Davis et al.; *J. Gen. Virol.* 74:2609–17 (1993)].

The best characterized of these neutralizing epitopes is in the C4 domain which has attracted special attention because antibodies binding to this area are known to block the binding of gp120 to CD4 [Moore et al.; *AIDS* 3:155–63 (1989); McKeating et al.; *AIDS Research and Human Retroviruses* 8:451–9 (1992)]. Because the epitope is located in a conserved (C) domain, naturally-occurring polymorphism in this region is far more limited than in other neutralizing epitopes. Nakamura et al.; *J. Virol.* 67:6179–91 (1993) reported that the binding of a number of neutralizing MAbs was dependent on K at position 429.

Comparison of the sequence of MN-rgp120 with other strains of HIV-1 showed that a common polymorphism, involving the substitution of E for K, occurs at this position. Indeed, substrains of the same virus isolate often show polymorphism at this position. The HXB2 substrain of HIV-$1_{LAI}$ contains K at position 429, whereas the BH10, IIIB, and LAV substrains of the HIV-$1_{LAI}$ contain E at this position [Nakamura et al.; *J. Virol.* 67:6179–91 (1993)]. Similarly, the 1984 isolate of HIV-$1_{MN}$ exhibited E at this position, while the 1990 isolate of HIV-$1_{MN}$, used to produce MN-rgp120, possessed K at this position.

When the sequences of the infected vaccine recipients were examined (FIG. 3), the virus from subject C17, like MN-rgp120 contained K at position 429, whereas the six other viruses that differed from the vaccine immunogen possessed E at this position. These results demonstrated that six of the seven breakthrough viruses differed from the vaccine immunogen at the CD4-blocking, neutralizing epitope in the C4 domain of gp120.

Studies with monoclonal antibodies have defined neutralizing epitopes in the V1 and V2 domains of gp120 [McKeating et al.; *J. Virol.* 67:4932–44 (1993); Moore et al.; *J. Virol.* 67:6136–6151 (1993); Davis et al.; *J. Gen. Virol.* 74:2609–17 (1993)]. Like the polymorphisms that occur in the C4 domain, the V2 domains exhibit several common polymorphisms that affect the binding of virus neutralizing antibodies. One such polymorphism occurs at position 171 which is critically important for the binding of murine MAb 1025, whereas residue 187 is important for the binding of MAb several MAbs represented by 1088.

When the V2 domain sequences were examined (FIG. 3), all of the infected-vaccinee viruses differed from MN-rgp120 in that R replaced G at position 171 and I or V replaced E at position 187. Antibodies recognizing these adjacent sites in the V2 domain of MN-rgp120 would not be expected to neutralize viruses with radical amino acid substitutions at these position. Thus, all seven breakthrough viruses differed from MN-rgp120 at a neutralizing epitope in the V2 domain of gp120.

Other neutralizing epitopes have been reported in the V1 domain of gp120 [O'Brien et al.; *Nature* (London) 348:69–73 (1990); McKeating et al.; *J. Virol.* 67:4932–44 (1993)]. Although the neutralizing epitopes in the V1 domain of MN-rgp120 have not been characterized, the polymorphism seen among the breakthrough viruses in this region was interesting. Particularly striking (FIG. 3) was that the length of this domain ranged from 20 amino acids (C17) to 45 amino acids (C6), and the number of N-linked glycosylation sites ranged from 2 to 6. In contrast, the V1 domain of MN-rgp120 is 31 amino acids in length and encodes three N-linked glycosylation sites.

Although examination of sequence databases suggest that variation in the V2 region is comparable to the V1 region, the V2 region of the breakthrough viruses showed less variation than expected. Specifically, the length of the V2 region ranged from 36 amino acids (C7) to 39 amino acids in length, with six of seven viruses containing three N-linked glycosylation sites in this domain. A high degree of polymorphism was found in the V4 region where sequences ranged from 26 (C10) to 33 (C15, C7) amino acids in length and contained either 4 or 5 N-linked glycosylation sites.

Figure 4:
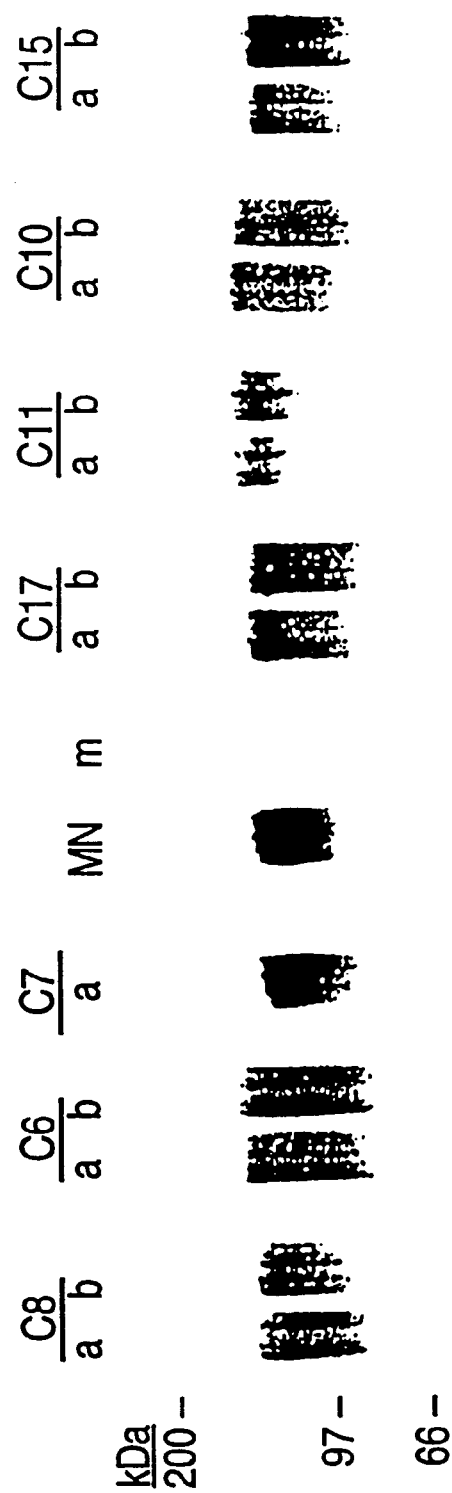
FIG. 4 illustrates immunoprecipitation of recombinant gp120 prepared from breakthrough viruses. Recombinant gp120s from the seven breakthrough viruses were prepared by transient transfection of 293s cells. Cells were metabolically labeled with $^{35}$S methionine and growth conditioned cell culture supernatants were immunoprecipitated with polyclonal antisera to MN-rgp120. Immunoprecipitates were resolved by SDS-PAGE and visualized by autoradiography. C8 lanes a and b correspond to clones C8.3 and C8.6; C6 lanes a and b correspond to clones C6.1 and C6.5; C7 lanes a and b correspond to clones C7.2 and C7.10; C17 lanes a and b correspond to C17.1 and C17.3; C11 lanes a and b correspond to clones C11.5 and C11.7; C10 lanes a and b correspond to clones C10.5 and C10.7; C15 lanes a and b correspond to clones C15.2 and C15.3.

Antigenicity of envelope glycoproteins from breakthrough viruses. To determine the significance of sequence variation on glycoprotein antigenicity, recombinant gp120 was prepared from the viruses of all seven infected vaccinees (FIG. 4). In these studies a series of MAbs was assembled and their binding to MN-rgp120 was compared to that of rgp120 from the vaccinee isolates by ELISA (Table 7).

TABLE 7

Relative Reactivity* of MAb Binding to rgp120 from Infected Subjects Compared with Binding to MN-rgp120

| gp120 | V3 | | Discontinuous | C8 | V2 |
| --- | --- | --- | --- | --- | --- |
| | 1034 | 50.1 | 1.5E | 1025 | 1024 | 1088 |
| MN | 1.0 | 1.00 | 1.00 | 1.00 | 1.00 | 1.00 |
| C6.1 | 0.37 | 0.37 | 0.17 | 0.00 | 0.00 | 0.00 |
| C6.5 | 0.33 | 0.33 | 0.75 | 0.00 | 0.00 | 0.00 |
| C8.3 | 0.11 | 0.37 | 0.38 | 0.00 | 0.00 | 0.00 |

TABLE 7-continued

Relative Reactivity* of MAb Binding to rgp120 from
Infected Subjects Compared with Binding to MN-rgp120

| gp120 | V3 | | Discontinuous | C8 | V2 |
|---|---|---|---|---|---|
| | 1034 | 50.1 | 1.5E | 1025 | 1024 | 1088 |
| C8.6 | 0.14 | 0.34 | 0.29 | 0.00 | 0.00 | 0.00 |
| C7.2 | 0.47 | 0.60 | 0.71 | 0.00 | 0.00 | 0.00 |
| C11.5 | 0.00 | 0.00 | 0.17 | 0.00 | 0.00 | 0.00 |
| C11.7 | 0.00 | 0.00 | 0.17 | 0.00 | 0.00 | 0.00 |
| C10.5 | 0.33 | 0.40 | 0.46 | 0.24 | 0.03 | 0.04 |
| C10.7 | 0.42 | 0.48 | 0.50 | 0.29 | 0.07 | 0.09 |
| C17.1 | 0.33 | 0.52 | 0.33 | 0.00 | 0.30 | 0.07 |
| C17.3 | 0.37 | 0.56 | 0.33 | 0.00 | 0.38 | 0.06 |
| C15.2 | 0.00 | 0.47 | 0.92 | 0.00 | 0.00 | 0.00 |
| C15.3 | 0.00 | 0.37 | 0.63 | 0.00 | 0.00 | 0.00 |

*Relative reactivity values represent ratio of optical densities obtained with rgp120 from patient isolates divided by optical density obtained for MN-rgp120 at a MAb concentration of 2 micrograms per milliliter.

Figure 5A:
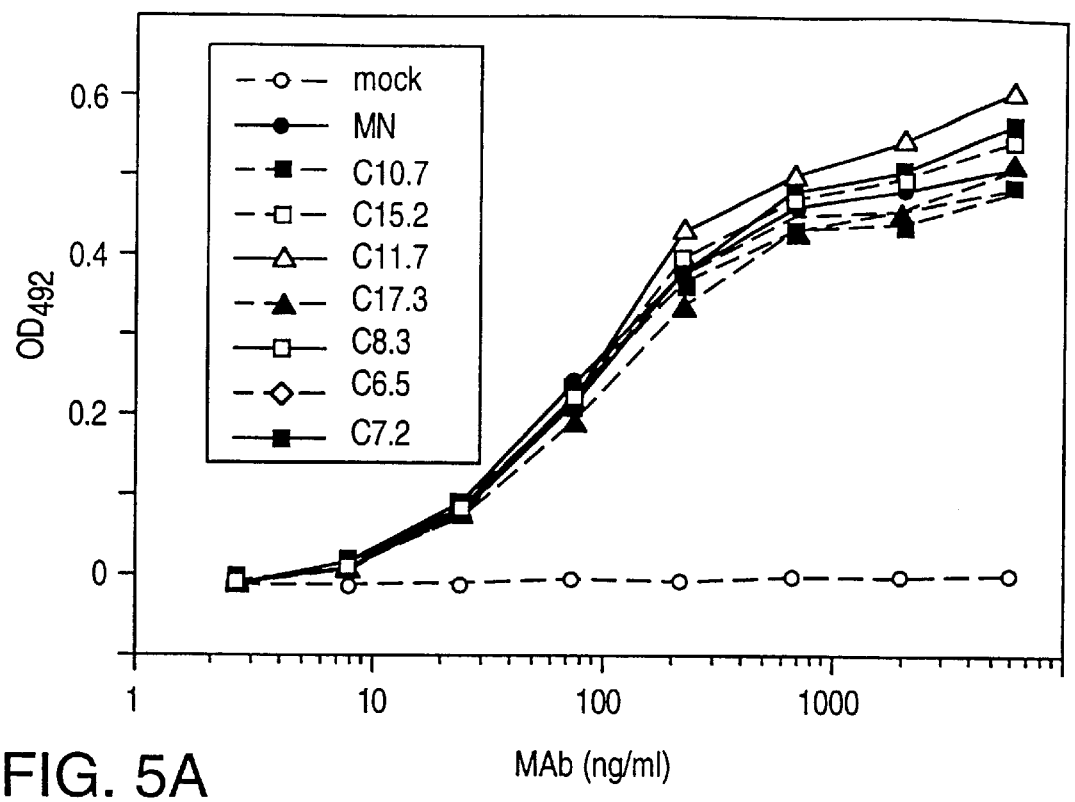
FIGS. 5A–5D illustrate binding of monoclonal antibodies to recombinant gp120 from breakthrough viruses. Growth-conditioned cell culture supernatants were collected from 293s cells transiently transfected with plasmids directing the expression of breakthrough virus envelope glycoproteins. The relative rgp120 concentrations were determined by ELISA using MAb 5B6 specific for the HSV-1 glycoprotein D flag epitope at the amino terminus of all of the rgp120 variants described herein. The resulting rgp120 preparations were captured onto wells of microtiter plates coated with a polyclonal antibody specific for a conserved sequence in the C-terminus of gp120. The binding of virus neutralizing monoclonal antibodies reactive with gp120 was determined by ELISA.

In control experiments, the binding of MAb 5B6 (which is specific for the HSV gD-1 flag epitope fused to the N terminus of all of the rgp120 protein) was used to standardize the amount of gp120 from each isolate (FIG. 5A). These studies demonstrated that the assay was carried out under conditions where equivalent amount of rgp120s were captured onto wells of microtiter plates.

Figure 5B:
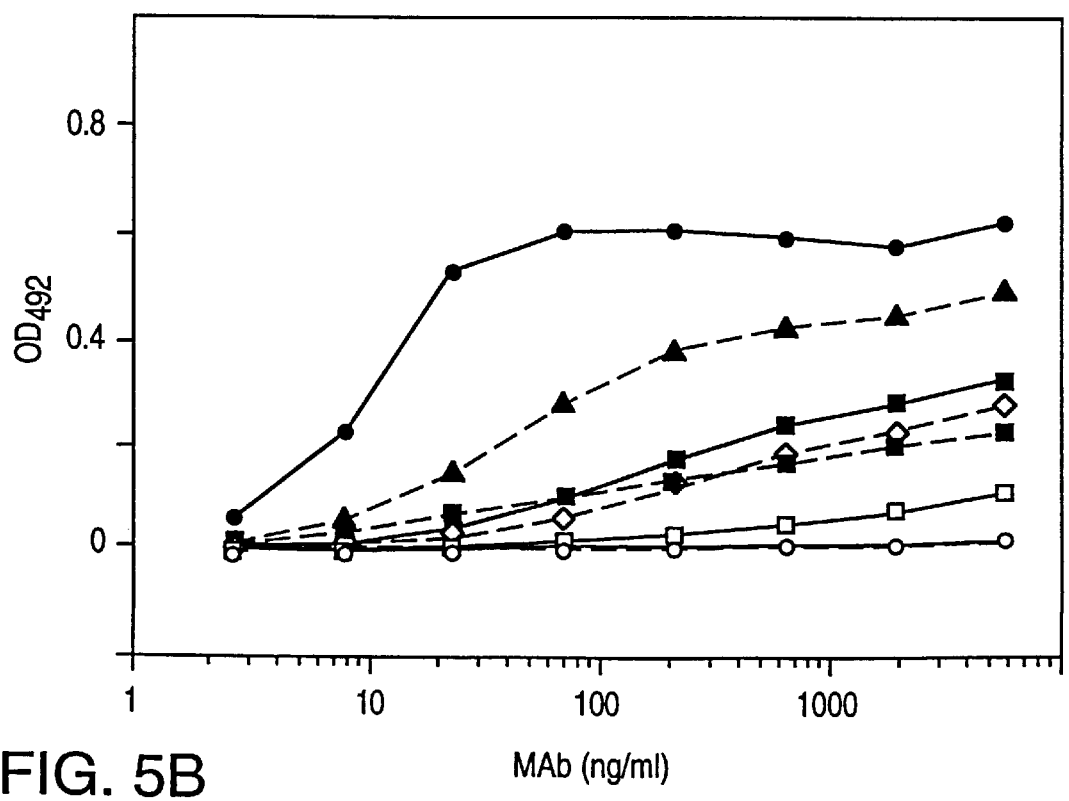
Figure 5C:
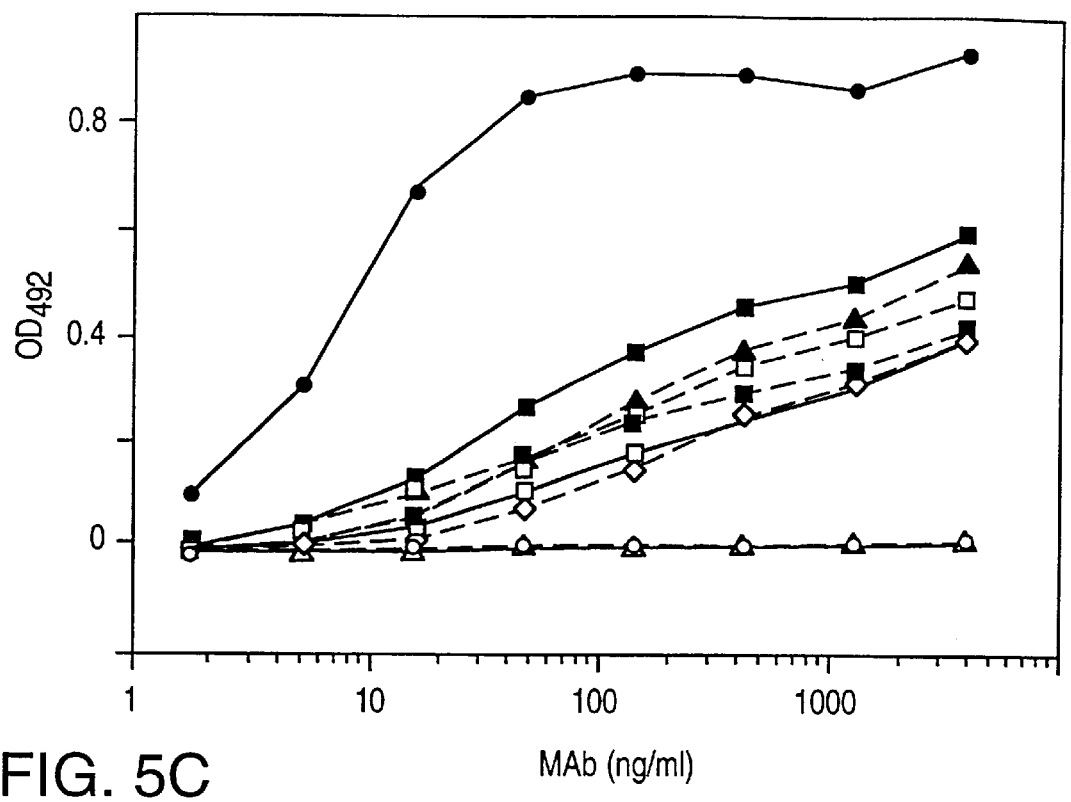
Figure 5D:
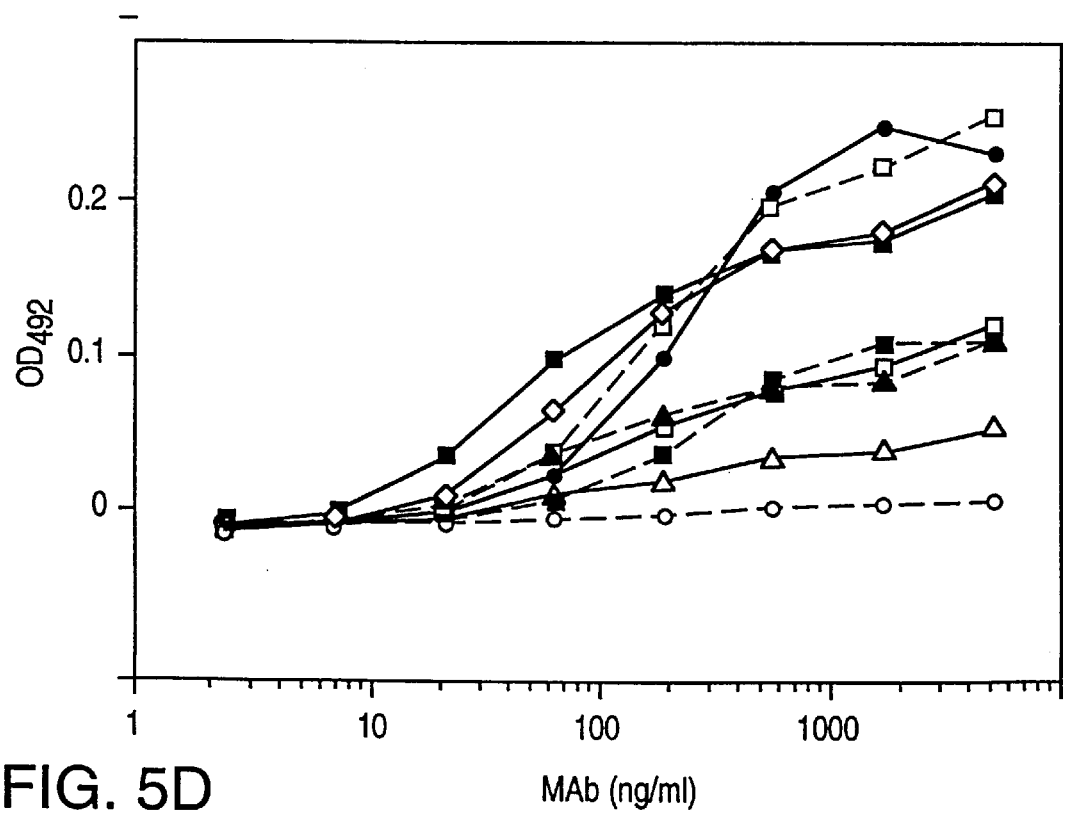
Figure 6:
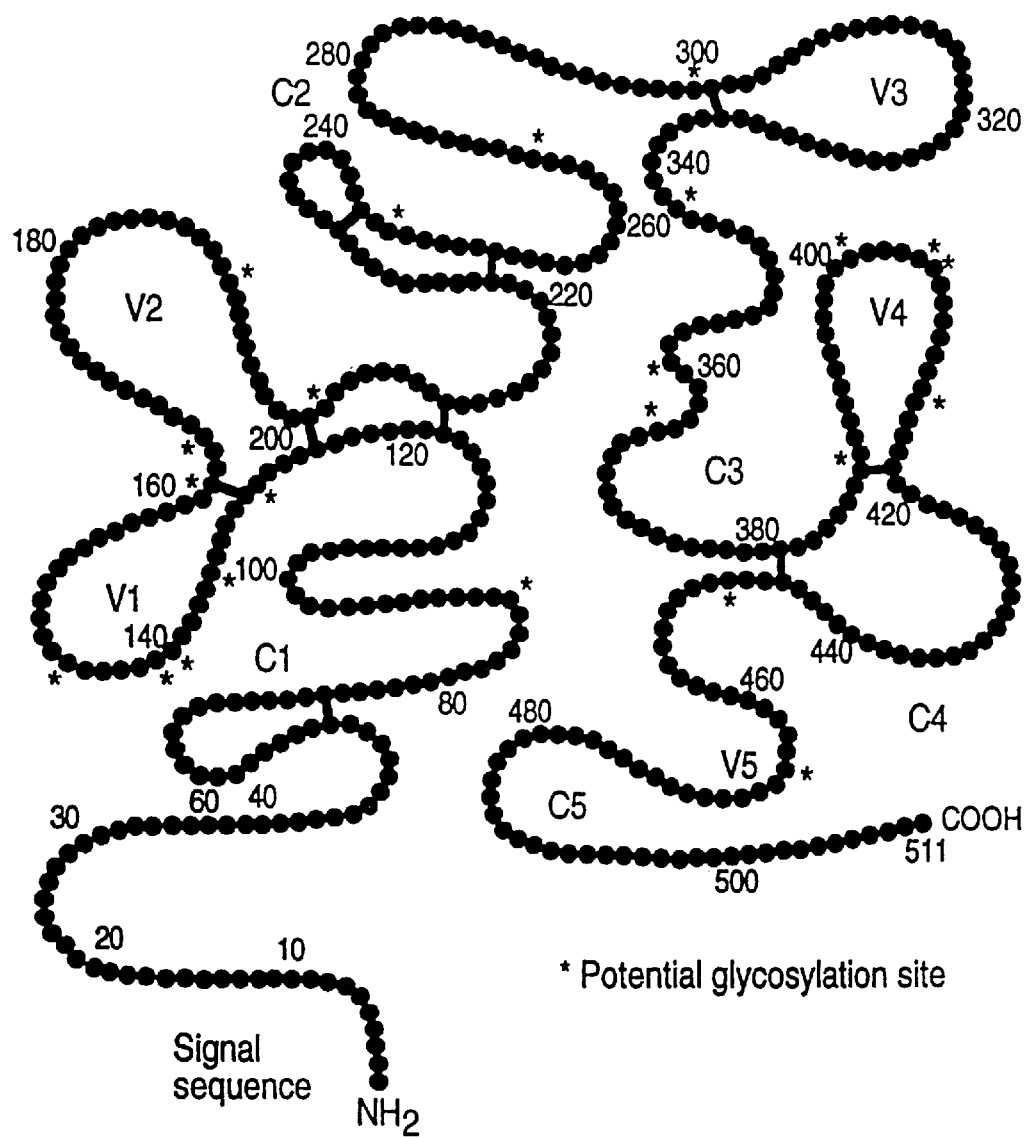
FIG. 6 depicts the mature envelope glycoprotein (gp120) from the MN clone of the MN strain of HIV-1 (SEQ. ID. NO:41). Hypervariable domains are indicated in bold, and the V and C regions are indicated (according to Modrow et al., *J. Virology* 61(2) :570 (1987). Potential glycosylation sites are marked with a (*).

The antigenic structure of the V3 domain was examined using the 1034 MAb (isolated from mice immunized with MN-rgp120 as described in Nakamura et al.; J. Virol. 67:6179–91 (1993) and the 50.1 MAb (prepared from mice immunized with a synthetic V3 domain peptide as described in Rini et al.; Proc. Natl. Acad. Sci. USA 90:6325–9 (1993). Both MAbs are known to exhibit potent virus neutralizing activity. When binding to the recombinant proteins was examined, the MAb binding to MN-rgp120 was at least 10-fold greater than to any of the breakthrough virus envelope proteins (FIGS. 5B and C). Surprisingly, rgp120 from the three patient isolates (C8, C6, and C17) that possessed the MN serotype-defining sequence, IGPGRAF (SEQ. ID. NO:32), varied from one another in their MAb binding activity. Thus, the binding of MAb 1034 and MAb 50.1 to rgp120 from C17 was significantly greater than the binding to rgp120s from C6 and C8.

A distinction in the epitopes recognized by these MAbs was evident since C6-rgp120 and C8-rgp120 gave comparable binding with 50.1, whereas 1034 bound better to the C6-derived protein than the C8-derived protein. The poorest MAb reactivity was with rgp120s from C11 and C15. This result was consistent with sequence analysis demonstrating that these two viruses both possessed the radical substitution of S for R at position 18 in the V3 domain. Surprisingly, both of these MAbs exhibited better than expected binding to rgp120 from the C7 and C10 viruses. Like MN-rgp120, both proteins contained the penta-peptide, IGPGR sequence (SEQ. ID. NO:57) in the V3 loop, but differed from MN-rgp120 in that V and L replaced A and F at positions 319 and 320 in gp120 from C10, and W replaced F at position 320 in gp120 from C7. These results indicate that R at position 318 is essential for the binding of these two MAbs, and that the epitopes recognized by 1034 and 50.1 are not completely destroyed by the hydrophobic substitutions at positions 319 and 320.

As predicted from the sequence data, there was little if any binding to the breakthrough virus rgp120s using MAbs (1088 and 1025) directed to the V2 region of MN-rgp120. Also consistent with sequence data was the observation that MAb 1024 directed to the C4 domain of MN-rgp120 gave some reactivity with C17-rgp120 which, like MN-rgp120 contained K at position 429, but gave no reactivity with the other isolates that contained E at residue 429.

Together, these studies demonstrated that the antigenic structure of all seven breakthrough viruses differed from the vaccine immunogen at three well characterized neutralizing epitopes.

A totally different pattern of reactivity was observed with the human hybridoma, MAb 15e, prepared from an HIV-1 infected individual as described in Ho et al.; J. Virol. 65:489–93 (1991). With this MAb, the greatest binding was achieved with MN-rgp120 and rgp120 from C7, and the poorest reactivity was seen with the two clones of rgp120 from the C11. Moderate, but comparable reactivity was seen with rgp120s from the C10 and C17.

These results demonstrate that the 15e epitope is polymorphic, and that the epitope is conserved on MN-rgp120 and rgp120 from C7, but has been lost on rgp120s from C11. Interestingly, the two different clones of gp120 derived from C6 gave strikingly different patterns of antibody binding. Thus, rgp120 from clone C6.5 exhibited strong reactivity with this antibody, whereas rgp120 from clones C6.1 exhibited significantly weaker activity with this MAb. Comparison of sequence data (FIG. 3) showed that the two C6 clones differed at 6 amino acid positions. Based on comparative binding to the other viral proteins of known sequence, it appeared that the substitution of K for I at position 351 in the C3 domain of gp120 could account for the difference in binding activity. This result is also consistent with both clones of C11 similarly containing a positively-charged K at this position, and also being poorly reactive with this MAb. Alternatively, a T for I substitution at position 439 in the C4 domain could account for the difference in 15e binding between C6.1 and C6.5. Although the inability of the two C11 clones to bind 15e cannot be explained by polymorphism at this position in the C4 domain, they could be affected by the adjacent T for M substitution at position 434.

DISCUSSION

In these studies, the viruses and immune responses in seven of nine vaccinees who became infected with HIV-1 through high risk activity while participating in Phase 1 or Phase 2 trials of MN-rgp120, a candidate HIV-1 vaccine were analyzed. Such infections would be expected to occur for one of two reasons: 1) lack of sufficient immune response at the time of infection; or 2) infection with viruses that fall outside of the antigenic spectrum expected to be covered by the vaccine immunogen. The data indicate that both explanations may be involved with the infections observed (Table 8).

TABLE 8

Summary of Breakthrough Infections

| Case No. | Adequate Immunization | MN-rgp120 Homology (%) | Homologous to MN-rgp120 | | |
|---|---|---|---|---|---|
| | | | V3 PND | C4 Epitope | V2 Epitope |
| C6 | − | 79 | + | − | − |
| C8 | − | 78 | + | − | − |
| C15 | − | 72 | − | − | − |
| C7 | − | 70 | − | − | − |
| C11 | + | 75 | − | − | − |

TABLE 8-continued

Summary of Breakthrough Infections MN-rgp120 Homologous to MN-rgp120

| Case No. | Adequate Immunization | Homology (%) | V3 PND | C4 Epitope | V2 Epitope |
|---|---|---|---|---|---|
| C10 | + | 69 | – | – | – |
| C17 | + | 80 | + | + | – |

Two of the infections occurred in individuals who failed to receive the minimum three doses of vaccine typically required for the induction of protective immunity with protein subunit vaccines (e.g. hepatitis B virus formulated in alum adjuvant as described in Francis et al.; Ann. Int. Med. 97:362–6 (1982). Two additional breakthrough infections occurred in vaccinees who had weak or undetectable primary (C7) and booster (C15) responses. Of the three individuals who became infected with HIV-1 after receiving three or more productive immunizations (C10, C11, and C17), at least two, and possibly all three, appear to have become infected more than six months after receiving their last immunization. Because antibody titers to MN-rgp120 typically decay with a half-time of 2 to 2.5 months [Belshe et al.; JAMA 272(6):475–80 (1994); Berman et al.; AIDS 8:591–601 (1994)], antibody titers would be expected to have decayed at least eight-fold and possibly as much as sixty four-fold at the time of infection. Thus, the lack of a sufficient immune response at the time of infection represents a potential explanation for at least six of the seven breakthrough infections.

Data from vaccine efficacy studies in gp160 immunized chimpanzees [McElrath et al.; Longitudinal Vaccine-Induced Immunity and Risk Behavior of Study Participants in AVEG Phase II Protocol 201. In: Abstracts from Eighth Annual Meeting of the National Cooperative Vaccine Development Groups for AIDS. Bethseda, Md. 1996:216] challenged with HIV-1, and gp120-immunized rhesus macaques challenged with a chimeric SIV/HIV-1 virus (SHIV) suggest that the magnitude of the neutralizing antibody response at the time of infection is a critical correlate of protective immunity. If maintaining neutralizing antibody titers proves to be a valid correlate of protective immunity in humans, then formulations (e.g. novel adjuvants) or immunization regimes (frequent boosting) designed to maximize the antibody responses may be required to achieve long lasting protection. Use of a booster every six months may be advantageous.

The other likely explanation for the late infections is the antigenic difference between the vaccine and the breakthrough virus envelope glycoproteins. This explanation is supported by the observation that four of the seven breakthrough viruses possessed envelope glycoproteins that differed from the MN-rgp120 by 25–30% at the amino acid level. Differences of this magnitude have historically [Myers et al.; Retroviruses and AIDS Database, Los Alamos National Laboratory (1992 and 1995)] been associated with inter-subtype variation and far exceeds the average 10–20% variation expected for viruses within the same subtype.

Although the biologic significance of sequence variation in many regions of the envelope glycoprotein is unclear, polymorphism at neutralizing epitopes is an important factor that affects vaccine efficacy. Previous studies [Salmon-Ceron et al.; AIDS Res. and Human Retroviruses 11:1479–86 (1995); Javaherian et al.; Science 250:1590–3 (1990)] have demonstrated that the breadth of neutralizing activity that could be elicited by HIV-1 envelope derived vaccines was critically dependent on the sequence of epitopes in the V3 domain (e.g.; the PND). Thus, candidate vaccines based on the LAI strain of HIV-1 (the prototypic "non-MN-like" subtype B virus), exhibited little or no cross neutralizing activity with subtype B viruses, whereas vaccines that contained the "MN-like-" PND sequence (IGPGRAF) (SEQ. ID. NO:52) exhibited broad cross neutralizing activity. That four of the seven breakthrough viruses possessed envelope glycoproteins with radical amino acid substitutions in the PND is consistent with the explanation that differences in antigenic structure explain some of these infections.

Over the last few years, it has become clear that polymorphism among "MN-like" viruses occurs at neutralizing epitopes outside of the PND. The best example occurs in the C4 domain where two antigenically distinct variants are distinguished by the presence of either K or E at position 429 [Moore et al.; AIDS 3:155–63 (1989)]. Because six of the seven breakthrough viruses differed from the vaccine strain in that they contained E rather than K at position 429, antibodies raised to the C4 domain of MN-rgp120 were unlikely to neutralize the viruses infecting in six of the seven vaccinees.

Other neutralizing epitopes are known to be present in the V1 and V2 domains of gp120. Although these regions are highly variable, due to insertions and deletions, neutralizing epitopes have been described by McKeating et al.; J. Virol. 67:4932–44 (1993); Moore et al.; J. Virol. 67:6136–6151 (1993); and Davis et al.; J. Gen. Virol. 74:2609–17 (1993). Several of these epitopes overlap an amino terminal sequence of the V2 domain containing the tri-peptide sequence RDK at positions corresponding to 142 to 144 of MN-rgp120 [McKeating et al.; J. Virol. 67:4932–44 (1993); Moore et al.; J. Virol. 67:6136–6151 (1993)]. Like the C4 epitope, variation in this sequence is known to occur between different substrains derived from the same parental isolate. Since all seven breakthrough viruses differed from MN-rgp120 in that they possessed the RDK sequence, rather than the GDK sequence present in the vaccine antigen, neutralizing antibodies to the V2 domain of MN-rgp120 would not have been expected neutralize any of the viruses recovered from the vaccinees immunized with MN-rgp120.

Although polymorphisms at neutralizing epitopes might account for the lack of protection in most of the infections, this does not appear to explain the infection of vaccinee C17, who was infected by a virus that matched MN-rgp120 in the V3 and C4 domains. If a difference in sequence was responsible for the lack of protection in this case, the critical difference might relate to the unusual sequence in the V1 domain of gp120 from this breakthrough virus. Several studies have shown that the V1 domain possesses epitopes recognized by virus neutralizing monoclonal antibodies [McKeating et al.; J. Virol. 67:4932–44 (1993); Davis et al.; J. Gen. Virol. 74:2609–17 (1993); Kayman et al.; J. Virol. 68:400–410 (1994)].

Although far less is known about the V1 epitopes relative to other neutralizing sites, the V1 epitopes appear to be conformation-dependent, and antisera from HIV-1 infected individuals recognize epitopes in the V1 and V2 domains [McKeating et al.; J. Virol. 67:4932–44 (1993); Kayman et al.; J. Virol. 68:400–410 (1994)]. The V1 sequence of the virus from C17 is noteworthy because it is smaller and contains fewer N-linked glycosylation sites than that of MN-rgp120 or any of the other breakthrough viruses. By the same token, the envelope glycoproteins from C11 and C6 are noteworthy because they are significantly larger and contain more glycosylation sites than MN-rgp120 or the other breakthrough viruses.

While differences in amino acid sequence can provide clues to differences in antigenic structure, the consequences of such polymorphism can only be proven through antibody binding studies. To correlate differences in sequence with differences in antigenic structure, gp120 from two clones each of all seven breakthrough viruses was expressed and the antigenicity of the clones with a panel of monoclonal antibodies was examined. As predicted from the sequence data, none of the breakthrough virus envelope glycoproteins reacted with neutralizing MAbs to the V2 domain of MN-rgp120. When MAbs to the C4 domain were examined, only the C17 envelope glycoprotein (that matched MN-rgp120 with respect to K429) showed significant, albeit lower, binding. Surprisingly, the three breakthrough envelope glycoproteins that contained the subtype B PND consensus sequence, IGPGRAF (SEQ. ID. NO:52), gave poor reactivity with all three PND directed MAbs, even though they possessed PND sequences closely related to the vaccine immunogen. Thus, all three of the vaccinee isolates appeared to possess changes outside of the recognition site that interfered with MAb binding.

It has been known for many years that resistance to neutralization in vitro can sometimes be attributed to mutations in remote sequences that alter the conformation of neutralizing epitopes and interfere with recognition by virus neutralizing antibodies [Nara et al.; *J. Virol.* 64:3779–91 (1990); Cordonnier et al.; *Nature* 340:571–4 (1989)]. Together, these results indicate that the antigenic structure of the envelope glycoproteins recovered from the breakthrough viruses differed significantly from that of the vaccine antigen.

A novel result was the localization of residues in the C3 domain that appeared to affect the binding of the virus neutralizing human MAb, 15e. This MAb is known to recognize a discontinuous epitope, block CD4 binding, and neutralize a variety of laboratory and primary isolates of HIV-1 [Ho et al.; *J. Virol.* 65:489–93 (1991); Thali et al.; *J. Virol.* 66:5635–5641 (1992); Moore et al.; *AIDS Res. Hum. Retroviruses* 9:1179–1187 (1993)].

Comparative binding to envelope glycoproteins from the breakthrough viruses indicated that recognition by this antibody is critically dependent on residues in the C3 or C4 domains of gp120. The unique occurrence of a positively charged K at position 351 in the C3 domain provides a common explanation for the inability of the C11.5, C11.7 and C6.1 strains of HIV-1 to bind to 15e. *Alternatively, it is possible that different amino acid substitutions in different locations account for the failure of* 15e to bind to rgp120s from the C6 and C11 clones. The only obvious positions where substitutions of this type occur are in the C4 domain where T replaces M at 434 (C11) and T replaces I at 439.

The present studies demonstrate that the current formulation of MN-rgp120 is less than 100% effective against HIV-1 infection. Based on previous in vitro and in vivo studies with MN-rgp120, protection from natural HIV-1 infection in humans is expected to depend on a threshold concentration of virus-neutralizing antibodies, and antigenic similarity between the vaccine immunogen and the challenge virus.

In this regard, only one of the seven breakthrough infections (C17) was unexpected. This individual received a full course of immunizations yet became infected with a virus similar to MN-rgp120 at at least two important neutralizing epitopes (V3 and C4 domains). This infection might be related to the magnitude of the antibody response at the time of infection, or antigenic differences between the breakthrough virus and the vaccine strain, or circumstances of infection (e.g., ulcerative lesions, infection by donor with acute infection or high viremia), not monitored in this protocol. Alternatively this individual may represent a true vaccine failure, without clear explanation.

On balance, the analysis of breakthrough infections described herein did not uncover any data that would discourage the continued development of MN-rgp120 as a vaccine to prevent HIV-1 infection. The results support speculation that enhancing vaccine immunogenicity (as by additional booster immunizations) may be required to maintain long term protective immunity, and that the addition of rgp120 from other antigenically different strains of virus in addition to MN-rgp120 are useful to expand the breadth of protection.

The availability of viruses and viral glycoproteins derived from breakthrough infections may provide an important means to streamline the process of identifying new antigens for inclusion into a multivalent vaccine. Recombinant viral glycoproteins prepared from breakthrough viruses, by definition, possess antigenic structures that are significantly different from MN-rgp120, and are be representative of viruses currently being transmitted. Thus, combining rgp120 from breakthrough viruses with MN-rgp120 is an effective way complement and significantly expand antigenic complexity and increase breadth of cross neutralizing activity.

What is claimed is:

1. An isolated polypeptide comprising an HIV gp 120 amino acid sequence selected from the group consisting of Sequence ID Nos: 2, 5, 8, 10, 12, 16, 19, 23, 25, 28, 31, 33, 36, and 39, and fragments thereof, wherein each of said fragments comprises at least the V2, V3, and C4 domains of gp120.

2. The polypeptide of claim 1 wherein the polypeptide additionally comprises a flag epitope sequence.

3. The polypeptide of claim 2 wherein the flag epitope sequence is the HSV gD-1 flag epitope sequence.

4. The polypeptide of claim 2 wherein the flag epitope sequence is fused to the HIV gp120 amino acid sequence.

5. The polypeptide of claim 1 wherein said HIV gp 120 amino acid sequence is a fragment lacking the gp120 signal sequence.

6. The polypeptide of claim 5 wherein the polypeptide additionally comprises a flag epitope sequence.

7. The polypeptide of claim 5 wherein the flag epitope sequence is the HSV gD-1 flag epitope sequence.

8. The polypeptide of claim 1 wherein the polypeptide comprises an amino acid sequence selected from the group consisting of Sequence ID Nos. 2 and 5 and fragments thereof, wherein each of said fragments comprises at least the V2, V3, and C4 domains of gp120.

9. The polypeptide of claim 1 wherein the polypeptide comprises an amino acid sequence selected from the group consisting of Sequence ID Nos. 8 and 10 and fragments thereof, wherein each of said fragments comprises at least the V2, V3, and C4 domains of gp120.

10. The polypeptide of claim 1 wherein the polypeptide comprises an amino acid sequence selected from the group consisting of Sequence ID Nos. 12 and 16 and fragments thereof, wherein each of said fragments comprises at least the V2, V3, and C4 domains of gp120.

11. The polypeptide of claim 1 wherein the polypeptide comprises an amino acid sequence selected from the group consisting of Sequence ID Nos. 19 and 23 and fragments thereof, wherein each of said fragments comprises at least the V2, V3, and C4 domains of gp120.

12. The polypeptide of claim 1 wherein the polypeptide comprises an amino acid sequence selected from the group consisting of Sequence ID Nos. 25 and 28 and fragments thereof, wherein each of said fragments comprises at least the V2, V3, and C4 domains of gp120.

13. The polypeptide of claim 1 wherein the polypeptide comprises an amino acid sequence selected from the group consisting of Sequence ID Nos. 31 and 33 and fragments thereof, wherein each of said fragments comprises at least the V2, V3, and C4 domains of gp120.

14. The polypeptide of claim 1 wherein the polypeptide comprises an amino acid sequence selected from the group consisting of Sequence ID Nos. 36 and 39 and fragments thereof, wherein each of said fragments comprises at least the V2, V3, and C4 domains of gp120.

15. An oligonucleotide of not more than five kilobases encoding an HIV gp120 polypeptide sequence comprising an amino acid sequence selected from the group consisting of Sequence ID Nos. 2, 5, 8, 10, 12, 16, 19, 23, 25, 28, 31, 33, 36, and 39, and fragments thereof, wherein each of said fragments encodes at least the V2, V3, and C4 domains of gp120.

16. The oligonucleotide of claim 15 wherein the oligonucleotide additionally encodes a flag epitope.

17. The oligonucleotide of claim 15 wherein the flag epitope is the HSV gD-1 flag epitope.

18. The oligonucleotide of claim 16 wherein the sequence encoding the flag epitope is fused to the sequence encoding the HIV gp120 amino acid sequence.

19. The oligonucleotide of claim 15 wherein said amino acid sequence is a fragment lacking the gp120 signal sequence.

20. The oligonucleotide of claim 19 wherein the nucleotide sequence encoding said fragment is joined to a nucleotide sequence encoding a heterologous signal sequence.

21. The oligonucleotide of claim 20 wherein said nucleotide sequences are joined via a nucleotide sequence encoding a flag epitope sequence.

22. The oligonucleotide of claim 20 wherein the signal sequence is the HSV gD1 signal sequence and the flag epitope sequence is the HSV gD-1 flag epitope sequence.

23. A vector comprising the oligonucleotide of claim 15.

24. A host cell comprising the vector of claim 23.

25. A method of producing a polypeptide comprising culturing the host cell of claim 24 and recovering the polypeptide.

26. An oligonucleotide of not more than 5 kilobases comprising a nucleotide sequence selected from the group consisting of Sequence ID Nos: 1, 4, 7, 9, 11, 15, 18, 22, 24, 27, 30, 32, 35, and 38, and fragments thereof, wherein each of said fragments encodes at least the V2, V3, and C4 domains of gp120.

27. The oligonucleotide of claim 26 wherein the oligonucleotide comprises a nucleotide sequence selected from the group consisting of Sequence ID Nos. 1 and 4 and fragments thereof, wherein each of said fragments encodes at least the V2, V3, and C4 domains of gp120.

28. The oligonucleotide of claim 26 wherein the oligonucleotide comprises a nucleotide sequence selected from the group consisting of Sequence ID Nos. 7 and 9 and fragments thereof, wherein each of said fragments encodes at least the V2, V3, and C4 domains of gp120.

29. The oligonucleotide of claim 26 wherein the oligonucleotide comprises a nucleotide sequence selected from the group consisting of Sequence ID Nos. 11 and 15 and fragments thereof, wherein each of said fragments encodes at least the V2, V3, and C4 domains of gp120.

30. The oligonucleotide of claim 26 wherein the oligonucleotide comprises a nucleotide sequence selected from the group consisting of Sequence ID Nos. 18 and 22 and fragments thereof, wherein each of said fragments encodes at least the V2, V3, and C4 domains of gp120.

31. The oligonucleotide of claim 26 wherein the oligonucleotide comprises a nucleotide sequence selected from the group consisting of Sequence ID Nos. 24 and 27 and fragments thereof, wherein each of said fragments encodes at least the V2, V3, and C4 domains of gp120.

32. The oligonucleotide of claim 26 wherein the oligonucleotide comprises a nucleotide sequence selected from the group consisting of Sequence ID Nos. 30 and 32 and fragments thereof, wherein each of said fragments encodes at least the V2, V3, and C4 domains of gp120.

33. The oligonucleotide of claim 26 wherein the oligonucleotide comprises a nucleotide sequence selected from the group consisting of Sequence ID Nos. 35 and 38 and fragments thereof, wherein each of said fragments encodes at least the V2, V3, and C4 domains of gp120.

* * * * *

SEQUENCE LISTING

<160> NUMBER OF SEQ ID NOS: 57

<210> SEQ ID NO 1
<211> LENGTH: 1503
<212> TYPE: DNA
<213> ORGANISM: HIV
<220> FEATURE:
<221> NAME/KEY: CDS
<222> LOCATION: (1)...(1503)

<400> SEQUENCE: 1

```
ggg gta cct gtg tgg aag gaa gca acc acc act cta ttt tgt gca tca      48
Gly Val Pro Val Trp Lys Glu Ala Thr Thr Thr Leu Phe Cys Ala Ser
  1               5                  10                  15
```

```
gat gct aaa gca tat gac aca gag gtg cat aat gtt tgg gcc aca cat        96
Asp Ala Lys Ala Tyr Asp Thr Glu Val His Asn Val Trp Ala Thr His
         20                  25                  30 gct tgt gta ccc aca gac cca aac cca caa gaa atg gta ttg gaa aat       144
Ala Cys Val Pro Thr Asp Pro Asn Pro Gln Glu Met Val Leu Glu Asn
     35                  40                  45 gtg aca gaa gat ttt aac atg tgg aaa aat gac atg gta gaa cag atg       192
Val Thr Glu Asp Phe Asn Met Trp Lys Asn Asp Met Val Glu Gln Met
 50                  55                  60 cat gag gat ata atc agt tta tgg gat caa agc cta aaa cca tgt gta       240
His Glu Asp Ile Ile Ser Leu Trp Asp Gln Ser Leu Lys Pro Cys Val
 65                  70                  75                  80 aaa tta acc cca ctc tgt att act tta aat tgc acc aat tgg aag aag       288
Lys Leu Thr Pro Leu Cys Ile Thr Leu Asn Cys Thr Asn Trp Lys Lys
                 85                  90                  95 aat gat act aaa act aat agt agt agt act aca act aat aat agt agt       336
Asn Asp Thr Lys Thr Asn Ser Ser Ser Thr Thr Thr Asn Asn Ser Ser
            100                 105                 110 gct aca gct aat agt agt agt act aca act aat agt agt tgg gga gag       384
Ala Thr Ala Asn Ser Ser Ser Thr Thr Thr Asn Ser Ser Trp Gly Glu
        115                 120                 125 ata aag gag gga gaa ata aag aac tgc tct ttc aat atc acc aca agc       432
Ile Lys Glu Gly Glu Ile Lys Asn Cys Ser Phe Asn Ile Thr Thr Ser
    130                 135                 140 ata aga gac aag gtg aag aaa gaa tat gca ctt ttt tat agc ctt gat       480
Ile Arg Asp Lys Val Lys Lys Glu Tyr Ala Leu Phe Tyr Ser Leu Asp
145                 150                 155                 160 gta gta cca ata gaa aat gat aat act agc tat agg ttg aga agt tgt       528
Val Val Pro Ile Glu Asn Asp Asn Thr Ser Tyr Arg Leu Arg Ser Cys
                165                 170                 175 aac acc tca gtc att aca caa gcc tgt cca aag gta act ttt gag cca       576
Asn Thr Ser Val Ile Thr Gln Ala Cys Pro Lys Val Thr Phe Glu Pro
            180                 185                 190 att ccc ata cat tat tgt acc ccg gct ggt ttt gcg att ctg aag tgt       624
Ile Pro Ile His Tyr Cys Thr Pro Ala Gly Phe Ala Ile Leu Lys Cys
        195                 200                 205 aga gat aaa aag ttc aat gga aca gga cca tgc aaa aat gtt agc aca       672
Arg Asp Lys Lys Phe Asn Gly Thr Gly Pro Cys Lys Asn Val Ser Thr
    210                 215                 220 gta caa tgt gca cat gga att aag cca gta gtg tca act caa ctg ctg       720
Val Gln Cys Ala His Gly Ile Lys Pro Val Val Ser Thr Gln Leu Leu
225                 230                 235                 240 tta aat ggc agc cta gca gaa gaa gag gta ata att aga tct gcc aat       768
Leu Asn Gly Ser Leu Ala Glu Glu Glu Val Ile Ile Arg Ser Ala Asn
                245                 250                 255 ttc tca aac aat gct aaa atc ata ata gta cag ttg agg gaa cct gta       816
Phe Ser Asn Asn Ala Lys Ile Ile Ile Val Gln Leu Arg Glu Pro Val
            260                 265                 270 gaa att aat tgt aca aga ccc agc aac aat aca ata aaa ggt ata cac       864
Glu Ile Asn Cys Thr Arg Pro Ser Asn Asn Thr Ile Lys Gly Ile His
        275                 280                 285 ata gga cca ggg aga gca ttt tat gca aca gga gac ata cga gga gat       912
Ile Gly Pro Gly Arg Ala Phe Tyr Ala Thr Gly Asp Ile Arg Gly Asp
    290                 295                 300 ata aga caa gca cat tgt aac att agt gga gca aaa tgg aat aac act       960
Ile Arg Gln Ala His Cys Asn Ile Ser Gly Ala Lys Trp Asn Asn Thr
305                 310                 315                 320 tta aag aag gta gtt aaa aaa tta aaa gaa caa ttt cca aat aaa aca      1008
Leu Lys Lys Val Val Lys Lys Leu Lys Glu Gln Phe Pro Asn Lys Thr
```

```
                    325                 330                 335
ata gtc ttt aac cat tcc tca gga ggg gac cca gaa att gta atg cac    1056
Ile Val Phe Asn His Ser Ser Gly Gly Asp Pro Glu Ile Val Met His
            340                 345                 350 agt ttt aat tgt caa ggg gaa ttt ttc tac tgt aat aca aca aag ctg    1104
Ser Phe Asn Cys Gln Gly Glu Phe Phe Tyr Cys Asn Thr Thr Lys Leu
            355                 360                 365 ttt aat agt act tgg aat gat act aca gag tca aat aac aat gat agt    1152
Phe Asn Ser Thr Trp Asn Asp Thr Thr Glu Ser Asn Asn Asn Asp Ser
            370                 375                 380 act att aca ctc cca tgc aga ata aaa caa att ata aac atg tgg cag    1200
Thr Ile Thr Leu Pro Cys Arg Ile Lys Gln Ile Ile Asn Met Trp Gln
385                 390                 395                 400 gaa ata gga aaa gca atg tat gcc cct ccc acc aga gga gaa att aaa    1248
Glu Ile Gly Lys Ala Met Tyr Ala Pro Pro Thr Arg Gly Glu Ile Lys
            405                 410                 415 tgt tca tca aat att aca gga cta ctg tta ata aga gat ggt ggt att    1296
Cys Ser Ser Asn Ile Thr Gly Leu Leu Leu Ile Arg Asp Gly Gly Ile
            420                 425                 430 aac act agc gat gcc acc gag acc ttc aga ccg gga gga gga gat atg    1344
Asn Thr Ser Asp Ala Thr Glu Thr Phe Arg Pro Gly Gly Gly Asp Met
            435                 440                 445 agg gac aat tgg aga agt gaa tta tat aaa tat aaa gta gtg aaa att    1392
Arg Asp Asn Trp Arg Ser Glu Leu Tyr Lys Tyr Lys Val Val Lys Ile
450                 455                 460 gag cca tta gga gta gca ccc acc aag gca aag aga aga gtg gtg cag    1440
Glu Pro Leu Gly Val Ala Pro Thr Lys Ala Lys Arg Arg Val Val Gln
465                 470                 475                 480 aga gaa aaa aga gca gta aca cta gga gct atg ttc ctt ggg ttc tta    1488
Arg Glu Lys Arg Ala Val Thr Leu Gly Ala Met Phe Leu Gly Phe Leu
            485                 490                 495 gga gca taa agc ttc                                                1503
Gly Ala  *  Ser Phe
            500

<210> SEQ ID NO 2
<211> LENGTH: 498
<212> TYPE: PRT
<213> ORGANISM: HIV

<400> SEQUENCE: 2

Gly Val Pro Val Trp Lys Glu Ala Thr Thr Thr Leu Phe Cys Ala Ser
1               5                   10                  15

Asp Ala Lys Ala Tyr Asp Thr Glu Val His Asn Val Trp Ala Thr His
            20                  25                  30

Ala Cys Val Pro Thr Asp Pro Asn Pro Gln Glu Met Val Leu Glu Asn
        35                  40                  45

Val Thr Glu Asp Phe Asn Met Trp Lys Asn Asp Met Val Glu Gln Met
    50                  55                  60

His Glu Asp Ile Ile Ser Leu Trp Asp Gln Ser Leu Lys Pro Cys Val
65                  70                  75                  80

Lys Leu Thr Pro Leu Cys Ile Thr Leu Asn Cys Thr Asn Trp Lys Lys
                85                  90                  95

Asn Asp Thr Lys Thr Asn Ser Ser Thr Thr Thr Asn Asn Ser Ser
            100                 105                 110

Ala Thr Ala Asn Ser Ser Ser Thr Thr Thr Asn Ser Ser Trp Gly Glu
        115                 120                 125

Ile Lys Glu Gly Glu Ile Lys Asn Cys Ser Phe Asn Ile Thr Thr Ser
```

```
        130                 135                 140
Ile Arg Asp Lys Val Lys Lys Glu Tyr Ala Leu Phe Tyr Ser Leu Asp
145                 150                 155                 160

Val Val Pro Ile Glu Asn Asp Asn Thr Ser Tyr Arg Leu Arg Ser Cys
                165                 170                 175

Asn Thr Ser Val Ile Thr Gln Ala Cys Pro Lys Val Thr Phe Glu Pro
            180                 185                 190

Ile Pro Ile His Tyr Cys Thr Pro Ala Gly Phe Ala Ile Leu Lys Cys
        195                 200                 205

Arg Asp Lys Lys Phe Asn Gly Thr Gly Pro Cys Lys Asn Val Ser Thr
    210                 215                 220

Val Gln Cys Ala His Gly Ile Lys Pro Val Val Ser Thr Gln Leu Leu
225                 230                 235                 240

Leu Asn Gly Ser Leu Ala Glu Glu Val Ile Ile Arg Ser Ala Asn
                245                 250                 255

Phe Ser Asn Asn Ala Lys Ile Ile Val Gln Leu Arg Glu Pro Val
                260                 265                 270

Glu Ile Asn Cys Thr Arg Pro Ser Asn Thr Ile Lys Gly Ile His
                275                 280                 285

Ile Gly Pro Gly Arg Ala Phe Tyr Ala Thr Gly Asp Ile Arg Gly Asp
290                 295                 300

Ile Arg Gln Ala His Cys Asn Ile Ser Gly Ala Lys Trp Asn Asn Thr
305                 310                 315                 320

Leu Lys Lys Val Val Lys Lys Leu Lys Glu Gln Phe Pro Asn Lys Thr
                325                 330                 335

Ile Val Phe Asn His Ser Ser Gly Gly Asp Pro Glu Ile Val Met His
                340                 345                 350

Ser Phe Asn Cys Gln Gly Glu Phe Phe Tyr Cys Asn Thr Thr Lys Leu
                355                 360                 365

Phe Asn Ser Thr Trp Asn Asp Thr Thr Glu Ser Asn Asn Asp Ser
    370                 375                 380

Thr Ile Thr Leu Pro Cys Arg Ile Lys Gln Ile Ile Asn Met Trp Gln
385                 390                 395                 400

Glu Ile Gly Lys Ala Met Tyr Ala Pro Pro Thr Arg Gly Glu Ile Lys
                405                 410                 415

Cys Ser Ser Asn Ile Thr Gly Leu Leu Leu Ile Arg Asp Gly Gly Ile
                420                 425                 430

Asn Thr Ser Asp Ala Thr Glu Thr Phe Arg Pro Gly Gly Gly Asp Met
            435                 440                 445

Arg Asp Asn Trp Arg Ser Glu Leu Tyr Lys Tyr Lys Val Val Lys Ile
    450                 455                 460

Glu Pro Leu Gly Val Ala Pro Thr Lys Ala Lys Arg Arg Val Val Gln
465                 470                 475                 480

Arg Glu Lys Arg Ala Val Thr Leu Gly Ala Met Phe Leu Gly Phe Leu
                485                 490                 495

Gly Ala

<210> SEQ ID NO 3
<211> LENGTH: 2
<212> TYPE: PRT
<213> ORGANISM: HIV

<400> SEQUENCE: 3

Ser Phe
```

```
<210> SEQ ID NO 4
<211> LENGTH: 1503
<212> TYPE: DNA
<213> ORGANISM: HIV
<220> FEATURE:
<221> NAME/KEY: CDS
<222> LOCATION: (1)...(1503)
<221> NAME/KEY: misc_feature
<222> LOCATION: (1)...(1503)
<223> OTHER INFORMATION: n = A,T,C or G

<400> SEQUENCE: 4
```

| | | | | | | | | | | | | | | | | |
|---|---|---|---|---|---|---|---|---|---|---|---|---|---|---|---|---|
| ggg | gta | cct | gta | tgg | aaa | gaa | gca | acc | acc | act | cta | ttt | tgt | gca | tca | 48 |
| Gly | Val | Pro | Val | Trp | Lys | Glu | Ala | Thr | Thr | Thr | Leu | Phe | Cys | Ala | Ser | |
| 1 | | | | 5 | | | | | 10 | | | | | 15 | | |
| gat | gct | aaa | gca | tat | gac | aca | gag | gtg | cat | aat | gtt | tgg | gcc | aca | cat | 96 |
| Asp | Ala | Lys | Ala | Tyr | Asp | Thr | Glu | Val | His | Asn | Val | Trp | Ala | Thr | His | |
| | | | | 20 | | | | | 25 | | | | | 30 | | |
| gct | tgt | gta | ccc | aca | gac | cca | aac | cca | caa | gaa | atg | gta | ttg | gaa | aat | 144 |
| Ala | Cys | Val | Pro | Thr | Asp | Pro | Asn | Pro | Gln | Glu | Met | Val | Leu | Glu | Asn | |
| | | 35 | | | | | 40 | | | | | 45 | | | | |
| gtg | aca | gaa | gat | ttt | aac | atg | tgg | aaa | aat | gac | atg | gta | gaa | cag | atg | 192 |
| Val | Thr | Glu | Asp | Phe | Asn | Met | Trp | Lys | Asn | Asp | Met | Val | Glu | Gln | Met | |
| | 50 | | | | | 55 | | | | | 60 | | | | | |
| cat | gag | ant | ata | atc | agt | tta | tgg | gat | caa | agc | cta | aaa | cca | tgt | gta | 240 |
| His | Glu | Xaa | Ile | Ile | Ser | Leu | Trp | Asp | Gln | Ser | Leu | Lys | Pro | Cys | Val | |
| 65 | | | | | 70 | | | | | 75 | | | | | 80 | |
| aaa | tta | acc | cca | ctc | tgt | att | act | tta | aat | tgc | acc | aat | tgg | aag | gag | 288 |
| Lys | Leu | Thr | Pro | Leu | Cys | Ile | Thr | Leu | Asn | Cys | Thr | Asn | Trp | Lys | Glu | |
| | | | | 85 | | | | | 90 | | | | | 95 | | |
| aat | gat | act | aaa | act | aat | agt | agt | agt | act | aca | act | aat | agt | agt | agt | 336 |
| Asn | Asp | Thr | Lys | Thr | Asn | Ser | Ser | Ser | Thr | Thr | Thr | Asn | Asn | Ser | Ser | |
| | | | | 100 | | | | | 105 | | | | | 110 | | |
| gct | aca | gct | aat | agt | agt | agt | act | aca | act | aat | agt | agt | tgg | gga | gag | 384 |
| Ala | Thr | Ala | Asn | Ser | Ser | Ser | Thr | Thr | Thr | Asn | Ser | Ser | Trp | Gly | Glu | |
| | | 115 | | | | | 120 | | | | | 125 | | | | |
| ata | aag | gag | gga | gaa | ata | aag | aac | tgc | tct | ttc | aat | atc | acc | aca | ggc | 432 |
| Ile | Lys | Glu | Gly | Glu | Ile | Lys | Asn | Cys | Ser | Phe | Asn | Ile | Thr | Thr | Gly | |
| | 130 | | | | | 135 | | | | | 140 | | | | | |
| ata | aga | gac | aag | gtg | aag | aaa | gaa | tat | gca | ctt | ttt | tat | agc | ctt | gat | 480 |
| Ile | Arg | Asp | Lys | Val | Lys | Lys | Glu | Tyr | Ala | Leu | Phe | Tyr | Ser | Leu | Asp | |
| 145 | | | | | 150 | | | | | 155 | | | | | 160 | |
| gta | gta | cca | ata | gaa | aat | gat | aat | act | agc | tat | agg | ttg | aga | agt | tgt | 528 |
| Val | Val | Pro | Ile | Glu | Asn | Asp | Asn | Thr | Ser | Tyr | Arg | Leu | Arg | Ser | Cys | |
| | | | | 165 | | | | | 170 | | | | | 175 | | |
| aac | acc | tca | gtc | att | aca | caa | gcc | tgt | cca | aag | gta | act | ttt | gag | cca | 576 |
| Asn | Thr | Ser | Val | Ile | Thr | Gln | Ala | Cys | Pro | Lys | Val | Thr | Phe | Glu | Pro | |
| | | | | 180 | | | | | 185 | | | | | 190 | | |
| att | ccc | ata | cat | tat | tgt | acc | ccg | gct | ggt | ttt | gcg | att | ctg | aag | tgt | 624 |
| Ile | Pro | Ile | His | Tyr | Cys | Thr | Pro | Ala | Gly | Phe | Ala | Ile | Leu | Lys | Cys | |
| | | 195 | | | | | 200 | | | | | 205 | | | | |
| aaa | gat | aaa | aag | ttc | aat | gga | aca | gga | cca | tgc | aaa | aat | gtt | agc | aca | 672 |
| Lys | Asp | Lys | Lys | Phe | Asn | Gly | Thr | Gly | Pro | Cys | Lys | Asn | Val | Ser | Thr | |
| | 210 | | | | | 215 | | | | | 220 | | | | | |
| gta | caa | tgt | aca | cat | gga | att | aag | cca | gta | gtg | tca | act | caa | ctg | ctg | 720 |
| Val | Gln | Cys | Thr | His | Gly | Ile | Lys | Pro | Val | Val | Ser | Thr | Gln | Leu | Leu | |
| 225 | | | | | 230 | | | | | 235 | | | | | 240 | |
| tta | aat | ggc | agc | cta | gca | gaa | gaa | gag | gta | ata | att | aga | tct | gcc | aat | 768 |
| Leu | Asn | Gly | Ser | Leu | Ala | Glu | Glu | Glu | Val | Ile | Ile | Arg | Ser | Ala | Asn | |
| | | | | 245 | | | | | 250 | | | | | 255 | | |

```
ttc tca aac aat gct aaa atc ata ata gta cag ttg aag gaa cct gta      816
Phe Ser Asn Asn Ala Lys Ile Ile Ile Val Gln Leu Lys Glu Pro Val
            260                 265                 270 gaa att aat tgt aca aga ccc agc aac aat aca ata aaa ggt ata cac      864
Glu Ile Asn Cys Thr Arg Pro Ser Asn Asn Thr Ile Lys Gly Ile His
        275                 280                 285 ata gga cca ggg aga gca ttt tat gca aca gga gac ata cga gga gat      912
Ile Gly Pro Gly Arg Ala Phe Tyr Ala Thr Gly Asp Ile Arg Gly Asp
    290                 295                 300 ata aga caa gca cat tgt aac att agt gga gca aaa tgg aat aac act      960
Ile Arg Gln Ala His Cys Asn Ile Ser Gly Ala Lys Trp Asn Asn Thr
305                 310                 315                 320 tta aag aag gta gtt ata aaa tta aaa gaa caa ttt cca aat aaa aca     1008
Leu Lys Lys Val Val Ile Lys Leu Lys Glu Gln Phe Pro Asn Lys Thr
                325                 330                 335 ata gtc ttt aac cat tcc tca gga ggg gac cca gaa att gta atg cac     1056
Ile Val Phe Asn His Ser Ser Gly Gly Asp Pro Glu Ile Val Met His
            340                 345                 350 agt ttt aat tgt caa ggg gaa ttt ttc tac tgt aat aca acg aag ctg     1104
Ser Phe Asn Cys Gln Gly Glu Phe Phe Tyr Cys Asn Thr Thr Lys Leu
        355                 360                 365 ttt aat agt act tgg aat gat act aca gag tca aat aac aat gat agt     1152
Phe Asn Ser Thr Trp Asn Asp Thr Thr Glu Ser Asn Asn Asn Asp Ser
    370                 375                 380 act att aca ctc cca tgc aga ata aaa caa att ata aac atg tgg cag     1200
Thr Ile Thr Leu Pro Cys Arg Ile Lys Gln Ile Ile Asn Met Trp Gln
385                 390                 395                 400 gaa gta gga aaa gca atg tat gcc cct ccc atc aga gga gaa att aaa     1248
Glu Val Gly Lys Ala Met Tyr Ala Pro Pro Ile Arg Gly Glu Ile Lys
                405                 410                 415 tgt tca tca aat att aca gga cta ctg tta aca aga gat ggt ggt att     1296
Cys Ser Ser Asn Ile Thr Gly Leu Leu Leu Thr Arg Asp Gly Gly Ile
            420                 425                 430 aac act agc gat gcc acc gag acc ttc aga ccg gga gga gga gat atg     1344
Asn Thr Ser Asp Ala Thr Glu Thr Phe Arg Pro Gly Gly Gly Asp Met
        435                 440                 445 agg gac aat tgg aga agt gaa tta tat aaa tat aaa gta gtg aaa att     1392
Arg Asp Asn Trp Arg Ser Glu Leu Tyr Lys Tyr Lys Val Val Lys Ile
    450                 455                 460 gag cca tta gga gta gca ccc acc aag gca aag aga aga gtg gtg cag     1440
Glu Pro Leu Gly Val Ala Pro Thr Lys Ala Lys Arg Arg Val Val Gln
465                 470                 475                 480 aga gaa aaa aga gca gta aca cta gga gct atg ttc ctt ggg ttc ttg     1488
Arg Glu Lys Arg Ala Val Thr Leu Gly Ala Met Phe Leu Gly Phe Leu
                485                 490                 495 gga gca taa agc ttc                                                  1503
Gly Ala  *  Ser Phe
             500

<210> SEQ ID NO 5
<211> LENGTH: 498
<212> TYPE: PRT
<213> ORGANISM: HIV
<220> FEATURE:
<221> NAME/KEY: VARIANT
<222> LOCATION: (1)...(498)
<223> OTHER INFORMATION: Xaa = Any Amino Acid

<400> SEQUENCE: 5

Gly Val Pro Val Trp Lys Glu Ala Thr Thr Thr Leu Phe Cys Ala Ser
 1               5                  10                  15
```

-continued

```
Asp Ala Lys Ala Tyr Asp Thr Glu Val His Asn Val Trp Ala Thr His
             20                  25                  30
Ala Cys Val Pro Thr Asp Pro Asn Pro Gln Glu Met Val Leu Glu Asn
         35                  40                  45
Val Thr Glu Asp Phe Asn Met Trp Lys Asn Asp Met Val Glu Gln Met
 50                  55                  60
His Glu Xaa Ile Ile Ser Leu Trp Asp Gln Ser Leu Lys Pro Cys Val
 65                  70                  75                  80
Lys Leu Thr Pro Leu Cys Ile Thr Leu Asn Cys Thr Asn Trp Lys Glu
                 85                  90                  95
Asn Asp Thr Lys Thr Asn Ser Ser Thr Thr Thr Asn Asn Ser Ser
             100                 105                 110
Ala Thr Ala Asn Ser Ser Ser Thr Thr Thr Asn Ser Ser Trp Gly Glu
         115                 120                 125
Ile Lys Glu Gly Glu Ile Lys Asn Cys Ser Phe Asn Ile Thr Thr Gly
             130                 135                 140
Ile Arg Asp Lys Val Lys Lys Glu Tyr Ala Leu Phe Tyr Ser Leu Asp
145                 150                 155                 160
Val Val Pro Ile Glu Asn Asp Asn Thr Ser Tyr Arg Leu Arg Ser Cys
                 165                 170                 175
Asn Thr Ser Val Ile Thr Gln Ala Cys Pro Lys Val Thr Phe Glu Pro
             180                 185                 190
Ile Pro Ile His Tyr Cys Thr Pro Ala Gly Phe Ala Ile Leu Lys Cys
             195                 200                 205
Lys Asp Lys Lys Phe Asn Gly Thr Gly Pro Cys Lys Asn Val Ser Thr
210                 215                 220
Val Gln Cys Thr His Gly Ile Lys Pro Val Val Ser Thr Gln Leu Leu
225                 230                 235                 240
Leu Asn Gly Ser Leu Ala Glu Glu Glu Val Ile Ile Arg Ser Ala Asn
                 245                 250                 255
Phe Ser Asn Asn Ala Lys Ile Ile Ile Val Gln Leu Lys Glu Pro Val
             260                 265                 270
Glu Ile Asn Cys Thr Arg Pro Ser Asn Asn Thr Ile Lys Gly Ile His
         275                 280                 285
Ile Gly Pro Gly Arg Ala Phe Tyr Ala Thr Gly Asp Ile Arg Gly Asp
 290                 295                 300
Ile Arg Gln Ala His Cys Asn Ile Ser Gly Ala Lys Trp Asn Asn Thr
305                 310                 315                 320
Leu Lys Lys Val Val Ile Lys Leu Lys Glu Gln Phe Pro Asn Lys Thr
                 325                 330                 335
Ile Val Phe Asn His Ser Ser Gly Gly Asp Pro Glu Ile Val Met His
             340                 345                 350
Ser Phe Asn Cys Gln Gly Glu Phe Phe Tyr Cys Asn Thr Thr Lys Leu
         355                 360                 365
Phe Asn Ser Thr Trp Asn Asp Thr Thr Glu Ser Asn Asn Asn Asp Ser
     370                 375                 380
Thr Ile Thr Leu Pro Cys Arg Ile Lys Gln Ile Ile Asn Met Trp Gln
385                 390                 395                 400
Glu Val Gly Lys Ala Met Tyr Ala Pro Pro Ile Arg Gly Glu Ile Lys
                 405                 410                 415
Cys Ser Ser Asn Ile Thr Gly Leu Leu Leu Thr Arg Asp Gly Gly Ile
             420                 425                 430
```

```
Asn Thr Ser Asp Ala Thr Glu Thr Phe Arg Pro Gly Gly Gly Asp Met
        435                 440                 445

Arg Asp Asn Trp Arg Ser Glu Leu Tyr Lys Tyr Lys Val Val Lys Ile
        450                 455                 460

Glu Pro Leu Gly Val Ala Pro Thr Lys Ala Lys Arg Arg Val Val Gln
465                 470                 475                 480

Arg Glu Lys Arg Ala Val Thr Leu Gly Ala Met Phe Leu Gly Phe Leu
                485                 490                 495

Gly Ala

<210> SEQ ID NO 6
<211> LENGTH: 2
<212> TYPE: PRT
<213> ORGANISM: HIV

<400> SEQUENCE: 6

Ser Phe
 1

<210> SEQ ID NO 7
<211> LENGTH: 1461
<212> TYPE: DNA
<213> ORGANISM: HIV
<220> FEATURE:
<221> NAME/KEY: CDS
<222> LOCATION: (2)...(1459)

<400> SEQUENCE: 7 g gta cct gta tgg aaa gaa gca acc acc act cta ttt tgt gca tca gat      49
  Val Pro Val Trp Lys Glu Ala Thr Thr Thr Leu Phe Cys Ala Ser Asp
   1               5                  10                  15 gct aaa gca tat gat aca gag gta cat aat gtt tgg gct aca cat gcc        97
Ala Lys Ala Tyr Asp Thr Glu Val His Asn Val Trp Ala Thr His Ala
             20                  25                  30 tgt gta ccc aca gac ccc aac cca caa gaa gta gta ttg gaa aat gta       145
Cys Val Pro Thr Asp Pro Asn Pro Gln Glu Val Val Leu Glu Asn Val
         35                  40                  45 aca gaa aat ttt aac atg tgg aaa aat aac atg gta gaa cag atg cat       193
Thr Glu Asn Phe Asn Met Trp Lys Asn Asn Met Val Glu Gln Met His
     50                  55                  60 gag gat ata atc agt tta tgg gat caa agt cta aag cca tgt gta aaa       241
Glu Asp Ile Ile Ser Leu Trp Asp Gln Ser Leu Lys Pro Cys Val Lys
 65                  70                  75                  80 tta acc cca ctc tgt gtt act tta aat tgc act aat ttg gag aat gct       289
Leu Thr Pro Leu Cys Val Thr Leu Asn Cys Thr Asn Leu Glu Asn Ala
                 85                  90                  95 aat aat acc gag aat gct aat aat acc aat aat tat acc ttg ggg atg       337
Asn Asn Thr Glu Asn Ala Asn Asn Thr Asn Asn Tyr Thr Leu Gly Met
            100                 105                 110 gag aga ggt gaa ata aaa aac tgc tct ttc aat atc acc aca agc tta       385
Glu Arg Gly Glu Ile Lys Asn Cys Ser Phe Asn Ile Thr Thr Ser Leu
        115                 120                 125 aga gat aag gtg aaa aaa gaa tat gca ttg ttt tat aaa ctt gat gta       433
Arg Asp Lys Val Lys Lys Glu Tyr Ala Leu Phe Tyr Lys Leu Asp Val
    130                 135                 140 gta caa ata gat aat agt acc aac tat agg ctg ata agt tgt aat acc       481
Val Gln Ile Asp Asn Ser Thr Asn Tyr Arg Leu Ile Ser Cys Asn Thr
145                 150                 155                 160 tca gtc att aca cag gcc tgt cca aag gta tcc ttt gag cta att ccc       529
Ser Val Ile Thr Gln Ala Cys Pro Lys Val Ser Phe Glu Leu Ile Pro
                165                 170                 175
```

-continued

```
ata cat tat tgt gcc ccg gct ggt ttt gcg att cta aag tgt aaa gat      577
Ile His Tyr Cys Ala Pro Ala Gly Phe Ala Ile Leu Lys Cys Lys Asp
            180                 185                 190 aag aag ttc aat gga aca gga cca tgt aaa aat gtc agc aca gta caa      625
Lys Lys Phe Asn Gly Thr Gly Pro Cys Lys Asn Val Ser Thr Val Gln
        195                 200                 205 tgt aca cat gga att aga cca gta gta tca act caa cta ctg tta aat      673
Cys Thr His Gly Ile Arg Pro Val Val Ser Thr Gln Leu Leu Leu Asn
        210                 215                 220 ggc agt cta gca gaa gaa gag ata gta att aga tct gaa aat atc aca      721
Gly Ser Leu Ala Glu Glu Glu Ile Val Ile Arg Ser Glu Asn Ile Thr
225                 230                 235                 240 gac aat gct aaa acc ata ata gtg cag cta aat gaa tct ata gtg att      769
Asp Asn Ala Lys Thr Ile Ile Val Gln Leu Asn Glu Ser Ile Val Ile
                245                 250                 255 aat tgt aca aga ccc aat aac aac aca aga aaa agt ata aat ata gga      817
Asn Cys Thr Arg Pro Asn Asn Asn Thr Arg Lys Ser Ile Asn Ile Gly
                260                 265                 270 cca ggg aga gca ttc tat aca aca gga gac ata ata gga gat ata aga      865
Pro Gly Arg Ala Phe Tyr Thr Thr Gly Asp Ile Ile Gly Asp Ile Arg
            275                 280                 285 caa gca cat tgt aac ctt agt aaa aca caa tgg gaa aaa acg tta aga      913
Gln Ala His Cys Asn Leu Ser Lys Thr Gln Trp Glu Lys Thr Leu Arg
        290                 295                 300 cag ata gct ata aaa tta gaa gaa aaa ttt aag aat aaa aca ata gcc      961
Gln Ile Ala Ile Lys Leu Glu Glu Lys Phe Lys Asn Lys Thr Ile Ala
305                 310                 315                 320 ttt aat aaa tcc tca gga ggg gac cca gaa att gta atg cac agt ttt     1009
Phe Asn Lys Ser Ser Gly Gly Asp Pro Glu Ile Val Met His Ser Phe
                325                 330                 335 aat tgt gga ggg gaa ttt ttc tac tgt aat aca aca aaa ctg ttt aat     1057
Asn Cys Gly Gly Glu Phe Phe Tyr Cys Asn Thr Thr Lys Leu Phe Asn
                340                 345                 350 agt acc tgg aat tta aca caa ccg ttt agt aat acc ggg aat cgt act     1105
Ser Thr Trp Asn Leu Thr Gln Pro Phe Ser Asn Thr Gly Asn Arg Thr
            355                 360                 365 gaa gag tta aat att aca ctc cca tgc aga ata aaa caa atc ata aac     1153
Glu Glu Leu Asn Ile Thr Leu Pro Cys Arg Ile Lys Gln Ile Ile Asn
370                 375                 380 ttg tgg cag gaa gta ggc aaa gca atg tat gcc cct ccc atc aga gga     1201
Leu Trp Gln Glu Val Gly Lys Ala Met Tyr Ala Pro Pro Ile Arg Gly
385                 390                 395                 400 caa att aga tgt tca tca aat att aca ggg cta cta tta aca aga gat     1249
Gln Ile Arg Cys Ser Ser Asn Ile Thr Gly Leu Leu Leu Thr Arg Asp
                405                 410                 415 ggt gga agt aac acc ggt gac aac agg act gag acc ttt aga cct gga     1297
Gly Gly Ser Asn Thr Gly Asp Asn Arg Thr Glu Thr Phe Arg Pro Gly
            420                 425                 430 gga gga gat atg agg gac aat tgg aga agt gaa tta tat aaa tat aaa     1345
Gly Gly Asp Met Arg Asp Asn Trp Arg Ser Glu Leu Tyr Lys Tyr Lys
        435                 440                 445 gta gta aga att gaa cca tta gga gta gca ccc acc cag gca aag aga     1393
Val Val Arg Ile Glu Pro Leu Gly Val Ala Pro Thr Gln Ala Lys Arg
        450                 455                 460 aga gtg gtg caa aga gaa aaa aga gca gtg ggg ata gga gct atg ttc     1441
Arg Val Val Gln Arg Glu Lys Arg Ala Val Gly Ile Gly Ala Met Phe
465                 470                 475                 480 ctt ggg ttc ttg gga gat aa                                          1461
Leu Gly Phe Leu Gly Asp
```

485

```
<210> SEQ ID NO 8
<211> LENGTH: 486
<212> TYPE: PRT
<213> ORGANISM: HIV

<400> SEQUENCE: 8
```

| | | | | | | | | | | | | | | |
|---|---|---|---|---|---|---|---|---|---|---|---|---|---|---|
|Val|Pro|Val|Trp|Lys|Glu|Ala|Thr|Thr|Thr|Leu|Phe|Cys|Ala|Ser|Asp
|1| | | |5| | | | |10| | | | |15|
|Ala|Lys|Ala|Tyr|Asp|Thr|Glu|Val|His|Asn|Val|Trp|Ala|Thr|His|Ala
| | | | |20| | | | |25| | | | |30| |
|Cys|Val|Pro|Thr|Asp|Pro|Asn|Pro|Gln|Glu|Val|Val|Leu|Glu|Asn|Val
| | | | |35| | | | |40| | | | |45| |
|Thr|Glu|Asn|Phe|Asn|Met|Trp|Lys|Asn|Asn|Met|Val|Glu|Gln|Met|His
| |50| | | | |55| | | | |60| | | | |
|Glu|Asp|Ile|Ile|Ser|Leu|Trp|Asp|Gln|Ser|Leu|Lys|Pro|Cys|Val|Lys
|65| | | | |70| | | | |75| | | | |80|
|Leu|Thr|Pro|Leu|Cys|Val|Thr|Leu|Asn|Cys|Thr|Asn|Leu|Glu|Asn|Ala
| | | | |85| | | | |90| | | | |95| |
|Asn|Asn|Thr|Glu|Asn|Ala|Asn|Asn|Thr|Asn|Asn|Tyr|Thr|Leu|Gly|Met
| | | | |100| | | | |105| | | | |110| |
|Glu|Arg|Gly|Glu|Ile|Lys|Asn|Cys|Ser|Phe|Asn|Ile|Thr|Thr|Ser|Leu
| | | | |115| | | | |120| | | | |125| |
|Arg|Asp|Lys|Val|Lys|Lys|Glu|Tyr|Ala|Leu|Phe|Tyr|Lys|Leu|Asp|Val
| | | | |130| | | | |135| | | | |140| |
|Val|Gln|Ile|Asp|Asn|Ser|Thr|Asn|Tyr|Arg|Leu|Ile|Ser|Cys|Asn|Thr
|145| | | | |150| | | | |155| | | | |160|
|Ser|Val|Ile|Thr|Gln|Ala|Cys|Pro|Lys|Val|Ser|Phe|Glu|Leu|Ile|Pro
| | | | |165| | | | |170| | | | |175| |
|Ile|His|Tyr|Cys|Ala|Pro|Ala|Gly|Phe|Ala|Ile|Leu|Lys|Cys|Lys|Asp
| | | | |180| | | | |185| | | | |190| |
|Lys|Lys|Phe|Asn|Gly|Thr|Gly|Pro|Cys|Lys|Asn|Val|Ser|Thr|Val|Gln
| | | | |195| | | | |200| | | | |205| |
|Cys|Thr|His|Gly|Ile|Arg|Pro|Val|Val|Ser|Thr|Gln|Leu|Leu|Leu|Asn
| | | | |210| | | | |215| | | | |220| |
|Gly|Ser|Leu|Ala|Glu|Glu|Glu|Ile|Val|Ile|Arg|Ser|Glu|Asn|Ile|Thr
|225| | | | |230| | | | |235| | | | |240|
|Asp|Asn|Ala|Lys|Thr|Ile|Ile|Val|Gln|Leu|Asn|Glu|Ser|Ile|Val|Ile
| | | | |245| | | | |250| | | | |255| |
|Asn|Cys|Thr|Arg|Pro|Asn|Asn|Asn|Thr|Arg|Lys|Ser|Ile|Asn|Ile|Gly
| | | | |260| | | | |265| | | | |270| |
|Pro|Gly|Arg|Ala|Phe|Tyr|Thr|Thr|Gly|Asp|Ile|Ile|Gly|Asp|Ile|Arg
| | | | |275| | | | |280| | | | |285| |
|Gln|Ala|His|Cys|Asn|Leu|Ser|Lys|Thr|Gln|Trp|Glu|Lys|Thr|Leu|Arg
| | | | |290| | | | |295| | | | |300| |
|Gln|Ile|Ala|Ile|Lys|Leu|Glu|Glu|Lys|Phe|Lys|Asn|Lys|Thr|Ile|Ala
|305| | | | |310| | | | |315| | | | |320|
|Phe|Asn|Lys|Ser|Ser|Gly|Gly|Asp|Pro|Glu|Ile|Val|Met|His|Ser|Phe
| | | | |325| | | | |330| | | | |335| |
|Asn|Cys|Gly|Gly|Glu|Phe|Phe|Tyr|Cys|Asn|Thr|Thr|Lys|Leu|Phe|Asn
| | | | |340| | | | |345| | | | |350| |
|Ser|Thr|Trp|Asn|Leu|Thr|Gln|Pro|Phe|Ser|Asn|Thr|Gly|Asn|Arg|Thr
| | | | |355| | | | |360| | | | |365| |

```
Glu Glu Leu Asn Ile Thr Leu Pro Cys Arg Ile Lys Gln Ile Ile Asn
    370                 375                 380
Leu Trp Gln Glu Val Gly Lys Ala Met Tyr Ala Pro Pro Ile Arg Gly
385                 390                 395                 400
Gln Ile Arg Cys Ser Ser Asn Ile Thr Gly Leu Leu Leu Thr Arg Asp
                405                 410                 415
Gly Gly Ser Asn Thr Gly Asp Asn Arg Thr Glu Thr Phe Arg Pro Gly
            420                 425                 430
Gly Gly Asp Met Arg Asp Asn Trp Arg Ser Glu Leu Tyr Lys Tyr Lys
            435                 440                 445
Val Val Arg Ile Glu Pro Leu Gly Val Ala Pro Thr Gln Ala Lys Arg
        450                 455                 460
Arg Val Val Gln Arg Glu Lys Arg Ala Val Gly Ile Gly Ala Met Phe
465                 470                 475                 480
Leu Gly Phe Leu Gly Asp
                485

<210> SEQ ID NO 9
<211> LENGTH: 1474
<212> TYPE: DNA
<213> ORGANISM: HIV
<220> FEATURE:
<221> NAME/KEY: CDS
<222> LOCATION: (2)...(1474)

<400> SEQUENCE: 9 g gta cct gtg tgg aaa gaa gca acc acc act cta ttt tgt gca tca gat      49
  Val Pro Val Trp Lys Glu Ala Thr Thr Thr Leu Phe Cys Ala Ser Asp
  1               5                   10                  15 gct aaa gca tat gat aca gag gta cat aat gtt tgg gct aca cat gcc      97
Ala Lys Ala Tyr Asp Thr Glu Val His Asn Val Trp Ala Thr His Ala
            20                  25                  30 tgt gta ccc aca gac ccc aac cca caa gaa gta gta ttg gaa aat gta     145
Cys Val Pro Thr Asp Pro Asn Pro Gln Glu Val Val Leu Glu Asn Val
        35                  40                  45 aca gaa aat ttt aac atg tgg aaa aat aac atg gta gaa cag atg cat     193
Thr Glu Asn Phe Asn Met Trp Lys Asn Asn Met Val Glu Gln Met His
    50                  55                  60 gag gat ata atc agt tta tgg gat caa agt cta aag cca tgt gta aaa     241
Glu Asp Ile Ile Ser Leu Trp Asp Gln Ser Leu Lys Pro Cys Val Lys
65                  70                  75                  80 tta acc cca ctc tgt gtt act tta aat tgc act aat ttg gag aat gct     289
Leu Thr Pro Leu Cys Val Thr Leu Asn Cys Thr Asn Leu Glu Asn Ala
                85                  90                  95 aat aat acc gag aat gct aat aat acc aat aat tat acc ttg ggg atg     337
Asn Asn Thr Glu Asn Ala Asn Asn Thr Asn Asn Tyr Thr Leu Gly Met
            100                 105                 110 gag aga ggt gaa aga aaa aac tgc tct ttc aat atc acc aca agc tta     385
Glu Arg Gly Glu Arg Lys Asn Cys Ser Phe Asn Ile Thr Thr Ser Leu
        115                 120                 125 aga gat aag ggg aaa aaa gaa tat gca ttg ttt tat aaa ctt gat gta     433
Arg Asp Lys Gly Lys Lys Glu Tyr Ala Leu Phe Tyr Lys Leu Asp Val
    130                 135                 140 gta caa ata gat aat agt acc aac tat agg ctg ata agt tgt aat acc     481
Val Gln Ile Asp Asn Ser Thr Asn Tyr Arg Leu Ile Ser Cys Asn Thr
145                 150                 155                 160 tca gtc att aca cag gcc tgt cca aag gta tcc ttt gag cca att ccc     529
Ser Val Ile Thr Gln Ala Cys Pro Lys Val Ser Phe Glu Pro Ile Pro
                165                 170                 175
```

```
ata cat tat tgt gcc ccg gct ggt ttt gcg att cta aag tgt aaa gat     577
Ile His Tyr Cys Ala Pro Ala Gly Phe Ala Ile Leu Lys Cys Lys Asp
        180                 185                 190 aag aag ttc aat gga aca gga cca tgt aaa aat gtc agg aca gta caa     625
Lys Lys Phe Asn Gly Thr Gly Pro Cys Lys Asn Val Arg Thr Val Gln
            195                 200                 205 tgt aca cat gga att aga cca gta gta tca act caa cta ctg tta aat     673
Cys Thr His Gly Ile Arg Pro Val Val Ser Thr Gln Leu Leu Leu Asn
        210                 215                 220 ggc agt cta gca gaa gaa gag ata gta att aga tct gaa aat atc aca     721
Gly Ser Leu Ala Glu Glu Glu Ile Val Ile Arg Ser Glu Asn Ile Thr
225                 230                 235                 240 gac aat gct aaa acc ata ata gtg cag cta aat gaa tct ata gtg att     769
Asp Asn Ala Lys Thr Ile Ile Val Gln Leu Asn Glu Ser Ile Val Ile
                245                 250                 255 aat tgt aca aga ccc aat aac aac aca aga aaa agt ata aat ata gga     817
Asn Cys Thr Arg Pro Asn Asn Asn Thr Arg Lys Ser Ile Asn Ile Gly
            260                 265                 270 cca ggg aga gca ttc tat aca aca gga gac ata ata gga gat ata aga     865
Pro Gly Arg Ala Phe Tyr Thr Thr Gly Asp Ile Ile Gly Asp Ile Arg
        275                 280                 285 caa gca cat tgt aac ctt agt aaa aca caa tgg gaa aaa acg tta aga     913
Gln Ala His Cys Asn Leu Ser Lys Thr Gln Trp Glu Lys Thr Leu Arg
    290                 295                 300 cag ata gct ata aaa tta gaa gaa aaa ttt aag aat aaa aca ata gcc     961
Gln Ile Ala Ile Lys Leu Glu Glu Lys Phe Lys Asn Lys Thr Ile Ala
305                 310                 315                 320 ttt aat aaa tcc tca gga ggg gac cca gaa att gta atg cac agt ttt    1009
Phe Asn Lys Ser Ser Gly Gly Asp Pro Glu Ile Val Met His Ser Phe
                325                 330                 335 aat tgt gga ggg gga ttt ttc tac tgt agt acg aga aaa ctg ttt aat    1057
Asn Cys Gly Gly Gly Phe Phe Tyr Cys Ser Thr Arg Lys Leu Phe Asn
            340                 345                 350 agt acc tgg aat tta aca caa ccg ttt agt aat acc ggg gat cgt act    1105
Ser Thr Trp Asn Leu Thr Gln Pro Phe Ser Asn Thr Gly Asp Arg Thr
        355                 360                 365 gaa gag tta aat att aca ctc cca tgc aga ata aaa caa atc ata aac    1153
Glu Glu Leu Asn Ile Thr Leu Pro Cys Arg Ile Lys Gln Ile Ile Asn
    370                 375                 380 ttg tgg cag gaa gta ggc aaa gca atg tat gcc cct ccc atc aga gga    1201
Leu Trp Gln Glu Val Gly Lys Ala Met Tyr Ala Pro Pro Ile Arg Gly
385                 390                 395                 400 caa att aga tgt tca tca aat att aca ggg cta cta tta agg aga gat    1249
Gln Ile Arg Cys Ser Ser Asn Ile Thr Gly Leu Leu Leu Arg Arg Asp
                405                 410                 415 ggt gga agt aac acc agt gac aac cag act gag acc ttt aga cct ggg    1297
Gly Gly Ser Asn Thr Ser Asp Asn Gln Thr Glu Thr Phe Arg Pro Gly
            420                 425                 430 gga gga gat atg agg gac aag tgg aga agt gaa tta tat aaa tat aaa    1345
Gly Gly Asp Met Arg Asp Lys Trp Arg Ser Glu Leu Tyr Lys Tyr Lys
        435                 440                 445 gta gta aga att gaa cca tta gga gta gca ccc acc cag gca aag aga    1393
Val Val Arg Ile Glu Pro Leu Gly Val Ala Pro Thr Gln Ala Lys Arg
    450                 455                 460 aga gtg gtg caa aga gaa aaa aga gca gtg ggg ata gga gct atg ttc    1441
Arg Val Val Gln Arg Glu Lys Arg Ala Val Gly Ile Gly Ala Met Phe
465                 470                 475                 480 ctt agg ttc tta gga gat aaa gct tct aga gtc                        1474
Leu Arg Phe Leu Gly Asp Lys Ala Ser Arg Val
                485                 490
```

```
<210> SEQ ID NO 10
<211> LENGTH: 491
<212> TYPE: PRT
<213> ORGANISM: HIV

<400> SEQUENCE: 10

Val Pro Val Trp Lys Glu Ala Thr Thr Thr Leu Phe Cys Ala Ser Asp
  1               5                  10                  15

Ala Lys Ala Tyr Asp Thr Glu Val His Asn Val Trp Ala Thr His Ala
             20                  25                  30

Cys Val Pro Thr Asp Pro Asn Pro Gln Glu Val Val Leu Glu Asn Val
         35                  40                  45

Thr Glu Asn Phe Asn Met Trp Lys Asn Asn Met Val Glu Gln Met His
 50                  55                  60

Glu Asp Ile Ile Ser Leu Trp Asp Gln Ser Leu Lys Pro Cys Val Lys
 65                  70                  75                  80

Leu Thr Pro Leu Cys Val Thr Leu Asn Cys Thr Asn Leu Glu Asn Ala
                 85                  90                  95

Asn Asn Thr Glu Asn Ala Asn Asn Thr Asn Asn Tyr Thr Leu Gly Met
            100                 105                 110

Glu Arg Gly Glu Arg Lys Asn Cys Ser Phe Asn Ile Thr Thr Ser Leu
        115                 120                 125

Arg Asp Lys Gly Lys Lys Glu Tyr Ala Leu Phe Tyr Lys Leu Asp Val
130                 135                 140

Val Gln Ile Asp Asn Ser Thr Asn Tyr Arg Leu Ile Ser Cys Asn Thr
145                 150                 155                 160

Ser Val Ile Thr Gln Ala Cys Pro Lys Val Ser Phe Glu Pro Ile Pro
                165                 170                 175

Ile His Tyr Cys Ala Pro Ala Gly Phe Ala Ile Leu Lys Cys Lys Asp
            180                 185                 190

Lys Lys Phe Asn Gly Thr Gly Pro Cys Lys Asn Val Arg Thr Val Gln
        195                 200                 205

Cys Thr His Gly Ile Arg Pro Val Val Ser Thr Gln Leu Leu Leu Asn
210                 215                 220

Gly Ser Leu Ala Glu Glu Glu Ile Val Ile Arg Ser Glu Asn Ile Thr
225                 230                 235                 240

Asp Asn Ala Lys Thr Ile Ile Val Gln Leu Asn Glu Ser Ile Val Ile
                245                 250                 255

Asn Cys Thr Arg Pro Asn Asn Asn Thr Arg Lys Ser Ile Asn Ile Gly
            260                 265                 270

Pro Gly Arg Ala Phe Tyr Thr Thr Gly Asp Ile Ile Gly Asp Ile Arg
        275                 280                 285

Gln Ala His Cys Asn Leu Ser Lys Thr Gln Trp Glu Lys Thr Leu Arg
290                 295                 300

Gln Ile Ala Ile Lys Leu Glu Glu Lys Phe Lys Asn Lys Thr Ile Ala
305                 310                 315                 320

Phe Asn Lys Ser Ser Gly Gly Asp Pro Glu Ile Val Met His Ser Phe
                325                 330                 335

Asn Cys Gly Gly Gly Phe Phe Tyr Cys Ser Thr Arg Lys Leu Phe Asn
            340                 345                 350

Ser Thr Trp Asn Leu Thr Gln Pro Phe Ser Asn Thr Gly Asp Arg Thr
        355                 360                 365

Glu Glu Leu Asn Ile Thr Leu Pro Cys Arg Ile Lys Gln Ile Ile Asn
```

```
        370                 375                 380
Leu Trp Gln Glu Val Gly Lys Ala Met Tyr Ala Pro Pro Ile Arg Gly
385                 390                 395                 400

Gln Ile Arg Cys Ser Ser Asn Ile Thr Gly Leu Leu Arg Arg Asp
                405                 410                 415

Gly Gly Ser Asn Thr Ser Asp Asn Gln Thr Glu Thr Phe Arg Pro Gly
                420                 425                 430

Gly Gly Asp Met Arg Asp Lys Trp Arg Ser Glu Leu Tyr Lys Tyr Lys
                435                 440                 445

Val Val Arg Ile Glu Pro Leu Gly Val Ala Pro Thr Gln Ala Lys Arg
                450                 455                 460

Arg Val Val Gln Arg Glu Lys Arg Ala Val Gly Ile Gly Ala Met Phe
465                 470                 475                 480

Leu Arg Phe Leu Gly Asp Lys Ala Ser Arg Val
                485                 490

<210> SEQ ID NO 11
<211> LENGTH: 1512
<212> TYPE: DNA
<213> ORGANISM: HIV
<220> FEATURE:
<221> NAME/KEY: CDS
<222> LOCATION: (1)...(1512)

<400> SEQUENCE: 11
```

| | | | | | | | | | | | | | | | | |
|---|---|---|---|---|---|---|---|---|---|---|---|---|---|---|---|---|
| ctc | gag | gta | cct | gta | tgg | aaa | gaa | gca | act | acc | act | cta | ttt | tgt | gca | 48 |
| Leu | Glu | Val | Pro | Val | Trp | Lys | Glu | Ala | Thr | Thr | Thr | Leu | Phe | Cys | Ala | |
| 1 | | | | 5 | | | | | 10 | | | | | 15 | | |
| tca | gat | gct | aaa | gca | tat | aat | aca | gag | aaa | cat | aat | gtt | tgg | gcc | aca | 96 |
| Ser | Asp | Ala | Lys | Ala | Tyr | Asn | Thr | Glu | Lys | His | Asn | Val | Trp | Ala | Thr | |
| | | | 20 | | | | | 25 | | | | | 30 | | | |
| cac | gcc | tgt | gta | ccc | aca | gat | ccc | aac | cca | caa | gaa | gta | gta | ttg | gga | 144 |
| His | Ala | Cys | Val | Pro | Thr | Asp | Pro | Asn | Pro | Gln | Glu | Val | Val | Leu | Gly | |
| | | 35 | | | | | 40 | | | | | 45 | | | | |
| aat | gtg | aca | gaa | aat | ttt | aac | atg | tgg | aaa | aat | aac | atg | gta | gaa | caa | 192 |
| Asn | Val | Thr | Glu | Asn | Phe | Asn | Met | Trp | Lys | Asn | Asn | Met | Val | Glu | Gln | |
| | 50 | | | | | 55 | | | | | 60 | | | | | |
| atg | cat | gaa | gat | ata | atc | agt | tta | tgg | gat | caa | agt | cta | aag | cca | tgt | 240 |
| Met | His | Glu | Asp | Ile | Ile | Ser | Leu | Trp | Asp | Gln | Ser | Leu | Lys | Pro | Cys | |
| 65 | | | | | 70 | | | | | 75 | | | | | 80 | |
| gta | aaa | tta | acc | cca | ctc | tgt | gtt | act | tta | aat | tgc | act | gat | gat | tta | 288 |
| Val | Lys | Leu | Thr | Pro | Leu | Cys | Val | Thr | Leu | Asn | Cys | Thr | Asp | Asp | Leu | |
| | | | | 85 | | | | | 90 | | | | | 95 | | |
| ggg | aat | gct | act | aat | acc | aat | agt | agt | gcc | act | acc | aat | agt | agt | agt | 336 |
| Gly | Asn | Ala | Thr | Asn | Thr | Asn | Ser | Ser | Ala | Thr | Thr | Asn | Ser | Ser | Ser | |
| | | | 100 | | | | | 105 | | | | | 110 | | | |
| tgg | gaa | gaa | atg | aag | ggg | gaa | atg | aaa | aga | tgc | tct | ttc | aat | atc | acc | 384 |
| Trp | Glu | Glu | Met | Lys | Gly | Glu | Met | Lys | Arg | Cys | Ser | Phe | Asn | Ile | Thr | |
| | | | 115 | | | | | 120 | | | | | 125 | | | |
| aca | agc | ata | aga | gat | aag | att | aag | aaa | gaa | cat | gca | ctt | ttc | tat | aga | 432 |
| Thr | Ser | Ile | Arg | Asp | Lys | Ile | Lys | Lys | Glu | His | Ala | Leu | Phe | Tyr | Arg | |
| | | 130 | | | | | 135 | | | | | 140 | | | | |
| ctt | gat | gta | gta | cca | ata | gat | aat | gat | aat | acc | aca | tat | agg | ttg | ata | 480 |
| Leu | Asp | Val | Val | Pro | Ile | Asp | Asn | Asp | Asn | Thr | Thr | Tyr | Arg | Leu | Ile | |
| 145 | | | | | 150 | | | | | 155 | | | | | 160 | |
| aat | tgt | aat | acc | tca | gtc | att | aca | cag | gcc | tgt | cca | aag | gta | tca | ttt | 528 |
| Asn | Cys | Asn | Thr | Ser | Val | Ile | Thr | Gln | Ala | Cys | Pro | Lys | Val | Ser | Phe | |
| | | | | 165 | | | | | 170 | | | | | 175 | | |
| gag | cca | att | ccc | ata | cat | ttt | tgt | gcc | ccg | gct | ggt | ttt | gcg | att | cta | 576 |

```
                Glu Pro Ile Pro Ile His Phe Cys Ala Pro Ala Gly Phe Ala Ile Leu
                                180                 185                 190 aag tgt aat aat aag acg ttc gag gga aaa gga cca tgt aaa aat gtc          624
Lys Cys Asn Asn Lys Thr Phe Glu Gly Lys Gly Pro Cys Lys Asn Val
            195                 200                 205 agt aca gta caa tgc aca cat gga att agg cca gta gtg tca act caa          672
Ser Thr Val Gln Cys Thr His Gly Ile Arg Pro Val Val Ser Thr Gln
        210                 215                 220 ctg ctg tta aat ggc agt cta gca gaa gaa gag gta ata att aga tct          720
Leu Leu Leu Asn Gly Ser Leu Ala Glu Glu Glu Val Ile Ile Arg Ser
225                 230                 235                 240 gac aat atc aca gac aat act aaa acc att ata gta cag cta aac gaa          768
Asp Asn Ile Thr Asp Asn Thr Lys Thr Ile Ile Val Gln Leu Asn Glu
                245                 250                 255 tct gta gta att aat tgt aca aga ccc aac aac aat aca aga aaa agt          816
Ser Val Val Ile Asn Cys Thr Arg Pro Asn Asn Asn Thr Arg Lys Ser
            260                 265                 270 ata cat ata gga cca ggg agt gca ttt ttt gca aca gga gaa ata ata          864
Ile His Ile Gly Pro Gly Ser Ala Phe Phe Ala Thr Gly Glu Ile Ile
        275                 280                 285 gga gat ata aga caa gca cac tgt aac ctt agt aga aca caa tgg aat          912
Gly Asp Ile Arg Gln Ala His Cys Asn Leu Ser Arg Thr Gln Trp Asn
290                 295                 300 aac act tta gga aag ata gtc ata aaa tta aga gaa caa ttt aga aaa          960
Asn Thr Leu Gly Lys Ile Val Ile Lys Leu Arg Glu Gln Phe Arg Lys
305                 310                 315                 320 caa ttt gga gaa aaa aca ata gtc ttt aat cga tcc tca gga ggg gac         1008
Gln Phe Gly Glu Lys Thr Ile Val Phe Asn Arg Ser Ser Gly Gly Asp
                325                 330                 335 ccg gaa att gca atg cac agt ttt aat tgt gga ggg gaa ttt ttc tac         1056
Pro Glu Ile Ala Met His Ser Phe Asn Cys Gly Gly Glu Phe Phe Tyr
            340                 345                 350 tgt aac aca aca gca ctg ttt aat agt acc tgg aat gtt act aaa ggg         1104
Cys Asn Thr Thr Ala Leu Phe Asn Ser Thr Trp Asn Val Thr Lys Gly
        355                 360                 365 ttg aat aac act gaa gga aat agc aca gga gat gaa aat atc ata ctc         1152
Leu Asn Asn Thr Glu Gly Asn Ser Thr Gly Asp Glu Asn Ile Ile Leu
    370                 375                 380 cca tgt aga ata aaa caa att ata aac atg tgg cag gaa gta gga aaa         1200
Pro Cys Arg Ile Lys Gln Ile Ile Asn Met Trp Gln Glu Val Gly Lys
385                 390                 395                 400 gca atg tat gcc cct ccc atc agt gga caa att aga tgt tca tca aac         1248
Ala Met Tyr Ala Pro Pro Ile Ser Gly Gln Ile Arg Cys Ser Ser Asn
                405                 410                 415 att aca ggg ctg cta cta aca aga gat ggt ggt agt aag aac gag agc         1296
Ile Thr Gly Leu Leu Leu Thr Arg Asp Gly Gly Ser Lys Asn Glu Ser
            420                 425                 430 atc acc acc gag gtc ttc aga cct gga gga gga gat atg agg gac aat         1344
Ile Thr Thr Glu Val Phe Arg Pro Gly Gly Gly Asp Met Arg Asp Asn
        435                 440                 445 tgg aga agt gaa tta tat aaa tat aaa gta gta aaa att gaa cca tta         1392
Trp Arg Ser Glu Leu Tyr Lys Tyr Lys Val Val Lys Ile Glu Pro Leu
    450                 455                 460 gga gta gcg ccc acc aag gca aag aga aga gtg gtg cag aga gaa aaa         1440
Gly Val Ala Pro Thr Lys Ala Lys Arg Arg Val Val Gln Arg Glu Lys
465                 470                 475                 480 aga gca gtg gga aca ata gga gct atg ttc ctt ggg ttc ttg gga gca         1488
Arg Ala Val Gly Thr Ile Gly Ala Met Phe Leu Gly Phe Leu Gly Ala
                485                 490                 495
```

-continued

```
taa agc ttc tag agt cga cct gca                                              1512
 *  Ser Phe  *  Ser Arg Pro Ala
            500
```

<210> SEQ ID NO 12
<211> LENGTH: 496
<212> TYPE: PRT
<213> ORGANISM: HIV

<400> SEQUENCE: 12

```
Leu Glu Val Pro Val Trp Lys Glu Ala Thr Thr Thr Leu Phe Cys Ala
 1               5                  10                  15

Ser Asp Ala Lys Ala Tyr Asn Thr Glu Lys His Asn Val Trp Ala Thr
             20                  25                  30

His Ala Cys Val Pro Thr Asp Pro Asn Pro Gln Glu Val Val Leu Gly
         35                  40                  45

Asn Val Thr Glu Asn Phe Asn Met Trp Lys Asn Asn Met Val Glu Gln
     50                  55                  60

Met His Glu Asp Ile Ile Ser Leu Trp Asp Gln Ser Leu Lys Pro Cys
 65                  70                  75                  80

Val Lys Leu Thr Pro Leu Cys Val Thr Leu Asn Cys Thr Asp Asp Leu
                 85                  90                  95

Gly Asn Ala Thr Asn Thr Asn Ser Ser Ala Thr Thr Asn Ser Ser Ser
            100                 105                 110

Trp Glu Glu Met Lys Gly Glu Met Lys Arg Cys Ser Phe Asn Ile Thr
        115                 120                 125

Thr Ser Ile Arg Asp Lys Ile Lys Lys Glu His Ala Leu Phe Tyr Arg
    130                 135                 140

Leu Asp Val Val Pro Ile Asp Asn Asp Asn Thr Thr Tyr Arg Leu Ile
145                 150                 155                 160

Asn Cys Asn Thr Ser Val Ile Thr Gln Ala Cys Pro Lys Val Ser Phe
                165                 170                 175

Glu Pro Ile Pro Ile His Phe Cys Ala Pro Ala Gly Phe Ala Ile Leu
            180                 185                 190

Lys Cys Asn Asn Lys Thr Phe Glu Gly Lys Gly Pro Cys Lys Asn Val
        195                 200                 205

Ser Thr Val Gln Cys Thr His Gly Ile Arg Pro Val Val Ser Thr Gln
    210                 215                 220

Leu Leu Leu Asn Gly Ser Leu Ala Glu Glu Val Ile Ile Arg Ser
225                 230                 235                 240

Asp Asn Ile Thr Asp Asn Thr Lys Thr Ile Ile Val Gln Leu Asn Glu
                245                 250                 255

Ser Val Val Ile Asn Cys Thr Arg Pro Asn Asn Asn Thr Arg Lys Ser
            260                 265                 270

Ile His Ile Gly Pro Gly Ser Ala Phe Phe Ala Thr Gly Glu Ile Ile
        275                 280                 285

Gly Asp Ile Arg Gln Ala His Cys Asn Leu Ser Arg Thr Gln Trp Asn
    290                 295                 300

Asn Thr Leu Gly Lys Ile Val Ile Lys Leu Arg Glu Gln Phe Arg Lys
305                 310                 315                 320

Gln Phe Gly Glu Lys Thr Ile Val Phe Asn Arg Ser Ser Gly Gly Asp
                325                 330                 335

Pro Glu Ile Ala Met His Ser Phe Asn Cys Gly Gly Glu Phe Phe Tyr
            340                 345                 350

Cys Asn Thr Thr Ala Leu Phe Asn Ser Thr Trp Asn Val Thr Lys Gly
```

```
                    355                 360                 365
Leu Asn Asn Thr Glu Gly Asn Ser Thr Gly Asp Glu Asn Ile Ile Leu
                370                 375                 380

Pro Cys Arg Ile Lys Gln Ile Ile Asn Met Trp Gln Glu Val Gly Lys
385                 390                 395                 400

Ala Met Tyr Ala Pro Pro Ile Ser Gly Gln Ile Arg Cys Ser Ser Asn
                    405                 410                 415

Ile Thr Gly Leu Leu Leu Thr Arg Asp Gly Gly Ser Lys Asn Glu Ser
                420                 425                 430

Ile Thr Thr Glu Val Phe Arg Pro Gly Gly Gly Asp Met Arg Asp Asn
                435                 440                 445

Trp Arg Ser Glu Leu Tyr Lys Tyr Lys Val Val Lys Ile Glu Pro Leu
    450                 455                 460

Gly Val Ala Pro Thr Lys Ala Lys Arg Val Val Gln Arg Glu Lys
465                 470                 475                 480

Arg Ala Val Gly Thr Ile Gly Ala Met Phe Leu Gly Phe Leu Gly Ala
                    485                 490                 495
```

<210> SEQ ID NO 13
<211> LENGTH: 2
<212> TYPE: PRT
<213> ORGANISM: HIV

<400> SEQUENCE: 13

Ser Phe
1

<210> SEQ ID NO 14
<211> LENGTH: 4
<212> TYPE: PRT
<213> ORGANISM: HIV

<400> SEQUENCE: 14

Ser Arg Pro Ala
1

<210> SEQ ID NO 15
<211> LENGTH: 1501
<212> TYPE: DNA
<213> ORGANISM: HIV
<220> FEATURE:
<221> NAME/KEY: CDS
<222> LOCATION: (1)...(1500)

<400> SEQUENCE: 15

```
ctc gag gta cct gtg tgg aaa gaa gca act acc act cta ttt tgt gca    48
Leu Glu Val Pro Val Trp Lys Glu Ala Thr Thr Thr Leu Phe Cys Ala
1               5                   10                  15 tca gat gct aaa gca tat aat aca gag aaa cat aat gtt tgg gcc aca    96
Ser Asp Ala Lys Ala Tyr Asn Thr Glu Lys His Asn Val Trp Ala Thr
            20                  25                  30 cac gcc tgt gta ccc aca gat ccc aac cca caa gaa gta gta ttg gga   144
His Ala Cys Val Pro Thr Asp Pro Asn Pro Gln Glu Val Val Leu Gly
        35                  40                  45 aat gtg aca gaa aat ttt aac atg tgg aaa aat aac atg gta gaa caa   192
Asn Val Thr Glu Asn Phe Asn Met Trp Lys Asn Asn Met Val Glu Gln
    50                  55                  60 atg cat gaa gat ata atc agt tta tgg gat caa agt cta aag cca tgt   240
Met His Glu Asp Ile Ile Ser Leu Trp Asp Gln Ser Leu Lys Pro Cys
65                  70                  75                  80
```

```
gta aaa tta acc cca ctc tgt gtt act tta aat tgc act gat gat tta         288
Val Lys Leu Thr Pro Leu Cys Val Thr Leu Asn Cys Thr Asp Asp Leu
            85                  90                  95 ggg aat gct act aat acc aat agc agt gcc act acc aat agt agt agt         336
Gly Asn Ala Thr Asn Thr Asn Ser Ser Ala Thr Thr Asn Ser Ser Ser
            100                 105                 110 tgg gaa gaa atg aag ggg gaa atg aaa agg tgc tct ttc aat atc acc         384
Trp Glu Glu Met Lys Gly Glu Met Lys Arg Cys Ser Phe Asn Ile Thr
            115                 120                 125 aca agc ata aga gat aag att aag aaa gaa cat gca ctt ttc tat aga         432
Thr Ser Ile Arg Asp Lys Ile Lys Lys Glu His Ala Leu Phe Tyr Arg
        130                 135                 140 ctt gat gta gta cca ata gat aat gat aat acc aca tat agg ttg ata         480
Leu Asp Val Val Pro Ile Asp Asn Asp Asn Thr Thr Tyr Arg Leu Ile
145                 150                 155                 160 aat tgt aat acc tca gtc att aca cag gcc tgt cca aag gta tca ttt         528
Asn Cys Asn Thr Ser Val Ile Thr Gln Ala Cys Pro Lys Val Ser Phe
                165                 170                 175 gag cca att ccc ata cat ttt tgt gcc ccg gct ggt ttt gcg att cta         576
Glu Pro Ile Pro Ile His Phe Cys Ala Pro Ala Gly Phe Ala Ile Leu
                180                 185                 190 aag tgt aat aat aag acg ttc gag gga aaa gga cca tgt aaa aat gtc         624
Lys Cys Asn Asn Lys Thr Phe Glu Gly Lys Gly Pro Cys Lys Asn Val
            195                 200                 205 agt aca gta caa tgc aca cat gga att agg cca gta gtg tca act caa         672
Ser Thr Val Gln Cys Thr His Gly Ile Arg Pro Val Val Ser Thr Gln
        210                 215                 220 ctg ctg tta aat ggc agt cta gca gaa gaa gag gta ata att aga tct         720
Leu Leu Leu Asn Gly Ser Leu Ala Glu Glu Glu Val Ile Ile Arg Ser
225                 230                 235                 240 ggc aat atc aca gac aat act aaa acc att ata gta cag cta aac gaa         768
Gly Asn Ile Thr Asp Asn Thr Lys Thr Ile Ile Val Gln Leu Asn Glu
                245                 250                 255 tct gta gta att aat tgt aca aga tcc aac aac aat aca aga aaa agt         816
Ser Val Val Ile Asn Cys Thr Arg Ser Asn Asn Asn Thr Arg Lys Ser
                260                 265                 270 ata cat ata gga cca ggg agt gca ttt ttt gca aca gga gaa ata ata         864
Ile His Ile Gly Pro Gly Ser Ala Phe Phe Ala Thr Gly Glu Ile Ile
            275                 280                 285 gga gat ata aga caa gca cac tgt aac ctt agt aga aca caa tgg aat         912
Gly Asp Ile Arg Gln Ala His Cys Asn Leu Ser Arg Thr Gln Trp Asn
        290                 295                 300 aac act tta gga aag ata gtc ata aaa tta aga gaa caa ttt aga aaa         960
Asn Thr Leu Gly Lys Ile Val Ile Lys Leu Arg Glu Gln Phe Arg Lys
305                 310                 315                 320 caa ttt gga gaa aaa aca ata gtc ttt aat cga tcc tca gga ggg gac        1008
Gln Phe Gly Glu Lys Thr Ile Val Phe Asn Arg Ser Ser Gly Gly Asp
                325                 330                 335 ccg gaa att gca atg cac agt ttt aat tgt gga ggg gaa ttt ttc tac        1056
Pro Glu Ile Ala Met His Ser Phe Asn Cys Gly Gly Glu Phe Phe Tyr
            340                 345                 350 tgt aac aca aca gca ctg ttt aat agt acc tgg aat gtt act aaa ggg        1104
Cys Asn Thr Thr Ala Leu Phe Asn Ser Thr Trp Asn Val Thr Lys Gly
        355                 360                 365 ttg aat aac act gaa gga aat agc aca ggg gat gaa aat atc ata ctc        1152
Leu Asn Asn Thr Glu Gly Asn Ser Thr Gly Asp Glu Asn Ile Ile Leu
370                 375                 380 cca tgt aga ata aaa caa att ata aac atg tgg cag gaa gta gga aaa        1200
Pro Cys Arg Ile Lys Gln Ile Ile Asn Met Trp Gln Glu Val Gly Lys
                385                 390                 395                 400
```

-continued

```
gca atg tat gcc cct ccc atc agt gga caa att aga tgt tca tca aat    1248
Ala Met Tyr Ala Pro Pro Ile Ser Gly Gln Ile Arg Cys Ser Ser Asn
            405                 410                 415 att aca ggg ctg cta cta aca aga gat ggt ggt agt aag aac gag agc    1296
Ile Thr Gly Leu Leu Leu Thr Arg Asp Gly Gly Ser Lys Asn Glu Ser
            420                 425                 430 atc acc acc gag gtc ttc aga cct gga gga gga gat atg agg gac aat    1344
Ile Thr Thr Glu Val Phe Arg Pro Gly Gly Gly Asp Met Arg Asp Asn
            435                 440                 445 tgg aga agt gaa tta tat aaa tat aaa gta gta aaa att gaa cca tta    1392
Trp Arg Ser Glu Leu Tyr Lys Tyr Lys Val Val Lys Ile Glu Pro Leu
450                 455                 460 gga gta gcg ccc acc aag gca aag aga aga gtg gtg cag aga gaa aaa    1440
Gly Val Ala Pro Thr Lys Ala Lys Arg Arg Val Val Gln Arg Glu Lys
465                 470                 475                 480 aga gca gtg gga aca ata gga gct atg ttc ctt ggg ttc tta gga gca    1488
Arg Ala Val Gly Thr Ile Gly Ala Met Phe Leu Gly Phe Leu Gly Ala
            485                 490                 495 taa agc ttc tag a                                                   1501
 *  Ser Phe
```

<210> SEQ ID NO 16
<211> LENGTH: 496
<212> TYPE: PRT
<213> ORGANISM: HIV

<400> SEQUENCE: 16

```
Leu Glu Val Pro Val Trp Lys Glu Ala Thr Thr Thr Leu Phe Cys Ala
  1               5                  10                  15

Ser Asp Ala Lys Ala Tyr Asn Thr Glu Lys His Asn Val Trp Ala Thr
                 20                  25                  30

His Ala Cys Val Pro Thr Asp Pro Asn Pro Gln Glu Val Val Leu Gly
             35                  40                  45

Asn Val Thr Glu Asn Phe Asn Met Trp Lys Asn Asn Met Val Glu Gln
 50                  55                  60

Met His Glu Asp Ile Ile Ser Leu Trp Asp Gln Ser Leu Lys Pro Cys
 65                  70                  75                  80

Val Lys Leu Thr Pro Leu Cys Val Thr Leu Asn Cys Thr Asp Asp Leu
                 85                  90                  95

Gly Asn Ala Thr Asn Thr Asn Ser Ser Ala Thr Thr Asn Ser Ser Ser
                100                 105                 110

Trp Glu Glu Met Lys Gly Glu Met Lys Arg Cys Ser Phe Asn Ile Thr
            115                 120                 125

Thr Ser Ile Arg Asp Lys Ile Lys Lys Glu His Ala Leu Phe Tyr Arg
130                 135                 140

Leu Asp Val Val Pro Ile Asp Asn Asp Asn Thr Thr Tyr Arg Leu Ile
145                 150                 155                 160

Asn Cys Asn Thr Ser Val Ile Thr Gln Ala Cys Pro Lys Val Ser Phe
                165                 170                 175

Glu Pro Ile Pro Ile His Phe Cys Ala Pro Ala Gly Phe Ala Ile Leu
            180                 185                 190

Lys Cys Asn Asn Lys Thr Phe Glu Gly Lys Gly Pro Cys Lys Asn Val
            195                 200                 205

Ser Thr Val Gln Cys Thr His Gly Ile Arg Pro Val Val Ser Thr Gln
            210                 215                 220

Leu Leu Leu Asn Gly Ser Leu Ala Glu Glu Glu Val Ile Ile Arg Ser
```

-continued

```
                225                 230                 235                 240
        Gly Asn Ile Thr Asp Asn Thr Lys Thr Ile Ile Val Gln Leu Asn Glu
                        245                 250                 255

Ser Val Val Ile Asn Cys Thr Arg Ser Asn Asn Thr Arg Lys Ser
                        260                 265                 270

Ile His Ile Gly Pro Gly Ser Ala Phe Phe Ala Thr Gly Glu Ile Ile
                        275                 280                 285

Gly Asp Ile Arg Gln Ala His Cys Asn Leu Ser Arg Thr Gln Trp Asn
                290                 295                 300

Asn Thr Leu Gly Lys Ile Val Ile Lys Leu Arg Glu Gln Phe Arg Lys
        305                 310                 315                 320

Gln Phe Gly Glu Lys Thr Ile Val Phe Asn Arg Ser Ser Gly Gly Asp
                        325                 330                 335

Pro Glu Ile Ala Met His Ser Phe Asn Cys Gly Gly Glu Phe Phe Tyr
                        340                 345                 350

Cys Asn Thr Thr Ala Leu Phe Asn Ser Thr Trp Asn Val Thr Lys Gly
                        355                 360                 365

Leu Asn Asn Thr Glu Gly Asn Ser Thr Gly Asp Glu Asn Ile Ile Leu
                        370                 375                 380

Pro Cys Arg Ile Lys Gln Ile Ile Asn Met Trp Gln Glu Val Gly Lys
        385                 390                 395                 400

Ala Met Tyr Ala Pro Pro Ile Ser Gly Gln Ile Arg Cys Ser Ser Asn
                        405                 410                 415

Ile Thr Gly Leu Leu Leu Thr Arg Asp Gly Ser Lys Asn Glu Ser
                        420                 425                 430

Ile Thr Thr Glu Val Phe Arg Pro Gly Gly Gly Asp Met Arg Asp Asn
                        435                 440                 445

Trp Arg Ser Glu Leu Tyr Lys Tyr Lys Val Val Lys Ile Glu Pro Leu
        450                 455                 460

Gly Val Ala Pro Thr Lys Ala Lys Arg Arg Val Val Gln Arg Glu Lys
        465                 470                 475                 480

Arg Ala Val Gly Thr Ile Gly Ala Met Phe Leu Gly Phe Leu Gly Ala
                        485                 490                 495

<210> SEQ ID NO 17
<211> LENGTH: 2
<212> TYPE: PRT
<213> ORGANISM: HIV

<400> SEQUENCE: 17

Ser Phe
 1

<210> SEQ ID NO 18
<211> LENGTH: 1514
<212> TYPE: DNA
<213> ORGANISM: HIV
<220> FEATURE:
<221> NAME/KEY: CDS
<222> LOCATION: (3)...(1514)

<400> SEQUENCE: 18 gg gaa ttc gga tcc ggg gta cct gtg tgg aag gaa gca acc acc act     47
   Glu Phe Gly Ser Gly Val Pro Val Trp Lys Glu Ala Thr Thr Thr
    1               5                  10                  15 cta ttc tgt gca tca gat gct aga gca tat gac aca gag gta cat aat    95
Leu Phe Cys Ala Ser Asp Ala Arg Ala Tyr Asp Thr Glu Val His Asn
                20                  25                  30
```

```
gtt tgg gcc aca cat gcc tgt gta ccc aca gac cct agt cca caa gaa      143
Val Trp Ala Thr His Ala Cys Val Pro Thr Asp Pro Ser Pro Gln Glu
            35                  40                  45 gta gtt ttg gaa aat gtg aca gaa aat ttt aac atg tgg aaa aat aac      191
Val Val Leu Glu Asn Val Thr Glu Asn Phe Asn Met Trp Lys Asn Asn
         50                  55                  60 atg gta gaa caa atg cat gag gat ata att agt tta tgg gat caa agc      239
Met Val Glu Gln Met His Glu Asp Ile Ile Ser Leu Trp Asp Gln Ser
 65                  70                  75 tta aag cca tgt gta aaa tta acc cca ctc tgt gtt act tta aat tgc      287
Leu Lys Pro Cys Val Lys Leu Thr Pro Leu Cys Val Thr Leu Asn Cys
 80                  85                  90                  95 agt gat tat agg aat gct act gat tat aag aat gct act gat acc act      335
Ser Asp Tyr Arg Asn Ala Thr Asp Tyr Lys Asn Ala Thr Asp Thr Thr
                100                 105                 110 agt agt aac gag gga aag atg gag aga gga gaa ata aaa aac tgc tct      383
Ser Ser Asn Glu Gly Lys Met Glu Arg Gly Glu Ile Lys Asn Cys Ser
            115                 120                 125 ttc aat att acc aca agc ata aaa aat aag atg cag aaa gaa tat gca      431
Phe Asn Ile Thr Thr Ser Ile Lys Asn Lys Met Gln Lys Glu Tyr Ala
        130                 135                 140 ctt ttc tat aaa ctt gat ata gta cca ata gat aat aca agc tat aca      479
Leu Phe Tyr Lys Leu Asp Ile Val Pro Ile Asp Asn Thr Ser Tyr Thr
    145                 150                 155 ttg ata agt tgt aac acc tca gtc att aca cag gcc tgt cca aag gta      527
Leu Ile Ser Cys Asn Thr Ser Val Ile Thr Gln Ala Cys Pro Lys Val
160                 165                 170                 175 tcc ttt gaa cca act ccc ata cat tat tgt gct ccg gct ggt ttt gcg      575
Ser Phe Glu Pro Thr Pro Ile His Tyr Cys Ala Pro Ala Gly Phe Ala
                180                 185                 190 att cta aag tgt aat gat aag aag ttc agt gga aaa gga gaa tgt aaa      623
Ile Leu Lys Cys Asn Asp Lys Lys Phe Ser Gly Lys Gly Glu Cys Lys
            195                 200                 205 aat gtc agc aca gta caa tgt aca cat gga att agg cca gta gta tca      671
Asn Val Ser Thr Val Gln Cys Thr His Gly Ile Arg Pro Val Val Ser
        210                 215                 220 act caa ctg ctg tta aat ggc agt cta gca gaa gaa gag gtg gta att      719
Thr Gln Leu Leu Leu Asn Gly Ser Leu Ala Glu Glu Glu Val Val Ile
    225                 230                 235 aga tct gac aat ttc ata gac aat act aaa acc ata ata gta cag ctg      767
Arg Ser Asp Asn Phe Ile Asp Asn Thr Lys Thr Ile Ile Val Gln Leu
240                 245                 250                 255 aaa gaa tct gta gaa att aat tgt ata aga ccc aac aat aat aca aga      815
Lys Glu Ser Val Glu Ile Asn Cys Ile Arg Pro Asn Asn Asn Thr Arg
                260                 265                 270 aaa ggt ata cat ata gga cca ggg aga gca tgg tat gca aca gga gaa      863
Lys Gly Ile His Ile Gly Pro Gly Arg Ala Trp Tyr Ala Thr Gly Glu
            275                 280                 285 ata gta gga gat ata aga aag gca tat tgt aac att agt aga aca aaa      911
Ile Val Gly Asp Ile Arg Lys Ala Tyr Cys Asn Ile Ser Arg Thr Lys
        290                 295                 300 tgg aat aac act tta ata cag ata gct aac aaa tta aaa gaa aaa tat      959
Trp Asn Asn Thr Leu Ile Gln Ile Ala Asn Lys Leu Lys Glu Lys Tyr
    305                 310                 315 aat aca aca ata agc ttt aat cga tcc tca gga ggg gac cca gaa att      1007
Asn Thr Thr Ile Ser Phe Asn Arg Ser Ser Gly Gly Asp Pro Glu Ile
320                 325                 330                 335 gta acg cat agt ttt aat tgt gga ggg gag ttt ttc tac tgt gat tca      1055
Val Thr His Ser Phe Asn Cys Gly Gly Glu Phe Phe Tyr Cys Asp Ser
```

```
                 340              345              350
aca caa ctg ttt aat agt act tgg aat tta aat ggt act tgg aat ttt    1103
Thr Gln Leu Phe Asn Ser Thr Trp Asn Leu Asn Gly Thr Trp Asn Phe
             355              360              365 act gca ggg tca aat gaa act gaa ggc aat atc aca ctc cca tgc aga    1151
Thr Ala Gly Ser Asn Glu Thr Glu Gly Asn Ile Thr Leu Pro Cys Arg
         370              375              380 ata aaa caa att ata aac agg tgg cag gaa gta ggg aaa gca atg tat    1199
Ile Lys Gln Ile Ile Asn Arg Trp Gln Glu Val Gly Lys Ala Met Tyr
385              390              395 gcc cct ccc atc agt gga caa ata aaa tgc tca tca aac att aca ggg    1247
Ala Pro Pro Ile Ser Gly Gln Ile Lys Cys Ser Ser Asn Ile Thr Gly
400              405              410              415 atg ata tta aca agg gat ggt ggt aac gag aac aat aat gag agc agt    1295
Met Ile Leu Thr Arg Asp Gly Gly Asn Glu Asn Asn Asn Glu Ser Ser
             420              425              430 act act gag acc ttc aga ccg gga gga gga gat atg agg aac aat tgg    1343
Thr Thr Glu Thr Phe Arg Pro Gly Gly Gly Asp Met Arg Asn Asn Trp
         435              440              445 aga agt gaa tta tat aaa tat aaa gta gta aaa att gaa cca tta gga    1391
Arg Ser Glu Leu Tyr Lys Tyr Lys Val Val Lys Ile Glu Pro Leu Gly
             450              455              460 gta gca ccc acc aag gca aag aga aga gtg gtg cag aga gaa aaa aga    1439
Val Ala Pro Thr Lys Ala Lys Arg Arg Val Val Gln Arg Glu Lys Arg
465              470              475 gca gtg gga gcg cta gga gct atg ttc ctt ggg ttc tta gga gca taa    1487
Ala Val Gly Ala Leu Gly Ala Met Phe Leu Gly Phe Leu Gly Ala
480              485              490              495 agc ttc tag acc gac tct aga gga tcc                                1514
Ser Phe  *  Thr Asp Ser Arg Gly Ser
             500
```

<210> SEQ ID NO 19
<211> LENGTH: 494
<212> TYPE: PRT
<213> ORGANISM: HIV

<400> SEQUENCE: 19

```
Glu Phe Gly Ser Gly Val Pro Val Trp Lys Glu Ala Thr Thr Thr Leu
1               5                   10                  15

Phe Cys Ala Ser Asp Ala Arg Ala Tyr Asp Thr Glu Val His Asn Val
            20                  25                  30

Trp Ala Thr His Ala Cys Val Pro Thr Asp Pro Ser Pro Gln Glu Val
        35                  40                  45

Val Leu Glu Asn Val Thr Glu Asn Phe Asn Met Trp Lys Asn Asn Met
    50                  55                  60

Val Glu Gln Met His Glu Asp Ile Ile Ser Leu Trp Asp Gln Ser Leu
65                  70                  75                  80

Lys Pro Cys Val Lys Leu Thr Pro Leu Cys Val Thr Leu Asn Cys Ser
                85                  90                  95

Asp Tyr Arg Asn Ala Thr Asp Tyr Lys Asn Ala Thr Asp Thr Thr Ser
            100                 105                 110

Ser Asn Glu Gly Lys Met Glu Arg Gly Glu Ile Lys Asn Cys Ser Phe
        115                 120                 125

Asn Ile Thr Thr Ser Ile Lys Asn Lys Met Gln Lys Glu Tyr Ala Leu
    130                 135                 140

Phe Tyr Lys Leu Asp Ile Val Pro Ile Asp Asn Thr Ser Tyr Thr Leu
145                 150                 155                 160
```

```
Ile Ser Cys Asn Thr Ser Val Ile Thr Gln Ala Cys Pro Lys Val Ser
                165                 170                 175

Phe Glu Pro Thr Pro Ile His Tyr Cys Ala Pro Ala Gly Phe Ala Ile
            180                 185                 190

Leu Lys Cys Asn Asp Lys Lys Phe Ser Gly Lys Gly Glu Cys Lys Asn
            195                 200                 205

Val Ser Thr Val Gln Cys Thr His Gly Ile Arg Pro Val Val Ser Thr
        210                 215                 220

Gln Leu Leu Leu Asn Gly Ser Leu Ala Glu Glu Val Val Ile Arg
225                 230                 235                 240

Ser Asp Asn Phe Ile Asp Asn Thr Lys Thr Ile Val Gln Leu Lys
                245                 250                 255

Glu Ser Val Glu Ile Asn Cys Ile Arg Pro Asn Asn Asn Thr Arg Lys
                260                 265                 270

Gly Ile His Ile Gly Pro Gly Arg Ala Trp Tyr Ala Thr Gly Glu Ile
                275                 280                 285

Val Gly Asp Ile Arg Lys Ala Tyr Cys Asn Ile Ser Arg Thr Lys Trp
        290                 295                 300

Asn Asn Thr Leu Ile Gln Ile Ala Asn Lys Leu Lys Glu Lys Tyr Asn
305                 310                 315                 320

Thr Thr Ile Ser Phe Asn Arg Ser Ser Gly Gly Asp Pro Glu Ile Val
                325                 330                 335

Thr His Ser Phe Asn Cys Gly Gly Glu Phe Phe Tyr Cys Asp Ser Thr
                340                 345                 350

Gln Leu Phe Asn Ser Thr Trp Asn Leu Asn Gly Thr Trp Asn Phe Thr
                355                 360                 365

Ala Gly Ser Asn Glu Thr Glu Gly Asn Ile Thr Leu Pro Cys Arg Ile
                370                 375                 380

Lys Gln Ile Ile Asn Arg Trp Gln Glu Val Gly Lys Ala Met Tyr Ala
385                 390                 395                 400

Pro Pro Ile Ser Gly Gln Ile Lys Cys Ser Ser Asn Ile Thr Gly Met
                405                 410                 415

Ile Leu Thr Arg Asp Gly Gly Asn Glu Asn Asn Asn Glu Ser Ser Thr
                420                 425                 430

Thr Glu Thr Phe Arg Pro Gly Gly Gly Asp Met Arg Asn Asn Trp Arg
                435                 440                 445

Ser Glu Leu Tyr Lys Tyr Lys Val Val Lys Ile Glu Pro Leu Gly Val
                450                 455                 460

Ala Pro Thr Lys Ala Lys Arg Arg Val Val Gln Arg Glu Lys Arg Ala
465                 470                 475                 480

Val Gly Ala Leu Gly Ala Met Phe Leu Gly Phe Leu Gly Ala
                485                 490

<210> SEQ ID NO 20
<211> LENGTH: 2
<212> TYPE: PRT
<213> ORGANISM: HIV

<400> SEQUENCE: 20

Ser Phe
 1

<210> SEQ ID NO 21
<211> LENGTH: 6
<212> TYPE: PRT
```

-continued

<213> ORGANISM: HIV

<400> SEQUENCE: 21

Thr Asp Ser Arg Gly Ser
 1               5

<210> SEQ ID NO 22
<211> LENGTH: 1408
<212> TYPE: DNA
<213> ORGANISM: HIV
<220> FEATURE:
<221> NAME/KEY: CDS
<222> LOCATION: (2)...(1408)

<400> SEQUENCE: 22

```
g gta cct gtg tgg aag gaa gca acc acc act cta ttc tgt gca tca gat      49
  Val Pro Val Trp Lys Glu Ala Thr Thr Thr Leu Phe Cys Ala Ser Asp
   1               5                  10                  15 gct aga gca tat gac aca gag gta cat aat gtt tgg gcc aca cat gcc        97
Ala Arg Ala Tyr Asp Thr Glu Val His Asn Val Trp Ala Thr His Ala
             20                  25                  30 tgt gta ccc aca gac cct agt cca caa gaa gta ttt ttg gga aat gtg       145
Cys Val Pro Thr Asp Pro Ser Pro Gln Glu Val Phe Leu Gly Asn Val
         35                  40                  45 aca gaa aat ttt aat atg tgg aaa aat aac atg gta gaa caa atg tat       193
Thr Glu Asn Phe Asn Met Trp Lys Asn Asn Met Val Glu Gln Met Tyr
     50                  55                  60 gag gat ata att agt tta tgg gat caa agc tta aag cca tgt gta aaa       241
Glu Asp Ile Ile Ser Leu Trp Asp Gln Ser Leu Lys Pro Cys Val Lys
 65                  70                  75                  80 tta acc cca ctc tgt gtt act tta aat tgc agt gat tat agg aat gct       289
Leu Thr Pro Leu Cys Val Thr Leu Asn Cys Ser Asp Tyr Arg Asn Ala
                 85                  90                  95 act gat tat aag aat gct act gat acc act agt agt aac gag gga aag       337
Thr Asp Tyr Lys Asn Ala Thr Asp Thr Thr Ser Ser Asn Glu Gly Lys
            100                 105                 110 atg gag aga gga gaa ata aaa aac tgc tct ttc aat atc acc aca agc       385
Met Glu Arg Gly Glu Ile Lys Asn Cys Ser Phe Asn Ile Thr Thr Ser
        115                 120                 125 ata aaa aat aag atg cag aaa gaa tat gca ctt ttc tat aaa ctt aat       433
Ile Lys Asn Lys Met Gln Lys Glu Tyr Ala Leu Phe Tyr Lys Leu Asn
    130                 135                 140 ata gta cca ata gat aat aca agc tat aca ttg ata agt tgt aac acc       481
Ile Val Pro Ile Asp Asn Thr Ser Tyr Thr Leu Ile Ser Cys Asn Thr
145                 150                 155                 160 tca gtc att aca cag gcc tgt cca aag gta tcc ttt gaa cca att ccc       529
Ser Val Ile Thr Gln Ala Cys Pro Lys Val Ser Phe Glu Pro Ile Pro
                165                 170                 175 ata cat tat tgt gct ccg gct ggt ttt gcg att cta aag tgt aat gat       577
Ile His Tyr Cys Ala Pro Ala Gly Phe Ala Ile Leu Lys Cys Asn Asp
            180                 185                 190 aag aag ttc agt gga aaa gga gaa tgt aaa aat gtc agc aca gta caa       625
Lys Lys Phe Ser Gly Lys Gly Glu Cys Lys Asn Val Ser Thr Val Gln
        195                 200                 205 tgt aca cat gga att agg cca gta gta tca act caa ctg ctg tta aat       673
Cys Thr His Gly Ile Arg Pro Val Val Ser Thr Gln Leu Leu Leu Asn
    210                 215                 220 ggc agt cta gca gaa gaa gag gtg gta att aga tct gac aat ttc aca       721
Gly Ser Leu Ala Glu Glu Glu Val Val Ile Arg Ser Asp Asn Phe Thr
225                 230                 235                 240 gac aat act aaa acc ata ata gta cag ctg aaa gaa tct gta gaa att       769
```

```
                Asp Asn Thr Lys Thr Ile Ile Val Gln Leu Lys Glu Ser Val Glu Ile
                            245                 250                 255 aat tgt ata aga ccc aac aat aat aca aga aaa ggt ata cat ata gga          817
Asn Cys Ile Arg Pro Asn Asn Asn Thr Arg Lys Gly Ile His Ile Gly
            260                 265                 270 cca ggg aga gca tgg tat gca aca gga gaa ata gta gga gat ata aga          865
Pro Gly Arg Ala Trp Tyr Ala Thr Gly Glu Ile Val Gly Asp Ile Arg
            275                 280                 285 cag gca tat tgt aac att agt aga aca aaa tgg aat aac act tta ata          913
Gln Ala Tyr Cys Asn Ile Ser Arg Thr Lys Trp Asn Asn Thr Leu Ile
        290                 295                 300 cag ata gct aac aaa tta aaa gaa aaa tat aat aca aca ata agc ttt          961
Gln Ile Ala Asn Lys Leu Lys Glu Lys Tyr Asn Thr Thr Ile Ser Phe
305                 310                 315                 320 aat cga tcc tca gga ggg gac cca gaa att gta acc cat agt ttt aat         1009
Asn Arg Ser Ser Gly Gly Asp Pro Glu Ile Val Thr His Ser Phe Asn
                325                 330                 335 tgt gga ggg gaa ttt ttc tac tgt aat tca aca caa ctg ttt aat agt         1057
Cys Gly Gly Glu Phe Phe Tyr Cys Asn Ser Thr Gln Leu Phe Asn Ser
                340                 345                 350 act tgg aat tta aat ggt act tgg aat ttt act gca ggg tca aat gaa         1105
Thr Trp Asn Leu Asn Gly Thr Trp Asn Phe Thr Ala Gly Ser Asn Glu
            355                 360                 365 act gaa ggc aat atc aca ctc cca tgc aga ata aaa caa att ata aac         1153
Thr Glu Gly Asn Ile Thr Leu Pro Cys Arg Ile Lys Gln Ile Ile Asn
370                 375                 380 agg tgg cag gaa gta gga aaa gca atg tat gcc cct ccc atc agt gga         1201
Arg Trp Gln Glu Val Gly Lys Ala Met Tyr Ala Pro Pro Ile Ser Gly
385                 390                 395                 400 caa ata aga tgc tca tca aac att aca ggg atg ata tta aca agg gat         1249
Gln Ile Arg Cys Ser Ser Asn Ile Thr Gly Met Ile Leu Thr Arg Asp
                405                 410                 415 ggt ggt aac gag aac aat aat gag agc agt act act gag acc ttc aga         1297
Gly Gly Asn Glu Asn Asn Asn Glu Ser Ser Thr Thr Glu Thr Phe Arg
                420                 425                 430 ccg gga gga gga gat atg agg aac aat tgg aga agt gaa tta tat aaa         1345
Pro Gly Gly Gly Asp Met Arg Asn Asn Trp Arg Ser Glu Leu Tyr Lys
            435                 440                 445 tat aaa gta gta aaa att gag cca tta gga gta gca ccc acc gac tct         1393
Tyr Lys Val Val Lys Ile Glu Pro Leu Gly Val Ala Pro Thr Asp Ser
        450                 455                 460 aga gga tcc tct aga                                                     1408
Arg Gly Ser Ser Arg
465

<210> SEQ ID NO 23
<211> LENGTH: 469
<212> TYPE: PRT
<213> ORGANISM: HIV

<400> SEQUENCE: 23

Val Pro Val Trp Lys Glu Ala Thr Thr Thr Leu Phe Cys Ala Ser Asp
  1               5                  10                  15

Ala Arg Ala Tyr Asp Thr Glu Val His Asn Val Trp Ala Thr His Ala
                20                  25                  30

Cys Val Pro Thr Asp Pro Ser Pro Gln Glu Val Phe Leu Gly Asn Val
            35                  40                  45

Thr Glu Asn Phe Asn Met Trp Lys Asn Asn Met Val Glu Gln Met Tyr
    50                  55                  60
```

-continued

```
Glu Asp Ile Ile Ser Leu Trp Asp Gln Ser Leu Lys Pro Cys Val Lys
 65                  70                  75                  80

Leu Thr Pro Leu Cys Val Thr Leu Asn Cys Ser Asp Tyr Arg Asn Ala
                 85                  90                  95

Thr Asp Tyr Lys Asn Ala Thr Asp Thr Thr Ser Ser Asn Glu Gly Lys
            100                 105                 110

Met Glu Arg Gly Glu Ile Lys Asn Cys Ser Phe Asn Ile Thr Thr Ser
        115                 120                 125

Ile Lys Asn Lys Met Gln Lys Glu Tyr Ala Leu Phe Tyr Lys Leu Asn
    130                 135                 140

Ile Val Pro Ile Asp Asn Thr Ser Tyr Thr Leu Ile Ser Cys Asn Thr
145                 150                 155                 160

Ser Val Ile Thr Gln Ala Cys Pro Lys Val Ser Phe Glu Pro Ile Pro
                165                 170                 175

Ile His Tyr Cys Ala Pro Ala Gly Phe Ala Ile Leu Lys Cys Asn Asp
            180                 185                 190

Lys Lys Phe Ser Gly Lys Gly Glu Cys Lys Asn Val Ser Thr Val Gln
        195                 200                 205

Cys Thr His Gly Ile Arg Pro Val Val Ser Thr Gln Leu Leu Leu Asn
    210                 215                 220

Gly Ser Leu Ala Glu Glu Val Val Ile Arg Ser Asp Asn Phe Thr
225                 230                 235                 240

Asp Asn Thr Lys Thr Ile Ile Val Gln Leu Lys Glu Ser Val Glu Ile
                245                 250                 255

Asn Cys Ile Arg Pro Asn Asn Asn Thr Arg Lys Gly Ile His Ile Gly
            260                 265                 270

Pro Gly Arg Ala Trp Tyr Ala Thr Gly Glu Ile Val Gly Asp Ile Arg
        275                 280                 285

Gln Ala Tyr Cys Asn Ile Ser Arg Thr Lys Trp Asn Asn Thr Leu Ile
    290                 295                 300

Gln Ile Ala Asn Lys Leu Lys Glu Lys Tyr Asn Thr Thr Ile Ser Phe
305                 310                 315                 320

Asn Arg Ser Ser Gly Gly Asp Pro Glu Ile Val Thr His Ser Phe Asn
                325                 330                 335

Cys Gly Gly Glu Phe Phe Tyr Cys Asn Ser Thr Gln Leu Phe Asn Ser
            340                 345                 350

Thr Trp Asn Leu Asn Gly Thr Trp Asn Phe Thr Ala Gly Ser Asn Glu
        355                 360                 365

Thr Glu Gly Asn Ile Thr Leu Pro Cys Arg Ile Lys Gln Ile Ile Asn
    370                 375                 380

Arg Trp Gln Glu Val Gly Lys Ala Met Tyr Ala Pro Pro Ile Ser Gly
385                 390                 395                 400

Gln Ile Arg Cys Ser Ser Asn Ile Thr Gly Met Ile Leu Thr Arg Asp
                405                 410                 415

Gly Gly Asn Glu Asn Asn Asn Glu Ser Ser Thr Thr Glu Thr Phe Arg
            420                 425                 430

Pro Gly Gly Gly Asp Met Arg Asn Asn Trp Arg Ser Glu Leu Tyr Lys
        435                 440                 445

Tyr Lys Val Val Lys Ile Glu Pro Leu Gly Val Ala Pro Thr Asp Ser
    450                 455                 460

Arg Gly Ser Ser Arg
465
```

```
<210> SEQ ID NO 24
<211> LENGTH: 1499
<212> TYPE: DNA
<213> ORGANISM: HIV
<220> FEATURE:
<221> NAME/KEY: CDS
<222> LOCATION: (1)...(1497)

<400> SEQUENCE: 24
```

| | | | | | | | | | | | | | | | | |
|---|---|---|---|---|---|---|---|---|---|---|---|---|---|---|---|---|
| gag | gta | cct | gtg | tgg | aaa | gaa | gca | acc | act | act | cta | ttt | tgt | gca | tca | 48 |
| Glu | Val | Pro | Val | Trp | Lys | Glu | Ala | Thr | Thr | Thr | Leu | Phe | Cys | Ala | Ser | |
| 1 | | | | 5 | | | | | 10 | | | | | 15 | | |
| gat | gct | aaa | gca | tat | gac | aca | ggg | gtg | cat | aat | gtt | tgg | gcc | aca | cat | 96 |
| Asp | Ala | Lys | Ala | Tyr | Asp | Thr | Gly | Val | His | Asn | Val | Trp | Ala | Thr | His | |
| | | | 20 | | | | | 25 | | | | | 30 | | | |
| gcc | tgt | gta | ccc | aca | gac | ccc | aac | cca | caa | gaa | ata | gaa | ttg | gta | aat | 144 |
| Ala | Cys | Val | Pro | Thr | Asp | Pro | Asn | Pro | Gln | Glu | Ile | Glu | Leu | Val | Asn | |
| | | 35 | | | | | 40 | | | | | 45 | | | | |
| gtg | aca | gaa | gat | ttt | aac | atg | tgg | aaa | aat | aaa | atg | gta | gac | cag | atg | 192 |
| Val | Thr | Glu | Asp | Phe | Asn | Met | Trp | Lys | Asn | Lys | Met | Val | Asp | Gln | Met | |
| | 50 | | | | | 55 | | | | | 60 | | | | | |
| cat | gag | gat | ata | atc | agt | tta | tgg | gat | gaa | agc | cta | aag | cca | tgt | gta | 240 |
| His | Glu | Asp | Ile | Ile | Ser | Leu | Trp | Asp | Glu | Ser | Leu | Lys | Pro | Cys | Val | |
| 65 | | | | | 70 | | | | | 75 | | | | | 80 | |
| aag | tta | acc | cca | ctt | tgt | gtt | act | cta | aac | tgc | agt | gat | gtg | aac | aat | 288 |
| Lys | Leu | Thr | Pro | Leu | Cys | Val | Thr | Leu | Asn | Cys | Ser | Asp | Val | Asn | Asn | |
| | | | | 85 | | | | | 90 | | | | | 95 | | |
| tcc | aca | aat | cct | aat | gat | act | aat | act | aat | tcc | act | aat | act | act | tcc | 336 |
| Ser | Thr | Asn | Pro | Asn | Asp | Thr | Asn | Thr | Asn | Ser | Thr | Asn | Thr | Thr | Ser | |
| | | | 100 | | | | | 105 | | | | | 110 | | | |
| tct | act | cct | acg | gcc | act | act | agt | agc | gag | gaa | aag | atg | gag | aag | gga | 384 |
| Ser | Thr | Pro | Thr | Ala | Thr | Thr | Ser | Ser | Glu | Glu | Lys | Met | Glu | Lys | Gly | |
| | | 115 | | | | | 120 | | | | | 125 | | | | |
| gaa | ata | aaa | aac | tgc | tct | ttc | aat | atc | acc | aca | cac | atg | aaa | gat | aag | 432 |
| Glu | Ile | Lys | Asn | Cys | Ser | Phe | Asn | Ile | Thr | Thr | His | Met | Lys | Asp | Lys | |
| | 130 | | | | | 135 | | | | | 140 | | | | | |
| gca | cag | aaa | gaa | tat | gca | ctt | ttt | tat | aaa | ctt | gat | ata | gta | cca | ata | 480 |
| Ala | Gln | Lys | Glu | Tyr | Ala | Leu | Phe | Tyr | Lys | Leu | Asp | Ile | Val | Pro | Ile | |
| 145 | | | | | 150 | | | | | 155 | | | | | 160 | |
| gat | gat | aat | aat | gcc | agc | tat | agg | ttg | ata | agt | tgt | aat | acc | tca | gac | 528 |
| Asp | Asp | Asn | Asn | Ala | Ser | Tyr | Arg | Leu | Ile | Ser | Cys | Asn | Thr | Ser | Asp | |
| | | | | 165 | | | | | 170 | | | | | 175 | | |
| att | aca | cag | gcc | tgt | cca | aag | gtg | acc | ttt | gag | cca | att | ccc | ata | cat | 576 |
| Ile | Thr | Gln | Ala | Cys | Pro | Lys | Val | Thr | Phe | Glu | Pro | Ile | Pro | Ile | His | |
| | | | 180 | | | | | 185 | | | | | 190 | | | |
| tat | tgt | gcc | ccg | gct | ggt | ttt | gcg | att | cta | aag | tgt | aaa | gat | aag | aag | 624 |
| Tyr | Cys | Ala | Pro | Ala | Gly | Phe | Ala | Ile | Leu | Lys | Cys | Lys | Asp | Lys | Lys | |
| | | 195 | | | | | 200 | | | | | 205 | | | | |
| ttc | aat | gga | aca | gga | cca | tgt | tca | aag | gtc | agc | aca | gta | caa | tgt | aca | 672 |
| Phe | Asn | Gly | Thr | Gly | Pro | Cys | Ser | Lys | Val | Ser | Thr | Val | Gln | Cys | Thr | |
| | 210 | | | | | 215 | | | | | 220 | | | | | |
| cat | gga | att | agg | cca | gta | gta | tca | act | caa | ctg | ttg | tta | aat | ggc | agt | 720 |
| His | Gly | Ile | Arg | Pro | Val | Val | Ser | Thr | Gln | Leu | Leu | Leu | Asn | Gly | Ser | |
| 225 | | | | | 230 | | | | | 235 | | | | | 240 | |
| ctt | gca | gaa | gaa | gaa | gta | gta | att | aga | tct | gtc | aat | ttc | aca | gac | aat | 768 |
| Leu | Ala | Glu | Glu | Glu | Val | Val | Ile | Arg | Ser | Val | Asn | Phe | Thr | Asp | Asn | |
| | | | | 245 | | | | | 250 | | | | | 255 | | |
| gct | aaa | atc | ata | ata | gta | cag | ctg | aaa | gaa | cct | gta | gca | att | aat | tgt | 816 |
| Ala | Lys | Ile | Ile | Ile | Val | Gln | Leu | Lys | Glu | Pro | Val | Ala | Ile | Asn | Cys | |
| | | | 260 | | | | | 265 | | | | | 270 | | | |
| aca | aga | ccc | aac | aac | aat | aca | aga | aaa | ggt | ata | cat | cta | gga | cca | ggg | 864 |

-continued

```
Thr Arg Pro Asn Asn Asn Thr Arg Lys Gly Ile His Leu Gly Pro Gly
            275                 280                 285 agc aca ttt tat aca aca gga gaa ata ata gga gac ata aga aaa gca      912
Ser Thr Phe Tyr Thr Thr Gly Glu Ile Ile Gly Asp Ile Arg Lys Ala
    290                 295                 300 tat tgc aag att agt aaa gaa aaa tgg aat aac act tta aga cag gta      960
Tyr Cys Lys Ile Ser Lys Glu Lys Trp Asn Asn Thr Leu Arg Gln Val
305                 310                 315                 320 gtt aaa aaa tta aga gaa caa ttt ggg aat aaa aca ata att ttt aat     1008
Val Lys Lys Leu Arg Glu Gln Phe Gly Asn Lys Thr Ile Ile Phe Asn
                325                 330                 335 cga tcc tca gga ggg gac cca gaa att gta atg cac agt ttt aac tgt     1056
Arg Ser Ser Gly Gly Asp Pro Glu Ile Val Met His Ser Phe Asn Cys
            340                 345                 350 gga ggg gag ttt ttc tac tgt aat aca aca caa ctg ttt aat agt act     1104
Gly Gly Glu Phe Phe Tyr Cys Asn Thr Thr Gln Leu Phe Asn Ser Thr
        355                 360                 365 tgg aat aat act gaa ggg aca aat agc act gaa gga aat agc aca atc     1152
Trp Asn Asn Thr Glu Gly Thr Asn Ser Thr Glu Gly Asn Ser Thr Ile
    370                 375                 380 aca ctc cca tgc aga ata aaa caa att ata aat atg tgg cag gaa gta     1200
Thr Leu Pro Cys Arg Ile Lys Gln Ile Ile Asn Met Trp Gln Glu Val
385                 390                 395                 400 gga aaa gca acg tat gcc cct ccc atc aga gga cga att aga tgc ata     1248
Gly Lys Ala Thr Tyr Ala Pro Pro Ile Arg Gly Arg Ile Arg Cys Ile
                405                 410                 415 tca aat att aca gga ctg cta tta aca aga gat ggt ggt agg aat gtc     1296
Ser Asn Ile Thr Gly Leu Leu Leu Thr Arg Asp Gly Gly Arg Asn Val
            420                 425                 430 aca aac aat acc gaa acc ttc aga cct gga gga gga gac atg agg gac     1344
Thr Asn Asn Thr Glu Thr Phe Arg Pro Gly Gly Gly Asp Met Arg Asp
        435                 440                 445 aat tgg aga agt gaa tta tat aaa tat aaa gta gta aaa gtt gaa cca     1392
Asn Trp Arg Ser Glu Leu Tyr Lys Tyr Lys Val Val Lys Val Glu Pro
    450                 455                 460 tta gga ata gca ccc acc aag gca aag aga aga gtg gtg cac aga gac     1440
Leu Gly Ile Ala Pro Thr Lys Ala Lys Arg Arg Val Val His Arg Asp
465                 470                 475                 480 aaa aga gca gca cta gga gcc ttg ttc ctt ggg ttc tta gga gca taa     1488
Lys Arg Ala Ala Leu Gly Ala Leu Phe Leu Gly Phe Leu Gly Ala
                485                 490                 495 aag ctt cta ga                                                      1499
Lys Leu Leu
```

<210> SEQ ID NO 25
<211> LENGTH: 495
<212> TYPE: PRT
<213> ORGANISM: HIV

<400> SEQUENCE: 25

```
Glu Val Pro Val Trp Lys Glu Ala Thr Thr Thr Leu Phe Cys Ala Ser
1               5                   10                  15

Asp Ala Lys Ala Tyr Asp Thr Gly Val His Asn Val Trp Ala Thr His
                20                  25                  30

Ala Cys Val Pro Thr Asp Pro Asn Pro Gln Glu Ile Glu Leu Val Asn
            35                  40                  45

Val Thr Glu Asp Phe Asn Met Trp Lys Asn Lys Met Val Asp Gln Met
        50                  55                  60

His Glu Asp Ile Ile Ser Leu Trp Asp Glu Ser Leu Lys Pro Cys Val
```

```
                65                  70                  75                  80
            Lys Leu Thr Pro Leu Cys Val Thr Leu Asn Cys Ser Asp Val Asn Asn
                            85                  90                  95

Ser Thr Asn Pro Asn Asp Thr Asn Thr Asn Ser Thr Asn Thr Thr Ser
                        100                 105                 110

Ser Thr Pro Thr Ala Thr Thr Ser Ser Glu Glu Lys Met Glu Lys Gly
                        115                 120                 125

Glu Ile Lys Asn Cys Ser Phe Asn Ile Thr Thr His Met Lys Asp Lys
                    130                 135                 140

Ala Gln Lys Glu Tyr Ala Leu Phe Tyr Lys Leu Asp Ile Val Pro Ile
            145                 150                 155                 160

Asp Asp Asn Asn Ala Ser Tyr Arg Leu Ile Ser Cys Asn Thr Ser Asp
                            165                 170                 175

Ile Thr Gln Ala Cys Pro Lys Val Thr Phe Glu Pro Ile Pro Ile His
                        180                 185                 190

Tyr Cys Ala Pro Ala Gly Phe Ala Ile Leu Lys Cys Lys Asp Lys Lys
                        195                 200                 205

Phe Asn Gly Thr Gly Pro Cys Ser Lys Val Ser Thr Val Gln Cys Thr
                    210                 215                 220

His Gly Ile Arg Pro Val Val Ser Thr Gln Leu Leu Leu Asn Gly Ser
            225                 230                 235                 240

Leu Ala Glu Glu Glu Val Val Ile Arg Ser Val Asn Phe Thr Asp Asn
                            245                 250                 255

Ala Lys Ile Ile Ile Val Gln Leu Lys Glu Pro Val Ala Ile Asn Cys
                        260                 265                 270

Thr Arg Pro Asn Asn Asn Thr Arg Lys Gly Ile His Leu Gly Pro Gly
                        275                 280                 285

Ser Thr Phe Tyr Thr Thr Gly Glu Ile Ile Gly Asp Ile Arg Lys Ala
                    290                 295                 300

Tyr Cys Lys Ile Ser Lys Glu Lys Trp Asn Asn Thr Leu Arg Gln Val
            305                 310                 315                 320

Val Lys Lys Leu Arg Glu Gln Phe Gly Asn Lys Thr Ile Ile Phe Asn
                            325                 330                 335

Arg Ser Ser Gly Gly Asp Pro Glu Ile Val Met His Ser Phe Asn Cys
                        340                 345                 350

Gly Gly Glu Phe Phe Tyr Cys Asn Thr Thr Gln Leu Phe Asn Ser Thr
                        355                 360                 365

Trp Asn Asn Thr Glu Gly Thr Asn Ser Thr Glu Gly Asn Ser Thr Ile
                    370                 375                 380

Thr Leu Pro Cys Arg Ile Lys Gln Ile Ile Asn Met Trp Gln Glu Val
            385                 390                 395                 400

Gly Lys Ala Thr Tyr Ala Pro Pro Ile Arg Gly Arg Ile Arg Cys Ile
                            405                 410                 415

Ser Asn Ile Thr Gly Leu Leu Leu Thr Arg Asp Gly Gly Arg Asn Val
                        420                 425                 430

Thr Asn Asn Thr Glu Thr Phe Arg Pro Gly Gly Gly Asp Met Arg Asp
                        435                 440                 445

Asn Trp Arg Ser Glu Leu Tyr Lys Tyr Lys Val Val Lys Val Glu Pro
                    450                 455                 460

Leu Gly Ile Ala Pro Thr Lys Ala Lys Arg Arg Val Val His Arg Asp
            465                 470                 475                 480

Lys Arg Ala Ala Leu Gly Ala Leu Phe Leu Gly Phe Leu Gly Ala
                            485                 490                 495
```

```
<210> SEQ ID NO 26
<211> LENGTH: 3
<212> TYPE: PRT
<213> ORGANISM: HIV

<400> SEQUENCE: 26

Lys Leu Leu
  1

<210> SEQ ID NO 27
<211> LENGTH: 1499
<212> TYPE: DNA
<213> ORGANISM: HIV
<220> FEATURE:
<221> NAME/KEY: CDS
<222> LOCATION: (1)...(1497)
<221> NAME/KEY: misc_feature
<222> LOCATION: (1)...(1499)
<223> OTHER INFORMATION: n = A,T,C or G

<400> SEQUENCE: 27 gag gta cct gta tgg aaa gaa gca acc act act cta ttt tgt gca tca        48
Glu Val Pro Val Trp Lys Glu Ala Thr Thr Thr Leu Phe Cys Ala Ser
  1               5                  10                  15 gat gct aaa gca tat gac aca gag gtg cat aat gtt tgg gcc aca cat        96
Asp Ala Lys Ala Tyr Asp Thr Glu Val His Asn Val Trp Ala Thr His
             20                  25                  30 gcc tgt gta ccc aca gac ccc aac cca caa gaa ata gaa ttg gta aat       144
Ala Cys Val Pro Thr Asp Pro Asn Pro Gln Glu Ile Glu Leu Val Asn
         35                  40                  45 gtg aca gaa gat ttt aac atg tgg aaa aat aaa atg gta gac cag atg       192
Val Thr Glu Asp Phe Asn Met Trp Lys Asn Lys Met Val Asp Gln Met
     50                  55                  60 cat gag gat ata atc agt tta tgg gat gaa agc cta aag cca tgt gta       240
His Glu Asp Ile Ile Ser Leu Trp Asp Glu Ser Leu Lys Pro Cys Val
 65                  70                  75                  80 aag tta acc cca ctt tgt gtt act cta aac tgc agt gat gtg aac aat       288
Lys Leu Thr Pro Leu Cys Val Thr Leu Asn Cys Ser Asp Val Asn Asn
                 85                  90                  95 tcc aca aat cct aat gat act aat act aat tcc act aat act act tcc       336
Ser Thr Asn Pro Asn Asp Thr Asn Thr Asn Ser Thr Asn Thr Thr Ser
            100                 105                 110 tct act cct acg gcc act act agt agc gag gaa aag atg gag aag gga       384
Ser Thr Pro Thr Ala Thr Thr Ser Ser Glu Glu Lys Met Glu Lys Gly
        115                 120                 125 gaa ata aaa aac tgc tct ttc aat atc acc aca cac atg aaa gat aag       432
Glu Ile Lys Asn Cys Ser Phe Asn Ile Thr Thr His Met Lys Asp Lys
    130                 135                 140 gta cag aaa gaa tat gca ctt ttt tat aaa ctt gat ata gta cca ata       480
Val Gln Lys Glu Tyr Ala Leu Phe Tyr Lys Leu Asp Ile Val Pro Ile
145                 150                 155                 160 gat gat aat aat acc agc tat agg ttg ata agt tgt aat acc tca gtc       528
Asp Asp Asn Asn Thr Ser Tyr Arg Leu Ile Ser Cys Asn Thr Ser Val
                165                 170                 175 att aca cag gcc tgt cca atg gtg acc ttt gag cca att ccc ata cat       576
Ile Thr Gln Ala Cys Pro Met Val Thr Phe Glu Pro Ile Pro Ile His
            180                 185                 190 tat tgt gcc ccg gct ggt ttt gcg att cta aag tgt aaa gat aag aag       624
Tyr Cys Ala Pro Ala Gly Phe Ala Ile Leu Lys Cys Lys Asp Lys Lys
        195                 200                 205 ttc aat gga aca gga cca tgt tca aag gtc agc aca gta caa tgt aca       672
```

|     |     |     |     |     |     |     |     |     |     |     |     |      |
|-----|-----|-----|-----|-----|-----|-----|-----|-----|-----|-----|-----|------|
| Phe | Asn | Gly | Thr | Gly | Pro | Cys | Ser | Lys | Val | Ser | Thr | Val Gln Cys Thr |
|     | 210 |     |     |     | 215 |     |     |     | 220 |     |     |      |

```
cat gga att agg cca gta gta tca act caa ctg ttg tta aat ggc agt         720
His Gly Ile Arg Pro Val Val Ser Thr Gln Leu Leu Leu Asn Gly Ser
225                 230                 235                 240 ctt gca gaa gaa gaa gta gta att aga tct gtc aat ttc aca gac aat         768
Leu Ala Glu Glu Glu Val Val Ile Arg Ser Val Asn Phe Thr Asp Asn
                245                 250                 255 gct aaa atc ata ata gta cag ctg aaa gaa cct gta gca att aat tgt         816
Ala Lys Ile Ile Ile Val Gln Leu Lys Glu Pro Val Ala Ile Asn Cys
                260                 265                 270 aca aga ccc aac aac aat aca aga aaa ggt ata cat cta gga cca ggg         864
Thr Arg Pro Asn Asn Asn Thr Arg Lys Gly Ile His Leu Gly Pro Gly
            275                 280                 285 agc aca ttt tat aca aca gga gaa ata ata gga gac ata aga aaa gca         912
Ser Thr Phe Tyr Thr Thr Gly Glu Ile Ile Gly Asp Ile Arg Lys Ala
        290                 295                 300 tat tgc aag att agt aaa gaa aaa tgg aat aac act tta aga cag gta         960
Tyr Cys Lys Ile Ser Lys Glu Lys Trp Asn Asn Thr Leu Arg Gln Val
305                 310                 315                 320 gtt aaa aaa tta aga gaa caa ttt ggg aat aaa aca ata att ttt aat        1008
Val Lys Lys Leu Arg Glu Gln Phe Gly Asn Lys Thr Ile Ile Phe Asn
                325                 330                 335 cga tcc tca gga ggg gac cca gaa att gta atg cac agt ttt aac tgt        1056
Arg Ser Ser Gly Gly Asp Pro Glu Ile Val Met His Ser Phe Asn Cys
                340                 345                 350 gga ggg gag ttt ttc tac tgt aat aca aca caa ctg ttt aat agt act        1104
Gly Gly Glu Phe Phe Tyr Cys Asn Thr Thr Gln Leu Phe Asn Ser Thr
                355                 360                 365 tgg aat aat act gaa ggg aca aat agc act gaa gga aat agc aca atc        1152
Trp Asn Asn Thr Glu Gly Thr Asn Ser Thr Glu Gly Asn Ser Thr Ile
370                 375                 380 aca ctc cca tgc aga ata aaa caa att ata aat atg tgg cag gaa gta        1200
Thr Leu Pro Cys Arg Ile Lys Gln Ile Ile Asn Met Trp Gln Glu Val
385                 390                 395                 400 gga aaa gca acg tat gcc cct ccc atc aga gga cga att aga tgc ata        1248
Gly Lys Ala Thr Tyr Ala Pro Pro Ile Arg Gly Arg Ile Arg Cys Ile
                405                 410                 415 tca aat att aca gga ctg cta tta aca aga gat ggt ggt agg aat gtc        1296
Ser Asn Ile Thr Gly Leu Leu Leu Thr Arg Asp Gly Gly Arg Asn Val
                420                 425                 430 aca aac aat acc gan ncc ttc aga cct gga gga gga gac atg agg gac        1344
Thr Asn Asn Thr Xaa Xaa Phe Arg Pro Gly Gly Gly Asp Met Arg Asp
                435                 440                 445 aat tgg aga agt gaa tta tat aaa tat aaa gta gta aaa gtt gaa cca        1392
Asn Trp Arg Ser Glu Leu Tyr Lys Tyr Lys Val Val Lys Val Glu Pro
450                 455                 460 tta gga ata gca ccc acc aag gca aag aga aga gtg gtg cac aga gac        1440
Leu Gly Ile Ala Pro Thr Lys Ala Lys Arg Arg Val Val His Arg Asp
465                 470                 475                 480 aaa aga gca gca cta gga gct ttg ttc ctt ggg ttc tta gga gca taa        1488
Lys Arg Ala Ala Leu Gly Ala Leu Phe Leu Gly Phe Leu Gly Ala
                485                 490                 495 aag ctt cta ga                                                         1499
Lys Leu Leu

<210> SEQ ID NO 28
<211> LENGTH: 495
<212> TYPE: PRT
<213> ORGANISM: HIV
```

```
<220> FEATURE:
<221> NAME/KEY: VARIANT
<222> LOCATION: (1)...(495)
<223> OTHER INFORMATION: Xaa = Any Amino Acid

<400> SEQUENCE: 28
```

| | | | | | | | | | | | | | | |
|---|---|---|---|---|---|---|---|---|---|---|---|---|---|---|
| Glu | Val | Pro | Val | Trp | Lys | Glu | Ala | Thr | Thr | Thr | Leu | Phe | Cys | Ala | Ser |
| 1 | | | | 5 | | | | | 10 | | | | | 15 |
| Asp | Ala | Lys | Ala | Tyr | Asp | Thr | Glu | Val | His | Asn | Val | Trp | Ala | Thr | His |
| | | | 20 | | | | | 25 | | | | | 30 | |
| Ala | Cys | Val | Pro | Thr | Asp | Pro | Asn | Pro | Gln | Glu | Ile | Glu | Leu | Val | Asn |
| | | 35 | | | | | 40 | | | | | 45 | | |
| Val | Thr | Glu | Asp | Phe | Asn | Met | Trp | Lys | Asn | Lys | Met | Val | Asp | Gln | Met |
| | 50 | | | | | 55 | | | | | 60 | | | | |
| His | Glu | Asp | Ile | Ile | Ser | Leu | Trp | Asp | Glu | Ser | Leu | Lys | Pro | Cys | Val |
| 65 | | | | | 70 | | | | | 75 | | | | | 80 |
| Lys | Leu | Thr | Pro | Leu | Cys | Val | Thr | Leu | Asn | Cys | Ser | Asp | Val | Asn | Asn |
| | | | | 85 | | | | | 90 | | | | | 95 | |
| Ser | Thr | Asn | Pro | Asn | Asp | Thr | Asn | Thr | Asn | Ser | Thr | Asn | Thr | Thr | Ser |
| | | | 100 | | | | | 105 | | | | | 110 | | |
| Ser | Thr | Pro | Thr | Ala | Thr | Thr | Ser | Ser | Glu | Glu | Lys | Met | Glu | Lys | Gly |
| | | 115 | | | | | 120 | | | | | 125 | | | |
| Glu | Ile | Lys | Asn | Cys | Ser | Phe | Asn | Ile | Thr | Thr | His | Met | Lys | Asp | Lys |
| | 130 | | | | | 135 | | | | | 140 | | | | |
| Val | Gln | Lys | Glu | Tyr | Ala | Leu | Phe | Tyr | Lys | Leu | Asp | Ile | Val | Pro | Ile |
| 145 | | | | | 150 | | | | | 155 | | | | | 160 |
| Asp | Asp | Asn | Asn | Thr | Ser | Tyr | Arg | Leu | Ile | Ser | Cys | Asn | Thr | Ser | Val |
| | | | | 165 | | | | | 170 | | | | | 175 | |
| Ile | Thr | Gln | Ala | Cys | Pro | Met | Val | Thr | Phe | Glu | Pro | Ile | Pro | Ile | His |
| | | | 180 | | | | | 185 | | | | | 190 | | |
| Tyr | Cys | Ala | Pro | Ala | Gly | Phe | Ala | Ile | Leu | Lys | Cys | Lys | Asp | Lys | Lys |
| | | 195 | | | | | 200 | | | | | 205 | | | |
| Phe | Asn | Gly | Thr | Gly | Pro | Cys | Ser | Lys | Val | Ser | Thr | Val | Gln | Cys | Thr |
| 210 | | | | | 215 | | | | | 220 | | | | | |
| His | Gly | Ile | Arg | Pro | Val | Val | Ser | Thr | Gln | Leu | Leu | Leu | Asn | Gly | Ser |
| 225 | | | | | 230 | | | | | 235 | | | | | 240 |
| Leu | Ala | Glu | Glu | Glu | Val | Val | Ile | Arg | Ser | Val | Asn | Phe | Thr | Asp | Asn |
| | | | | 245 | | | | | 250 | | | | | 255 | |
| Ala | Lys | Ile | Ile | Ile | Val | Gln | Leu | Lys | Glu | Pro | Val | Ala | Ile | Asn | Cys |
| | | | 260 | | | | | 265 | | | | | 270 | | |
| Thr | Arg | Pro | Asn | Asn | Asn | Thr | Arg | Lys | Gly | Ile | His | Leu | Gly | Pro | Gly |
| | | 275 | | | | | 280 | | | | | 285 | | | |
| Ser | Thr | Phe | Tyr | Thr | Thr | Gly | Glu | Ile | Ile | Gly | Asp | Ile | Arg | Lys | Ala |
| | 290 | | | | | 295 | | | | | 300 | | | | |
| Tyr | Cys | Lys | Ile | Ser | Lys | Glu | Lys | Trp | Asn | Asn | Thr | Leu | Arg | Gln | Val |
| 305 | | | | | 310 | | | | | 315 | | | | | 320 |
| Val | Lys | Lys | Leu | Arg | Glu | Gln | Phe | Gly | Asn | Lys | Thr | Ile | Ile | Phe | Asn |
| | | | | 325 | | | | | 330 | | | | | 335 | |
| Arg | Ser | Ser | Gly | Gly | Asp | Pro | Glu | Ile | Val | Met | His | Ser | Phe | Asn | Cys |
| | | | 340 | | | | | 345 | | | | | 350 | | |
| Gly | Gly | Glu | Phe | Phe | Tyr | Cys | Asn | Thr | Thr | Gln | Leu | Phe | Asn | Ser | Thr |
| | | 355 | | | | | 360 | | | | | 365 | | | |
| Trp | Asn | Asn | Thr | Glu | Gly | Thr | Ser | Thr | Glu | Gly | Asn | Ser | Thr | Ile | |
| 370 | | | | | 375 | | | | | 380 | | | | | |

```
Thr Leu Pro Cys Arg Ile Lys Gln Ile Ile Asn Met Trp Gln Glu Val
385                 390                 395                 400

Gly Lys Ala Thr Tyr Ala Pro Pro Ile Arg Gly Arg Ile Arg Cys Ile
                405                 410                 415

Ser Asn Ile Thr Gly Leu Leu Thr Arg Asp Gly Gly Arg Asn Val
                420                 425                 430

Thr Asn Asn Thr Xaa Xaa Phe Arg Pro Gly Gly Gly Asp Met Arg Asp
                435                 440                 445

Asn Trp Arg Ser Glu Leu Tyr Lys Tyr Lys Val Val Lys Val Glu Pro
450                 455                 460

Leu Gly Ile Ala Pro Thr Lys Ala Lys Arg Arg Val Val His Arg Asp
465                 470                 475                 480

Lys Arg Ala Ala Leu Gly Ala Leu Phe Leu Gly Phe Leu Gly Ala
                485                 490                 495

<210> SEQ ID NO 29
<211> LENGTH: 3
<212> TYPE: PRT
<213> ORGANISM: HIV

<400> SEQUENCE: 29

Lys Leu Leu
 1

<210> SEQ ID NO 30
<211> LENGTH: 1475
<212> TYPE: DNA
<213> ORGANISM: HIV
<220> FEATURE:
<221> NAME/KEY: CDS
<222> LOCATION: (2)...(1450)

<400> SEQUENCE: 30 g gta cct gtg tgg aaa gaa gca aac aca act cta ttt tgt gca tca gat      49
  Val Pro Val Trp Lys Glu Ala Asn Thr Thr Leu Phe Cys Ala Ser Asp
   1               5                  10                  15 gct aaa gca tat gat aga gaa gta cat aat gtt tgg gca aca cat gcc        97
Ala Lys Ala Tyr Asp Arg Glu Val His Asn Val Trp Ala Thr His Ala
            20                  25                  30 tgt gta ccc aca gac ccc aac cca caa gaa ata gta ttg gga aat gtg       145
Cys Val Pro Thr Asp Pro Asn Pro Gln Glu Ile Val Leu Gly Asn Val
        35                  40                  45 aca gaa aat ttt aac atg tgg aaa aat aac atg gta gaa caa atg cat       193
Thr Glu Asn Phe Asn Met Trp Lys Asn Asn Met Val Glu Gln Met His
 50                  55                  60 gag gat ata atc aat tta tgg gat caa agc tta aag cca tgt gta aag       241
Glu Asp Ile Ile Asn Leu Trp Asp Gln Ser Leu Lys Pro Cys Val Lys
 65                  70                  75                  80 tta act cca ctc tgt gtt act tta aag tgc aag gat ctg gag agg aat       289
Leu Thr Pro Leu Cys Val Thr Leu Lys Cys Lys Asp Leu Glu Arg Asn
                85                  90                  95 act acc tat aat agc act att acc aat aat agt agt ttg gag gga cta       337
Thr Thr Tyr Asn Ser Thr Ile Thr Asn Asn Ser Ser Leu Glu Gly Leu
            100                 105                 110 aga gaa caa atg aca aac tgc tct ttc aac atc acc aca agt ata aga       385
Arg Glu Gln Met Thr Asn Cys Ser Phe Asn Ile Thr Thr Ser Ile Arg
        115                 120                 125 gat aag gtg cag aaa gaa tat gca ctt ttg tat aaa ctt gat gta gta       433
Asp Lys Val Gln Lys Glu Tyr Ala Leu Leu Tyr Lys Leu Asp Val Val
    130                 135                 140
```

```
cca ata gaa gaa gat gac aat act agc tat aga ttg ata agt tgt aac      481
Pro Ile Glu Glu Asp Asp Asn Thr Ser Tyr Arg Leu Ile Ser Cys Asn
145                 150                 155                 160 acc tca gtc att aca cag gct tgt cca aag aca tcc ttt gag cca att      529
Thr Ser Val Ile Thr Gln Ala Cys Pro Lys Thr Ser Phe Glu Pro Ile
                165                 170                 175 ccc ata cat tat tgt gcc ccg gct ggt ttt gcg att cta aag tgt aat      577
Pro Ile His Tyr Cys Ala Pro Ala Gly Phe Ala Ile Leu Lys Cys Asn
            180                 185                 190 gat aag aag ttc aat gga aca gga cca tgt aaa aat gtc agc aca gta      625
Asp Lys Lys Phe Asn Gly Thr Gly Pro Cys Lys Asn Val Ser Thr Val
        195                 200                 205 caa tgt aca cat gga att agg cca gta gta tca act caa ctg ttg tta      673
Gln Cys Thr His Gly Ile Arg Pro Val Val Ser Thr Gln Leu Leu Leu
210                 215                 220 aat ggc agt cta gca gaa gaa gag gta gta atc aga tct gcc aat ttc      721
Asn Gly Ser Leu Ala Glu Glu Glu Val Val Ile Arg Ser Ala Asn Phe
225                 230                 235                 240 aca gac aat gct aaa acc ata ata gta cat cta aat gaa act gta aaa      769
Thr Asp Asn Ala Lys Thr Ile Ile Val His Leu Asn Glu Thr Val Lys
                245                 250                 255 att aat tgt aca aga ctt ggc aac aat aca aga aaa agt ata aat ata      817
Ile Asn Cys Thr Arg Leu Gly Asn Asn Thr Arg Lys Ser Ile Asn Ile
            260                 265                 270 gga cca ggg aga gta ctc tat gca aca gga gaa ata ata gga gac ata      865
Gly Pro Gly Arg Val Leu Tyr Ala Thr Gly Glu Ile Ile Gly Asp Ile
        275                 280                 285 aga caa gca cat tgt aac att agt aga gca caa tgg aat aag act tta      913
Arg Gln Ala His Cys Asn Ile Ser Arg Ala Gln Trp Asn Lys Thr Leu
    290                 295                 300 gaa aag gta gtt gac aaa tta aga aaa caa ttt ggg gat aat aca aca      961
Glu Lys Val Val Asp Lys Leu Arg Lys Gln Phe Gly Asp Asn Thr Thr
305                 310                 315                 320 ata gct ttt aat cga tcc tca gga ggg gac cca gaa att gta atg cac     1009
Ile Ala Phe Asn Arg Ser Ser Gly Gly Asp Pro Glu Ile Val Met His
                325                 330                 335 act ttt aat tgt gga ggg gaa ttt ttc tac tgt aat aca aca caa ctg     1057
Thr Phe Asn Cys Gly Gly Glu Phe Phe Tyr Cys Asn Thr Thr Gln Leu
            340                 345                 350 ttt aat agt act tgg aat aat act tgg aag gat cct aac agg agt gac     1105
Phe Asn Ser Thr Trp Asn Asn Thr Trp Lys Asp Pro Asn Arg Ser Asp
        355                 360                 365 aat atc aca ctc cca tgc aga ata aaa caa att ata aac atg tgg cag     1153
Asn Ile Thr Leu Pro Cys Arg Ile Lys Gln Ile Ile Asn Met Trp Gln
    370                 375                 380 gaa gta gga aaa gca atg tac gcc cct ccc atc aga ggg gaa att aga     1201
Glu Val Gly Lys Ala Met Tyr Ala Pro Pro Ile Arg Gly Glu Ile Arg
385                 390                 395                 400 tgt tca tca aat atc aca ggg ctg cta cta aca aga gat ggt ggt aat     1249
Cys Ser Ser Asn Ile Thr Gly Leu Leu Leu Thr Arg Asp Gly Gly Asn
                405                 410                 415 gac gat ggt aat gac acg acc aca aac agg acc gag atc ttc aga cct     1297
Asp Asp Gly Asn Asp Thr Thr Thr Asn Arg Thr Glu Ile Phe Arg Pro
            420                 425                 430 gga gga gga gat atg agg gac aat tgg aga agt gaa tta tat aga tat     1345
Gly Gly Gly Asp Met Arg Asp Asn Trp Arg Ser Glu Leu Tyr Arg Tyr
        435                 440                 445 aaa gta gta aaa att gaa cca tta gga ata gca ccc acc agg gca aag     1393
Lys Val Val Lys Ile Glu Pro Leu Gly Ile Ala Pro Thr Arg Ala Lys
    450                 455                 460
```

```
aga aga gtg gtg cag aga gaa aaa aga gca gta gga cta gga gct ttg         1441
Arg Arg Val Val Gln Arg Glu Lys Arg Ala Val Gly Leu Gly Ala Leu
465             470                 475                 480 ttc ctt ggg ttcttaggag cataaagctt ctaga                                 1475
Phe Leu Gly

<210> SEQ ID NO 31
<211> LENGTH: 483
<212> TYPE: PRT
<213> ORGANISM: HIV

<400> SEQUENCE: 31

Val Pro Val Trp Lys Glu Ala Asn Thr Thr Leu Phe Cys Ala Ser Asp
 1               5                  10                  15

Ala Lys Ala Tyr Asp Arg Glu Val His Asn Val Trp Ala Thr His Ala
             20                  25                  30

Cys Val Pro Thr Asp Pro Asn Pro Gln Glu Ile Val Leu Gly Asn Val
         35                  40                  45

Thr Glu Asn Phe Asn Met Trp Lys Asn Met Val Glu Gln Met His
     50                  55                  60

Glu Asp Ile Ile Asn Leu Trp Asp Gln Ser Leu Lys Pro Cys Val Lys
65                  70                  75                  80

Leu Thr Pro Leu Cys Val Thr Leu Lys Cys Lys Asp Leu Glu Arg Asn
                 85                  90                  95

Thr Thr Tyr Asn Ser Thr Ile Thr Asn Ser Ser Leu Glu Gly Leu
            100                 105                 110

Arg Glu Gln Met Thr Asn Cys Ser Phe Asn Ile Thr Thr Ser Ile Arg
        115                 120                 125

Asp Lys Val Gln Lys Glu Tyr Ala Leu Leu Tyr Lys Leu Asp Val Val
    130                 135                 140

Pro Ile Glu Glu Asp Asp Asn Thr Ser Tyr Arg Leu Ile Ser Cys Asn
145                 150                 155                 160

Thr Ser Val Ile Thr Gln Ala Cys Pro Lys Thr Ser Phe Glu Pro Ile
                165                 170                 175

Pro Ile His Tyr Cys Ala Pro Ala Gly Phe Ala Ile Leu Lys Cys Asn
            180                 185                 190

Asp Lys Lys Phe Asn Gly Thr Gly Pro Cys Lys Asn Val Ser Thr Val
        195                 200                 205

Gln Cys Thr His Gly Ile Arg Pro Val Val Ser Thr Gln Leu Leu Leu
    210                 215                 220

Asn Gly Ser Leu Ala Glu Glu Val Val Ile Arg Ser Ala Asn Phe
225                 230                 235                 240

Thr Asp Asn Ala Lys Thr Ile Ile Val His Leu Asn Glu Thr Val Lys
                245                 250                 255

Ile Asn Cys Thr Arg Leu Gly Asn Asn Thr Arg Lys Ser Ile Asn Ile
            260                 265                 270

Gly Pro Gly Arg Val Leu Tyr Ala Thr Gly Glu Ile Ile Gly Asp Ile
        275                 280                 285

Arg Gln Ala His Cys Asn Ile Ser Arg Ala Gln Trp Asn Lys Thr Leu
    290                 295                 300

Glu Lys Val Val Asp Lys Leu Arg Lys Gln Phe Gly Asp Asn Thr Thr
305                 310                 315                 320

Ile Ala Phe Asn Arg Ser Ser Gly Gly Asp Pro Glu Ile Val Met His
                325                 330                 335
```

```
Thr Phe Asn Cys Gly Gly Glu Phe Phe Tyr Cys Asn Thr Thr Gln Leu
            340                 345                 350

Phe Asn Ser Thr Trp Asn Asn Thr Trp Lys Asp Pro Asn Arg Ser Asp
            355                 360                 365

Asn Ile Thr Leu Pro Cys Arg Ile Lys Gln Ile Ile Asn Met Trp Gln
            370                 375                 380

Glu Val Gly Lys Ala Met Tyr Ala Pro Pro Ile Arg Gly Glu Ile Arg
385                 390                 395                 400

Cys Ser Ser Asn Ile Thr Gly Leu Leu Leu Thr Arg Asp Gly Gly Asn
                    405                 410                 415

Asp Asp Gly Asn Asp Thr Thr Asn Arg Thr Glu Ile Phe Arg Pro
                    420                 425                 430

Gly Gly Gly Asp Met Arg Asp Asn Trp Arg Ser Glu Leu Tyr Arg Tyr
                    435                 440                 445

Lys Val Val Lys Ile Glu Pro Leu Gly Ile Ala Pro Thr Arg Ala Lys
            450                 455                 460

Arg Arg Val Val Gln Arg Glu Lys Arg Ala Val Gly Leu Gly Ala Leu
465                 470                 475                 480

Phe Leu Gly

<210> SEQ ID NO 32
<211> LENGTH: 1475
<212> TYPE: DNA
<213> ORGANISM: HIV
<220> FEATURE:
<221> NAME/KEY: CDS
<222> LOCATION: (2)...(1474)

<400> SEQUENCE: 32 g gta cct gtg tgg aaa gaa gca aac aca act cta ttt tgt gca tca gat      49
  Val Pro Val Trp Lys Glu Ala Asn Thr Thr Leu Phe Cys Ala Ser Asp
  1               5                   10                  15 gct aaa gca tat gat aga gaa gta cat aat gtt tgg gca aca cat gcc       97
Ala Lys Ala Tyr Asp Arg Glu Val His Asn Val Trp Ala Thr His Ala
            20                  25                  30 tgt gta ccc aca gac ccc aac cca caa gaa ata gta ttg gga aat gtg      145
Cys Val Pro Thr Asp Pro Asn Pro Gln Glu Ile Val Leu Gly Asn Val
        35                  40                  45 aca gaa aat ttt aac atg tgg aaa aat aac atg gta gaa caa atg cat      193
Thr Glu Asn Phe Asn Met Trp Lys Asn Asn Met Val Glu Gln Met His
    50                  55                  60 gag gat ata atc aat tta tgg gat caa agc tta aag cca tgt gta aag      241
Glu Asp Ile Ile Asn Leu Trp Asp Gln Ser Leu Lys Pro Cys Val Lys
65                  70                  75                  80 tta act cca ctc tgt gtt act tta aag tgc aag gat ctg gag agg aat      289
Leu Thr Pro Leu Cys Val Thr Leu Lys Cys Lys Asp Leu Glu Arg Asn
                85                  90                  95 act acc tat aat agc act att acc aat aat agt agt ttg gag gga cta      337
Thr Thr Tyr Asn Ser Thr Ile Thr Asn Asn Ser Ser Leu Glu Gly Leu
            100                 105                 110 aga gaa caa atg aca aac tgc tct ttc aac atc acc aca agt ata aga      385
Arg Glu Gln Met Thr Asn Cys Ser Phe Asn Ile Thr Thr Ser Ile Arg
        115                 120                 125 gat aag gtg cag aaa gaa tat gca ctt ttg tat aaa ctt gat gta gta      433
Asp Lys Val Gln Lys Glu Tyr Ala Leu Leu Tyr Lys Leu Asp Val Val
    130                 135                 140 cca ata gaa gaa gat gac aat act agc tat aga ttg ata agt tgt aac      481
Pro Ile Glu Glu Asp Asp Asn Thr Ser Tyr Arg Leu Ile Ser Cys Asn
145                 150                 155                 160
```

```
acc tca gtc att aca cag gct tgt cca aag aca tcc ttt gag cca att      529
Thr Ser Val Ile Thr Gln Ala Cys Pro Lys Thr Ser Phe Glu Pro Ile
            165                 170                 175 ccc ata cat tat tgt gcc ccg gct ggt ttt gcg att cta aag tgt aat      577
Pro Ile His Tyr Cys Ala Pro Ala Gly Phe Ala Ile Leu Lys Cys Asn
            180                 185                 190 gat aag aag ttc aat gga aca gga cca tgt aaa aat gtc agc aca gta      625
Asp Lys Lys Phe Asn Gly Thr Gly Pro Cys Lys Asn Val Ser Thr Val
            195                 200                 205 caa tgt aca cat gga att agg cca gta gta tca act caa ctg ttg tta      673
Gln Cys Thr His Gly Ile Arg Pro Val Val Ser Thr Gln Leu Leu Leu
            210                 215                 220 aat ggc agt cta gca gaa gaa gag gta gta atc aga tct gcc aat ttc      721
Asn Gly Ser Leu Ala Glu Glu Glu Val Val Ile Arg Ser Ala Asn Phe
225                 230                 235                 240 aca gac aat gct aaa acc ata ata gta cat cta aat gaa act gta aaa      769
Thr Asp Asn Ala Lys Thr Ile Ile Val His Leu Asn Glu Thr Val Lys
            245                 250                 255 att aat tgt aca aga ctt ggc aac aat aca aga aaa agt ata aat ata      817
Ile Asn Cys Thr Arg Leu Gly Asn Asn Thr Arg Lys Ser Ile Asn Ile
            260                 265                 270 gga cca ggg aga gta ctc tat gca aca gga gaa ata ata gga gac ata      865
Gly Pro Gly Arg Val Leu Tyr Ala Thr Gly Glu Ile Ile Gly Asp Ile
            275                 280                 285 aga caa gca cat tgt aac att agt aga gca caa tgg aat aag act tta      913
Arg Gln Ala His Cys Asn Ile Ser Arg Ala Gln Trp Asn Lys Thr Leu
            290                 295                 300 gaa aag gta gtt gac aag tta aga aaa caa ttt ggg gat aat aca aca      961
Glu Lys Val Val Asp Lys Leu Arg Lys Gln Phe Gly Asp Asn Thr Thr
305                 310                 315                 320 ata gct ttt aat cga tcc tca gga ggg gac cca gaa att gta atg cac     1009
Ile Ala Phe Asn Arg Ser Ser Gly Gly Asp Pro Glu Ile Val Met His
            325                 330                 335 act ttt aat tgt gga ggg gaa ttt ttc tac tgt aat aca aca caa ctg     1057
Thr Phe Asn Cys Gly Gly Glu Phe Phe Tyr Cys Asn Thr Thr Gln Leu
            340                 345                 350 ttt aat agt act tgg aat aat act tgg aag gat cct aac agg agt gac     1105
Phe Asn Ser Thr Trp Asn Asn Thr Trp Lys Asp Pro Asn Arg Ser Asp
            355                 360                 365 aat atc aca ctc cca tgc aga ata aaa caa att ata aac atg tgg cag     1153
Asn Ile Thr Leu Pro Cys Arg Ile Lys Gln Ile Ile Asn Met Trp Gln
            370                 375                 380 gaa gta gga aaa gca atg tac gcc cct ccc atc aga ggg gaa att aga     1201
Glu Val Gly Lys Ala Met Tyr Ala Pro Pro Ile Arg Gly Glu Ile Arg
385                 390                 395                 400 tgt tca tca aat atc aca ggg ctg cta cta aca aga gat ggt ggt aat     1249
Cys Ser Ser Asn Ile Thr Gly Leu Leu Leu Thr Arg Asp Gly Gly Asn
            405                 410                 415 gac gat ggt aat gac acg acc aca aac agg acc gag atc ttc aga cct     1297
Asp Asp Gly Asn Asp Thr Thr Thr Asn Arg Thr Glu Ile Phe Arg Pro
            420                 425                 430 gga gga gga gat atg agg gac aat tgg aga agt gaa tta tat aga tat     1345
Gly Gly Gly Asp Met Arg Asp Asn Trp Arg Ser Glu Leu Tyr Arg Tyr
            435                 440                 445 aaa gta gta aaa att gaa cca tta gga ata gca ccc acc agg gca aag     1393
Lys Val Val Lys Ile Glu Pro Leu Gly Ile Ala Pro Thr Arg Ala Lys
            450                 455                 460 aga aga gtg gtg cag aga gaa aaa aga gca gta gga cta gga gct ttg     1441
Arg Arg Val Val Gln Arg Glu Lys Arg Ala Val Gly Leu Gly Ala Leu
```

```
                465                 470                 475                 480
ttc ctt ggg ttc ttg gga gca taa agc ttc tag a                                       1475
Phe Leu Gly Phe Leu Gly Ala  *  Ser Phe
                485
```

<210> SEQ ID NO 33
<211> LENGTH: 487
<212> TYPE: PRT
<213> ORGANISM: HIV

<400> SEQUENCE: 33

```
Val Pro Val Trp Lys Glu Ala Asn Thr Thr Leu Phe Cys Ala Ser Asp
 1               5                  10                  15
Ala Lys Ala Tyr Asp Arg Glu Val His Asn Val Trp Ala Thr His Ala
            20                  25                  30
Cys Val Pro Thr Asp Pro Asn Pro Gln Glu Ile Val Leu Gly Asn Val
        35                  40                  45
Thr Glu Asn Phe Asn Met Trp Lys Asn Asn Met Val Glu Gln Met His
    50                  55                  60
Glu Asp Ile Ile Asn Leu Trp Asp Gln Ser Leu Lys Pro Cys Val Lys
65                  70                  75                  80
Leu Thr Pro Leu Cys Val Thr Leu Lys Cys Lys Asp Leu Glu Arg Asn
                85                  90                  95
Thr Thr Tyr Asn Ser Thr Ile Thr Asn Asn Ser Ser Leu Glu Gly Leu
            100                 105                 110
Arg Glu Gln Met Thr Asn Cys Ser Phe Asn Ile Thr Thr Ser Ile Arg
        115                 120                 125
Asp Lys Val Gln Lys Glu Tyr Ala Leu Leu Tyr Lys Leu Asp Val Val
    130                 135                 140
Pro Ile Glu Glu Asp Asp Asn Thr Ser Tyr Arg Leu Ile Ser Cys Asn
145                 150                 155                 160
Thr Ser Val Ile Thr Gln Ala Cys Pro Lys Thr Ser Phe Glu Pro Ile
                165                 170                 175
Pro Ile His Tyr Cys Ala Pro Ala Gly Phe Ala Ile Leu Lys Cys Asn
            180                 185                 190
Asp Lys Lys Phe Asn Gly Thr Gly Pro Cys Lys Asn Val Ser Thr Val
        195                 200                 205
Gln Cys Thr His Gly Ile Arg Pro Val Val Ser Thr Gln Leu Leu Leu
    210                 215                 220
Asn Gly Ser Leu Ala Glu Glu Val Val Ile Arg Ser Ala Asn Phe
225                 230                 235                 240
Thr Asp Asn Ala Lys Thr Ile Ile Val His Leu Asn Glu Thr Val Lys
                245                 250                 255
Ile Asn Cys Thr Arg Leu Gly Asn Asn Thr Arg Lys Ser Ile Asn Ile
            260                 265                 270
Gly Pro Gly Arg Val Leu Tyr Ala Thr Gly Glu Ile Ile Gly Asp Ile
        275                 280                 285
Arg Gln Ala His Cys Asn Ile Ser Arg Ala Gln Trp Asn Lys Thr Leu
    290                 295                 300
Glu Lys Val Val Asp Lys Leu Arg Lys Gln Phe Gly Asp Asn Thr Thr
305                 310                 315                 320
Ile Ala Phe Asn Arg Ser Ser Gly Gly Asp Pro Glu Ile Val Met His
                325                 330                 335
Thr Phe Asn Cys Gly Gly Glu Phe Phe Tyr Cys Asn Thr Thr Gln Leu
            340                 345                 350
```

```
Phe Asn Ser Thr Trp Asn Asn Thr Trp Lys Asp Pro Asn Arg Ser Asp
            355                 360                 365

Asn Ile Thr Leu Pro Cys Arg Ile Lys Gln Ile Ile Asn Met Trp Gln
        370                 375                 380

Glu Val Gly Lys Ala Met Tyr Ala Pro Pro Ile Arg Gly Glu Ile Arg
385                 390                 395                 400

Cys Ser Ser Asn Ile Thr Gly Leu Leu Leu Thr Arg Asp Gly Gly Asn
                405                 410                 415

Asp Asp Gly Asn Asp Thr Thr Thr Asn Arg Thr Glu Ile Phe Arg Pro
            420                 425                 430

Gly Gly Gly Asp Met Arg Asp Asn Trp Arg Ser Glu Leu Tyr Arg Tyr
        435                 440                 445

Lys Val Val Lys Ile Glu Pro Leu Gly Ile Ala Pro Thr Arg Ala Lys
450                 455                 460

Arg Arg Val Val Gln Arg Glu Lys Arg Ala Val Gly Leu Gly Ala Leu
465                 470                 475                 480

Phe Leu Gly Phe Leu Gly Ala
                485
```

<210> SEQ ID NO 34
<211> LENGTH: 2
<212> TYPE: PRT
<213> ORGANISM: HIV

<400> SEQUENCE: 34

Ser Phe
 1

<210> SEQ ID NO 35
<211> LENGTH: 1435
<212> TYPE: DNA
<213> ORGANISM: HIV
<220> FEATURE:
<221> NAME/KEY: CDS
<222> LOCATION: (1)...(1434)

<400> SEQUENCE: 35

```
ctc gag gta cct gtg tgg aaa gaa gca acc acc act cta ttt tgt gca        48
Leu Glu Val Pro Val Trp Lys Glu Ala Thr Thr Thr Leu Phe Cys Ala
 1               5                  10                  15 tca gat gct aaa gca tat gat tca gag gca cat aat gtt tgg gcc aca        96
Ser Asp Ala Lys Ala Tyr Asp Ser Glu Ala His Asn Val Trp Ala Thr
             20                  25                  30 cat gcc tgt gta ccc aca gac ccc aac cca caa gaa gta gaa ttg gaa       144
His Ala Cys Val Pro Thr Asp Pro Asn Pro Gln Glu Val Glu Leu Glu
         35                  40                  45 aat gtg aca gaa aat ttt aac atg tgg aaa aat aac atg gta gaa cag       192
Asn Val Thr Glu Asn Phe Asn Met Trp Lys Asn Asn Met Val Glu Gln
     50                  55                  60 atg cat ggg gat ata att agt tta tgg gat caa agc cta aag cca tgt       240
Met His Gly Asp Ile Ile Ser Leu Trp Asp Gln Ser Leu Lys Pro Cys
 65                  70                  75                  80 gta aaa tta acc cca ctc tgt gtt acg tta aat tgc act gac cca aat       288
Val Lys Leu Thr Pro Leu Cys Val Thr Leu Asn Cys Thr Asp Pro Asn
                 85                  90                  95 gtt act aat agc gag aga acg ata gag ggg gga gaa ata aaa aat tgc       336
Val Thr Asn Ser Glu Arg Thr Ile Glu Gly Gly Glu Ile Lys Asn Cys
            100                 105                 110 tct ttc aat atc acc aca aac ata aga gat agg ttt cag aaa gaa tat       384
```

```
                                                                                       -continued Ser Phe Asn Ile Thr Thr Asn Ile Arg Asp Arg Phe Gln Lys Glu Tyr
        115                 120                 125 gca ctt ttt tat aaa ctt gat gta ata cca tta ggt aat gat aat act       432
Ala Leu Phe Tyr Lys Leu Asp Val Ile Pro Leu Gly Asn Asp Asn Thr
130                 135                 140 agc tat agg ttg ata agt tgt aac acc tca gtc att aca cag gcc tgt       480
Ser Tyr Arg Leu Ile Ser Cys Asn Thr Ser Val Ile Thr Gln Ala Cys
145                 150                 155                 160 cca aag gta tcc ttt gag cca att ccc ata cat tat tgt gcc ccg gct       528
Pro Lys Val Ser Phe Glu Pro Ile Pro Ile His Tyr Cys Ala Pro Ala
                165                 170                 175 ggt ttt gcg att cta aag tgt aaa gat aag aag ttc aat gga aca gga       576
Gly Phe Ala Ile Leu Lys Cys Lys Asp Lys Lys Phe Asn Gly Thr Gly
            180                 185                 190 cca tgt aca aat gtc agc aca gta caa tgt aca cat gga att aag cca       624
Pro Cys Thr Asn Val Ser Thr Val Gln Cys Thr His Gly Ile Lys Pro
        195                 200                 205 gta gta tca act caa ctg ttg tta aat ggc agt cta gca gaa gaa gac       672
Val Val Ser Thr Gln Leu Leu Leu Asn Gly Ser Leu Ala Glu Glu Asp
    210                 215                 220 ata gta att aga tcc gcc aat ctc aca gac aat gct aaa aac ata ata       720
Ile Val Ile Arg Ser Ala Asn Leu Thr Asp Asn Ala Lys Asn Ile Ile
225                 230                 235                 240 gta cag ctg aat gaa tct gta aca atg aat tgt aca aga ccc aac aac       768
Val Gln Leu Asn Glu Ser Val Thr Met Asn Cys Thr Arg Pro Asn Asn
                245                 250                 255 aat aca atg aaa agt ata cat ata gga cca ggc aga gca ttt tat gca       816
Asn Thr Met Lys Ser Ile His Ile Gly Pro Gly Arg Ala Phe Tyr Ala
            260                 265                 270 aca gga aac ata ata gga gat ata aga caa gca cat tgt aac att agt       864
Thr Gly Asn Ile Ile Gly Asp Ile Arg Gln Ala His Cys Asn Ile Ser
        275                 280                 285 gga aca aaa tgg aat gac act ttg aaa aag ata gct ata aaa tta aga       912
Gly Thr Lys Trp Asn Asp Thr Leu Lys Lys Ile Ala Ile Lys Leu Arg
    290                 295                 300 gaa caa ttt aat aag aca ata gtc ttt aat caa tcc tca gga ggg gac       960
Glu Gln Phe Asn Lys Thr Ile Val Phe Asn Gln Ser Ser Gly Gly Asp
305                 310                 315                 320 cca gaa att gca acg ctc agt ttt aat tgt gga ggg gaa ttt ttc tac      1008
Pro Glu Ile Ala Thr Leu Ser Phe Asn Cys Gly Gly Glu Phe Phe Tyr
                325                 330                 335 tgt aat tca aca caa ctg ttt aat agt act tgg aat agt act ggg tca      1056
Cys Asn Ser Thr Gln Leu Phe Asn Ser Thr Trp Asn Ser Thr Gly Ser
            340                 345                 350 aat aac act aaa gga aat gac aca atc aca ctc cca tgc aga ata aga      1104
Asn Asn Thr Lys Gly Asn Asp Thr Ile Thr Leu Pro Cys Arg Ile Arg
        355                 360                 365 caa att ata aac atg tgg cag aaa ata gga aaa gca atg tat gcc cct      1152
Gln Ile Ile Asn Met Trp Gln Lys Ile Gly Lys Ala Met Tyr Ala Pro
    370                 375                 380 ccc atc aaa ggg caa att aga tgt tca tca aat att aca ggg cta ata      1200
Pro Ile Lys Gly Gln Ile Arg Cys Ser Ser Asn Ile Thr Gly Leu Ile
385                 390                 395                 400 tta aca aga gat ggt ggt aac aac aac atg agc aag acc acc gag acc      1248
Leu Thr Arg Asp Gly Gly Asn Asn Asn Met Ser Lys Thr Thr Glu Thr
                405                 410                 415 ttc aga cct gga gga gga gat atg agg gac aat tgg aga agt gaa tta      1296
Phe Arg Pro Gly Gly Gly Asp Met Arg Asp Asn Trp Arg Ser Glu Leu
            420                 425                 430
```

```
tat aaa tat aaa gta gta aaa att gaa cca tta gga gta gca ccc acc      1344
Tyr Lys Tyr Lys Val Val Lys Ile Glu Pro Leu Gly Val Ala Pro Thr
        435                 440                 445 agg gca aag aga aga gtg gtg cag aga gaa aaa aga gca gtg gga ata      1392
Arg Ala Lys Arg Arg Val Val Gln Arg Glu Lys Arg Ala Val Gly Ile
    450                 455                 460 gga gct gtg ttc ctt ggg ttc ttg gga gca taa agc ttc tag              1434
Gly Ala Val Phe Leu Gly Phe Leu Gly Ala  *  Ser Phe
465                 470                 475 a                                                                    1435

<210> SEQ ID NO 36
<211> LENGTH: 474
<212> TYPE: PRT
<213> ORGANISM: HIV

<400> SEQUENCE: 36
```

| Leu | Glu | Val | Pro | Val | Trp | Lys | Glu | Ala | Thr | Thr | Thr | Leu | Phe | Cys | Ala |
|---|---|---|---|---|---|---|---|---|---|---|---|---|---|---|---|
| 1 | | | | 5 | | | | | 10 | | | | | 15 | |

Ser Asp Ala Lys Ala Tyr Asp Ser Glu Ala His Asn Val Trp Ala Thr
                20                  25                  30

His Ala Cys Val Pro Thr Asp Pro Asn Pro Gln Glu Val Glu Leu Glu
            35                  40                  45

Asn Val Thr Glu Asn Phe Asn Met Trp Lys Asn Asn Met Val Glu Gln
50                  55                  60

Met His Gly Asp Ile Ile Ser Leu Trp Asp Gln Ser Leu Lys Pro Cys
65                  70                  75                  80

Val Lys Leu Thr Pro Leu Cys Val Thr Leu Asn Cys Thr Asp Pro Asn
                85                  90                  95

Val Thr Asn Ser Glu Arg Thr Ile Glu Gly Gly Glu Ile Lys Asn Cys
            100                 105                 110

Ser Phe Asn Ile Thr Thr Asn Ile Arg Asp Arg Phe Gln Lys Glu Tyr
        115                 120                 125

Ala Leu Phe Tyr Lys Leu Asp Val Ile Pro Leu Gly Asn Asp Asn Thr
    130                 135                 140

Ser Tyr Arg Leu Ile Ser Cys Asn Thr Ser Val Ile Thr Gln Ala Cys
145                 150                 155                 160

Pro Lys Val Ser Phe Glu Pro Ile Pro Ile His Tyr Cys Ala Pro Ala
                165                 170                 175

Gly Phe Ala Ile Leu Lys Cys Lys Asp Lys Lys Phe Asn Gly Thr Gly
            180                 185                 190

Pro Cys Thr Asn Val Ser Thr Val Gln Cys Thr His Gly Ile Lys Pro
        195                 200                 205

Val Val Ser Thr Gln Leu Leu Leu Asn Gly Ser Leu Ala Glu Glu Asp
    210                 215                 220

Ile Val Ile Arg Ser Ala Asn Leu Thr Asp Asn Ala Lys Asn Ile Ile
225                 230                 235                 240

Val Gln Leu Asn Glu Ser Val Thr Met Asn Cys Thr Arg Pro Asn Asn
                245                 250                 255

Asn Thr Met Lys Ser Ile His Ile Gly Pro Gly Arg Ala Phe Tyr Ala
            260                 265                 270

Thr Gly Asn Ile Ile Gly Asp Ile Arg Gln Ala His Cys Asn Ile Ser
        275                 280                 285

Gly Thr Lys Trp Asn Asp Thr Leu Lys Lys Ile Ala Ile Lys Leu Arg
    290                 295                 300

```
Glu Gln Phe Asn Lys Thr Ile Val Phe Asn Gln Ser Ser Gly Gly Asp
305                 310                 315                 320

Pro Glu Ile Ala Thr Leu Ser Phe Asn Cys Gly Gly Glu Phe Phe Tyr
                325                 330                 335

Cys Asn Ser Thr Gln Leu Phe Asn Ser Thr Trp Asn Ser Thr Gly Ser
            340                 345                 350

Asn Asn Thr Lys Gly Asn Asp Thr Ile Thr Leu Pro Cys Arg Ile Arg
        355                 360                 365

Gln Ile Ile Asn Met Trp Gln Lys Ile Gly Lys Ala Met Tyr Ala Pro
370                 375                 380

Pro Ile Lys Gly Gln Ile Arg Cys Ser Ser Asn Ile Thr Gly Leu Ile
385                 390                 395                 400

Leu Thr Arg Asp Gly Gly Asn Asn Asn Met Ser Lys Thr Glu Thr
                405                 410                 415

Phe Arg Pro Gly Gly Gly Asp Met Arg Asp Asn Trp Arg Ser Glu Leu
                420                 425                 430

Tyr Lys Tyr Lys Val Val Lys Ile Glu Pro Leu Gly Val Ala Pro Thr
            435                 440                 445

Arg Ala Lys Arg Arg Val Val Gln Arg Glu Lys Arg Ala Val Gly Ile
450                 455                 460

Gly Ala Val Phe Leu Gly Phe Leu Gly Ala
465                 470
```

<210> SEQ ID NO 37
<211> LENGTH: 2
<212> TYPE: PRT
<213> ORGANISM: HIV

<400> SEQUENCE: 37

Ser Phe
1

<210> SEQ ID NO 38
<211> LENGTH: 1435
<212> TYPE: DNA
<213> ORGANISM: HIV
<220> FEATURE:
<221> NAME/KEY: CDS
<222> LOCATION: (1)...(1434)

<400> SEQUENCE: 38

```
ctc gag gta cct gtg tgg aaa gaa gca acc acc act cta ttt tgt gca        48
Leu Glu Val Pro Val Trp Lys Glu Ala Thr Thr Thr Leu Phe Cys Ala
1               5                   10                  15 tca gat gct aaa gca tat gat tca gag gca cat aat gtt tgg gcc aca        96
Ser Asp Ala Lys Ala Tyr Asp Ser Glu Ala His Asn Val Trp Ala Thr
            20                  25                  30 cat gcc tgt gta ccc aca gac ccc aac cca caa gaa gta gaa ttg gaa       144
His Ala Cys Val Pro Thr Asp Pro Asn Pro Gln Glu Val Glu Leu Glu
        35                  40                  45 aat gtg aca gaa aat ttt aac atg tgg aaa aat aac atg gta gaa cag       192
Asn Val Thr Glu Asn Phe Asn Met Trp Lys Asn Asn Met Val Glu Gln
    50                  55                  60 atg cat ggg gat ata att agt tta tgg gat caa agc cta aag cca tgt       240
Met His Gly Asp Ile Ile Ser Leu Trp Asp Gln Ser Leu Lys Pro Cys
65                  70                  75                  80 gta aaa tta acc cca ctc tgt gtt acg tta aat tgc act gac cca aat       288
Val Lys Leu Thr Pro Leu Cys Val Thr Leu Asn Cys Thr Asp Pro Asn
                85                  90                  95
```

```
gtt act aat agc gag aga acg ata gag ggg gga gaa ata aaa aat tgc        336
Val Thr Asn Ser Glu Arg Thr Ile Glu Gly Gly Glu Ile Lys Asn Cys
            100                 105                 110 tct ttc aat atc acc aca aac ata aga gat agg ttt cag aaa gaa tat        384
Ser Phe Asn Ile Thr Thr Asn Ile Arg Asp Arg Phe Gln Lys Glu Tyr
            115                 120                 125 gca ctt ttt tat aaa ctt gat gta ata cca tta ggt aat gat aat act        432
Ala Leu Phe Tyr Lys Leu Asp Val Ile Pro Leu Gly Asn Asp Asn Thr
130                 135                 140 agc tat agg ttg ata agt tgt aac acc tca gtc att aca cag gcc tgt        480
Ser Tyr Arg Leu Ile Ser Cys Asn Thr Ser Val Ile Thr Gln Ala Cys
145                 150                 155                 160 cca aag gta tcc ttt gag cca att ccc ata cat tat tgt gcc ccg gct        528
Pro Lys Val Ser Phe Glu Pro Ile Pro Ile His Tyr Cys Ala Pro Ala
                165                 170                 175 ggt ttt gcg att cta aag tgt aaa gat aag aag ttc aat gga aca gga        576
Gly Phe Ala Ile Leu Lys Cys Lys Asp Lys Lys Phe Asn Gly Thr Gly
                180                 185                 190 cca tgt aca aat gtc agc aca gta caa tgt aca cat gga att aag cca        624
Pro Cys Thr Asn Val Ser Thr Val Gln Cys Thr His Gly Ile Lys Pro
            195                 200                 205 gta gta tca act caa ctg ttg tta aat ggc agt cta gca gaa gaa gac        672
Val Val Ser Thr Gln Leu Leu Leu Asn Gly Ser Leu Ala Glu Glu Asp
210                 215                 220 ata gta att aga tcc gcc aat ctc aca gac aat gct aaa aac ata ata        720
Ile Val Ile Arg Ser Ala Asn Leu Thr Asp Asn Ala Lys Asn Ile Ile
225                 230                 235                 240 gta cag ctg aat gaa tct gta aca atg aat tgt aca aga ccc aac aac        768
Val Gln Leu Asn Glu Ser Val Thr Met Asn Cys Thr Arg Pro Asn Asn
                245                 250                 255 aat aca atg aaa agt ata cat ata gga cca ggc aga gca ttt tat gca        816
Asn Thr Met Lys Ser Ile His Ile Gly Pro Gly Arg Ala Phe Tyr Ala
                260                 265                 270 aca gga aac ata ata gga gat ata aga caa gca cat tgt aac att agt        864
Thr Gly Asn Ile Ile Gly Asp Ile Arg Gln Ala His Cys Asn Ile Ser
            275                 280                 285 gga aca aaa tgg aat gac act ttg aaa aag ata gct ata aaa tta aga        912
Gly Thr Lys Trp Asn Asp Thr Leu Lys Lys Ile Ala Ile Lys Leu Arg
290                 295                 300 gaa caa ttt aat aag aca ata gtc ttt aat caa tcc tca gga ggg gac        960
Glu Gln Phe Asn Lys Thr Ile Val Phe Asn Gln Ser Ser Gly Gly Asp
305                 310                 315                 320 cca gaa att gca acg ctc agt ttt aat tgt gga ggg gaa ttt ttc tac       1008
Pro Glu Ile Ala Thr Leu Ser Phe Asn Cys Gly Gly Glu Phe Phe Tyr
                325                 330                 335 tgt aat tca aca caa ctg ttt aat agt act tgg aat agt act ggg tca       1056
Cys Asn Ser Thr Gln Leu Phe Asn Ser Thr Trp Asn Ser Thr Gly Ser
            340                 345                 350 aat aac act aaa gga aat gac aca atc aca ctc cca tgc aga ata aga       1104
Asn Asn Thr Lys Gly Asn Asp Thr Ile Thr Leu Pro Cys Arg Ile Arg
            355                 360                 365 caa att ata aac atg tgg cag aaa ata gga aaa gca atg tat gcc cct       1152
Gln Ile Ile Asn Met Trp Gln Lys Ile Gly Lys Ala Met Tyr Ala Pro
370                 375                 380 ccc atc aaa ggg caa att aga tgt tca tca aat att aca ggg cta ata       1200
Pro Ile Lys Gly Gln Ile Arg Cys Ser Ser Asn Ile Thr Gly Leu Ile
385                 390                 395                 400 tta aca aga gat ggt ggt aac aac aac atg agc aag acc acc gag acc       1248
Leu Thr Arg Asp Gly Gly Asn Asn Asn Met Ser Lys Thr Thr Glu Thr
                405                 410                 415
```

-continued

| | | | | | | | | | | | | | | |
|---|---|---|---|---|---|---|---|---|---|---|---|---|---|---|
| ttc | aga | cct | gga | gga | gga | gat | atg | agg | gac | aat | tgg | aga | agt | gaa | tta | 1296 |
| Phe | Arg | Pro | Gly | Gly | Gly | Asp | Met | Arg | Asp | Asn | Trp | Arg | Ser | Glu | Leu | |
| | | | 420 | | | | 425 | | | | 430 | | | | | |
| tat | aaa | tat | aaa | gta | gta | aaa | att | gaa | cca | tta | gga | gta | gca | ccc | acc | 1344 |
| Tyr | Lys | Tyr | Lys | Val | Val | Lys | Ile | Glu | Pro | Leu | Gly | Val | Ala | Pro | Thr | |
| | | 435 | | | | 440 | | | | | 445 | | | | | |
| agg | gca | aag | aga | aga | gtg | gtg | cag | aga | gaa | aaa | aga | gca | gtg | gga | ata | 1392 |
| Arg | Ala | Lys | Arg | Arg | Val | Val | Gln | Arg | Glu | Lys | Arg | Ala | Val | Gly | Ile | |
| | 450 | | | | | 455 | | | | | 460 | | | | | |
| gga | gct | gtg | ttc | ctt | ggg | ttc | ttg | gga | gca | taa | agc | ttc | tag | | | 1434 |
| Gly | Ala | Val | Phe | Leu | Gly | Phe | Leu | Gly | Ala | * | Ser | Phe | | | | |
| 465 | | | | | 470 | | | | | | 475 | | | | | |
| a | | | | | | | | | | | | | | | | 1435 |

<210> SEQ ID NO 39
<211> LENGTH: 474
<212> TYPE: PRT
<213> ORGANISM: HIV

<400> SEQUENCE: 39

| | | | | | | | | | | | | | | |
|---|---|---|---|---|---|---|---|---|---|---|---|---|---|---|
| Leu | Glu | Val | Pro | Val | Trp | Lys | Glu | Ala | Thr | Thr | Thr | Leu | Phe | Cys | Ala |
| 1 | | | | 5 | | | | | 10 | | | | | 15 | |
| Ser | Asp | Ala | Lys | Ala | Tyr | Asp | Ser | Glu | Ala | His | Asn | Val | Trp | Ala | Thr |
| | | | 20 | | | | | 25 | | | | | 30 | | |
| His | Ala | Cys | Val | Pro | Thr | Asp | Pro | Asn | Pro | Gln | Glu | Val | Glu | Leu | Glu |
| | | 35 | | | | | 40 | | | | | 45 | | | |
| Asn | Val | Thr | Glu | Asn | Phe | Asn | Met | Trp | Lys | Asn | Asn | Met | Val | Glu | Gln |
| | 50 | | | | | 55 | | | | | 60 | | | | |
| Met | His | Gly | Asp | Ile | Ile | Ser | Leu | Trp | Asp | Gln | Ser | Leu | Lys | Pro | Cys |
| 65 | | | | | 70 | | | | | 75 | | | | | 80 |
| Val | Lys | Leu | Thr | Pro | Leu | Cys | Val | Thr | Leu | Asn | Cys | Thr | Asp | Pro | Asn |
| | | | | 85 | | | | | 90 | | | | | 95 | |
| Val | Thr | Asn | Ser | Glu | Arg | Thr | Ile | Glu | Gly | Gly | Glu | Ile | Lys | Asn | Cys |
| | | | 100 | | | | | 105 | | | | | 110 | | |
| Ser | Phe | Asn | Ile | Thr | Thr | Asn | Ile | Arg | Asp | Arg | Phe | Gln | Lys | Glu | Tyr |
| | | 115 | | | | | 120 | | | | | 125 | | | |
| Ala | Leu | Phe | Tyr | Lys | Leu | Asp | Val | Ile | Pro | Leu | Gly | Asn | Asp | Asn | Thr |
| | 130 | | | | | 135 | | | | | 140 | | | | |
| Ser | Tyr | Arg | Leu | Ile | Ser | Cys | Asn | Thr | Ser | Val | Ile | Thr | Gln | Ala | Cys |
| 145 | | | | | 150 | | | | | 155 | | | | | 160 |
| Pro | Lys | Val | Ser | Phe | Glu | Pro | Ile | Pro | Ile | His | Tyr | Cys | Ala | Pro | Ala |
| | | | | 165 | | | | | 170 | | | | | 175 | |
| Gly | Phe | Ala | Ile | Leu | Lys | Cys | Lys | Asp | Lys | Lys | Phe | Asn | Gly | Thr | Gly |
| | | | 180 | | | | | 185 | | | | | 190 | | |
| Pro | Cys | Thr | Asn | Val | Ser | Thr | Val | Gln | Cys | Thr | His | Gly | Ile | Lys | Pro |
| | | 195 | | | | | 200 | | | | | 205 | | | |
| Val | Val | Ser | Thr | Gln | Leu | Leu | Leu | Asn | Gly | Ser | Leu | Ala | Glu | Glu | Asp |
| | 210 | | | | | 215 | | | | | 220 | | | | |
| Ile | Val | Ile | Arg | Ser | Ala | Asn | Leu | Thr | Asp | Asn | Ala | Lys | Asn | Ile | Ile |
| 225 | | | | | 230 | | | | | 235 | | | | | 240 |
| Val | Gln | Leu | Asn | Glu | Ser | Val | Thr | Met | Asn | Cys | Thr | Arg | Pro | Asn | Asn |
| | | | | 245 | | | | | 250 | | | | | 255 | |
| Asn | Thr | Met | Lys | Ser | Ile | His | Ile | Gly | Pro | Gly | Arg | Ala | Phe | Tyr | Ala |
| | | | 260 | | | | | 265 | | | | | 270 | | |
| Thr | Gly | Asn | Ile | Ile | Gly | Asp | Ile | Arg | Gln | Ala | His | Cys | Asn | Ile | Ser |

-continued

```
            275                 280                 285
Gly Thr Lys Trp Asn Asp Thr Leu Lys Lys Ile Ala Ile Lys Leu Arg
    290                 295                 300

Glu Gln Phe Asn Lys Thr Ile Val Phe Asn Gln Ser Ser Gly Gly Asp
305                 310                 315                 320

Pro Glu Ile Ala Thr Leu Ser Phe Asn Cys Gly Gly Glu Phe Phe Tyr
                325                 330                 335

Cys Asn Ser Thr Gln Leu Phe Asn Ser Thr Trp Asn Ser Thr Gly Ser
                340                 345                 350

Asn Asn Thr Lys Gly Asn Asp Thr Ile Thr Leu Pro Cys Arg Ile Arg
                355                 360                 365

Gln Ile Ile Asn Met Trp Gln Lys Ile Gly Lys Ala Met Tyr Ala Pro
    370                 375                 380

Pro Ile Lys Gly Gln Ile Arg Cys Ser Ser Asn Ile Thr Gly Leu Ile
385                 390                 395                 400

Leu Thr Arg Asp Gly Gly Asn Asn Met Ser Lys Thr Thr Glu Thr
                405                 410                 415

Phe Arg Pro Gly Gly Gly Asp Met Arg Asp Asn Trp Arg Ser Glu Leu
                420                 425                 430

Tyr Lys Tyr Lys Val Val Lys Ile Glu Pro Leu Gly Val Ala Pro Thr
                435                 440                 445

Arg Ala Lys Arg Arg Val Val Gln Arg Glu Lys Arg Ala Val Gly Ile
    450                 455                 460

Gly Ala Val Phe Leu Gly Phe Leu Gly Ala
465                 470
```

<210> SEQ ID NO 40
<211> LENGTH: 2
<212> TYPE: PRT
<213> ORGANISM: HIV

<400> SEQUENCE: 40

Ser Phe
 1

<210> SEQ ID NO 41
<211> LENGTH: 511
<212> TYPE: PRT
<213> ORGANISM: HIV

<400> SEQUENCE: 41

```
Met Arg Val Lys Gly Ile Arg Arg Asn Tyr Gln His Trp Trp Gly Arg
 1               5                  10                  15

Gly Thr Met Leu Leu Gly Leu Leu Met Ile Cys Ser Ala Thr Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Ala
        50                  55                  60

His Asn Val Trp Ala Thr His Ala Cys Val Pro Thr Asp Pro Asn Pro
65                  70                  75                  80

Gln Glu Val Glu Leu Val Asn Val Thr Glu Asn Phe Asn Met Trp Lys
                85                  90                  95

Asn Asn Met Val Glu Gln Met His Glu Asp Ile Ile Ser Leu Trp Asn
                100                 105                 110

Gln Ser Leu Lys Pro Cys Val Lys Leu Thr Pro Leu Cys Val Thr Leu
```

```
                  115                 120                 125
Asn Cys Thr Asp Leu Arg Asn Thr Thr Asn Thr Asn Asn Ser Thr Asp
    130                 135                 140

Asn Asn Asn Ser Lys Ser Glu Gly Thr Ile Lys Gly Gly Glu Met Lys
145                 150                 155                 160

Asn Cys Ser Phe Asn Ile Thr Thr Ser Ile Gly Asp Lys Met Gln Lys
                165                 170                 175

Glu Tyr Ala Leu Leu Tyr Lys Leu Asp Ile Glu Pro Ile Asp Asn Asp
                180                 185                 190

Ser Thr Ser Tyr Arg Leu Ile Ser Cys Asn Thr Ser Val Ile Thr Gln
            195                 200                 205

Ala Cys Pro Lys Ile Ser Phe Glu Pro Ile Pro Ile His Tyr Cys Ala
    210                 215                 220

Pro Ala Gly Phe Ala Ile Leu Lys Cys Asn Asp Lys Lys Phe Ser Gly
225                 230                 235                 240

Lys Gly Ser Cys Lys Asn Val Ser Thr Val Gln Cys Thr His Gly Ile
                245                 250                 255

Arg Pro Val Val Ser Thr Gln Leu Leu Leu Asn Gly Ser Leu Ala Glu
                260                 265                 270

Glu Glu Val Val Ile Arg Ser Glu Asp Phe Thr Asp Asn Ala Lys Thr
            275                 280                 285

Ile Ile Val His Leu Lys Glu Ser Val Gln Ile Asn Cys Thr Arg Pro
    290                 295                 300

Asn Tyr Asn Lys Arg Lys Arg Ile His Ile Gly Pro Gly Arg Ala Phe
305                 310                 315                 320

Tyr Thr Thr Lys Asn Ile Lys Gly Thr Ile Arg Gln Ala His Cys Ile
                325                 330                 335

Ile Ser Arg Ala Lys Trp Asn Asp Thr Leu Arg Gln Ile Val Ser Lys
                340                 345                 350

Leu Lys Glu Gln Phe Lys Asn Lys Thr Ile Val Phe Asn Pro Ser Ser
            355                 360                 365

Gly Gly Asp Pro Glu Ile Val Met His Ser Phe Asn Cys Gly Gly Glu
    370                 375                 380

Phe Phe Tyr Cys Asn Thr Ser Pro Leu Phe Asn Ser Ile Trp Asn Gly
385                 390                 395                 400

Asn Asn Thr Trp Asn Asn Thr Thr Gly Ser Asn Asn Asn Ile Thr Leu
                405                 410                 415

Gln Cys Lys Ile Lys Gln Ile Ile Asn Met Trp Gln Lys Val Gly Lys
                420                 425                 430

Ala Met Tyr Ala Pro Pro Ile Glu Gly Gln Ile Arg Cys Ser Ser Asn
            435                 440                 445

Ile Thr Gly Leu Leu Leu Thr Arg Asp Gly Gly Glu Asp Thr Asp Thr
    450                 455                 460

Asn Asp Thr Glu Ile Phe Arg Pro Gly Gly Gly Asp Met Arg Asp Asn
465                 470                 475                 480

Trp Arg Ser Glu Leu Tyr Lys Tyr Lys Val Val Thr Ile Glu Pro Leu
                485                 490                 495

Gly Val Ala Pro Thr Lys Ala Lys Arg Arg Val Val Gln Arg Glu
                500                 505                 510

<210> SEQ ID NO 42
<211> LENGTH: 2800
<212> TYPE: DNA
<213> ORGANISM: HIV
```

-continued

```
<220> FEATURE:
<221> NAME/KEY: CDS
<222> LOCATION: (683)...(2419)

<400> SEQUENCE: 42
ttcgagctcg cccgacattg attattgact agagtcgatc gacagctgtg gaatgtgtgt      60
cagttagggt gtggaaagtc cccaggctcc ccagcaggca gaagtatgca aagcatgcat     120
ctcaattagt cagcaaccag gtgtggaaag tccccaggct ccccagcagg cagaagtatg     180
caaagcatgc atctcaatta gtcagcaacc atagtcccgc ccctaactcc gcccatcccg     240
cccctaactc cgcccagttc cgcccattct ccgccccatg gctgactaat ttttttttatt     300 tatgcagagg ccgaggccgc ctcggcctct gagctattcc agaagtagtg aggaggcttt     360
tttggaggcc taggcttttg caaaaagcta gcttatccgg ccgggaacgg tgcattggaa     420
cgcggattcc ccgtgccaag agtcaggtaa gtaccgccta tagagtctat aggcccaccc     480
ccttggcttc gttagaacgc ggctacaatt aatacataac cttttggatc gatcctactg     540
acactgacat ccacttttc ttttctcca caggtgtcca ctcccaggtc caactgcacc        600
tcggttcgcg aagctagctt gggctgcatc gattgaattc cactgccttc caccaagctc     660
tgcaggatcc cagagtcagg gg tct gta tct tcc tgc tgg tgg ctc cag ttc      712
                        Ser Val Ser Ser Cys Trp Trp Leu Gln Phe
                         1               5                  10 agg aac agt aaa ccc tgc tcc gaa tat tgc ctc tca cat ctc gtc aat        760
Arg Asn Ser Lys Pro Cys Ser Glu Tyr Cys Leu Ser His Leu Val Asn
             15                  20                  25 ctc cgc gag gac tgg gga ccc tct gac aag ctt cag cgc gaa cga cca        808
Leu Arg Glu Asp Trp Gly Pro Ser Asp Lys Leu Gln Arg Glu Arg Pro
         30                  35                  40 act acc ccg atc atc agt tat cct taa ggt ctc ttt tgt gtg gtg cgt        856
Thr Thr Pro Ile Ile Ser Tyr Pro  *  Gly Leu Phe Cys Val Val Arg
     45                  50                  55 tcc ggt atg ggg ggg act gcc gcc agg ttg ggg gcc gtg att ttg ttt        904
Ser Gly Met Gly Gly Thr Ala Ala Arg Leu Gly Ala Val Ile Leu Phe
 60                  65                  70 gtc gtc ata gtg ggc ctc cat ggg gtc cgc ggc aaa tat gcc ttg gcg        952
Val Val Ile Val Gly Leu His Gly Val Arg Gly Lys Tyr Ala Leu Ala
 75                  80                  85                  90 gat gcc tct ctc aag atg gcc gac ccc aat cga ttt cgc ggc aaa gac       1000
Asp Ala Ser Leu Lys Met Ala Asp Pro Asn Arg Phe Arg Gly Lys Asp
                 95                 100                 105 ctt ccg gtc ctg gac cag ctg ctc gag gta cct gtg tgg aaa gaa gca       1048
Leu Pro Val Leu Asp Gln Leu Leu Glu Val Pro Val Trp Lys Glu Ala
             110                 115                 120 aac acc act cta ttt tgt gca tca gat gct aaa gca tat aag aca gag       1096
Asn Thr Thr Leu Phe Cys Ala Ser Asp Ala Lys Ala Tyr Lys Thr Glu
         125                 130                 135 gca cat aat gtt tgg gcc aca cat gcc tgt gta ccc aca gac ccc aaa       1144
Ala His Asn Val Trp Ala Thr His Ala Cys Val Pro Thr Asp Pro Lys
     140                 145                 150 cca caa gaa ata aaa ttg gaa aat gtg aca gaa aat ttt aac atg tgg       1192
Pro Gln Glu Ile Lys Leu Glu Asn Val Thr Glu Asn Phe Asn Met Trp
155                 160                 165                 170 aaa aat aac atg gta gaa cag atg cat gag gat ata atc agt tta tgg       1240
Lys Asn Asn Met Val Glu Gln Met His Glu Asp Ile Ile Ser Leu Trp
                 175                 180                 185 gat caa agc cta aag cca tgt gta aaa tta acc cca ctc tgt gtt act       1288
Asp Gln Ser Leu Lys Pro Cys Val Lys Leu Thr Pro Leu Cys Val Thr
             190                 195                 200
```

-continued

| | | |
|---|---|---|
| tta aat tgc act gat ttg agg aat aat act aat acc aat agt acc tac<br>Leu Asn Cys Thr Asp Leu Arg Asn Asn Thr Asn Thr Asn Ser Thr Tyr<br>205 210 215 | 1336 |
| gga aaa ata atg gag gga gga gag ata aaa aac tgc tct ttc aat atc<br>Gly Lys Ile Met Glu Gly Gly Glu Ile Lys Asn Cys Ser Phe Asn Ile<br>220 225 230 | 1384 |
| acc aca agc ata aaa gat aag ctg aaa gat atg tca ctt ttt tat aaa<br>Thr Thr Ser Ile Lys Asp Lys Leu Lys Asp Met Ser Leu Phe Tyr Lys<br>235 240 245 250 | 1432 |
| ctt gat gta gta cca ata ggt aat aat agt aat act act agt tat agg<br>Leu Asp Val Val Pro Ile Gly Asn Asn Ser Asn Thr Thr Ser Tyr Arg<br>255 260 265 | 1480 |
| ttg ata agt tgt aac acc tca gtc att aca caa gcc tgt cca aag aca<br>Leu Ile Ser Cys Asn Thr Ser Val Ile Thr Gln Ala Cys Pro Lys Thr<br>270 275 280 | 1528 |
| tcc ttt gag cca att ccc ata cat tat tgt gcc ccg gct ggt ttt gcg<br>Ser Phe Glu Pro Ile Pro Ile His Tyr Cys Ala Pro Ala Gly Phe Ala<br>285 290 295 | 1576 |
| att ctc aag tgt aat gat aat aag ttc aat gga aca gga cca tgt cca<br>Ile Leu Lys Cys Asn Asp Asn Lys Phe Asn Gly Thr Gly Pro Cys Pro<br>300 305 310 | 1624 |
| aat gtc agc aca gta caa tgt aca cat gga att agg cca gta gta tca<br>Asn Val Ser Thr Val Gln Cys Thr His Gly Ile Arg Pro Val Val Ser<br>315 320 325 330 | 1672 |
| act caa ctg ctg tta aat ggc agt cta gca gaa aaa gag gta gtc ctt<br>Thr Gln Leu Leu Leu Asn Gly Ser Leu Ala Glu Lys Glu Val Val Leu<br>335 340 345 | 1720 |
| aga tct gaa aat ttc acg gac aat gct aaa acc ata ata gta cag ctg<br>Arg Ser Glu Asn Phe Thr Asp Asn Ala Lys Thr Ile Ile Val Gln Leu<br>350 355 360 | 1768 |
| aac gaa tct gta ata att gat tgt atg aga ccc aac aac aat aca aga<br>Asn Glu Ser Val Ile Ile Asp Cys Met Arg Pro Asn Asn Asn Thr Arg<br>365 370 375 | 1816 |
| aca agt ata cct atg gga cca ggg aaa gca ttt tat gca aca gga gat<br>Thr Ser Ile Pro Met Gly Pro Gly Lys Ala Phe Tyr Ala Thr Gly Asp<br>380 385 390 | 1864 |
| gta ata gga gat ata aga cga gca cat tgt aac att agt aga gca gga<br>Val Ile Gly Asp Ile Arg Arg Ala His Cys Asn Ile Ser Arg Ala Gly<br>395 400 405 410 | 1912 |
| tgg aat acc act tta caa cag ata gct aaa aaa tta aga gaa aaa ttt<br>Trp Asn Thr Thr Leu Gln Gln Ile Ala Lys Lys Leu Arg Glu Lys Phe<br>415 420 425 | 1960 |
| gag aac aaa aca ata gtt ttt aat cac tcc tca gga ggg gac cca gaa<br>Glu Asn Lys Thr Ile Val Phe Asn His Ser Ser Gly Gly Asp Pro Glu<br>430 435 440 | 2008 |
| att gta atg cac act ttt aat tgt gga ggg gaa ttt ttc tgc tgt aat<br>Ile Val Met His Thr Phe Asn Cys Gly Gly Glu Phe Phe Cys Cys Asn<br>445 450 455 | 2056 |
| tca aca cca ctg ttt aat agt act tgg aat gat gca caa ctg ttt aat<br>Ser Thr Pro Leu Phe Asn Ser Thr Trp Asn Asp Ala Gln Leu Phe Asn<br>460 465 470 | 2104 |
| agt act tgg gat gat act aaa tgg tca aaa ggc act aac gaa aat gac<br>Ser Thr Trp Asp Asp Thr Lys Trp Ser Lys Gly Thr Asn Glu Asn Asp<br>475 480 485 490 | 2152 |
| aca atc acc ctc cat tgc aga ata aaa caa att ata aat atg tgg cag<br>Thr Ile Thr Leu His Cys Arg Ile Lys Gln Ile Ile Asn Met Trp Gln<br>495 500 505 | 2200 |
| gaa gta gga aaa gca atg tat gcc cct ccc atc aaa gga caa att aga<br>Glu Val Gly Lys Ala Met Tyr Ala Pro Pro Ile Lys Gly Gln Ile Arg | 2248 |

|  |  |  |  |  |  |  |  |  |  |  |  |  |  |  |  |
|---|---|---|---|---|---|---|---|---|---|---|---|---|---|---|---|
| | | | 510 | | | | | 515 | | | | | 520 | | |
| tgt | gaa | tca | aat | att | aca | ggg | ctg | cta | tta | aca | aga | gat | ggt | ggt | aac | 2296
| Cys | Glu | Ser | Asn | Ile | Thr | Gly | Leu | Leu | Leu | Thr | Arg | Asp | Gly | Gly | Asn |
| | | 525 | | | | | 530 | | | | | 535 | | | |
| gac | acg | agc | aag | aat | aac | act | gag | att | ttc | aga | cct | gga | gga | gga | aat | 2344
| Asp | Thr | Ser | Lys | Asn | Asn | Thr | Glu | Ile | Phe | Arg | Pro | Gly | Gly | Gly | Asn |
| | | 540 | | | | | 545 | | | | | 550 | | | |
| atg | aag | gac | aat | tgg | aga | agt | gaa | tta | tat | aaa | tat | aaa | gta | ata | aaa | 2392
| Met | Lys | Asp | Asn | Trp | Arg | Ser | Glu | Leu | Tyr | Lys | Tyr | Lys | Val | Ile | Lys |
| 555 | | | | | 560 | | | | | 565 | | | | | 570 |
| att | gaa | cca | tta | gga | gta | gca | ccc | atc | taggcaaaga | | | gaagagtggt | | | | 2439
| Ile | Glu | Pro | Leu | Gly | Val | Ala | Pro | Ile | | | | | | | |
| | | | | 575 | | | | | | | | | | | |

| | |
|---|---|
| gcagagagaa aaaagagcag tgacactagg agctatgttc cttgggttct tgggagcagc | 2499 |
| aggaagcact atgggcgata agctttaatg cggtagttta tcacagttaa attcgtaacg | 2559 |
| cagtcaggca ccgtgtatga atctaacaa tgcgacctgc agaagcttag aaccgaggaa | 2619 |
| cttgtttatt gcagcttata atggttacaa ataaagcaat agcatcacaa atttcacaaa | 2679 |
| taaagcattt ttttcactgc attctagttg tggtttgtcc aaactcatca atgtatctta | 2739 |
| tcatgtctgg atcgggaatt aattcggcgc agcaccatgg cctgaaataa cctctgaaag | 2799 |
| a | 2800 |

<210> SEQ ID NO 43
<211> LENGTH: 50
<212> TYPE: PRT
<213> ORGANISM: HIV

<400> SEQUENCE: 43

Ser Val Ser Ser Cys Trp Trp Leu Gln Phe Arg Asn Ser Lys Pro Cys
  1               5                  10                  15

Ser Glu Tyr Cys Leu Ser His Leu Val Asn Leu Arg Glu Asp Trp Gly
             20                  25                  30

Pro Cys Asp Lys Leu Gln Arg Glu Arg Pro Thr Thr Pro Ile Ile Ser
         35                  40                  45

Tyr Pro
     50

<210> SEQ ID NO 44
<211> LENGTH: 528
<212> TYPE: PRT
<213> ORGANISM: HIV

<400> SEQUENCE: 44

Gly Leu Phe Cys Val Val Arg Ser Gly Met Gly Gly Thr Ala Ala Arg
  1               5                  10                  15

Leu Gly Ala Val Ile Leu Phe Val Val Ile Val Gly Leu His Gly Val
             20                  25                  30

Arg Gly Lys Tyr Ala Leu Ala Asp Ala Ser Leu Lys Met Ala Asp Pro
         35                  40                  45

Asn Arg Phe Arg Gly Lys Asp Leu Pro Val Leu Asp Gln Leu Leu Glu
     50                  55                  60

Val Pro Val Trp Lys Glu Ala Asn Thr Thr Leu Phe Cys Ala Ser Asp
 65                  70                  75                  80

Ala Lys Ala Tyr Lys Thr Glu Ala His Asn Val Trp Ala Thr His Ala
             85                  90                  95

Cys Val Pro Thr Asp Pro Lys Pro Gln Glu Ile Lys Leu Glu Asn Val

-continued

```
            100                 105                 110
Thr Glu Asn Phe Asn Met Trp Lys Asn Asn Met Val Glu Gln Met His
        115                 120                 125
Glu Asp Ile Ile Ser Leu Trp Asp Gln Ser Leu Lys Pro Cys Val Lys
    130                 135                 140
Leu Thr Pro Leu Cys Val Thr Leu Asn Cys Thr Asp Leu Arg Asn Asn
145                 150                 155                 160
Thr Asn Thr Asn Ser Thr Tyr Gly Lys Ile Met Glu Gly Gly Glu Ile
                165                 170                 175
Lys Asn Cys Ser Phe Asn Ile Thr Thr Ser Ile Lys Asp Lys Leu Lys
                180                 185                 190
Asp Met Ser Leu Phe Tyr Lys Leu Asp Val Val Pro Ile Gly Asn Asn
            195                 200                 205
Ser Asn Thr Thr Ser Tyr Arg Leu Ile Ser Cys Asn Thr Ser Val Ile
        210                 215                 220
Thr Gln Ala Cys Pro Lys Thr Ser Phe Glu Pro Ile Pro Ile His Tyr
225                 230                 235                 240
Cys Ala Pro Ala Gly Phe Ala Ile Leu Lys Cys Asn Asp Asn Lys Phe
                245                 250                 255
Asn Gly Thr Gly Pro Cys Pro Asn Val Ser Thr Val Gln Cys Thr His
                260                 265                 270
Gly Ile Arg Pro Val Val Ser Thr Gln Leu Leu Asn Gly Ser Leu
            275                 280                 285
Ala Glu Lys Glu Val Val Leu Arg Ser Glu Asn Phe Thr Asp Asn Ala
        290                 295                 300
Lys Thr Ile Ile Val Gln Leu Asn Glu Ser Val Ile Ile Asp Cys Met
305                 310                 315                 320
Arg Pro Asn Asn Asn Thr Arg Thr Ser Ile Pro Met Gly Pro Gly Lys
                325                 330                 335
Ala Phe Tyr Ala Thr Gly Asp Val Ile Gly Asp Ile Arg Arg Ala His
                340                 345                 350
Cys Asn Ile Ser Arg Ala Gly Trp Asn Thr Thr Leu Gln Gln Ile Ala
            355                 360                 365
Lys Lys Leu Arg Glu Lys Phe Glu Asn Lys Thr Ile Val Phe Asn His
        370                 375                 380
Ser Ser Gly Gly Asp Pro Glu Ile Val Met His Thr Phe Asn Cys Gly
385                 390                 395                 400
Gly Glu Phe Phe Cys Cys Asn Ser Thr Pro Leu Phe Asn Ser Thr Trp
                405                 410                 415
Asn Asp Ala Gln Leu Phe Asn Ser Thr Trp Asp Thr Lys Trp Ser
                420                 425                 430
Lys Gly Thr Asn Glu Asn Asp Thr Ile Thr Leu His Cys Arg Ile Lys
        435                 440                 445
Gln Ile Ile Asn Met Trp Gln Glu Val Gly Lys Ala Met Tyr Ala Pro
    450                 455                 460
Pro Ile Lys Gly Gln Ile Arg Cys Glu Ser Asn Ile Thr Gly Leu Leu
465                 470                 475                 480
Leu Thr Arg Asp Gly Gly Asn Asp Thr Ser Lys Asn Asn Thr Glu Ile
                485                 490                 495
Phe Arg Pro Gly Gly Gly Asn Met Lys Asp Asn Trp Arg Ser Glu Leu
                500                 505                 510
Tyr Lys Tyr Lys Val Ile Lys Ile Glu Pro Leu Gly Val Ala Pro Ile
        515                 520                 525
```

```
<210> SEQ ID NO 45
<211> LENGTH: 1533
<212> TYPE: DNA
<213> ORGANISM: HIV
<220> FEATURE:
<221> NAME/KEY: CDS
<222> LOCATION: (166)...(1533)

<400> SEQUENCE: 45
atggggggga ctgccgccag gttgggggcc gtgattttgt tgtcgtcat agtgggcctc         60 catgggtcc gcggcaaata tgccttggcg gatgcctctc tcaagatggc cgaccccaat       120
cgatttcgcg gcaaagacct tccggtcctg gaccagctgc tcgag gta cct gtg tgg       177
                                                  Val Pro Val Trp
                                                   1 aaa gaa gca acc acc act cta ttt tgt gca tca gat gct aaa gca tat         225
Lys Glu Ala Thr Thr Thr Leu Phe Cys Ala Ser Asp Ala Lys Ala Tyr
 5              10                  15                  20 gat aca gag gta cat aat gtt tgg gcc aca cat gcc tgt gta ccc aca         273
Asp Thr Glu Val His Asn Val Trp Ala Thr His Ala Cys Val Pro Thr
             25                  30                  35 gac ccc aac cca caa gaa ata gga ttg gaa aat gta aca gaa aat ttt         321
Asp Pro Asn Pro Gln Glu Ile Gly Leu Glu Asn Val Thr Glu Asn Phe
         40                  45                  50 aac atg tgg aaa aat aac atg gta gaa cag atg cat gag gat ata atc         369
Asn Met Trp Lys Asn Asn Met Val Glu Gln Met His Glu Asp Ile Ile
     55                  60                  65 agt tta tgg gat caa agc tta aag cca tgt gta aaa tta acc cca cta         417
Ser Leu Trp Asp Gln Ser Leu Lys Pro Cys Val Lys Leu Thr Pro Leu
 70                  75                  80 tgt gtt act tta aat tgc act gat ttg aaa aat gct act aat acc act         465
Cys Val Thr Leu Asn Cys Thr Asp Leu Lys Asn Ala Thr Asn Thr Thr
 85                  90                  95                 100 agt agc agc tgg gga aag atg gag aga gga gaa ata aaa aac tgc tct         513
Ser Ser Ser Trp Gly Lys Met Glu Arg Gly Glu Ile Lys Asn Cys Ser
                105                 110                 115 ttc aat gtc acc aca agt ata aga gat aag atg aag aat gaa tat gca         561
Phe Asn Val Thr Thr Ser Ile Arg Asp Lys Met Lys Asn Glu Tyr Ala
            120                 125                 130 ctt ttt tat aaa ctt gat gta gta cca ata gat aat gat aat act agc         609
Leu Phe Tyr Lys Leu Asp Val Val Pro Ile Asp Asn Asp Asn Thr Ser
        135                 140                 145 tat agg ttg ata agt tgt aac acc tca gtc att aca cag gcc tgt cca         657
Tyr Arg Leu Ile Ser Cys Asn Thr Ser Val Ile Thr Gln Ala Cys Pro
    150                 155                 160 aag gtg tcc ttt gag cca att ccc ata cat tat tgt gcc ccg gct ggt         705
Lys Val Ser Phe Glu Pro Ile Pro Ile His Tyr Cys Ala Pro Ala Gly
165                 170                 175                 180 ttt gcg att cta aag tgt aga gat aaa aag ttc aac gga aca gga cca         753
Phe Ala Ile Leu Lys Cys Arg Asp Lys Lys Phe Asn Gly Thr Gly Pro
                185                 190                 195 tgt aca aat gtc agc aca gta caa tgt aca cat gga att agg cca gta         801
Cys Thr Asn Val Ser Thr Val Gln Cys Thr His Gly Ile Arg Pro Val
            200                 205                 210 gta tca act caa ctg ctg tta aat ggc agt tta gca gaa gaa gaa gta         849
Val Ser Thr Gln Leu Leu Leu Asn Gly Ser Leu Ala Glu Glu Glu Val
        215                 220                 225 gta att aga tct gcc aat ttc tcg gac aat gct aaa acc ata ata gta         897
Val Ile Arg Ser Ala Asn Phe Ser Asp Asn Ala Lys Thr Ile Ile Val

```
cag ctg aac gaa tct gta gaa att aat tgt aca aga ccc aac aac aat      945
Gln Leu Asn Glu Ser Val Glu Ile Asn Cys Thr Arg Pro Asn Asn Asn
245                 250                 255                 260 aca aga aga agt ata cat ata gga cca ggg aga gca ttt tat gca aca      993
Thr Arg Arg Ser Ile His Ile Gly Pro Gly Arg Ala Phe Tyr Ala Thr
                265                 270                 275 gga gaa ata ata gga gac ata aga caa gca cat tgt aac ctt agt agc     1041
Gly Glu Ile Ile Gly Asp Ile Arg Gln Ala His Cys Asn Leu Ser Ser
            280                 285                 290 aca aaa tgg aat aat act tta aaa cag ata gtt aca aaa tta aga gaa     1089
Thr Lys Trp Asn Asn Thr Leu Lys Gln Ile Val Thr Lys Leu Arg Glu
        295                 300                 305 cat ttt aat aaa aca ata gtc ttt aat cac tcc tca gga ggg gac cca     1137
His Phe Asn Lys Thr Ile Val Phe Asn His Ser Ser Gly Gly Asp Pro
    310                 315                 320 gaa att gta atg cac agt ttt aat tgt gga ggg gaa ttt ttc tac tgt     1185
Glu Ile Val Met His Ser Phe Asn Cys Gly Gly Glu Phe Phe Tyr Cys
325                 330                 335                 340 aat aca aca cca ctg ttt aat agt act tgg aat tat act tat act tgg     1233
Asn Thr Thr Pro Leu Phe Asn Ser Thr Trp Asn Tyr Thr Tyr Thr Trp
                345                 350                 355 aat aat act gaa ggg tca aat gac act gga aga aat atc aca ctc caa     1281
Asn Asn Thr Glu Gly Ser Asn Asp Thr Gly Arg Asn Ile Thr Leu Gln
            360                 365                 370 tgc aga ata aaa caa att ata aac atg tgg cag gaa gta gga aaa gca     1329
Cys Arg Ile Lys Gln Ile Ile Asn Met Trp Gln Glu Val Gly Lys Ala
        375                 380                 385 atg tat gcc cct ccc ata aga gga caa att aga tgc tca tca aat att     1377
Met Tyr Ala Pro Pro Ile Arg Gly Gln Ile Arg Cys Ser Ser Asn Ile
    390                 395                 400 aca ggg ctg cta tta aca aga gat ggt ggt aat aac agc gaa acc gag     1425
Thr Gly Leu Leu Leu Thr Arg Asp Gly Gly Asn Asn Ser Glu Thr Glu
405                 410                 415                 420 atc ttc aga cct gga gga gga gat atg agg gac aat tgg aga agt gaa     1473
Ile Phe Arg Pro Gly Gly Gly Asp Met Arg Asp Asn Trp Arg Ser Glu
                425                 430                 435 tta tat aaa tat aaa gta gta aaa att gaa cca tta gga gta gca ccc     1521
Leu Tyr Lys Tyr Lys Val Val Lys Ile Glu Pro Leu Gly Val Ala Pro
            440                 445                 450 acc aag gca taa                                                      1533
Thr Lys Ala
        455

<210> SEQ ID NO 46
<211> LENGTH: 455
<212> TYPE: PRT
<213> ORGANISM: HIV

<400> SEQUENCE: 46

Val Pro Val Trp Lys Glu Ala Thr Thr Thr Leu Phe Cys Ala Ser Asp
  1               5                  10                  15

Ala Lys Ala Tyr Asp Thr Glu Val His Asn Val Trp Ala Thr His Ala
                20                  25                  30

Cys Val Pro Thr Asp Pro Asn Pro Gln Glu Ile Gly Leu Glu Asn Val
            35                  40                  45

Thr Glu Asn Phe Asn Met Trp Lys Asn Asn Met Val Glu Gln Met His
        50                  55                  60

Glu Asp Ile Ile Ser Leu Trp Asp Gln Ser Leu Lys Pro Cys Val Lys
 65                  70                  75                  80
```

-continued

```
Leu Thr Pro Leu Cys Val Thr Leu Asn Cys Thr Asp Leu Lys Asn Ala
                85                  90                  95
Thr Asn Thr Thr Ser Ser Ser Trp Gly Lys Met Glu Arg Gly Glu Ile
            100                 105                 110
Lys Asn Cys Ser Phe Asn Val Thr Thr Ser Ile Arg Asp Lys Met Lys
        115                 120                 125
Asn Glu Tyr Ala Leu Phe Tyr Lys Leu Asp Val Val Pro Ile Asp Asn
    130                 135                 140
Asp Asn Thr Ser Tyr Arg Leu Ile Ser Cys Asn Thr Ser Val Ile Thr
145                 150                 155                 160
Gln Ala Cys Pro Lys Val Ser Phe Glu Pro Ile Pro Ile His Tyr Cys
                165                 170                 175
Ala Pro Ala Gly Phe Ala Ile Leu Lys Cys Arg Asp Lys Lys Phe Asn
            180                 185                 190
Gly Thr Gly Pro Cys Thr Asn Val Ser Thr Val Gln Cys Thr His Gly
        195                 200                 205
Ile Arg Pro Val Val Ser Thr Gln Leu Leu Asn Gly Ser Leu Ala
    210                 215                 220
Glu Glu Glu Val Val Ile Arg Ser Ala Asn Phe Ser Asp Asn Ala Lys
225                 230                 235                 240
Thr Ile Ile Val Gln Leu Asn Glu Ser Val Glu Ile Asn Cys Thr Arg
                245                 250                 255
Pro Asn Asn Asn Thr Arg Arg Ser Ile His Ile Gly Pro Gly Arg Ala
            260                 265                 270
Phe Tyr Ala Thr Gly Glu Ile Ile Gly Asp Ile Arg Gln Ala His Cys
        275                 280                 285
Asn Leu Ser Ser Thr Lys Trp Asn Asn Thr Leu Lys Gln Ile Val Thr
    290                 295                 300
Lys Leu Arg Glu His Phe Asn Lys Thr Ile Val Phe Asn His Ser Ser
305                 310                 315                 320
Gly Gly Asp Pro Glu Ile Val Met His Ser Phe Asn Cys Gly Gly Glu
                325                 330                 335
Phe Phe Tyr Cys Asn Thr Thr Pro Leu Phe Asn Ser Thr Trp Asn Tyr
            340                 345                 350
Thr Tyr Thr Trp Asn Asn Thr Glu Gly Ser Asn Asp Thr Gly Arg Asn
        355                 360                 365
Ile Thr Leu Gln Cys Arg Ile Lys Gln Ile Ile Asn Met Trp Gln Glu
    370                 375                 380
Val Gly Lys Ala Met Tyr Ala Pro Pro Ile Arg Gly Gln Ile Arg Cys
385                 390                 395                 400
Ser Ser Asn Ile Thr Gly Leu Leu Leu Thr Arg Asp Gly Gly Asn Asn
                405                 410                 415
Ser Glu Thr Glu Ile Phe Arg Pro Gly Gly Asp Met Arg Asp Asn
            420                 425                 430
Trp Arg Ser Glu Leu Tyr Lys Tyr Lys Val Val Lys Ile Glu Pro Leu
        435                 440                 445
Gly Val Ala Pro Thr Lys Ala
    450                 455
```

<210> SEQ ID NO 47
<211> LENGTH: 37
<212> TYPE: DNA
<213> ORGANISM: Artificial Sequence
<220> FEATURE:

-continued

```
<223> OTHER INFORMATION: Primer

<400> SEQUENCE: 47
gggaattcgg atccagagca gaagacagtg gcaatga                              37

<210> SEQ ID NO 48
<211> LENGTH: 33
<212> TYPE: DNA
<213> ORGANISM: Artificial Sequence
<220> FEATURE:
<223> OTHER INFORMATION: Primer

<400> SEQUENCE: 48
ctcgagctcc tgaagacagt cagactcatc aag                                  33

<210> SEQ ID NO 49
<211> LENGTH: 39
<212> TYPE: DNA
<213> ORGANISM: Artificial Sequence
<220> FEATURE:
<223> OTHER INFORMATION: Primer

<400> SEQUENCE: 49
ggtctagaag ctttagccca tagtgcttcc tgctgctcc                            39

<210> SEQ ID NO 50
<211> LENGTH: 36
<212> TYPE: DNA
<213> ORGANISM: Artificial Sequence
<220> FEATURE:
<223> OTHER INFORMATION: Primer

<400> SEQUENCE: 50
gggcggatcc tcgaggtacc tgtrtggaaa gaagca                               36

<210> SEQ ID NO 51
<211> LENGTH: 38
<212> TYPE: DNA
<213> ORGANISM: Artificial Sequence
<220> FEATURE:
<223> OTHER INFORMATION: Primer

<400> SEQUENCE: 51
ggtctagaag ctttatgctc cyaagaaccc aaggaaca                             38

<210> SEQ ID NO 52
<211> LENGTH: 7
<212> TYPE: PRT
<213> ORGANISM: HIV

<400> SEQUENCE: 52

Ile Gly Pro Gly Arg Ala Phe
1               5

<210> SEQ ID NO 53
<211> LENGTH: 7
<212> TYPE: PRT
<213> ORGANISM: HIV

<400> SEQUENCE: 53

Ile Gly Pro Gly Arg Ala Trp
1               5

<210> SEQ ID NO 54
<211> LENGTH: 7
```

```
-continued

<212> TYPE: PRT
<213> ORGANISM: HIV

<400> SEQUENCE: 54

Leu Gly Pro Gly Ser Thr Phe
 1               5

<210> SEQ ID NO 55
<211> LENGTH: 7
<212> TYPE: PRT
<213> ORGANISM: HIV

<400> SEQUENCE: 55

Ile Gly Pro Gly Arg Val Leu
 1               5

<210> SEQ ID NO 56
<211> LENGTH: 7
<212> TYPE: PRT
<213> ORGANISM: HIV

<400> SEQUENCE: 56

Ile Gly Pro Gly Ser Ala Phe
 1               5

<210> SEQ ID NO 57
<211> LENGTH: 5
<212> TYPE: PRT
<213> ORGANISM: HIV

<400> SEQUENCE: 57

Ile Gly Pro Gly Arg
 1               5
```